(12) United States Patent
Corbascio et al.

(10) Patent No.: US 10,751,370 B2
(45) Date of Patent: Aug. 25, 2020

(54) IMMUNOMODULATORY COMPOSITIONS

(71) Applicant: ISLETONE AB, Huddinge (SE)

(72) Inventors: Matthias Corbascio, Vallentuna (SE); Makiko Kumagai, Enskede (SE)

(73) Assignee: Swedish Stromabio AB, Lidingö (SE)

( * ) Notice: Subject to any disclaimer, the term of this patent is extended or adjusted under 35 U.S.C. 154(b) by 67 days.

(21) Appl. No.: 15/103,832

(22) PCT Filed: Dec. 11, 2014

(86) PCT No.: PCT/SE2014/000148
§ 371 (c)(1),
(2) Date: Jun. 10, 2016

(87) PCT Pub. No.: WO2015/088414
PCT Pub. Date: Jun. 18, 2015

(65) Prior Publication Data
US 2016/0361364 A1 Dec. 15, 2016

(30) Foreign Application Priority Data
Dec. 13, 2013 (SE) ..................................... 1300777

(51) Int. Cl.
A61K 35/14 (2015.01)
A61K 35/28 (2015.01)
A61K 39/395 (2006.01)
C07K 16/28 (2006.01)

(52) U.S. Cl.
CPC .......... *A61K 35/28* (2013.01); *A61K 39/3955* (2013.01); *C07K 16/28* (2013.01); *C07K 16/2875* (2013.01)

(58) Field of Classification Search
None
See application file for complete search history.

(56) References Cited

U.S. PATENT DOCUMENTS 7,829,534 B2 * 11/2010 Larsen ............. C07K 14/70521
424/134.1
8,455,245 B2 * 6/2013 Frank ................... C12N 5/0625
435/325

2002/0044923 A1 4/2002 Mosca et al.
2012/0269806 A1 * 10/2012 Sykes ................ A61K 38/1709
424/134.1
2015/0139994 A1 * 5/2015 Xu .................... C07K 14/70521
424/134.1

FOREIGN PATENT DOCUMENTS

WO WO9947163 * 9/1999
WO 2007/143139 A1 12/2007

OTHER PUBLICATIONS

Corbascio et al., "CTLA4Ig Combined With Anti-Lfa-1 Prolongs Cardiac Allograft Survival Indefinitely", Transplant Immunology, vol. 10, 2002, pp. 55-61.
Engela et al., "Mesenchymal Stem Cells Control Alloreactive Cd8+Cd28—T Cells", Clinical and Experimental Immunology, vol. 174, 2013, pp. 449-458.
International Preliminary Report on Patentability received for PCT Patent Application No. PCT/SE2014/000148, dated Jun. 23, 2016, 8 pages.
International Search Report and Written Opinion received for PCT Patent Application No. PCT/SE2014/000148, dated Mar. 25, 2015, 11 Pages.
Larsson et al., "Simultaneous Inhibition of B7 and Lfa-1 Signaling Prevents Rejection of Discordant Neural Xenografts in Mice Lacking Cd40I", Xenotransplantation, vol. 9, 2002, pp. 68-76.
Zhang et al., "Immunomodulatory and Osteogenic Differentiation Effects of Mesenchymal Stem Cells by Adenovirus-Mediated Coexpression of Ctla4ig and Bmp2", Journal of Orthopaedic Research, vol. 26, 2008, pp. 314-321.
Dominici et al., "Minimal criteria for defining multipotent mesenchymal stromal cells. The International Society for Cellular Therapy position statement", Cytotherapy (2006) vol. 8, No. 4, 315-317.

* cited by examiner

*Primary Examiner* — Michail A Belyavskyi
(74) *Attorney, Agent, or Firm* — Morrison & Foerster LLP

(57) ABSTRACT

The present invention relates to pharmaceutical compositions comprising mesenchymal cells (MSCs) and additional agents for blocking co-stimulation of the immune system. The compositions may optionally further comprise a therapeutic cell, a therapeutic tissue, and/or a therapeutic organ implant. Additionally, the instant invention pertains to medical uses of such compositions in immune-mediated diseases and disorders, in essentially all inflammatory and/or autoimmune diseases and conditions, and also in transplantation-related conditions.

5 Claims, 17 Drawing Sheets
Specification includes a Sequence Listing.

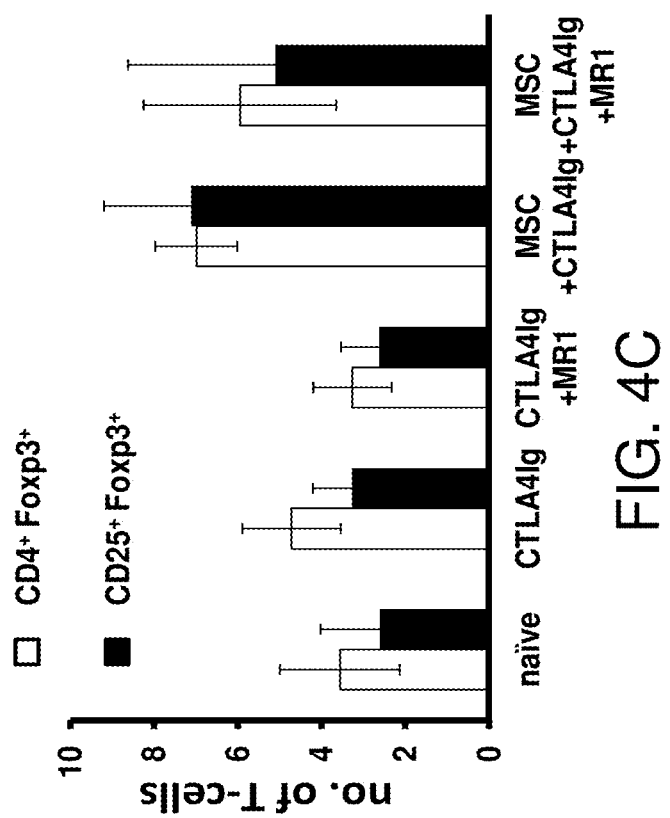

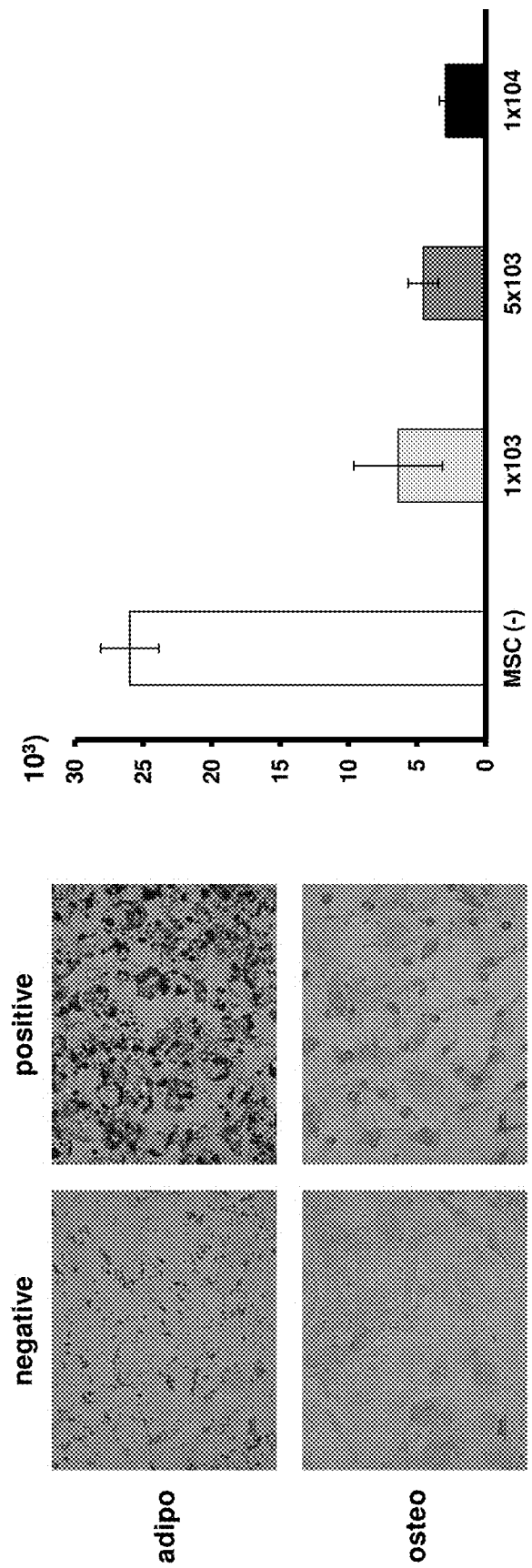

US 10,751,370 B2

IMMUNOMODULATORY COMPOSITIONS

CROSS-REFERENCE TO RELATED APPLICATIONS

This application is a U.S. National Stage of International Application Number PCT/SE2014/000148 filed Dec. 11, 2014, which claims priority to Swedish Patent Application Number 1300777-8 filed Dec. 13, 2013, the disclosures of which are hereby incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 737452000300SEQLIST.txt, date recorded: Jun. 9, 2016, size: 337 KB).

TECHNICAL FIELD

The present invention relates inter alia to compositions, treatment methods, and medical uses of a combination of mesenchymal stem cells (MSCs) and agents for blocking co-stimulation of the immune system, so called co-stimulation inhibitors. The invention also pertains to compositions further comprising a therapeutic transplant in the form of a cell, a therapeutic tissue, and/or a therapeutic organ.

BACKGROUND ART

The successful use of mesenchymal stem cells to treat steroid-resistant severe graft-versus-host disease (GVHD) was a milestone in regenerative medicine (Le Blanc et al., *Lancet*, 2004). Since those initial reports were published, multiple clinical trials have been initiated to test MSC treatment of GVHD, Crohn's disease, ulcerative colitis and multiple sclerosis (Le Blanc et al., *Nature Reviews Immunology*, 2012). This broad applicability is an implication of the ability of MSCs to modulate nearly every cellular component of the innate and adaptive immune system. This includes reducing inflammation and neutrophil activation, modulating macrophages towards an anti-inflammatory phenotype, inhibiting NK cell activation and cytotoxicity, modulating dendritic cell activation, as well as modulating CD4+ and CD8+ T cell responses (Selmani et al., *Stem Cells*, 2008).

Concurrently, costimulation blockade has emerged as a promising strategy for replacing immunity with tolerance. In a seminal article from 1996, it was demonstrated that by blocking B7 and CD40L with CTLA4Ig and anti-CD40L in the peri-operative period, indefinite survival of vascularised allografts could be achieved (Larsen et al., Nature, 1996). Inhibition of costimulatory signals, while allowing for TCR/MHC interactions to remain intact, renders T cells anergic to donor antigen. In later studies, tolerance toward the transplants was shown to be in part due to the development of intra-graft Foxp3+ regulatory T cells generated specifically towards donor antigen with the ability to specifically inhibit anti-donor immune responses.

Later studies would show however that this was not universal to all transplant models and heterologous immunity, cross-reactivity of memory T cells to donor antigen, will probably be a major barrier in a clinical setting.

Studies in mice indicate that tolerance can be induced efficiently using one or more costimulation inhibitors but translation into non-human primates and humans has not been without obstacles, due to the complexities of e.g. the human immune system. For instance, certain subsets of T cells such as memory T cells, which have a reduced reliance on costimulation pathways, are relatively resistant to treatment with the costimulation blockade, leading to e.g. increased incidence of transplant rejection (Kinnear et al., *Transplantation*, 2013)). Furthermore, it is noteworthy that the development of novel reagents for modulating the costimulation pathway has resulted in severe adverse events, for instance cytokine storms, etc.

Costimulation blockade and MSC treatment modulate many of the same components of the immune system and can induce the peripheral conversion of T cells to a regulatory T cells. These two treatment strategies are being tested independently in clinical organ transplantation with the hope of improving graft function and recipient survival but because these strategies converge on some of the same targets the two approaches have traditionally been seen as mutually exclusive. This therapeutic similarity is evidenced by a study by Sullivan and coworkers (Sullivan et al., *Stem Cells Dev*, 2013), wherein MSCs that were genetically modified to express CTLA4Ig failed to augment the immunosuppressive effects of unmodified MSCs when treating mice with collagen-induced arthritis.

SUMMARY OF THE INVENTION

The present invention pertains to safe and effective pharmaceutical compositions comprising mesenchymal stem cells (MSCs) (also called mesenchymal cells (MSCs), mesenchymal stromal cells (MSCs), multipotent stromal cells (MSCs), etc.)) and exogenous free (solubilized) agent(s) that inhibit secondary signals in immune activation, i.e. so-called co-stimulation inhibitors. The present invention hence aims to overcome and alleviate some of the technical and scientific problems of the prior art, namely to enhance the efficacy of both co-stimulation inhibitors and MSCs in the context of transplantation-related conditions and in the context of treatment of inflammatory and autoimmune diseases and disorders. The inventors have serendipitously discovered that a highly unexpected synergism between MSCs and at least one costimulation inhibitor can be achieved when combining MSCs with at least one systemically present exogenous costimulation inhibitor. Importantly, the present invention makes use of costimulation inhibitors which have an extended in vivo half life, meaning that they exert their effects in the patient for extended time periods whereas the MSC effects are relatively transient in nature, resulting in a highly efficacious combinatorial treatment strategy. The compositions of the present invention may be comprised of a set of (i.e. a plurality of) compositions, wherein the MSC population may be a first composition (e.g. in a separate vessel) and the at least one agent inhibiting co-stimulatory signal(s) (i.e. the co-stimulation inhibitor) may be a subsequent composition (or several subsequent compositions) (e.g. a first co-stimulation inhibitor is present in a second composition and a second co-stimulation inhibitor is present in a third composition).

The costimulation inhibitors may inhibit signaling between T cells and antigen-presenting cells (APCs), as well as signals between T cells and their targets. The inhibitory agents in question may normally be aimed at inhibiting the so called co-stimulatory pathways and said molecules may therefore be referred to as agent(s) inhibiting co-stimulatory signals, or co-stimulation inhibitors. These co-stimulation inhibitors may comprise at least one agent selected from the group comprising at least one fusion protein, at least one monoclonal antibody, at least one small molecule, and any combination thereof, and, unlike e.g. the work by Sullivan and coworkers, the co-stimulation inhibitors of the present invention are exogenous (i.e. not derived from the body itself or from the MSCs as such) and are present in a composition (which may be a solution) as free biopharmaceutical agents (and not expressed by MSCs or any other type of delivery vector). Using the approach of Sullivan et al. the in vivo behavior, the distribution in the patient, the transient local effects of CTLA4Ig, and the potential for posttranslational modifications of the endogenous CTLA4Ig (one of the first co-stimulation inhibitors) are all factors which may result in sub-optimal pharmacokinetic and/or pharmacodynamic properties. In complete contrast, the present invention teaches a combination of therapeutically evaluated, unaltered and unmodified MSCs with systemically administered exogenous co-stimulation inhibitors which may preferably have an extended in vivo half-life (preferably a half-life of at least 2 days) in order to ensure that synergistic effects between the MSCs and the co-stimulation inhibitors are seen, unlike in the work of Sullivan et al.

In one aspect, the present invention thus pertains to a composition and/or a pharmaceutical composition comprising a population of mesenchymal cells (MCs) and at least one exogenous agent inhibiting co-stimulatory signal(s). The mesenchymal cell (MC) may also be referred to as e.g. a mesenchymal stem cell and/or a mesenchymal stromal cell (MSC) and may be obtainable from bone marrow, cord blood, amnion tissue, Wharton's jelly, adipose tissue, skin, adult muscle (for instance heart muscle), and other suitable tissues.

In another aspect, the present invention relates to the compositions for use as medicaments, and more specifically in various immune-mediated diseases and disorders, in transplantation and implantation, and in virtually any diseases or disorders with autoimmunity and/or inflammatory involvement.

Furthermore, the present invention also pertains to a combination of an MSC population and at least one exogenous co-stimulation inhibitor for use as a medicament, and the invention also relates to the combinatorial approaches of (i) an MSC population for use as a medicament, wherein the MSC population is administered in combination with at least one exogenous co-stimulation inhibitor, and (ii) an exogenous co-stimulation inhibitor for use as a medicament, wherein the at least one exogenous co-stimulation inhibitor is administered in combination with an MSC population.

The instant invention also relates to a combination of an MSC population and at least one exogenous co-stimulation inhibitor for use in a method of suppressing and/or modulating the immune system in a subject, the method comprising the steps of (a) administering to the subject an MSC population and (b) administering to the subject at least one exogenous co-stimulation inhibitor, wherein steps (a) and (b) may be carried out simultaneously or sequentially in any sequence or order. The invention may further comprise the step (c) of administering to the subject a therapeutic transplant in the form of a cell, tissue, and/or organ, wherein steps (a), (b), and (c) may be carried out simultaneously or sequentially in any sequence or order.

The present invention thus offers a more effective, predictable, and practical treatment approach to autoimmune, inflammatory, and transplantation-related diseases, disorders, and conditions, by utilizing a combination of immunomodulatory MSCs and tolerance-inducing exogenous co-stimulation inhibitors (which may be present in the form of solubilized, pharmaceutical compositions for systemic administration to a patient).

As above-mentioned, the present invention pertains to combining the MSC population and the co-stimulation inhibitor(s) with a transplant or a graft, typically in the form of therapeutic cell, therapeutic tissue and/or therapeutic organ transplant/implant. Thus, the composition of the present invention may comprise, in addition to the MSC and the co-stimulation inhibitor, a cell, tissue, and/or organ of allogeneic and/or autologous origin which would treat a particular indication if successfully administered to the patient. In fact the therapeutic cell may also be an MSC. For a type 1 diabetes patient, the treatment modality may advantageously comprise at least one MSC, at least one agent inhibiting co-stimulatory signal(s), and at least one cell capable of producing insulin (i.e. a so called beta cell), in order to modulate the immune system of the patient to inhibit cell rejection and thereby to normalize blood glucose levels. Similarly, hepatocytes could be included in a composition for treating liver failure, and kidney cells could be included in a composition treating various kidney disorders.

The present invention thus represents completely novel treatment modalities for immune-mediated disorders and diseases, where a composition comprising MSCs and agent(s) inhibiting co-stimulation modulates and/or suppresses the immune system, which may in itself be a highly efficacious treatment for various inflammatory and/or autoimmune disorders and diseases, but it also allows for cell, tissue, and/or organ implantation and/or transplantation.

BRIEF DESCRIPTION OF THE DRAWINGS

FIG. 7: Characterization of MSCs and suppressive activity on T cell proliferation by MSCs. (FIG. 7B) MSCs were labeled with antibodies against CD44, CD90.2, SCA-1, CD11c, CD31, CD34, CD45 and MHC class II. Grey lines indicate isotype control. (FIG. 7C) Splenocytes from C57BL/6 ($2\times10^5$) were co-cultured with irradiated Balb/c splenocytes ($4\times10^5$) in the absence or presence of graded numbers of MSCs for 4 days. Cell proliferation was measured by $^3$H-thymidine uptake for the last 18 hours. Results are shown as mean cpms ±SD of quadricates and are representative of three experiments.

FIG. 8 shows a table of weight development after rectal infusion.

DETAILED DESCRIPTION OF THE INVENTION

Figure 1A:
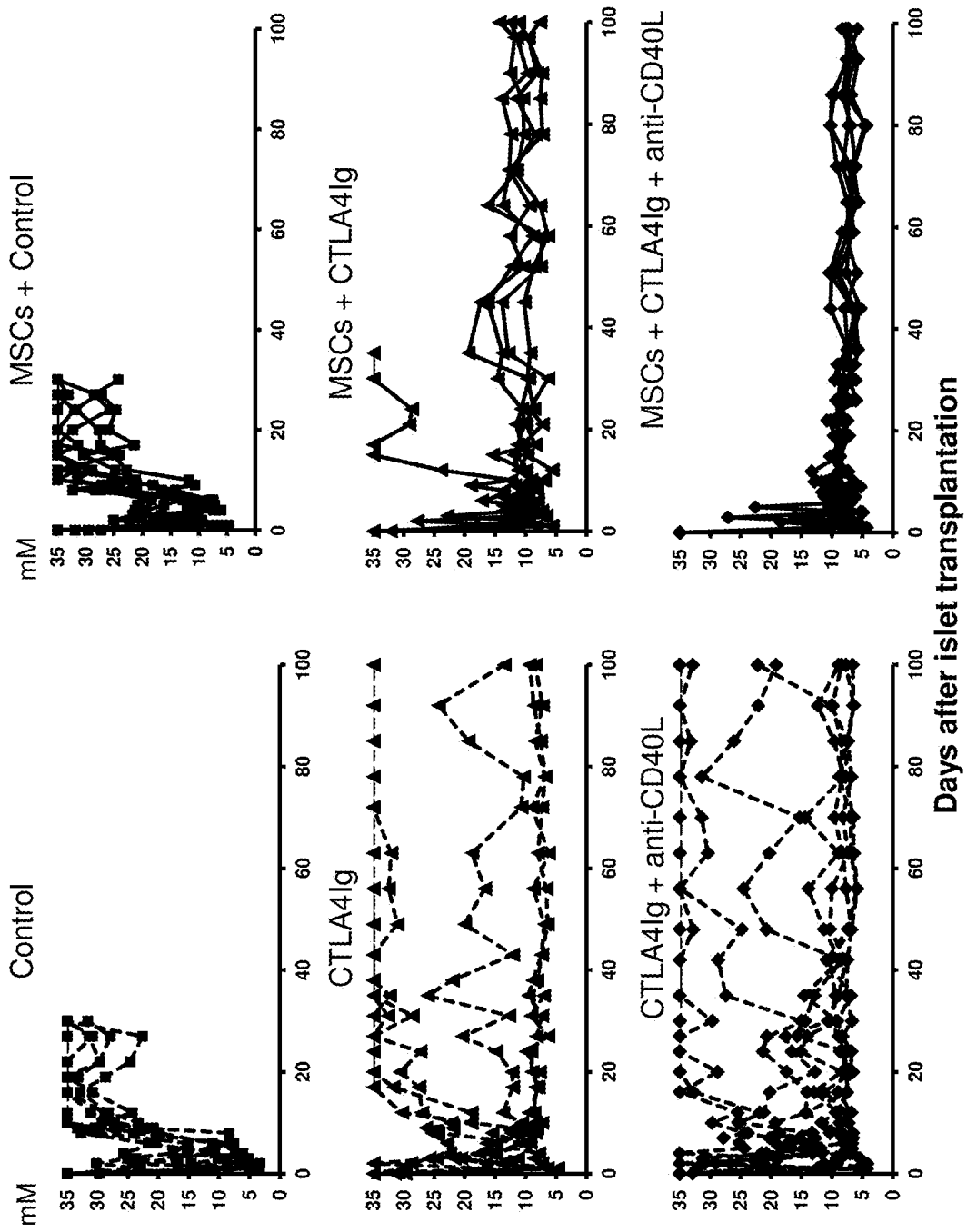
(FIG. 1A) Eight to 12-week-old diabetic C57BL/6 mice received 250 islets from fully MHC-mismatched Balb/c donors by portal vein injection. Recipients were randomized to co-transplantation with $2.5 \times 10^5$ MSC originating from recipient bone marrow and treatment with CTLA4Ig only or CTLA4Ig and anti-CD40L (or CTLA4Ig and anti-LFA1 or anti-CD40L and anti-LFA1 (data not shown)) or isotype control antibodies. Graft survival was followed by studying fasting blood glucose. Blood glucose higher than 20 mM on more than two consecutive days was considered rejection (FIG. 1B) % graft survival. MSC+CTLA4Ig+anti-CD40L vs. CTLA4Ig+anti-CD40L, ** P<0.01: MSC+CTLA4Ig+anti-CD40L vs. CTLA4Ig.

The present invention relates to highly efficacious and practically usable compositions comprising a mesenchymal cell (MC) population and at least one exogenous agent inhibiting at least one co-stimulatory signal, i.e. a so called co-stimulation inhibitor. The combinatorial use of MSCs (in the form of MSC populations) and at least one exogenous co-stimulation inhibitor (which in advantageous embodiments has an extended half-life) results in a highly surprising synergistic effect that improves treatment outcomes in numerous autoimmune, inflammatory, and transplantation-related diseases and conditions.

For clarity, the terms "mesenchymal cell" ("MC"), "mesenchymal stem cell" ("MSC"), "multipotent stromal cell" ("MSC"), "mesenchymal stromal cell" ("MSC"), and "multipotent mesenchymal stromal cell" may be used interchangeably and shall be understood to relate to cells with at least the minimal phenotype of $CD105^+$, $CD73^+$, $CD90^+$, and $CD45-$, $CD14-$, $CD34-$, $HLA-DR-$. MSCs may be allogeneic or autologous and may be isolated from different tissues including but not limited to bone marrow (BM), blood, dermis, periosteum, placenta, Wharton's jelly, fetal or embryonic tissue, umbilical cord blood, adipose tissue, liver, muscle, heart, kidney, pancreas, tooth bud, amniotic tissue, and they can differentiate into at least osteoblasts, chondroblasts, or adipocytes in vitro and in vivo. MSCs may be of either allogeneic origin (matched or unmatched to the patient) or of autologous origin (i.e. from the patient to be treated), or the MSC population may be a combination comprising both allogeneic and autologous cells. Generally, MSCs are able to form colony-forming unit fibroblasts and to proliferate extensively in vitro. In some embodiments, the MSCs of the present invention may display a spindle-shape morphology and expressing CD73, CD90, and CD105, and being negative for (i.e. devoid of) CD34, CD45, CD14, and CD31. The MSCs in accordance with the present invention may naturally also have undergone derivation and/or differentiation, for instance derivation to Isl1+ cells and/or further differentiation to cells of a certain type, e.g. cardiac cells, kidney cells, or neurons. By way of example, the MSCs of the present invention may be obtained from various types of tissue (e.g. bone marrow, adipose tissue, tooth bud, amniotic tissue, cord blood, Wharton's jelly, etc.), derived into Isl1+ mesenchymal cells, and differentiated into different cell types (for instance cardiac cells (such as cardiomyocytes)), and then administered to a patient together with the at least one agent inhibiting co-stimulatory signal(s). Further, the MSCs of the present invention may be derived from allogeneic sources, e.g. from a healthy donor (and this donor may also be the donor of a cell, tissue and/or organ transplant). Such a donor may preferably be below 50 years old, more preferably below 40 years old, even more preferably below 40 years old, yet even more preferably below 30 years old, and yet again even more preferably below 20 years old. Naturally, the MSCs and/or the cell, tissue, and/or organ transplant may also be of autologous origin.

For clarity, the expression "at least one" in the context of e.g. MSCs or more generally in the context of cells shall be understood to relate to populations of cells, e.g. a population of between one cell and several millions or even several billions of cells. In the context of agents inhibiting co-stimulatory signal(s), the term "at least one" shall be understood to relate to e.g. one (1), two (2), three (3), four (4), five (5), six (6), seven (7), eight (8), nine (9), ten (10), fifteen (15), or any other suitable number of agents that inhibit co-stimulation. Particularly advantageous numbers of agents inhibiting co-stimulatory signal(s) may be e.g. 1, 2, 3, 4, 5 or any other one-digit number of agents (for instance a combination of CTLA4Ig and anti-CD40, i.e. 2 inhibitory agents).

Generally, all polypeptides (primarily the co-stimulation inhibitors) and/or polynucleotides disclosed in the present application naturally encompass polypeptide and/or nucleotide sequences that have at least a reasonable resemblance to the polypeptide and/or polynucleotide in question, for instance a 50% sequence identity to the polypeptide and/or polynucleotide in question, preferably 70% sequence identity to the polypeptide and/or polynucleotide in question, more preferably a sequence identity of at least 80%, and even more preferably a sequence identify of at least 90% to the polypeptide and/or polynucleotide in question.

The terms "positive for" and "negative for" in the context of the present invention (e.g. an MSC and/or normally an MSC population which is "positive for" a polypeptide and/or polynucleotide in question) shall be understood in accordance with the meaning normally given to the term within the biological and medical sciences, in essence a cell that is positive for a certain polypeptide and/or polynucleotide expresses said polypeptide and/or polynucleotide. The polypeptide and/or polynucleotide in question may be identified via various means, for instance using fluorescence-activated cell sorting (FACS) and/or immunohistochemical techniques and/or proteomics techniques such as LC-MS and/or 2D-PAGE. The term "positive for" may in certain instances be understood to comprise cell populations where at least 50% of the cells express the polypeptide (or polynucleotide or any other marker) in question, but preferably at least 70% or even more preferably at least 90% of the population expresses the polypeptide in question. The term "negative for" may, in the same vein, naturally be understood to be the opposite of the term "positive for", i.e. at least 50% —but preferably at least 70% or even more preferably at least 90% —of the cells of the population shall not express the polypeptide (or other suitable marker) in question.

The terms "exogenous" or "exogenously derived" shall in the context of costimulation inhibitors be understood to pertain to agents coming/deriving from outside the body or outside an MSC, i.e. as opposed to an endogenous agent that originated within the body (by way of example an endogenous CTLA4Ig polypeptide that is expressed by a genetically modified MSC). The exogenous co-stimulation inhibitor polypeptides referred to herein are conventionally obtained via recombinant technology and may be produced in a suitable production microorganism, for instance bacterial or yeast cells.

The terms "systemic" or "systemically present" shall be understood to pertain to an agent (or agents) (typically the co-stimulation inhibitors) that is present systemically, e.g. essentially throughout the entire body of a subject, normally throughout the systemic circulation which is powered by the left ventricle of the heart. For clarity, this means that the inhibitors of costimulation are distributed throughout the body after administration to the patient, so that they can exert systemic immuno-modulatory and/or immunosuppressive effects.

The term "population", which may relate to MSCs or to extracellular vesicles such as exosomes (normally derived from the MSCs in question), shall be understood to encompass a plurality of entities constituting a given population, for instance the individual MSCs which when present in a plurality constitute an MSC population. Thus, naturally, the present invention pertains also to the individual cells and vesicles of e.g. an MSC population or a population of extracellular vesicles, respectively.

The terms "subject" and/or "individual" and/or "patient" may be used interchangeably herein and are to be understood to refer broadly to an animal, for instance a human being, from whom cells can be obtained and/or to whom treatment, including prophylaxis or preventative treatment (for instance using the cells as per the present invention) is provided. Advantageously, the subject of the treatments as described in the context of the present invention is a mammal, preferably a human, or other mammals, preferably domesticated or production mammals.

The term "therapeutically effective amount" is to be understood to refer to an amount which results in an improvement, alleviation, or remediation of the disease, disorder, or symptoms of the disease or condition.

The terms "administering," "introducing" and "transplanting" are used interchangeably for the purposes of the present invention, for instance in the context of the administration of the MSCs to a patient suffering from any of the diseases and/or disorders mentioned in the context of the present invention. A suitable method or route is one which leads to at least partial localization of the MSCs at a desired site. The MSCs and/or the co-stimulation inhibitors may be administered (delivered) by any appropriate route which results in delivery of the cells and/or paracrine factors excreted from the cells (e.g. exosomes) to a desired location/tissue/site in the subject. The modes of administration suitable for the purposes of the present invention comprise for instance (without limitation) intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The most advantageous modes of administration for most patients having the diseases and disorders described herein are probably intravenous injection, peripheral intravenous injection, central venous injection into the right atrium, injection into the right ventricle of the heart, and/or injection into the pulmonary trunk/artery.

The phrase "pharmaceutically acceptable excipient" as used herein is to be understood to relate to a pharmaceutically acceptable material, composition or vehicle, for instance a solid or liquid filler, a diluent, an excipient, a carrier, a solvent or an encapsulating material, involved in suspending, maintaining the activity of or carrying or transporting the subject agents from one organ, or portion of the body, to another organ, or portion of the body.

Where features, embodiments, aspects, or alternatives of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups. This also relates to any other groups or lists of members mentioned herein. Additionally, it should be noted that any embodiment, feature, aspect, or alternative described in connection with a certain embodiment, feature, aspect, or alternative of the present invention may also be applicable mutatis mutandis to all the other embodiments, features, aspects, and alternatives of the invention. For example, the at least one exogenous co-stimulation inhibitor described in connection with the compositions and/or the pharmaceutical compositions to be used in medical treatment of a patient shall be understood to be relevant also for in vitro use of said at least one agent. As another example, steps, features, alternatives, or aspects of the methods described herein for culturing MSCs may naturally be applicable, in isolation or taken together in any combination, to all aspects, embodiments, features, and alternatives relating to e.g. the MSCs comprised in the pharmaceutical compositions, meaning that the MSCs of the (pharmaceutical) compositions according to the present invention may be obtained through culturing using the culturing methods described herein or through using any apt aspects, embodiments, features, and alternative described in connection with those methods, in isolation or in any combination of such aspects, embodiments, features, and/or alternative. As yet another example, alternatives or embodiments described herein for instance in connection with the exogenous co-stimulation inhibitors in the (pharmaceutical) compositions are naturally also applicable, in isolation or taken together in any combination, to all aspects, embodiments, features, and alternatives relating to e.g. treatment methods and/or medical uses of MSCs in combination with the co-stimulation inhibitors. For instance, although the MSCs and the co-stimulation inhibitors may be described in connection with (pharmaceutical) compositions according to the present invention they may also be utilized together as a combinatorial treatment method and/or in a medical use without necessarily being present in one or more pharmaceutical composition(s). Thus, in summary, all aspects, embodiments, features, and alternatives of the present invention may be applicable, implemented, relevant, and transferable to all other aspects, embodiments, features, and alternatives herein without departing from the scope of the present invention.

In one aspect, the present invention relates to a composition comprising at least one mesenchymal stem cell (MSC) and at least one agent inhibiting at least one co-stimulatory signal (interchangeably referred to herein as a co-stimulation inhibitor). Co-stimulatory signals are sometimes also referred to as "adhesion signals" and the signals that are being inhibited by the agent(s) of the present invention thus also include relevant adhesion signals. LFA-1 binding to ICAM 1, 2, 3 is the seminal adhesion molecule central to the binding of leukocytes to an inflamed endothelium. However, LFA-1 is also one of most important costimulatory molecule in the activation of CD4+ and CD8+ T cells and thereby the LFA-1/ICAM axis can be considered both an adhesion molecule as well as a costimulatory molecule. Another important signaling axis is LFA-3 binding to CD2. This pathway is both adhesive stabilizing T cell receptor binding to antigen presenting cells as well as providing important signaling to activate T cells. Generally, co-stimulation is required for the mounting of an effective immune response and both B cells and T cells may be exposed to co-stimulatory signals. By way of example, T cells normally require two signals to become fully activated: the first signal is antigen-specific and is provided through the interaction between the T cell receptor and the major histocompability complex (MHC) receptor present on the membrane of an antigen-presenting cell (APC) (e.g. a dendritic cell (DC)). The second signal is co-stimulatory (and antigen-nonspecific) and is provided by the interaction between a co-stimulatory signal (which may be expressed by the APC) and a receptor present on the T cell. By inhibiting co-stimulatory signals, as proposed in the present invention, lymphocytes do not become fully activating, resulting in an immuno-modulatory effect.

The present invention relates to a combination of mesenchymal cells (MSCs) and at least one agent inhibiting co-stimulatory signal(s). This combination may advantageously take the form of a composition or several separate compositions but other physical forms are also within the scope of instant invention, for instance a cell culture or a kit comprising MSCs (and optionally other therapeutic cell or tissue types, e.g. islet cells, or organs, e.g. a kidney) combined with the at least one exogenous agent inhibiting co-stimulatory signal(s). This combination of MSCs and at least one agent inhibiting co-stimulatory signal(s) may be used in the prophylaxis and/or treatment of cell, tissue, or organ transplantation/implantation, or essentially any inflammatory and/or autoimmune disease.

Without wishing to be bound by any particular theory, it is surmised that the use of at least one co-stimulation inhibitor (e.g. CTLA4Ig) in combination with administration of MSCs may also enhance the efficacy of the MSCs per se. It may be surmised that the co-stimulation inhibition may contribute to longer MSC survival in vivo, giving the MSCs a longer time span to provide therapeutic effects to the subject. Thus, in one embodiment, the present invention relates to the use of at least one co-stimulation inhibitor to enhance the therapeutic efficacy of MSCs, both in vitro and in vivo. Furthermore, the inventors have unexpectedly realized that when combining MSCs with at least one agent inhibiting co-stimulation a clear synergistic immune-modulatory effect is achieved, in complete contrast to the decreased immune-modulatory effect seen when combining MSCs with standard immunosuppressants such as Cyclosporin A and/or dexamethasone. This finding was highly serendipitous in nature and results in an extremely potent combinatorial treatment.

Thus in one embodiment the present invention pertains to at least one exogenous co-stimulation inhibitor for use in a method of increasing in vivo survival of an MSC population. The method may comprise the steps of administering to a subject (a) an MSC population and (b) at least one exogenous co-stimulation inhibitor. Steps (a) and (b) may be carried out simultaneously or sequentially in any sequence or order, meaning that step (b) may precede step (a), or that step (a) and step (b) are carried out approximately at the same time.

In one embodiment, the at least one MSC may be obtained from virtually any suitable cell/tissue source, for instance from bone marrow, cord blood, amnion fluid, Wharton's jelly, adipose tissue, iPS cells, skin, human embryonic or fetal tissue, umbilical cord, etc., but also directly from adult organs such as kidney, liver, heart, pancreas, etc. By way of example, obtaining MSCs directly from e.g. a kidney could facilitate implantation/transplantation of a kidney together with application of the pharmaceutical composition comprising the at least one MSC and the at least one agent inhibiting co-stimulatory signal(s). Importantly, MSCs are essentially insensitive to co-stimulation as they are normally devoid of the required polypeptides involved in the co-stimulation pathways, meaning that MSCs and co-stimulation inhibitors can coexist in essentially any system. For instance, a single pharmaceutical composition may comprise both a population of MSCs and several co-stimulation inhibitors without any reactivity between the cellular and the polypeptide components of the composition.

In a further embodiment, the at least one MSC may be of allogeneic and/or autologous origin, depending on factors such as availability, immunological status of the patient, etc. In order to conserve the immuno-modulatory potency of the MSCs, it is preferable to passage the cells as few times as possible, for instance less than 20 times, preferably less than 10 times, and more preferably less than 5 times. In a further embodiment, the MSCs may be cultured in a culture medium comprising lyzed human trombocytes (platelets), preferably at least $10^7$ (or even higher numbers, such as $10^8$ or $10^9$) lyzed human trombocytes per ml of culture medium. In a further embodiment, when the cells are to be utilized for medical treatment of a patient suffering from any of the diseases and disorders that may be prevented, treated, cured or alleviated by MSCs, the cells may be harvested (and subsequently used for therapeutic treatment) when the population of MSCs have reached at most $5000\times10^6$, preferably at most $2500\times10^6$ cells, more preferably at most $1000\times10^6$, even more preferably at most $750\times10^6$ cells, yet even more preferably at most $500\times10^6$ cells, starting from at most 200 ml (cm$^3$), more preferably at most 100 ml, even more preferably at most 60 ml, of cell-containing sample (such as an aspirate), for instance obtained from bone marrow. Thus, by way of example, the entire procedure from obtaining the cells to the preparing a pharmaceutical composition may entail obtaining not more than 200 ml (preferably not more than 40 ml and even more preferably not more than 30 ml) of cell-containing sample from a healthy donor (by way of example for instance from crista iliaca and/or sternum), expanding the MSCs obtained from the cell-containing sample to not more than $750*10^6$ cells, and, finally, harvesting the cells to prepare a pharmaceutical composition to be administered to a patient. The MSCs obtained by the methods of the present invention display a highly surprising level of therapeutic potency and a significantly smaller number of cells may hence be administered to a patient without reducing the therapeutic efficacy, thereby simplifying and speeding up the entire procedure. One key aspect behind the enhanced therapeutic potency lies in the lower number of cell divisions the MSCs in accordance with the present invention have undergone, meaning that their beneficial immuno-modulating characteristics are conserved. When MSCs are obtained from the donor and/or the patient they may be frozen immediately, followed by thawing and starting of the cell culture upon the need for therapeutic intervention (alternatively, cells may be obtained (and cultivated directly) from a donor and/or patient when a clinical need for MSCs arises). As above-mentioned, it is important to not cultivate the MSCs for any longer period of time, preferably less than 30 passages (after obtaining the cells from the donor or after thawing), more preferably less than 20 passages, even more preferably not more than 10 passages, and yet even more preferably not more than 5 passages, in order to conserve the potency of the MSCs. Thus, through optimizing the properties of the MSCs and using them in combination with the at least one agent inhibiting co-stimulation the present invention provides a completely novel immuno-modulatory and/or immunosuppressive approach to autoimmune and/or inflammatory diseases and disorders, and also to transplant, tissue, and cell rejection.

In further aspects, the present invention pertains to MSCs displaying highly efficient immuno-modulatory potency, to ensure efficacy when combining MSCs with the at least one exogenous co-stimulation inhibitor. Ensuring that MSCs have clinically effective immuno-modulatory capacity is an important but in the prior art frequently overlooked aspect. The present invention therefore utilizes MSC populations fulfilling certain immuno-modulatory criteria, which can be determined through assessing the MSC population(s) to ensure that preferably at least one of the following immuno-modulation criteria are met:

(a) the MSC population is positive for at least one of the following polypeptides: vimentin (SEQ ID No 1), caldesmon (SEQ ID No 2), annexin A1 (SEQ ID No 3), 14-3-3 protein epsilon (SEQ ID No 4), ADP ribosylation factor 1 (SEQ ID No 5), calnexin (SEQ ID No 6), ADP ribosylation factor 5 (SEQ ID No 7), transforming protein RhoA (SEQ ID No 8), CD44 (SEQ ID No 9), coactosin-like protein (SEQ ID No 10), mitogen-activated protein kinase 3 (SEQ ID No 11), insulin-like growth factor-binding protein 7 (SEQ ID No 12), N-acetyl-glucosamine-6-sulfatase (SEQ ID No 13), cellular retinoic acid-binding protein 2 (SEQ ID No 14), transcription elongation factor B polypeptide 1 (SEQ ID No 15), NEDD8 (SEQ ID No 16), fatty acid-binding protein, heart (SEQ ID No 17). Preferably, the MSC population is positive for at least one of the following polypeptides: vimentin (SEQ ID No 1), annexin A1 (SEQ ID No 3) and/or insulin-like growth factor-binding protein 7 (SEQ ID No 12);

(b) a population of extracellular vesicles derived from the MSC population is positive for at least one of the following polypeptides: serotransferrin (SEQ ID No 18), versican core protein (SEQ ID No 19), annexin A2 (SEQ ID No 20), serine protease HTRA1 (SEQ ID No 21), insulin-like growth factor-binding protein 3 (SEQ ID No 22), connective tissue growth factor (SEQ ID No 23), vinculin (SEQ ID No 24), neuroblast differentiation associated protein AHNAK (SEQ ID No 25), microtubule-associated protein 1B (SEQ ID No 26), fatty acid-synthase (SEQ ID No 27), triosephosphate isomerase (SEQ ID No 28), ATP-citrate synthase (SEQ ID No 29), calreticulin (SEQ ID No 30), vigilin (SEQ ID No 31), DNA-dependent protein kinase catalytic subunit (SEQ ID No 32), Rab GDP dissociation inhibitor beta (SEQ ID No 33), ATP synthase subunit beta, mitochondrial (SEQ ID No 34).). Preferably, the population of extracellular vesicles derived from the MSC population is positive for at least one of the following polypeptides: serotransferrin (SEQ ID No 18), annexin A2 (SEQ ID No 20), and/or insulin-like growth factor-binding protein 3 (SEQ ID No 22);

(c) the MSC population in (a) displays the following order of polypeptide abundance: vimentin>Annexin A1. Preferably, the MSC population exhibits the following order of polypeptide abundance: vimentin>Annexin A1>CD44>insulin-like growth factor binding protein 7>fatty-acid binding protein 3;

(d) the extracellular vesicle population in (b) displays the following order of polypeptide abundance: serotransferrin>annexin A2. Preferably, the extracellular vesicle population displays the following polypeptide abundance: serotransferrin>annexin A2>connective tissue growth factor (e) the fold-increase expression of indoleamine 2,3-dioxygenase (IDO) in the MSC population is <10 when the MSCs are primed with 15 ng/mL TNF-alpha;

(f) the fold-increase expression of indoleamine 2,3-dioxygenase (IDO) in the MSC population is >100 when the MSCs are primed with 10 ng/mL IFN-gamma;

(g) the viability of polymorphonuclear neutrophils (PMNs) is increased by at least 20% (preferably at least 30% or even more preferably at least 50%) when co-cultured with MSCs from the MSC population primed with IFN-gamma or TNF-alpha in accordance with (e) or (f);

(h) the number of $CD14^+HLA-DR^{low}$ monocytes is increased at least 1.5-fold (more preferably at least 2-fold, or even more preferably at least 3-fold) when healthy control human peripheral blood mononuclear cells (PBMSCs) are co-cultured with the MSC population primed with IFN-gamma or TNF-alpha in accordance with (e) or (f);

(i) the number of $CD4^+CD25^{high}CD127^{low}$ regulatory T-cells ($TR_{Regs}$) is increased at least 1.5-fold (more preferably at least 2-fold, or even more preferably at least 3-fold) when healthy control human peripheral blood mononuclear cells (PBMSCs) are co-cultured with the MSC population primed with IFN-gamma or TNF-alpha in accordance with (e) or (f).

Furthermore, the extracellular vesicle population obtainable from the MSC population may preferably be negative for (i.e. devoid of) at least one of the following polypeptides: LIM domain only protein7 (SEQ ID No 35), LIM domain and actin-binding protein 1 (SEQ ID No 36), coatomer protein complex, subunit beta 2 (Beta prime), isoform CRA_b (SEQ ID No 37), ribonuclease inhibitor (SEQ ID No 38), PDZ and LIM domain protein 5 (SEQ ID No 39), reticulocalbin-1 (SEQ ID No 40), early endosome antigen 1 (SEQ ID No 41), septin-2 (SEQ ID No 42), actin-related protein 2/3 complex subunit 2 (SEQ ID No 43), septin 11 (SEQ ID No 44).

Naturally, the MSC culture (i.e. the MSC population, the population of extracellular vesicles derived from the MSCs, and both the MSC population and the population of extracellular vesicles derived from the MSCs) may fulfill only one (1) of the above criteria, but preferably several criteria are met. For instance, the culture may meet criteria (a) and (b), (a) and (c), (b) and (c), (a) and (d), (a) and (e), (b) and (d), (a) and (e), (a), (i), and (c), (a), (b), and (d), (b), (c), and (i), (c), (d), and (i), (d) and (e), (a), (f), and (g), (i), (f), and (g), (a), (b), and (g), (a), (g), and (f), etc., etc. Thus, the MSC culture may meet all possible combinations and permutations of the above criteria (a)-(i) without departing from the scope of the present invention.

In essence, based on screening of a large number of MSC cultures the inventors have realized that certain polypeptide profiles of both cells and extracellular components contribute strongly to the therapeutic immuno-modulatory efficacy, and when these cells are combined with the at least one exogenous co-stimulation inhibitor a highly effective therapeutic modality is obtained. Some of the key polypeptide expression features are summarized in the tables below but other polypeptide expression patterns in addition to the ones explicitly mentioned have also been linked to immuno-modulatory properties.

| Polypeptide Expression - Active MSC-derived Extracellular Vesicles | | | |
|---|---|---|---|
| Preferably positive for at least one of: | SEQ ID No | Preferably negative for at least one of: | SEQ ID No |
| Serotransferrin | 18 | LIM domain only protein 7 | 35 |
| Versican core protein | 19 | LIM domain and actin-binding protein 1 | 36 |

| Polypeptide Expression - Active MSC-derived Extracellular Vesicles | | | |
|---|---|---|---|
| Preferably positive for at least one of: | SEQ ID No | Preferably negative for at least one of: | SEQ ID No |
| Annexin A2 | 20 | Coatomer protein complex, subunit beta 2 (Beta prime), isoform CRA_b | 37 |
| Serine protease HTRA1 | 21 | Ribonuclease inhibitor | 38 |
| IGFBP3 | 22 | PDZ and LIM domain protein 5 | 39 |
| Connective tissue GF | 23 | Reticulocalbin-1 | 40 |
| Vinculin | 24 | Early endosome antigen 1 | 41 |
| Neuroblast differentiation-associated protein AHNAK | 25 | Septin-2 | 42 |
| Microtubule-associated protein | 26 | Actin-related protein 2/3 complex subunit 2 | 43 |
| Fatty acid-synthase | 27 | Septin 11 | 44 |
| Triosephosphate isomerise | 28 | | |
| ATP-citrate synthase | 29 | | |
| Calreticulin | 30 | | |
| Vigilin | 31 | | |
| DNA-dependent protein kinase catalytic subunit | 32 | | |
| Rab GDP dissociation inhibitor beta | 33 | | |
| ATP synthase subunit beta, mitochondrial | 34 | | |

| Polypeptide Abundance Patterns (Higher-to-Lower) of Active MSCs & Extracellular Vesicles | |
|---|---|
| MSCs | Extracellular Vesicles |
| Vimentin > Annexin A1 | Serotransferrin > Annexin A2 |
| Vimentin > Caldesmon | Serotransferrin > Versican core protein |
| Vimentin > Transforming protein RhoA | Serotransferrin > Annexin A2 > Connective tissue growth factor |
| Vimentin > CD44 | Serotransferrin > Vinculin |
| Vimentin > Annexin A1 > CD44 | Serotransferrin > Annexin A2 > Vinculin |

As above-mentioned, the present invention may relate to a population of immuno-modulatory MSCs having the following antigen profile: CD73+, CD90+, CD105+, CD34−, CD45−, CD14−, and CD3−. In a further embodiment, the MSC population may be positive for vimentin and/or Annexin A1, and also positive for insulin-like growth factor binding protein 7 and/or fatty-acid binding protein 3 and/or Annexin A1.

MSCs are normally defined as functional and biologically active through a colony unit forming (CFU) test and differentiation into adipocytes (fat cells), osteoblasts (bone cells), and chondrocytes (cartilage cells). Madeira and co-authors (*PLOS One*, 2012) have compared biologically active and inactive MSCs and found that in inactive cells, expression of annexin A1 is upregulated 1.5 fold. Annexin A1 is a known apoptosis-related protein, which impacts adaptive and innate immunity. In contrast, expression of vimentin, which is a cellular cytoskeleton component, is downregulated 2.5 fold in biologically inactive MSCs in comparison with that in the active ones. This probably reflects downregulation in proliferation capacity of the inactive MCSs. However, what the inventors of the present inventions have unexpectedly found is that it is clearly preferential with a larger abundance of vimentin (and related polypeptides) than of annexin A1 (and related polypeptides). Additionally, the present inventors have found that the abundance of both Annexin A1 and Annexin A2 are higher in the extracellular fraction (e.g. in extracellular vesicles such as exosomes) of immuno-modulatory MSCs than of non-immunomodulatory MSCs and that this is an important factor for immuno-modulatory capacity in various inflammatory disorders.

Similarly, the inventors have identified other abundance patterns which result in enhanced immuno-modulatory potency, for instance in the context of the whole cells lysates: Vimentin>Caldesmon, Vimentin>CD44, and Vimentin>Annexin A1>CD44. And, in the context of the lysate of the fraction containing extracellular vesicles: Serotransferrin>Versican core protein, Serotransferrin>Annexin A2>Connective tissue growth factor, and Serotransferrin>Annexin A2>Vinculin. Importantly, the different polypeptide profiles of the MSCs and the extracellular vesicles may co-exist, for instance in that the whole cell lysate (i.e. the MSC polypeptide pattern) may display a greater abundance of vimentin than of Annexin A1, whereas the extracellular vesicle fraction derived from the MSC population exhibits a greater abundance of serotransferrin than of Annexin A2.

In a further embodiment, the MSC population may be positive for the CD44 antigen, and CD44 may advantageously be present in a lower abundance than Annexin A1.

The present inventors have also realized that certain polypeptides related to glucose metabolism play an extraordinarily important role in the modulation of the immune system. Another immuno-modulation criteria as per the present invention relates to insulin-like growth factor binding protein 7 (IGFBP7), which is key to inducing T cells to switch to regulatory T cells and to stimulate prostacyclin production, which may be important mechanisms behind the immuno-modulatory capacity of MSCs. Thus, in a preferred embodiment the immuno-modulatory MSCs (and naturally the MSC populations thereof) effective in treating myocarditis of the present invention may also meet the criteria of being positive for IGFBP7, and further the cell fraction and the extracellular fraction (e.g. the extracellular vesicles) may express approximately equal amounts (+/−30%, but preferably +/−20%) of IGFBP7 (i.e have approximately equal abundance of the polypeptide in question). In contrast, the extracellular fraction from non-immunomodulatory MSCs (i.e. MSCs not meeting the immuno-modulation criteria as per the present invention) may be distinguished from immuno-modulatory MSCs by having a significantly lower IGFBP7 abundance.

Conversely, immuno-modulatory MSCs with therapeutic activity in inflammation, transplantation, and/or autoimmunity may be essentially devoid (or at least have a very low expression/abundance) of IGFBP2 (SEQ ID No 45) both in the whole cell fraction and in the extracellular fraction (e.g. in the extracellular vesicles), whereas MSCs without immuno-modulatory capacity may have a significantly higher IGFBP2 expression.

Naturally, the abovementioned profiles may be detected/assessed e.g. either at the point of obtaining the material from a donor, at various time points during the expansion/culturing of the MSCs prior to clinical application, at various time points after the cells have been cultured in vitro, and/or at the point when it is time to administer the MSCs and/or extracellular vesicles to a patient to be treated.

In a further embodiment, the at least one exogenous co-stimulation inhibitor may inhibit at least one of the following signaling pathways:
 a. the CD28/CTLA4: CD80/CD86 pathway;
 b. the CD40: CD154 pathway;
 c. the ICOS: ICOSL pathway;
 d. the 41BB: 41BBL pathway;
 e. the CD27: CD70 pathway;
 f. the LFA-1: ICAM pathway;
 g. the VLA-4: VCAM pathway;
 h. OX40: OX40L pathway,
 i. Fas (CD95): FasL (CD95L), and,
 j. the TIM pathway,
 k. The LFA-3:CD2 pathway.

The above pathways are all important for co-stimulation of immune cells and inhibition of at least one appropriate pathway, in combination with administration of MSCs, results in significant clinical benefits, for instance when combined with transplantation of insulin-producing islet cells (to treat type 1 diabetes), hepatocytes (to treat e.g. acute or chronic liver failure), or kidney cells (to treat e.g. acute or chronic kidney failure). Similarly, applying the composition (comprising MSCs and co-stimulation inhibitors) may be highly beneficial in the context of whole organ transplantation, for instance liver transplantation, kidney transplantation, heart transplantation, etc. Also, hematopoietic cell transplants may also be relevant within the context of the present invention. Nonetheless, administering the pharmaceutical composition of the present invention (i.e. a composition which comprises MSCs and co-stimulation inhibitors) alone may also be highly beneficial in the treatment and/or prophylaxis of numerous autoimmune and inflammatory diseases, for instance diabetes type 1, kidney failure, multiple sclerosis, Crohn's disease, ALS, MS, ARDS, ulcerative colitis, graft-vs-host disease (GvHD), kidney failure, autoimmune kidney diseases, liver failure, autoimmune liver diseases, rheumatoid arthritis, Parkinson's disease, hematopoietic cell transplantation, SLE, Alzheimer's disease, arteriosclerosis, chronic or acute inflammatory diseases, arthritis, asthma, chronic obstructive pulmonary disease, post-cardiotomy cardiac failure, allergic diseases of the skin or airways, autoimmune vasculitis, etc.

In a further embodiment, the at least one agent inhibiting at least one co-stimulatory signal (i.e. the co-stimulation inhibitor) may be selected from a group comprising virtually any agent that can inhibit the at least one of the co-stimulatory signals, for instance an antibody against any suitable pathway component(s) listed in a-j above (e.g. CD28, CD80, CD86, CD40, CD154, ICOS, ICOSL, 41BB, 41BBL, CD27, CD70L, LFA-1, ICAM, VLA-4, VCAM, OX40, OX40L, Fas (CD95), FasL (CD95L), TIM, etc.), LFA-3:CD2 or a fusion protein of any one of the components above with e.g. an Fc component. Normally, the at least one agent inhibiting at least one co-stimulatory signal comprises a polypeptide, i.e. these agents may be polypeptides, which may be synthesized but most often are derived through recombinant technology.

The at least one agent inhibiting at least one co-stimulatory signal may be selected from a group comprising CTLA4-Ig, anti-CD40, anti-CD40L, anti-B7.1 and anti-B7.2 (anti-CD80 and anti-CD86), CD40 and its ligand CD154, anti-LFA1 (CD11) and anti-ICAM-1 (CD54), anti-CD27/CD70, anti-OX40/OX40L, anti-41BB/41BBL, anti-VLA4, anti-VCAM, and any variants or derivatives thereof, and any combination thereof. Interestingly, in humans the CD40-CD40L axis is preferentially inhibited through blocking CD40 with e.g. an antibody against CD40, whereas in rodents inhibition of the CD40-CD40L pathway may be achieved via blocking of either anti-CD40 or anti-CD40L. However, agents blocking CD40L may be used in humans under certain conditions and/or with certain modifications, for instance in a preferred embodiment of the present invention the anti-CD40L-Tn3 molecule (which inhibits the CD40:CD40L axis without inducing platelet aggregation) may be used in humans together with the MSC population.

A particularly advantageous composition according to the present invention may comprise CTLA4-Ig and an MSC population. CTLA4-Ig is a fusion protein composed of the Fc fragment of a human IgG1 linked to the extracellular domain of CTLA-4, and it exists in various modified variants and derivatives that are all within the scope of the present invention, for instance belatacept (SEQ ID No 46) (also known as Nulojix) and abatacept (SEQ ID No 47) (also known as Orencia).

The combination of the present invention of MSCs with free, solubilized, exogenous and systemically present co-stimulation inhibitor(s) means that one can harness the positive effects of systemic distribution of the at least one inhibitor and the homing effects of MSCs to target sites within the body, e.g. sites of inflammation and/or injury/trauma. Thus, the present invention ensures efficacious and safe administration of at least one agent inhibiting co-stimulation combined with at least one MSC, optionally further combined with at least one therapeutic transplant in the form of a cell, tissue, and/or organ.

The at least one co-stimulation inhibitor used in combination with the MSCs may advantageously be modified to have an extended half-life. Thus, in one preferred embodiment, the at least one agent inhibiting co-stimulation has an in vivo half-life of at least 2 days, preferably at least 5 days, and even more preferably at least 8 days. In essence, the extended half-life of the at least one agent inhibiting co-stimulatory signals implies that the co-stimulation inhibitor(s) can be detected in the body of a patient for an extended period of time, normally at least 2 days but preferably for longer time periods.

The prior art (exemplified by Sullivan and coworkers) merely describes local administration of CTLA4Ig through adenoviral transduction of MSCs with a construct expressing CTLA4Ig. The present invention is based on systemic administration of co-stimulation inhibitors with extended half-life, which enables therapeutically efficacious and cost-effective treatment of patients over extended periods of time, in complete contrast to the teachings by Sullivan and coworkers who merely teach a theoretical concept with no clinical applicability. Furthermore, the synergistic immunomodulatory effects of MSCs and at least one agent inhibiting co-stimulation discovered by the present inventors are not seen when utilizing the technology described by Sullivan and coworkers, as the systemic presence of at least one exogenous co-stimulation inhibitor is needed. Specifically, Sullivan et al. did not detect any decrease in inflammatory cytokines such as IFN-gamma and TNF-alpha, in contrast to the present invention. Furthermore, by being able to administer the infusion of the at least one exogenous co-stimulation inhibitor systemically, the administration can be repeated in cases where relapse of a disease state can occur without having to re-administer the MSC-based delivery system described by Sullivan and coworkers, i.e. a cell which produces a certain co-stimulation inhibitor. Repeat administrations of cells may lead to sensitization with unknown effects including allergic reactions or anaphylaxis or rejection of the cell-based delivery system which limits half-life and thereby efficacy, as well as immunization which can increase cross-reactive towards eventual future transplantation or pregnancy.

Furthermore, by eliminating the need for a cellular carrier system for drug delivery, manipulation of the MSC is avoided, eliminating interference of the biology of the MSC and its capacity to modulate the immune system in the host. Genetically modified MSCs are not easily assessed for their immuno-modulatory properties and the need for viral vectors always increases the risk of adverse events. All the exogenous co-stimulatory inhibitors utilized in the context of the present invention are developed individually and safety is tested before combining with MSC therapy. Furthermore, the fact that the at least one co-stimulation inhibitor is systemic and exogenous (i.e. not produced endogenously by the MSC) results in a longer survival time of the MSCs and thereby enhances the cells' immuno-modulatory and/or immunosuppressive effects.

Thus, to optimize the immuno-modulatory combination of MSCs and co-stimulation inhibitors, in a further particularly advantageous embodiment the compositions as per the present invention may comprise at least two agents that inhibit co-stimulatory signals, for instance CTLA4-Ig and/or anti-CD40 and/or anti-LFA1 (or variants and/or derivatives thereof). Thus, in further advantageous embodiments, the pharmaceutical composition of the present invention may comprise at least one MSC, CTLA4-Ig, and any agent that could block for instance CD40 or LFA1, either directly or by interacting with any suitable target that would abrogate the activity of the CD40:CD40L axis and/or the LFA1 pathway. Anti-CD40 and anti-LFA1 may be antibodies against CD40 and LFA-1, respectively, but they could also be any type of polypeptide that bind to and inhibit the action of any of CD40/CD40L or LFA1/ICAM1-3. In a further advantageous embodiment, the pharmaceutical composition of the present invention may comprise at least one MC, anti-CD40 and/or anti-CD40L and anti-LFA1. The anti-LFA1 agent may be the clinically approved Efalizumab (also known as Raptiva) and the anti-CD40 agent may be anti-CD40L-Tn3 (i.e. a Tenascin 3 scaffold comprising a CD40L-specific monomer subunit), and/or an agent known as 4D11 and/or an agent known as ASKP1240 (monoclonal antibody against CD40), which are currently undergoing clinical evaluation. Furthermore, another costimulation inhibitor of interest may be an anti-B7RP1 monoclonal antibody.

In a further embodiment, the dosage of CTLA4-Ig (in the form of e.g. Belatacept) may range from as little as 0.1 mg/kg, to 1 mg/kg, to 10 mg/kg, to 100 mg/kg and to even higher doses if the condition to be treated so requires. The dosage of anti-LFA1 (e.g. in the form of Efalizumab (SEQ ID No 48 (heavy chain variable region) and SEQ ID No 49 (light chain variable region)) or Odulimomab) may range from as little as 0.01 mg/kg, to 0.1 mg/kg, to 10 mg/kg, to 100 mg/kg and to even higher doses if the condition to be treated so requires. Naturally, the dosage may vary heavily also outside of the indicative ranges above depending on e.g. the duration of the treatment, the frequency of administration of the agent, the disease to be treated, the combination with other agents, the medical and/or immunological condition of the patient to be treated, etc.

The pharmaceutical compositions according to the present invention may comprise various pharmaceutically acceptable excipients in order to ensure that the MSCs and the co-stimulation inhibitors can be delivered to the patient in an efficacious manner. The MSCs and the co-stimulation inhibitors may be present in different pharmaceutical compositions with different excipients, diluents, or properties; alternatively, the MSCs and the co-stimulation inhibitors may be present in the same pharmaceutical composition. The at least one excipient may be a liquid, a solvent, a solution, a filler, a matrix proteins such as a laminin, a carrier, an encapsulating material, or any combination thereof. In one advantageous embodiment, the MSCs and the optional therapeutic cell, tissue, and/or organ transplant/implant may be administered to a patient together with at least one laminin (LN), to improve inter alia engraftment and efficacy. Suitable laminins may be LN-111, LN-211, LN221, LN-511, LN-521, LN-411, LN-421, LN-311, LN-321, LN-332 and any combination thereof (such as LN-211 combined with LN-521, or LN-421 combined with LN-521).

In a further embodiment of the present invention, the MSC population and the at least one exogenous co-stimulation inhibitor may be present in separate containers or vessels. As above-mentioned, alternatively, the MSC and the at least one agent inhibiting co-stimulatory signal(s) may also be present in the same vessel, as MSCs are costimulation-inert and as the use of one single vessel for MSCs and co-stimulation inhibitors may be advantageous in a clinical setting, for instance the combination of MSC and inhibitors (in a container bag for infusion) are administered i.v. to a patient. The use of more than one container may allow administration of the MSCs and the co-stimulation inhibitors independently of one another (e.g. that that MSCs are administered first, followed by administration of the co-stimulation inhibitors, or vice versa, that the co-stimulation inhibitors are administered first followed by administration of the MSCs). When the MSCs and the co-stimulation inhibitors are present in separate containers the containers may be for different uses, for instance the MSCs may be delivered/implanted directly into a certain organ of the patient (in that case the container may be a syringe, etc.) whereas the co-stimulation inhibitors may be administered intravenously (in which case the container may be e.g. a syringe or a container bag for infusion, etc.).

Interestingly, in part due to their tendency to home to inflammation and/or trauma, the MSCs of the pharmaceutical composition of the present invention may be administered systemically (for instance via intravenous administration), but they may also be guided to a certain site, tissue, or organ via transplantation/implantation, or optionally as part of medical device.

In a further embodiment, the pharmaceutical composition may further comprise at least one therapeutic transplant in the form of a cell, tissue, and/or organ that is to be administered to a patient. A "therapeutic cell", "therapeutic tissue", and/or "therapeutic organ" shall be understood as a cell, tissue, and/or organ that is meant to perform a certain physiological function in the body of the patient receiving the cell, tissue, and/or organ in question. The therapeutic cell, tissue, and/or organ may be intended to provide the same function as it would have done in the donor: for instance, pancreatic islet cells that are administered to a patient with type 1 diabetes in combination with the composition as per the present invention would be intended to perform the same function in the patient receiving the pancreatic islet cells as they would have done in the donor, i.e. to produce insulin. The same reasoning is applicable to kidney transplantation, wherein a kidney from a donor would be intended to perform the same function in the patient receiving the kidney as in the donor. Thus, the terms "therapeutic cell", "therapeutic tissue", and "therapeutic organ" shall be understood as a cell, tissue, and/or organ that when administered to a patient in combination with the composition of the present invention restores a particular function or feature of the body of the patient. In one embodiment, a composition may thus comprise an MSC population, at least one agent inhibiting co-stimulatory signals, and at least one cell, for instance pancreatic islet cells, neurons, hepatocytes, nephrocytes, cardiomyocytes, etc. These cells may be autologous and/or allogeneic, depending on the purpose of the cell administration. Combining the pharmaceutical composition with implantation/ transplantation (basically any type of administration) of a cell (and/or tissue and/or organ) may result in significantly improved graft survival, for instance one would be able to administer islet cells to a person suffering from type 1 diabetes and due to the immuno-modulatory effects of the pharmaceutical composition according to the present invention the islet cells would not be the target of an attack by the host (patient's) immune system or that attack would be at least partially inhibited. The therapeutic cells to be administered (e.g. islet cells, neurons, or hepatocytes) may be comprised in the same composition as the MSCs and the co-stimulation inhibitors, but said cells may also be present in a separate composition (in a separate container). Alternatively, the MSCs and the therapeutic cells (e.g. islet cells, neurons, or hepatocytes) may be comprised in a separate composition (in a separate container) which may be administered directly into a suitable target tissue, organ, or site of the patient. The administration of the MSCs and the therapeutic cells may take place before, after, or at essentially the same time as the administration of the co-stimulation inhibitors.

MSC implantation can be given as an infusion to the patient or to an organ as a conditioning regime outside of the body before transplantation. MSCs can be implanted directly to the organ that is to be targeted in the patient or as a systemic treatment. MSCs can function as the cell therapy for autoimmune or inflammatory diseases and not necessarily with a concomitant transplant of another allogeneic or syngeneic cell type or organ. Co-stimulation inhibitors may be given at the time of MSC implantation or afterwards and both therapies may be repeated as maintenance therapy or as a single induction therapy or a series of repeated therapies at the time of disease activity or as a prophylactic therapy to prevent new episodes of disease occurrence. A temporal delay of the administration of MSC therapy and co-stimulation inhibitors may achieve beneficial effects as the half-life of biologically active therapies can be maintained in the host for weeks and even months. This includes any combination of local or systemic administration of MSC and co-stimulation inhibitor with or without another cellular or organ transplant or syngeneic cell implantation.

The pharmaceutical composition comprising the MSCs may advantageously be administered to a patient suffering from any of the herein mentioned diseases, disorders, and/or conditions more than once within a certain time period, for instance the pharmaceutical composition may be administered within 1 week of the first dose, within 2 weeks of the first dose, within 3 weeks of the first dose, within 1 month of the first dose, within 2 months of the first dose, within 6 months of the first dose, and even within 1 year of the first dose, in order to enhance the therapeutic effect. Additionally, the pharmaceutical composition comprising the MSCs may be administered with longer intervals as well, either in response to disease recidivism or as a part of the regular treatment.

Prior to administering the MSC+inhibitor compositions and/or the MSC+inhibitor combination the patient may be treated with fragmin and/or heparin to reduce cell trapping in the lungs and to prevent the MSCs to cause pulmonary clotting or emboli formation. Furthermore, the patient may also be pre-treated with corticosteroids (such as prednisolone), antihistamines, and antibiotics, in a conventional manner.

The compositions (comprising the MSCs and the at least one agent inhibiting co-stimulation) may advantageously be administered to the patient via infusion through a central venous catheter. This is particularly advantageous when targeting diseases of the lung where MSC tend to be sequestered after i.v. infusion. The administration route of the pharmaceutical composition may be important to achieve therapeutic efficacy and the compositions according to the present invention may thus be administered via various different routes, for instance auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes.

In a further embodiment of the present invention, the therapeutic dose of MSCs comprised in the pharmaceutical compositions may range from at least 100,000 MSCs per kg of body weight, or at least 500,000 MSCs per kg of body weight, or at least 1,000,000 MSCs per kg of body weight, or at least 2,000,000 MSCs per kg of body weight, or even higher numbers of MSCs per kg of body weight. The therapeutic range of MSCs may for most diseases range from 100,000 to 10,000,000 MSCs per kg of body weight of the patient. In one embodiment, the pharmaceutical composition may further comprise plasma of a for the patient to be treated suitable blood type. Surprisingly, plasma of blood type AB may advantageously be used irrespective of the blood type of the patient to which the pharmaceutical composition is to be administered. Without wishing to be bound by any theory, it is surmised that the absence of antibodies against either A or B antigens is advantageous when administering the pharmaceutical composition to a patient. The plasma may be present at any concentration above 1%, preferably around 10%. The plasma is obtained fresh, normally cryo-reduced, and subsequently stored at −20° C. until use. In one embodiment, the pharmaceutically acceptable carrier may be an aqueous solution comprising at least 5% w/v sodium chloride, but other pharmaceutically and physiologically acceptable carriers may also be employed. The concentration of sodium chloride in the aqueous solution is preferably around 9% w/v.

In a further embodiment, the pharmaceutical composition as per the present invention may be used in medicine, wherein the at least one cell, tissue or organ transplant/implant is co-administered together with the MSC population, and the co-stimulation inhibitors are administered separately before, after, or essentially at the same time as the combination of MSCs and the at least one cell, tissue or organ transplant/implant.

In yet another embodiment, the present invention may relate to an MSC population for use in a method of therapeutic and/or prophylactic treatment of a subject, the method comprising the step of administering to the subject the MSC population in combination with at least one exogenous co-stimulation inhibitor. And, in an additional embodiment, the invention may also relate to at least one exogenous co-stimulation inhibitor for use in a method of therapeutic and/or prophylactic treatment of a subject, the method comprising the step of administering to the subject at least one exogenous co-stimulation inhibitor in combination with an MSC population.

Aspect 1. An article of manufacture comprising a plurality of vessels, wherein a first vessel comprises an MSC population and at least one subsequent vessel comprises at least one exogenous co-stimulation inhibitor.

Aspect 2. The article of manufacture according to Aspect 1, further comprising a subsequent vessel comprising at least one therapeutic transplant in the form of a cell, tissue, and/or organ.

In a further embodiment, the present invention pertains to an article of manufacture comprising a plurality of vessels and/or containers, wherein a first vessel comprises an MSC population and at least one subsequent vessel comprises at least one exogenous co-stimulation inhibitor. The article of manufacture, which may be in the form of a kit for use as a medicament, may further comprise at least one transplant in the form of a therapeutic cell, tissue and/or organ, optionally in yet another subsequent vessel but also in either one of the vessels comprising MSCs and/or co-stimulation inhibitor(s). The article of manufacture may, by way of example, comprise in (a) a population of MSCs obtainable from any suitable source, separately (b) at least one agent which inhibits co-stimulation, for instance CTLA4-Ig, anti-CD40, or anti-LFA1, or any combination thereof, and, optionally, separately (c) at least one therapeutic cell, tissue and/or organ, for instance islet cell(s), kidney cell(s), hepatocyte(s), a kidney, a heart, a liver, or any combination thereof.

In a further embodiment, the present invention relates to at least one MSC and at least one agent inhibiting co-stimulatory signals for use in a method of therapeutic and/or prophylactic treatment of a subject, the method comprising the steps of (a) administering to the subject at least one MSC, and (b) administering to the subject at least one agent which inhibits at least one co-stimulatory signal. In a further embodiment, the method may comprise timing the administration of at least one MC and of at least one agent inhibiting co-stimulatory signals such that the administering is carried out essentially simultaneously or sequentially in any sequential manner. For instance, the at least one MC may be administered to the subject at a certain time point, and the administration of the at least one agent inhibiting co-stimulatory signal(s) may take place before the administration of the MC or after the administration of the MC, or both before and after. The administration of the co-stimulation inhibitor(s) may e.g. take place several weeks or months before the administration of the MSCs, or e.g. several days or hours before the administration of the MSCs. Conversely, the administration of the co-stimulation inhibitor(s) may e.g. take place several weeks or months after the administration of the MSCs, or e.g. several days or hours after the administration of the MSCs. In a further embodiment, the method may also comprise an additional step (c) of administering to a subject at least one therapeutic cell, tissue, and/or organ. Again, administering of the therapeutic cell, tissue, and/or organ may take place at essentially the same time as administering the MSCs and/or the co-stimulation inhibitor(s), or at later or earlier time points. Thus, the sequence of steps (a), (b), and the optional step (c) may vary, for instance as follows:

Step (a) followed by step (b)
Step (b) followed by step (a)
Step (a) followed by step (b) followed by step (c)
Step (a) followed by step (c) followed by step (b)
Step (b) followed by step (a) followed by step (c)
Step (b) followed by step (c) followed by step (a)
Step (c) followed by step (a) followed by step (b)
Step (c) followed by step (b) followed by step (a)
Step (a) and step (c) carried out at the same time followed by step (b)
Step (a) followed by step (b) and step (c) carried out at the same time
Step (b) followed by step (a) and step (c) carried out at the same time
Step (a) and step (b) carried out at the same time followed by step (c)

Naturally, all combinations of the three steps are within the scope of the present invention, and the choice of how to employ the method may be influenced by the disease or disorder, whether the intention is prophylactic and/or therapeutic, the medical state of the patient, the immunological state of the patient, etc.

In a further embodiment, the present invention relates to at least one MC for use in a method of therapeutic and/or prophylactic treatment of a subject, the method comprising the step of administering to the subject at least one agent which inhibits at least one co-stimulatory signal. In yet another embodiment, the present invention relates to at least one agent inhibiting co-stimulatory signal(s) for use in a method of therapeutic and/or prophylactic treatment of a subject, the method comprising the step of administering to the subject at least one MC. Thus, the present invention pertains to combining treatment of a patient with MSCs with treatment using at least one agent inhibiting co-stimulatory signals (e.g. CTLA4-Ig and/or anti-CD40 and/or anti-LFA1), or conversely combining treatment of a patient with at least one agent inhibiting co-stimulatory signals (e.g.

CTLA4-Ig and/or anti-CD40 and/or anti-LFA1) with treatment using MSCs. As above-mentioned, the subject to be treated may suffer from a range of autoimmune, inflammatory, and transplantation/implantation-related conditions, diseases, and disorders.

In yet another embodiment, the present invention relates to a combination of an MSC population and at least one exogenous co-stimulation inhibitor for use in a method of suppressing and/or modulating the immune system in a subject, the method comprising the steps of:
 (a) administering to the subject an MSC population; and,
 (b) administering to the subject at least one exogenous co-stimulation inhibitor,
  wherein steps (a) and (b) may be carried out simultaneously or sequentially in any sequence or order.

In a further embodiment, the present invention may relate to a method of treatment of a patient suffering from type I diabetes, comprising administering an MSC population, at least one agent inhibiting co-stimulatory signal(s), and optionally at least one pancreatic islet cell and/or a pancreas.

In a further embodiment, the present invention may relate to a method of treatment of a patient suffering from acute and/or chronic kidney failure, comprising administering an MSC population, at least one agent inhibiting co-stimulatory signal(s), and optionally at least one kidney cell and/or at least one kidney.

In a further embodiment, the present invention may relate to a method of treatment of a patient suffering from chronic and/or acute heart failure, comprising administering an MSC population, at least one agent inhibiting co-stimulatory signal(s), and optionally at least one heart cell and/or a heart.

In a further embodiment, the present invention may relate to a method of treatment of a patient suffering from acute and/or chronic liver failure, comprising administering at least one MC, at least one agent inhibiting co-stimulatory signal(s), and optionally at least one hepatocyte and/or a liver.

In one embodiment, the present invention relates to the use (in vivo or in vitro) of a combination of MSCs and at least one agent inhibiting co-stimulatory signals for modulating and/or suppressing the innate and/or the adaptive immune system. More specifically, the combination of an MSC population and at least one exogenous co-stimulation inhibitor may be used in vitro or in vivo for reducing immune response, inflammation and neutrophil activation, modulating macrophages towards an anti-inflammatory phenotype, inhibiting NK cell activation and cytotoxicity, modulating dendritic cell (DC) activation, modulating CD4+ and CD8+ T cell responses, and/or reprogramming conventional T cells into regulatory T cells.

In further embodiments, the present invention relates to reagents, kits, cell mediums, and cell culturing processes as described above. For instance, cell culturing processes utilizing the methods for obtaining the MSCs of the present invention may be employed in a variety of suitable settings, using any suitable combination of cell sources. In a further embodiment, the present invention pertains to the in vitro use of the compositions as per the present invention, i.e. compositions comprising an MSC population and at least one exogenous co-stimulation inhibitor, and optionally a further cell, tissue, or organ (which normally in itself has certain physiological functions). In a further embodiment, the present invention relates to a kit which may comprise in one container at least one MSC, in another container at least one agent inhibiting at least one co-stimulatory signal, and optionally additional containers and components for utilizing the kit in vitro.

It shall be understood that the above described exemplifying aspects, embodiments, and alternatives, and variants can be modified without departing from the scope of the invention, inter alia with respect to the described constituents, components, and materials, etc. (e.g. MSCs, the at least one exogenous co-stimulation inhibitor, the therapeutic cell, tissue, organ, etc. to be administered to a patient, etc.). The invention will now be further exemplified with the enclosed experimental section, which naturally also can be modified without departing from the scope of the invention.

Experimental Section

Experimental Animals

All animal experiments were approved by the local Ethics Committee for Animal Research and were performed in accordance with local institutional and Swedish national rules and regulations.

Isolation, Culture and Characterization of Mice MSCs

C57BL/6 bone marrow (BM) MSCs were flushed from the femurs and tibias and cultured with mouse mesenchymal stem cell basal media with supplements (STEMCELL Technologies, Grenoble, France). Passages 3 to 10 of MSCs were used and phenotyped as well as the ability to differentiate into adipocytes and osteocytes, and the ability to inhibit T cell activation was studied.

Isolation, Culture and Characterization of Human MSCs

Between 10 and 40 ml of bone marrow was aspirated from HLA-mismatched third party healthy volunteers. MSCs was additionally obtained from Wharton's jelly, from adipose tissue, and from cord blood. Clinical-grade MSCs were generated under good manufacturing practice (GMP) conditions according to a common protocol elaborated by the EBMT Developmental Committee, accredited by the Swedish National Board of Health and Welfare. Cells (around $150 \times 10^6$) were seeded into 175 cm$^2$ flasks (Falcon, Franklin Lakes, N.J., USA) in Dulbecco's modified Eagles Medium-Low Glucose (DMEM-LG, Life Technologies, Gaithersburg, Md., USA) supplemented with lysed human platelets (final concentrations ranging from $10^7$ to $10^9$, normally $10^8$/mL). When the cultures were near confluence (>80%), the cells were detached by treatment with trypsin and EDTA (Invitrogen, Grand Island, N.Y., USA) and re-plated once at a density of 4,000 cells/cm$^2$. MSCs were harvested and cryopreserved in 10% Dimethyl Sulfoxide (WAK-Chemie Medical GmbH, Germany). After thawing, the cells were washed three times in PBS and re-suspended in 0.9% saline solution with the addition of 10% AB plasma, to a final concentration of $2 \times 10^6$ cells/ml.

MSC release criteria for clinical use included: absence of visible clumps, spindle shape morphology, absence of contamination by pathogens (bacteria and mycoplasma) and viability >95%. MSCs expressed CD73, CD90, CD105, HLA-ABC and were negative for CD14, CD31, CD34, CD45 and HLA-DR.

Assessment of Immuno-Modulatory Capacity of MSCs

Ex-vivo expanded MSCs were pre-treated (primed MSCs, pMSCs) or not (MSCs) with 10 ng/ml of IFN-γ and 15 ng/ml of TNF-α for 48 hours before used in co-cultures with PMNs with or without activation by endotoxin (100 ng/ml of lipopolysaccharides (LPS)). Following inflammatory priming, the MSCs up-regulated cell surface expression of CD54 (ICAM-1), CD106 (VCAM-1) and HLA-ABC and -DR, as well as the expression of indoleamine 2,3-dioxygenase (IDO), a potent mediator of many MSC immune regulatory functions.

Fold increase of IDO expression after TNFα stimulation of donor cell MSCs should be <10 and fold increase of IDO expression after stimulation of INFγ should be more than >100 (p0.05). MSCs was cultured in the presence of TNF-α (15 ng/mL) or IFN-γ (10 ng/mL).

Viability of PMN is preferably significantly improved (p0.05), preferably improved by at least 10%, or more preferably by at least 20%, after adding in either MSCs and LPS or pMSC with or without LPS as a co-culture. Viability and expression levels of surface markers by control or LPS-stimulated PMNs were investigated after 40 hours of direct co-culture with either resting or pMSCs. CD16 (FcγR-III) expression was used as surrogate marker of PMN viability. In the absence of LPS, PMN survival was enhanced only in presence of pMSCs. When LPS was added to the co-culture, both resting and pMSCs protected PMNs from apoptosis. Accordingly, the percentage of CD16-positive PMNs matched with the percentage of viable PMNs in all culture conditions. In parallel, expression of CD11b and CD54 is typically associated with PMN activation status. As expected, the percentage of CD11b-positive PMNs was higher in the presence of MSCs and further enhanced by LPS treatment, while CD11b relative mean fluorescence intensity (rMFI) did not change significantly, suggesting that more PMNs are becoming activated following MSC or pMSC exposure. Meaning that CD11b should be significantly improved (p 0.05) in presence of MSCs, pMSCs with or without LPS. In contrast, CD54 rMFI should be significantly (p0.05) up-regulated by LPS treatment and this effect was enhanced by co-culture with MSCs. Overall, the higher PMN survival and activation triggered by MSCs suggests that MSCs may influence the PMN-dependent innate response through functional modifications rather than pro-apoptotic effects.

Donor MSCs is preferably increasing the number of myeloid-derived suppressor cells (MDSCs) by a factor 1.5, or more preferably a factor 2. Co-culturing PMNs with MSCs led to a marked increase in mature $CD11b^{bright}/CD16^{bright}/CD62L^{dim}$ (N2-type) cells with hypersegmented nuclei consistent with granulocytic MDSCs. Similarly, co-culturing MSCs with healthy control human peripheral blood mononuclear cells (PBMSCs) at different ratios promoted a significant increase (p0.05) $CD14^{+}HLA-DR^{low}$ monocytes resembling monocytic MDSCs.

Donor MSCs are preferably significantly increasing (p 0.05), preferably 1.5-fold or even more preferably 2-fold, the number of regulatory T-cells as exemplified by $CD4^{+}CD25^{high}CD127^{low}$ regulatory T-cells ($T_{Regs}$), a key immune regulatory cell population, was also expanded in co-culture experiments with PBMSCs. This corresponded with increased levels of circulating $CD4^{+}CD25^{high}CD127^{low}$ $T_{Regs}$ that was observed in observed in treated subjects peripheral blood for up to 20 days following MSC administration ($T_{Regs}$ among $CD4^{+}$ T-cells in healthy controls (n=11) 3.84+/-1.60%, $T_{Reg}$ range in patients 3.34-17.8%). This finding could have resulted from an elevated thymic output as indicated by the increased proportion of $CD31^{+}$ recent thymic emigrants among $CD45RA^{+}$ naive $T_{Regs}$ in patients and/or the MSC-stimulated conversion of conventional T-cells in the periphery.

Islet Transplantation in Type 1 Diabetes Mice Model
Isolation, Culture and Phenotypic Characterization of DCs C57BL/6 immature DCs (imDCs) were isolated according to methods described by Choi and coworkers (Choi et al., *Immunol Invest*, 2012). MSCs were added with 500 ng/ml LPS (Sigma-Aldrich, St. Louis, Mo.) to examine the inhibitory effect on DC maturation. CD11c+ DCs were stained with monoclonal antibodies (mAbs) against CD11c, CD80, CD86, MHC class II and isotype-matched controls (eBioscience, Hatfield, UK). The data was presented as the mean fluorescence intensity.

Islet Isolation and Transplantation

Balb/c islets were isolated by collagenase P (Roche Dagnostics GmbH, Mannheim, Germany). C57BL/6 recipient mice were rendered diabetic by intravenous injection of alloxan (75 mg/kg) (Sigma) 3 days before transplantation and transplanted with 250 Balb/c islet equivalents (IEQ) either alone or together with C57BL/6 MSCs (2.5×105 cells/mouse) via the portal vein. Mice were treated with CTLA4Ig and anti-CD40L (clone MRI) every other day until postoperative day 10 at doses of 0.5 mg on day 0 and 0.25 mg on day 2, 4, 6, 8, 10 or with isotype controls at similar doses. All antibodies were purchased from Bio X Cell (West Lebanon, N.H.). Treatments were also carried out with CTLA4Ig+anti-LFA1+MSCs, and with anti-LFA1+anti-CD40L+MSCs. Blood glucose levels of less than 11.1 mmol/l were considered to be reversal of diabetes and islet rejection was defined as >20 mmol/l non-fasting blood glucose for 2 consecutive days.

Immunohistochemistry

Livers from recipients surviving to 100 days after transplantation were snap-frozen, sectioned into 5 mm pieces and fixed in 4% formaldehyde. For FoxP3 staining 10% donkey serum (Jackson ImmunoResearch Laboratories Inc., West Grove, Pa.) was used as a blocking agent and for CD4/CD8 staining 5% donkey serum and 5% mouse serum (DAKO, Glostrup, Denmark). The sections were incubated with rat anti-mouse FoxP3 (eBioscience) or rat anti-mouse CD4/CD8 (Serotec, Oslo, Norway) over night. Donkey anti-rat-IgG (Alexa fluor) was added and the slides incubated for 1 h and mounted with the anti-fading reagent containing 4,6-diamidino-2-phenylindole (DAPI; Pierce, Rockford, Ill.). For insulin staining, the sections were incubated with rhodamine-conjugated anti-insulin antibody (Mabtech AB, Nacka, Sweden) for 1 h and followed by staining with DAPI.

Enzyme-Linked Immunospot (ELISPOT) Assay

To examine the graft-specific T cell activity, splenocytes and intrahepatic lymphocytes (IHLs) were isolated from the recipient livers and used as responder cells. Splenocytes (1×105/well) or IHLs (1×104/well) were seeded in triplicate with irradiated Balb/c splenocytes (4×105/well) for 18 hours. Pretreated 96-well plates and the anti-rat IFNγ ELISPOT kit were gifts from Mabtech AB. The calculation of the number of spot forming units and cytokine activity were determined by the ELISPOT counter software, version 3.5 (AID, Strasburg, Germany) and signifies a relative quantification of cytokine levels.

Expression of IDO, TGFβ, Insulin and Foxp3

Total RNA was isolated from recipient livers. Real-time PCR was performed with 2× FAST SYBR® Green Master Mix (Life Technologies) in triplicate using 7500 Fast Real-Time PCR System (Applied Biosystems, Foster City, Calif.). Primer sequences (Life Technologies) and fragment sizes of the genes are shown in Supplementary Table. The level of sample mRNA was normalized by GAPDH as internal control.

Mixed Lymphocyte Reaction (MLR)

CD4+ T cells (1×105/well) from naive C57BL/6 spleen and irradiated pan T cells (2×105/well) from naive Balb/c spleen were used as responder and stimulator cells, respectively. C57BL/6-derived mature DC (mDC) or MSCs-co-cultured DCs (MSC-DCs) were used as antigen presenting cells (APCs) (2×104/well). In some experiments, MSCs (2×104/well) were seeded onto the wells with mDC (mDC+MSCs). After 3 days culture, cells were pulsed with 1 μCi [3H] thymidine (Perkin Elmer, Waltham Mass.) for 18 h. The results are expressed as mean count per minutes (cpm) of relative increase which the syngeneic response was subtracted from.

Regulatory T Cells Analysis by Flow Cytometry

Splenocytes from recipients were harvested on POD 100 and labeled for surface CD4-FITC and CD25-PE, and intracellular FoxP3-PerCP (eBioscience). Naïve C57BL/6 CD4+ T cells (1×106/ml) and C57BL/6-derived CD11c+ DCs (2×105/ml) were co-cultured with Balb/c pan T cells (2×106/ml) with or without MSCs (2×105/ml) at a ratio of 5:1:1 (CD4+ T:DC:MSC). After 96 hour incubation, CD4+ T cells were purified again and labeled for CD4, CD25, and FoxP3. L-kynurenine concentrations from the supernatants were determined by ELISA (MyBioSource Inc., San Diego, Calif.).

Islet Transplant Survival

Figure 1C:
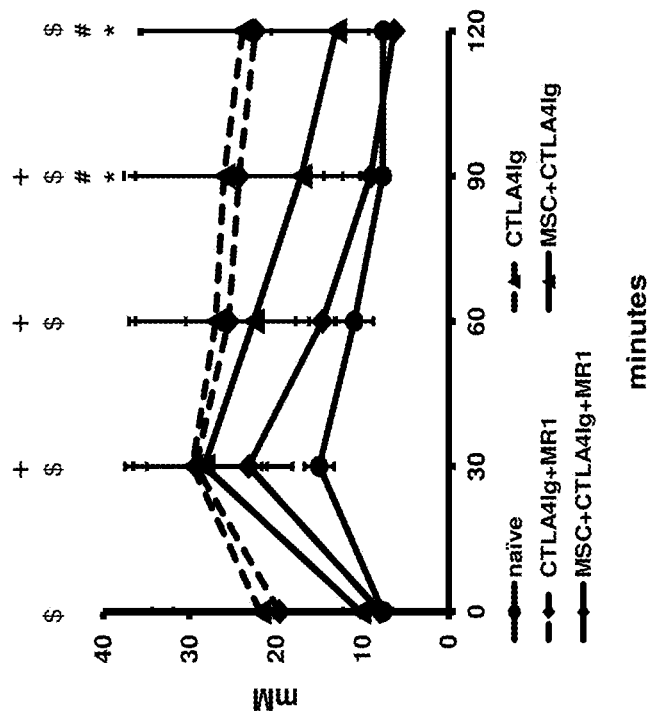
(FIG. 1C) IPGTT of different recipient groups at 30 days after transplantation. Recipients treated with MSC+CTLA4IG+anti-CD40L, MSC+CTLA4IG+anti-LFA1, or MSC+anti-CD40L+anti-LFA1 had similar blood glucose at 90 minutes as naive untransplanted mice.
Figure 1B:
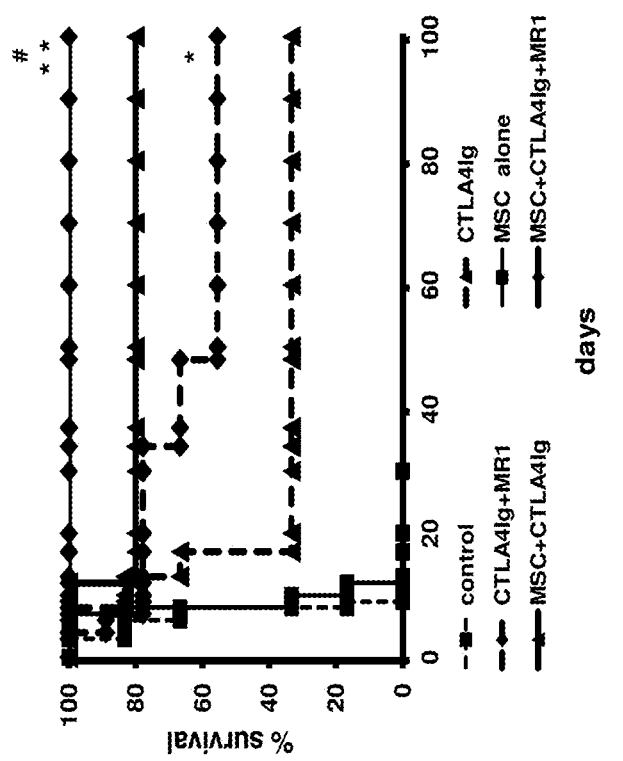
FIG. 1: Islet allograft survival and function.

Mice receiving islet cell transplants treated with isotype control antibodies rejected the transplant with a mean survival time (MST) of 7 days demonstrating the robust immune response to the fully MHC-mismatched islets after intraportal injection. Co-transplantation with recipient MSCs yielded a mean survival time of 8.83 days (FIG. 1A). In the group treated with CTLA4Ig only, 2 of 6 mice were normoglycemic to 100 days (MST=45.8 days). In the group treated with CTLA4Ig and anti-CD40L, 5 of 9 recipients achieved long term graft survival of 100 days (MST=65.9 days). When treated with MSCs and CTLA4Ig, MST was 82.4 days with 4 of 5 surviving to 100 days. MSC co-transplantation prolonged islet graft survival in all recipients when treated in addition with costimulation blockade in the form of CTLA4Ig and anti-CD40L (MST ≥100 days). Highly similar results were obtained when treating the animals with MSCs+anti-CD40L+anti-LFA1 and with MSCs+CTLA4-Ig+anti-LFA1. This increase in graft survival was significant when compared with all the other treatment groups (FIG. 1B). In order to test graft function IPGTTs was performed one month after transplantation. Recipients treated with MSCs, CTLA4Ig and anti-CD40L had significantly better IPGTTs compared to groups receiving only the co-stimulation blockade at 90 minutes ($p<0.05$) (FIG. 1C). IPGTT was equivalent in the MSCs, CTLA4Ig and anti-CD40L group to naive untransplanted mice at 90 minutes. Thus, in accordance with the present invention, it is possible to utilize only one agent that inhibits co-stimulatory signals (e.g. either one of CTLA4-Ig, anti-CD40L, or anti-LFA1) but it may be preferable to use at least two agents that inhibit co-stimulatory signals (e.g. any combination of CTLA4-Ig, anti-CD40L, and anti-LFA1).

Figure 2:
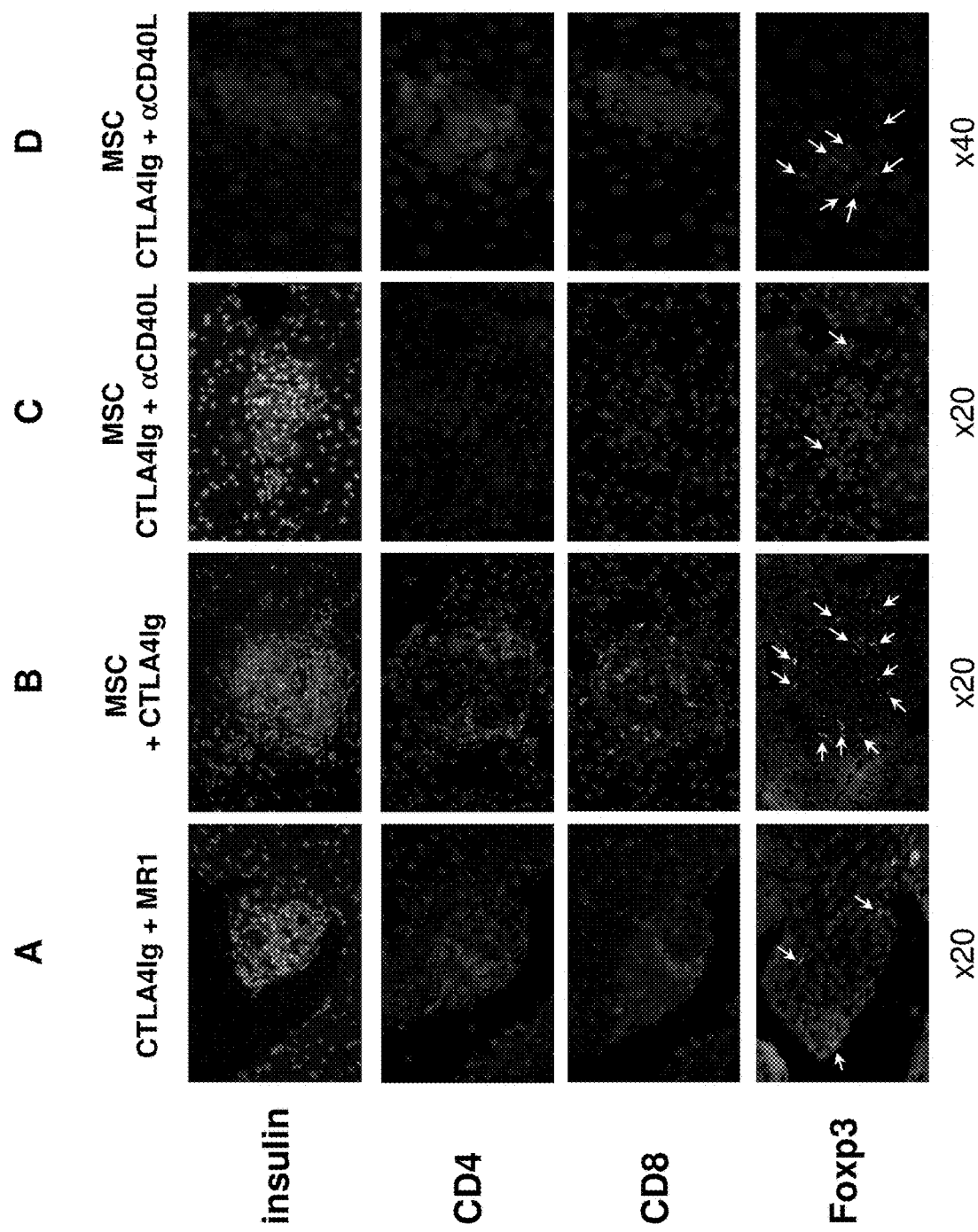
FIG. 2: Histological evaluation of islet grafts in the liver on postoperative day 100. Immunofluorescent staining for insulin (red), Foxp3, CD4 and CD8 (green) was performed on recipient livers treated with (A) CTLA4Ig+MR1 (anti-CD40L), (B) MSC+CTLA4Ig and (C,D) MSC+CTLA4Ig+MR1. Foxp3 stained cells were indicated by arrows.

Insulin-producing islets could be found in the different recipient groups in mice with normal glucose levels at 100 days after transplantation (FIG. 2). Recipients treated with CTLA4Ig and anti-CD40L having survived to 100 days after transplantation, had equivalent numbers of infiltrating $CD4^+$ and $CD8^+$ lymphocytes in the liver, but only a few staining positive for Foxp3 (FIG. 2). In mice treated with MSC and CTLA4Ig, a similar infiltration of $CD4^+$ and $CD8^+$ T cells was observed, but had more Foxp3+ cells then found in the liver of the CTLA4Ig, anti-CD40L treated recipients. In the group receiving MSCs, CTLA4Ig and anti-CD40L treatment, very little lymphocytic infiltrate could be found with the exception of Foxp3+ cells detected around the islets.

Figures 3A, 3B:
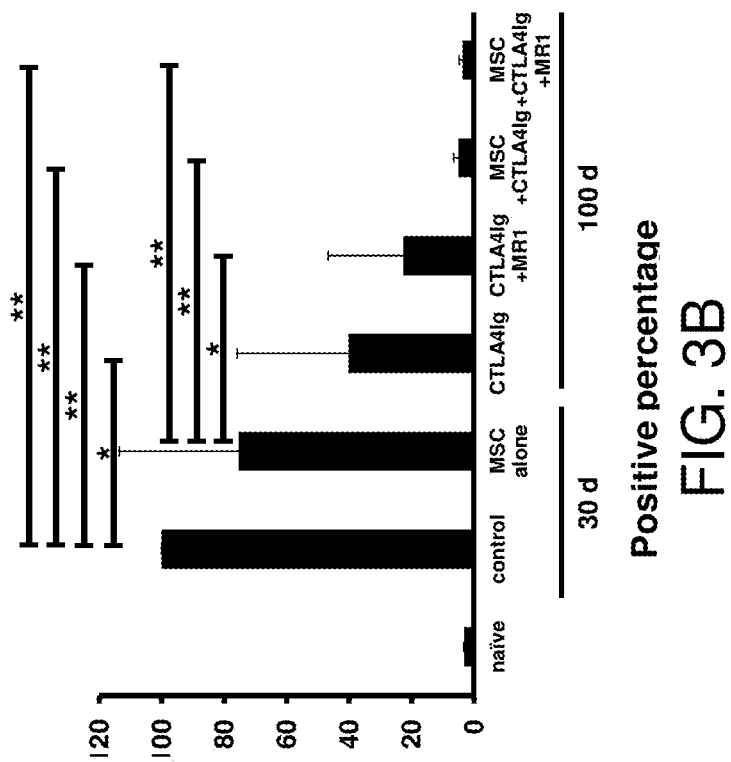
FIG. 3: Presence of donor specific antibodies and suppression of T-cell alloreactive response. Donor specific antibodies (DSA) in mouse serum was examined by flow_cytometry. MFI of each group was compared (FIG. 3A). * p<0.5. Control group showed significantly higher mean MCF compared with costimulation treated group with/without MSC co-injection. The MSCs, costimulation blockade treated recipients showed less positive staining of Balb/c cells than the costimulation blockade group as a percentage (FIG. 3B). Splenocytes from mice receiving CTLA4Ig and anti-CD4OL with or without MSCs (159.9.+-.43.8 or 164.1.+-.63.2%) had significantly reduced alloreactive responses compared to control (513.5.+-.190%) at 30 days. This effect was observed even if the recipients were treated with MSCs alone (240.7.+-.105.8%, p<0.05) (FIG. 3C). At 100 days, CTLA4Ig and anti-CD40L treated recipients induced significantly more alloreactive responses than naive (CTLA4Ig alone: 242.6.+-.70.3, CTLA4Ig+anti-CD40L mAb: 253.3.+-.124.5%, p<0.05). However, MSCs combined with costimulation blockade treated groups had reduced alloreactive responses and there were no significant difference compared to naive (FIG. 3D). Moreover, MSCs, CTLA4Ig and anti-CD40L treated recipients (122.3.+-.22.8%) had significantly reduced alloreactive T cell proliferation compared to the CTLA4Ig and anti-CD40L treated recipients (p<0.01) (FIG. 3D).

In order to study the presence of anti-donor antibody responses, Balb/c pan-T cells were exposed to sera and then stained with anti-IgG. Co-stimulation blockade treated recipients and MSC, co-stimulation blockade treated recipients had significanity less anti-donor antibodies at compared to control and MSCs treated recipients (FIG. 3A). The mean flourescence intensity (MFI) was equivalent to that found in naïve mice, indicating that B cell activation had not occurred at a substantial level in these recipients. The MSCs, costimulation blockade treated recipients showed less positive staining of Balb/c cells than the costimulation blockade group (FIG. 3B).

T Cell Responses and Increase of $CD4^+CD25^+Foxp3^+$ T Cells

Figures 3C, 3D:
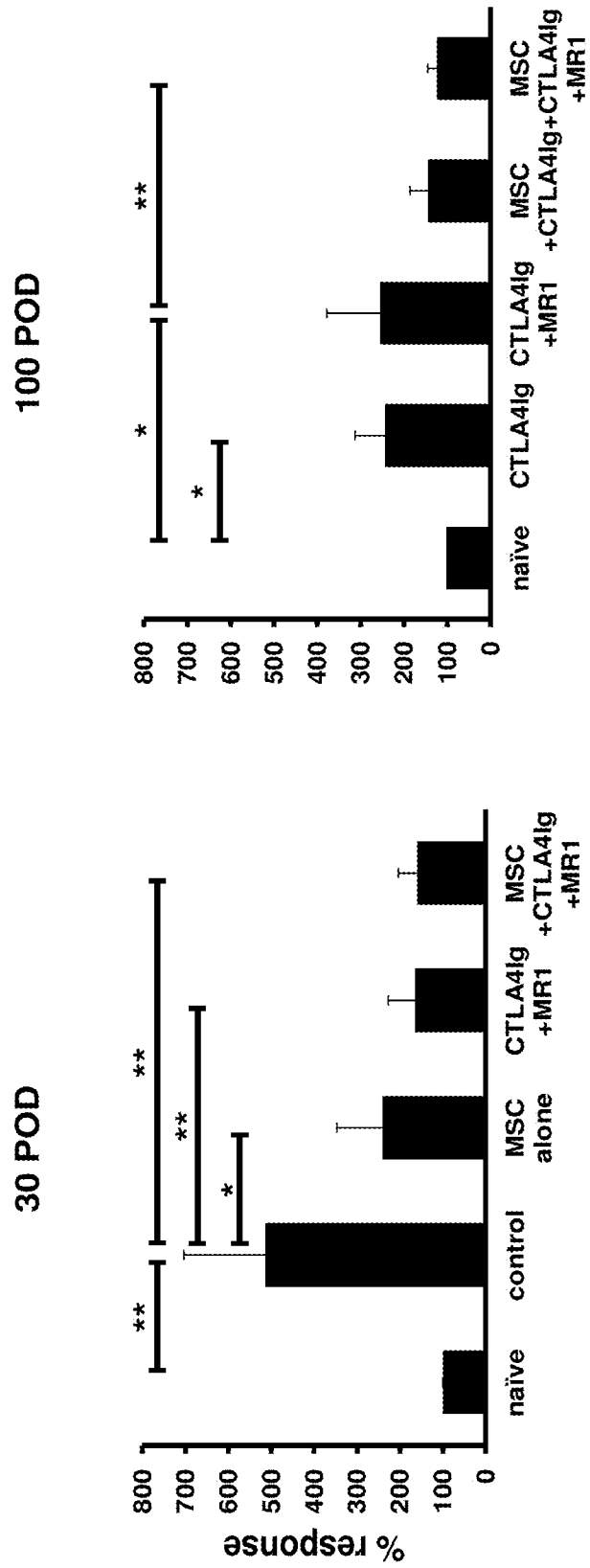

Splenocytes from mice receiving CTLA4Ig and anti-CD40L with or without MSCs (159.9±43.8 or 164.1±63.2%) had significantly reduced alloreactive responses compared to control (513.5±190%) at 30 days. This effect was observed even if the recipients were treated with MSCs alone (240.7±105.8%, $p<0.05$) (FIG. 3C). At 100 days, CTLA4Ig and anti-CD40L treated recipients induced significantly more alloreactive responses than naïve (CTLA4Ig alone: 242.6±70.3, CTLA4Ig+anti-CD40L mAb: 253.3±124.5%, $p<0.05$). However, MSCs combined with costimulation blockade treated groups had reduced alloreactive responses and there were no significant difference compared to naïve (FIG. 3D). Moreover, MSCs, CTLA4Ig and anti-CD40L treated recipients (122.3±22.8%) had significantly reduced alloreactive T cell proliferation compared to the CTLA4Ig and anti-CD40L treated recipients ($p<0.01$) (FIG. 3D). Similar results as for MSCs, CTLA4Ig and anti-CD40L were obtained when evaluating the following combinations: MSCs+anti-CD40L+anti-LFA1 and MSCs+CTLA4Ig+anti-LFA1.

Figure 4B:
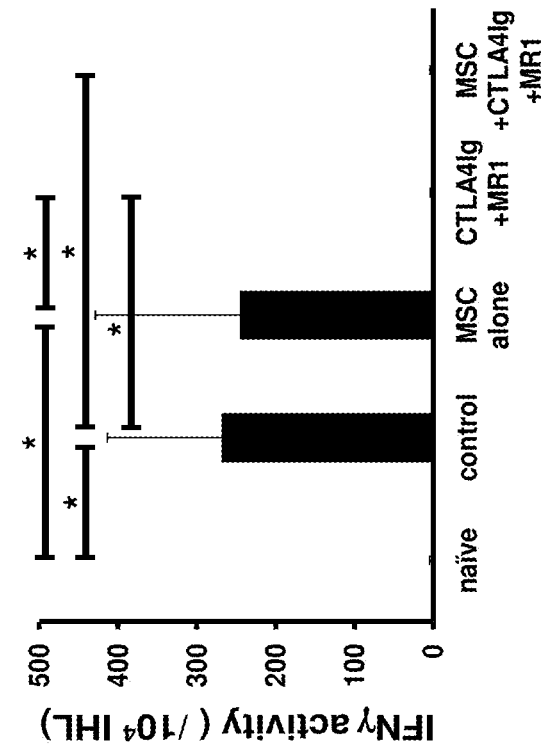
FIG. 4: Recipient T cell responses to donor antigen and quantification of $CD4^+CD25^+Foxp3^+$ T cells in spleen.
(FIG. 4A) Splenocytes ($1\times10^5$) or (FIG. 4B) Intrahepatic lymphocytes ($1\times10^4$) from C57BL/6 recipients were co-cultured with Balb/c splenocytes ($4\times10^5$) in capture antibody-mounted 96-well plates for 20 h and spot forming units and IFNg activity were measured. Results are shown as means ±SD. * $P<0.05$ and ** $P<0.01$.
(FIG. 4C) Splenocytes from C57BL/6 recipients were harvested at POD 100 and FACS analysis was performed for the detection of $CD4^+CD25^+Foxp3^+$ T cells. The percentage of $CD4^+Foxp3^+$ or $CD25^+Foxp3^+$ T cells is shown as means ±SD.
Figure 4A:
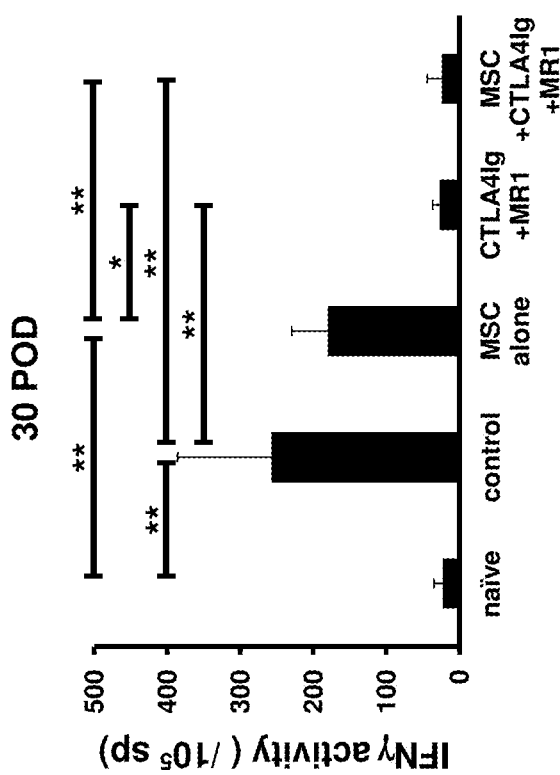

In order to characterize the T cell population in different recipient groups, spleenocytes and IHLs were isolated at 30 days after transplantation. These lymphocytes were cultured with naïve Balb/c spleenocytes and the IFN activity was measured. Spleenocytes from recipients treated with CTLA4Ig and anti-CD40L with or without MSCs (24.3±19.7 or 26.8±9.8 activities, respectively) showed significantly lower production of IFNγ compared to isotype control or MSCs only treated recipients (257.6±128.2 or 180.0±49.7 activities, respectively) ($p<0.01$ or $p<0.05$) (FIG. 4A). The activity of IFNγ producing IHLs from the CTLA4Ig and anti-CD40L with or without MSCs (1.5±2.6 or 0.6±3.1 activities) recipients was significantly lower than those from control (268.8±144.8 activities, $p<0.05$) and MSCs treated recipients (249±176) (FIG. 4B). The frequency of $CD4^+CD25^+Foxp3^+$ T cells in the spleen was evaluated at POD 100. Recipients treated with MSCs, CTLA4Ig and anti-CD40L (6.0±2.3%) and MSCs and CTLA4Ig only (7.0±1.0%) had significantly more $CD4^+CD25^+Foxp3^+$ T cells compared to mice receiving only CTLA4Ig and anti-CD40L (3.3±0.9%, $p<0.01$ or $p<0.05$) (FIG. 4C).

Intrahepatic Expression of IDO, TGFβ, Insulin and Foxp3

Figure 5B:
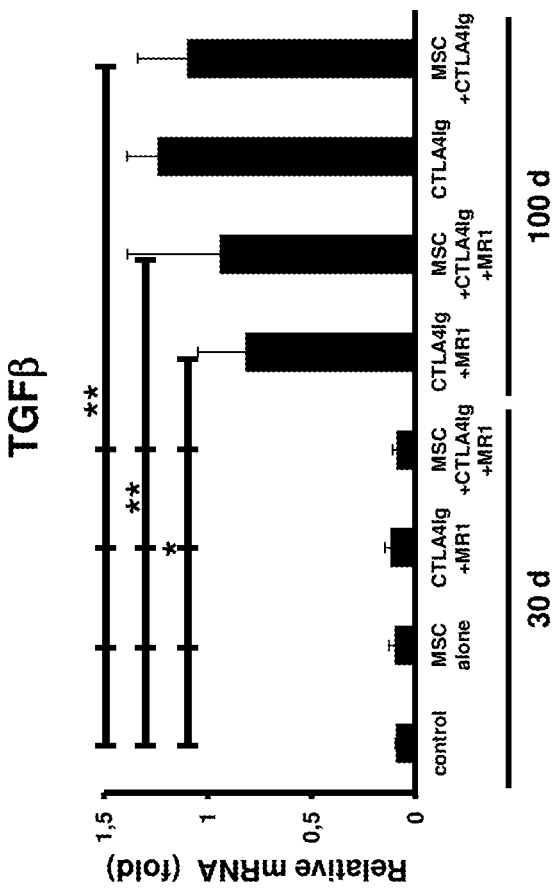
FIG. 5: Real-time PCR analysis of four genes from islet-transplanted livers. Total RNA was isolated from the livers in all islet transplanted recipients at the time of sacrifice. The expression of each gene transcript was normalized to the expression level of the house keeping gene, GAPDH and a relative value is given. Results are shown as means ±SD. * $P<0.05$ and ** $P<0.01$.
Figure 5A:
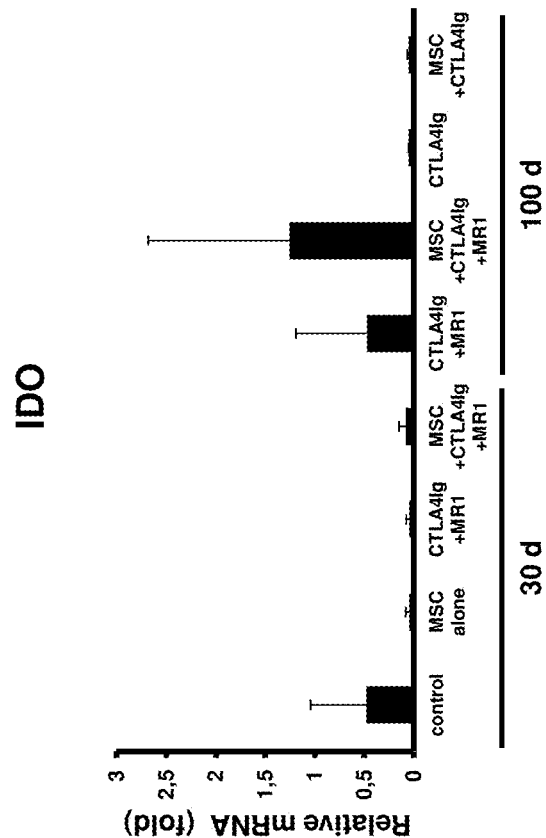
Figures 5C, 5D:
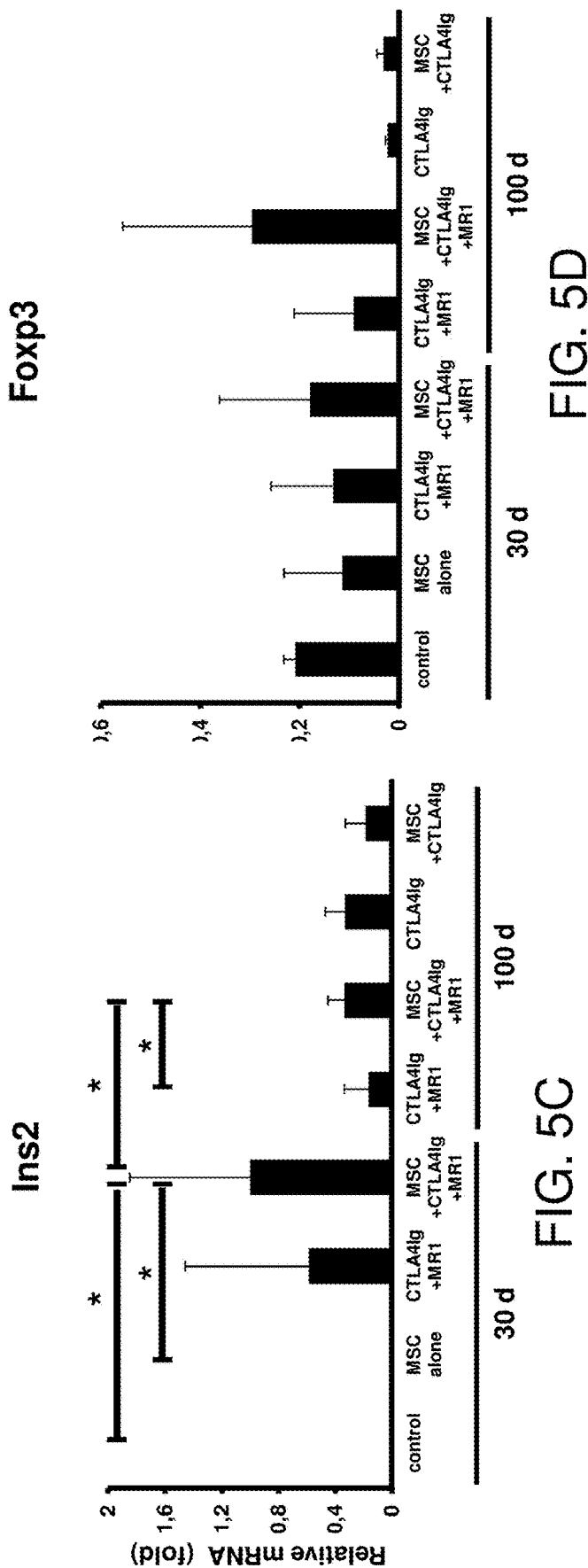

The IDO mRNA levels in islet grafted livers of mice treated with MSCs, CTLA4Ig and anti-CD40L (1.25±1.43) appeared to be higher than that of mice receiving CTLA4Ig and anti-CD40L (0.48±0.72) at POD 100, but was not statistically significant (FIG. 5A). IDO mRNA expression in the other groups was negligible. TGFβ mRNA expression levels were significantly upregulated on POD 100 in all long term functioning graft recipients compared to POD 30 in all groups (FIG. 5B). In order to estimate the functional islet-graft mass, Ins2 mRNA levels in livers were measured. Only when CTLA4Ig and anti-CD40L was combined with MSCs ($1.0\pm0.85\times10^{-3}$) did recipients maintain significantly higher Ins2 levels than those receiving control antibodies ($0.0002\pm3.79E^{-5}\times10^{-3}$) or MSCs alone ($0.0002\pm0.0002\times10^{-3}$, p<0.05). Ins2 mRNA expression in the MSCs, CTLA4Ig and anti-CD40L group decreased gradually, but was significantly higher than the CTLA4Ig and anti-CD40L group at 100 days ($0.33\pm0.11\times10^{-3}$ vs. $0.16\pm0.17\times10^{-3}$, p<0.05) (FIG. 5C). The combination of MSCs, CTLA4Ig and anti-CD40L ($0.3\pm0.26$) upregulated Foxp3 transcript levels more than CTLA4Ig and anti-CD40L ($0.09\pm0.12$), but statistical significance was not reached (FIG. 5D).

MSCs Attenuate DC Maturation

Figure 6B:
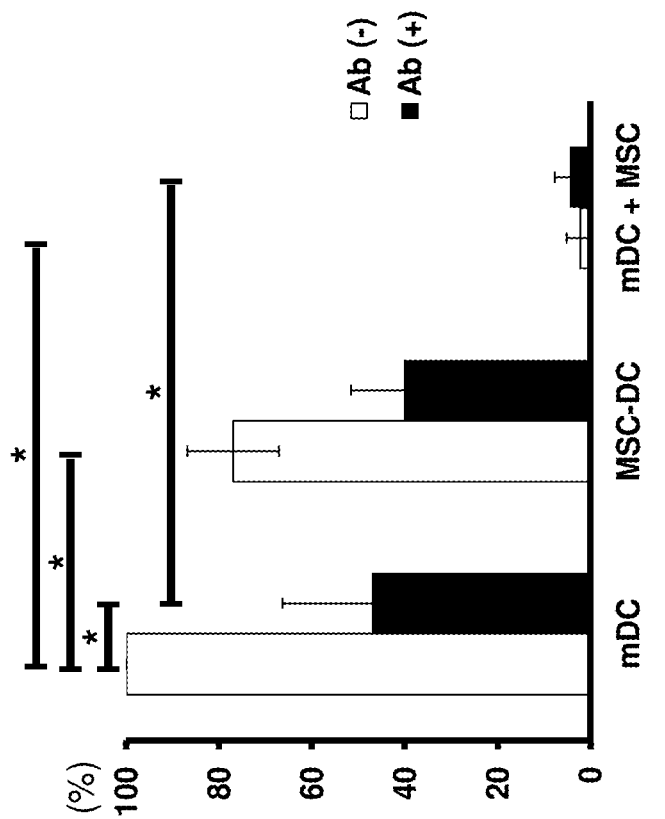
FIG. 6: Suppression of DCs maturation and alloreactive T cell proliferation or Foxp3 T cell induction by MSCs in vitro.
(FIG. 6A) After a 24 hour-stimulation with LPS, BM-DCs with or without MSCs were isolated using anti-$CD11c^+$ microbeads and their surface markers were analyzed by FACS. Results are representative of four independent experiments. MSC (L)-DC, MSC (H)-DC: low ($1\times10^4$) and high dose ($1\times10^5$) of MSC treated DC, respectively. * $P<0.05$ (FIG. 6B) C57BL/6CD4$^+$ T cells ($1\times10^5$) were co-cultured with syngeneic DCs ($2\times10^4$) and allogeneic Balb/c pan T cells ($2\times10^5$) in the presence or absence of mAbs for 4 days. Results are expressed as mean counts per minute (cpm) of relative increase which syngeneic response was subtracted from and shown as means ±SD of six independent experiments. * $P<0.05$ (FIG. 6C) C57BL/6 $CD4^+$ T cells ($2\times10^6$) were co-cultured with syngeneic DCs ($4\times10^5$) and Balb/c pan T cells ($4\times10^6$) in 12 well plates for 4 days. Non-adherent cells were harvested followed by $CD4^+$ isolation and stained with CD4, CD25 and Foxp3 for FACS analysis. Results are one of the representatives of three independent experiments.
(FIG. 6D) Supernatants after 4 days culture described in (FIG. 6C) were collected and Kynurenine concentrations were analyzed by ELISA. Results are expressed as means ±SD of three independent experiments. * $P<0.05$.
Figure 6A:
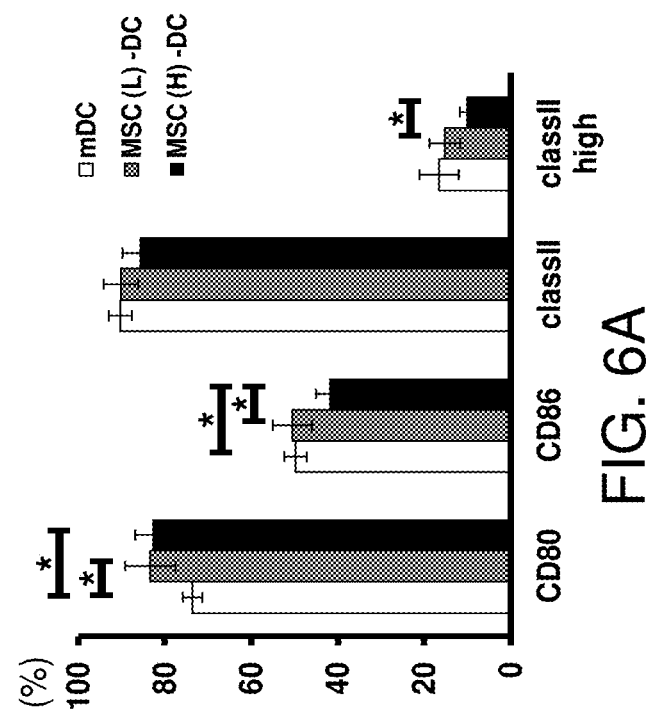

To determine potential mechanisms underlying the immune modulating function of MSCs on DCs, the direct effect of MSCs on DC maturation was examined. FACS analysis showed that CD86 and MHC class II expression was significantly (p<0.05) down-regulated in a dose-dependent fashion in DC co-cultured with MSCs (MSC-DCs) compared to in mature DCs (mDCs) (FIG. 6A). In contrast, CD80 expression on MSC-DCs was significantly up-regulated compared to on mDCs suggesting that DC maturation was impaired by MSCs.

To assess DCs function, MLRs were performed with naïve C57BL/6 CD4$^+$ T cells and naïve Balb/c pan-T cells in the presence of mDCs or MSC-DCs. T cell proliferation was significantly suppressed when mDCs were co-cultured with MSCs ($142.6\pm176.1$) compared to mDCs ($6960.7\pm2276.9$) or MSC-DCs ($4613.1\pm1268.1$) (p<0.01: FIG. 6B). The addition of CTLA4Ig and anti-CD40L significantly decreased proliferation when added to mDC and when added to MSC-DC. When mature DC (mDC) were cultured with MSC, T cell proliferation was completely abrogated independently of the presence of costimulation blockade.

Figure 6D:
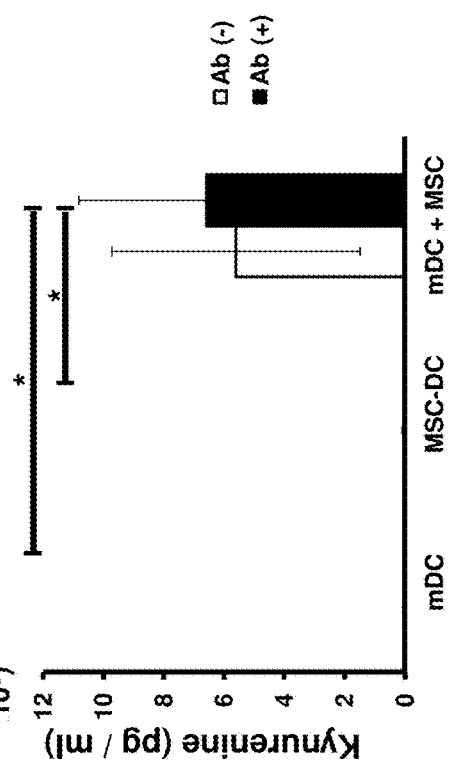
Figure 6C:
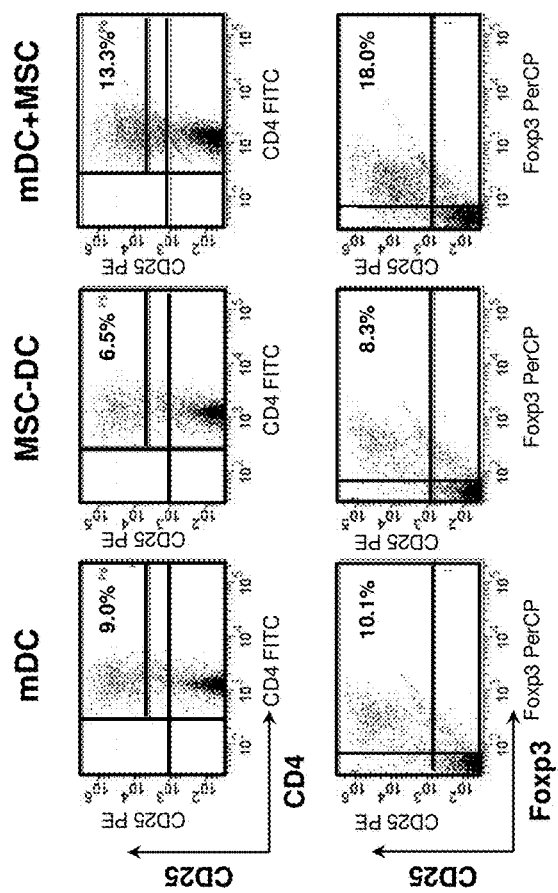
Figure 7A:
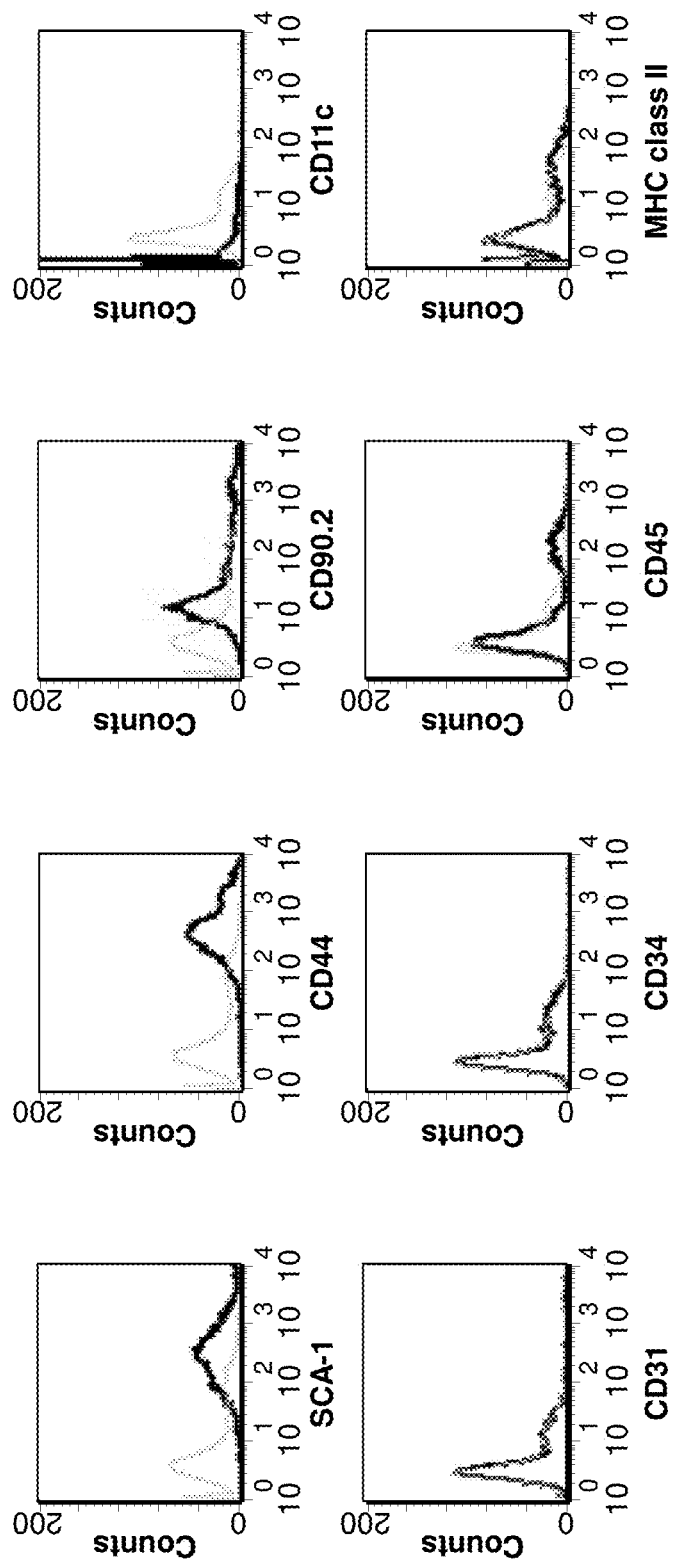
(FIG. 7A) MSCs obtained from bone marrow cells were differentiated into into adipocytes and osteocytes. Original magnification ×200. Scale bar: 20 mm.

In addition, increased numbers of CD4$^+$CD25$^+$Foxp3$^+$ T cells were observed in MLRs with CD4$^+$ T cells co-cultured with mDC and MSCs than in MLRs co-cultured with mDC or MSC-DCs, but the difference was not statistically significant (FIG. 6C). IDO activity in MLRs was also examined by means of quantifying the kynurenine levels in culture supernatant. The kynurenine levels in the supernatant were significantly higher with mDC cultured with MSCs ($6580\pm4234$ pg/ml) than with mDC ($17.3\pm30.0$ pg/ml) or MSC-DCs ($19.9\pm27.9$ pg/ml) only in the presence of CTLA4Ig and anti-CD40L (p<0.05) suggesting a synergistic effect of combining costimulation blockade with MSC co-culture on the level of IDO activity (FIG. 6D).

Treatment of Inflammatory Bowel Disease

Figure 8:
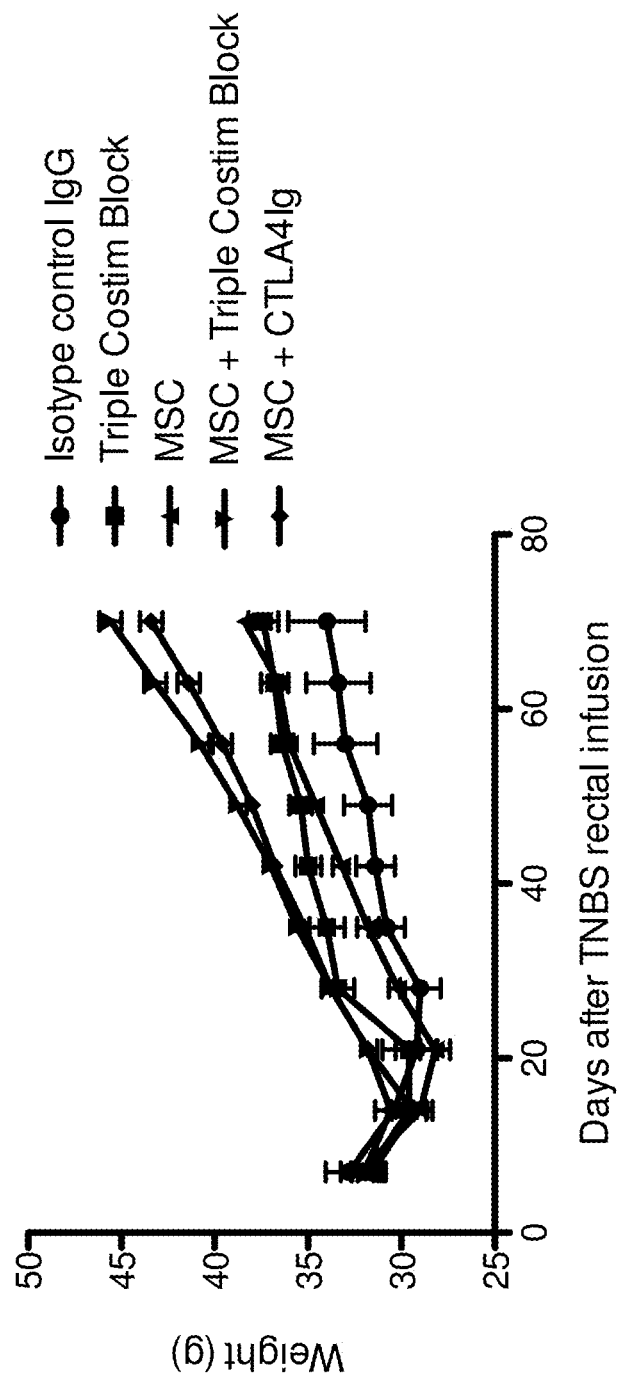
FIG. 8: Balb/c mice receive sensitization and then rectal infusion of TNBS. Mice are randomized to treatment with triple co-stimulation blockade (anti-LFA-1, CTLA4Ig and anti-CD40L), isotype control antibodies only or with MSC and costimulation blockade (MSC+CTLA4Ig+anti-LFA-1+anti-CD40L, MSC+CTLA4Ig) for the first week after sensitization. Mice are followed for ten weeks and weighed daily. Mice are then sacrificed and intestines are analyzed for the degree of inflammation.

Balb/c mice receive sensitization and then rectal infusion of TNBS. Mice are randomized to treatment with anti-LFA-1, CTLA4Ig and anti-CD40L, anti-LFA-1 only, CTLA4Ig and anti-CD40L only, isotype control antibodies only or with MSC and costimulation blockade (either MSC+CTLA4Ig, MSC+CTLA4Ig+anti-LFA-1, MSC+anti-LFA-1, MSC+CTLA4Ig+anti-LFA-1+anti-CD40L, MSC+anti-CD40L, MSC+anti-CD40L+anti-LFA1, MSC+anti-CD40L+CTLA4Ig) for the first week after sensitization. Mice are followed for six weeks and weighed daily. Mice are then sacrificed and intestines are analyzed for the degree of inflammation. FIG. 8 shows a table comprising immunohistochemical analysis performed to study the number of CD4+ and CD8+ T cells as well as macrophages and neutrophils. The number of CD4+CD25+ foxp3+ regulatory T cells is also quantitated.

Heart Transplantation in C57BL/6 Mice Model

Figure 9:
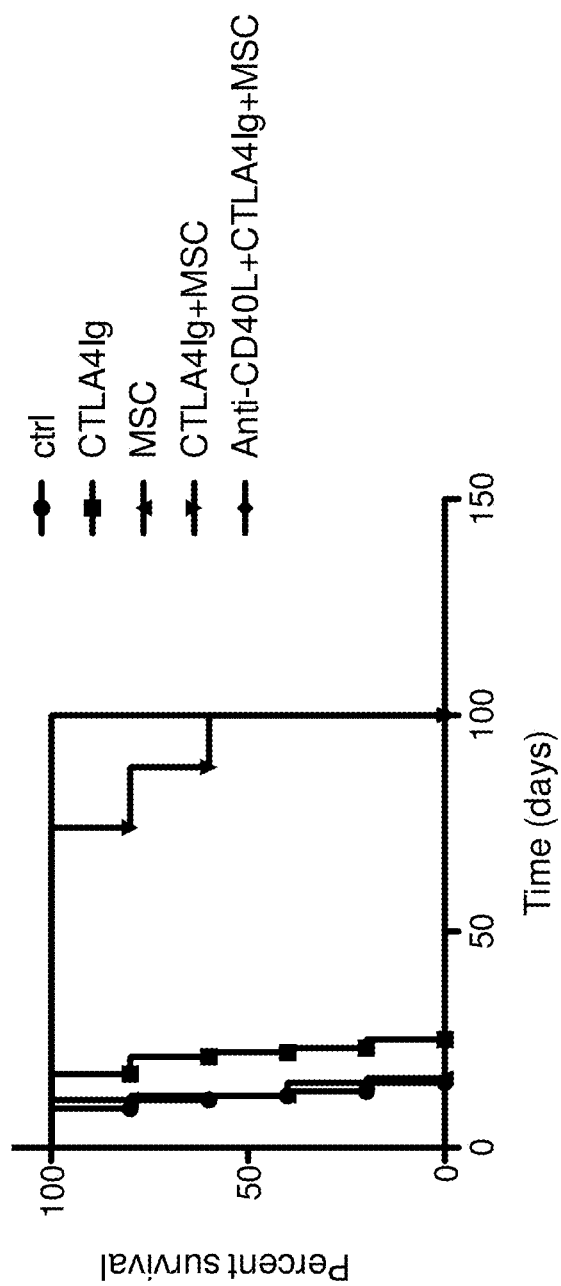
FIG. 9: C57BL/6 mice were transplanted with MHC-mismatched Balb/c hearts and treated with control human IgG, CTLA4Ig, MSC, or a combination of MSC and various co-stimulation inhibitors. Treatment with only MSC had no effect on the prevention of cardiac allograft rejection. Treatment with CTLA4Ig induced a significant prolongation of allograft survival with a median survival time of 25 days. Treatment with MSC therapy combined with (i) CTLA4Ig, (ii) CTLA4Ig and anti-CD40L induced strong allograft survival in four of five recipients. These results imply that there is a potentiating effect of combining MSC with at least one polypeptide inhibitor of co-stimulatory signaling.

C57BL/6 mice were transplanted with MHC-mismatched Balb/c hearts and treated with control human IgG, CTLA4Ig, MSC, or a combination of MSC and various polypeptides inhibiting co-stimulation. Treatment with only MSC had no effect on the prevention of cardiac allograft rejection. Treatment with CTLA4Ig induced a significant prolongation of allograft survival with a median survival time of 25 days. Treatment with MSC therapy combined with (i) CTLA4Ig, (ii) CTLA4Ig and anti-LFA1, and (iii) CTLA4Ig, anti-LFA1, and anti-CD40L induced indefinite allograft survival in four of five recipients (FIG. 9). One recipient rejected at 88 days after transplantation. These results imply that there is a potentiating effect of combining MSC with at least one inhibitor of co-stimulatory signaling.

Treatment of Collagen-Derived Arthritis

Figure 10:
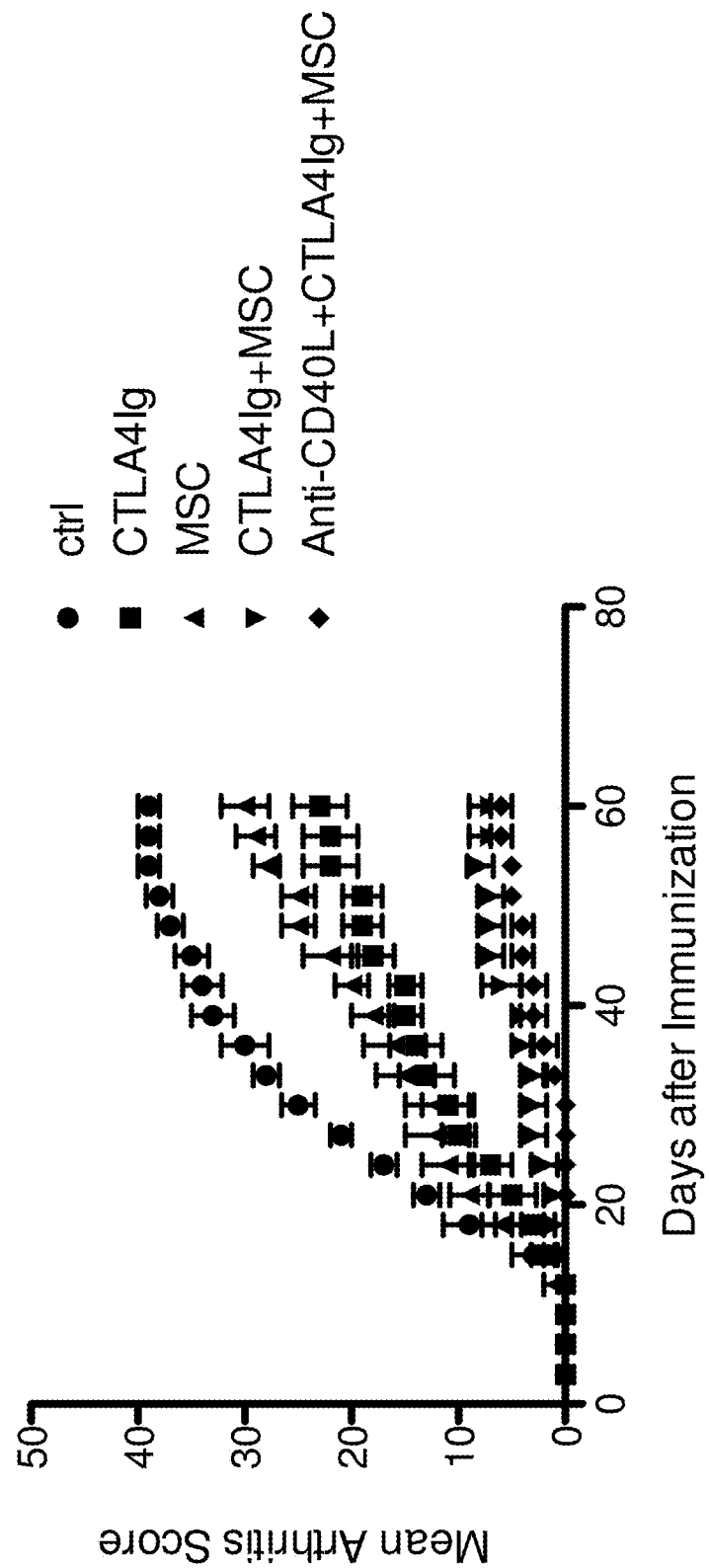
FIG. 10: C57BL/10Q mice were immunized by subcutaneous (s.c) injection at the base of the tail with 100 micrograms of rat collagen type II (CII) emulsified in an equal volume of Freund's adjuvant at a final concentration of 2 mg/ml. After 21 days, mice were boosted by injection near the first injection with 50 micrograms of rat CII. Severity of disease was followed by clinical scoring every fifth day starting on the fifth day after immunization. Recipients were randomised to receive human IgG control or CTLA4ig (500 microgram) on day 0, 2, 4, 6 after immunization and/or 2×10.6 bone marrow derived MSC from C57BL/10Q mice on the day of immunization. Treatment with MSC in combination with one co-stimulation inhibitor (CTLA4Ig) had an acceptable effect on reducing the mean arthritis score during a 60 day follow-up. Treatment with both MSC in combination with CTLA4Ig and anti-CD40L lead to a significant reduction in mean arthritis score in all observed time points at 30 days and thereafter.
Figure 11:
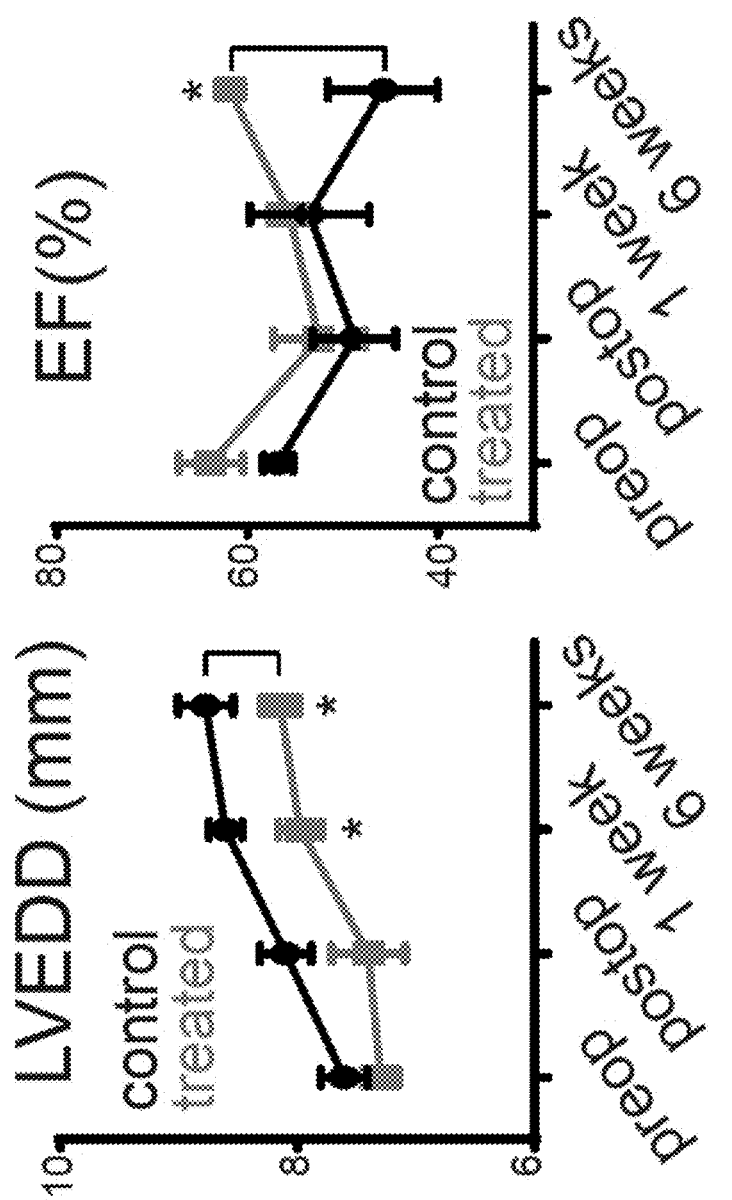
FIG. 11: Effect of Isl1 positive cell therapy in combination with triple costimulation blockade (i.e. CTLA4Ig+anti-CD40L+anti-LFA1) on left ventricular function and dimension following myocardial infarction. Rats (N=8) treated with a combination of Isl1+ mesenchymal cells (i.e. mesenchymal cells positive for Isl1) and costimulation blockade (grey squares) were compared to a placebo control group (N=8) (black circles). Pre- and postoperatively there was no significant difference in left-ventricular end diastolic diameter (LVEDD) or ejection fraction (EF) between the two groups. After 1 and 6 weeks, LVEDD was significantly reduced in the group treated with a combination of Isl positive mesenchymal cells and costimulation blockade, while at the same time the EF had improved towards preoperative level. Therapeutic efficacy was also seen with a combination of the MSC population and CTLA4Ig and anti-CD40L. Data presented as mean±SD. In figure: *p<0.05.

C57BL/10Q mice were immunized by subcutaneous (s.c) injection at the base of the tail with 100 micrograms of rat collagen type II (CII) emulsified in an equal volume of Freund's adjuvant at a final concentration of 2 mg/ml. After 21 days, mice were boosted by injection near the first injection with 50 micrograms of rat CII. Severity of disease was followed by clinical scoring every fifth day starting on the fifth day after immunization. Recipients were randomised to receive human IgG control or CTLA4ig (500 microgram) on day 0, 2, 4, 6 after immunization and/or 2×10.6 bone marrow derived MSC from C57BL/10Q mice on the day of immunization. Treatment with CTLA4Ig or MSC had an intermediary effect on reducing the mean arthritis score during a 60 day follow-up. Treatment with both MSC and CTLA4Ig lead to a significant reduction in mean arthritis score in all observed time points at 30 days and thereafter (FIG. 10).

Treatment of Myocardial Infarction

The effect of Isl1 positive cell therapy in combination with triple costimulation blockade (i.e. CTLA4Ig+anti-CD40L+anti-LFA1) on left ventricular function and dimension following myocardial infarction. Rats (N=8) treated with a combination of Isl1+ mesenchymal cells (i.e. mesenchymal cells positive for Isl1) and costimulation blockade (grey squares) were compared to a placebo control group (N=8) (black circles). Pre- and postoperatively there was no significant difference in left-ventricular end diastolic diameter (LVEDD) or ejection fraction (EF) between the two groups. After 1 and 6 weeks, LVEDD was significantly reduced in the group treated with a combination of Isl positive mesenchymal cells and costimulation blockade, while at the same time the EF had improved towards preoperative level. Therapeutic efficacy was also seen with a combination of the MSC population and CTLA4Ig and anti-CD40L. Data presented as mean±SD. In figure: *p<0.05.

Discussion

This invention demonstrates that by combining MSC administration with at least one exogenous inhibitor of co-stimulatory signal(s) a complementary and potentiated immuno-modulatory effect can be attained, which can be exploited in a large number of inflammatory and/or autoimmune disorders, and in transplantation and transplantation-related settings. MSCs as mono-therapy may not always have sufficient effects on graft survival and on different inflammatory disorders, whereas combining MSCs and at least one co-stimulation inhibitor (e.g. CTLA4Ig, anti-CD40L, anti-LFA1, etc.) results in highly efficacious therapeutic effects.

As a non-limiting example based on the above-described islet transplantation experiments, CTLA4Ig combined with anti-CD40L induced long-term normoglycemia in 5 of 9 recipients but many had unstable glucose control. The combination of CTLA4Ig with MSCs yielded long term graft survival in the majority of recipients, the presence of Foxp3$^+$ T cells around the islet grafts, decreased IFNγ upon re-exposure to donor antigen and elevated numbers of regulatory T cells in the spleen. Expression of TGFβ and insulin was significantly up-regulated in the recipient liver.

The addition of MSCs to CTLA4Ig and anti-CD40L (or to anti-CD40L and anti-LFA1, or to anti-LFA1 and CTLA4Ig) lead to normoglycemia and indefinite graft survival in all recipients. When graft function was tested with IPGTT, these recipients demonstrated better glucose control and had similar blood glucose levels as naïve untransplanted mice. Histological analysis of these recipients showed low levels of lymphocytic infiltrates. The cells that were present were CD4$^+$ and expressed Foxp3. No CD8$^+$ infiltrates were found in the livers of these recipients. Anti-donor IgG levels were lower in these mice compared to recipients receiving only costimulation blockade indicating an increased inhibition of B cell responses. Splenocytes from these recipients when co-cultured with donor antigen demonstrated reduced proliferation both at 30 and 100 days implying that the inhibited T cell response was maintained in the long term. Spleenocytes and IHLs from these donors expressed low levels of IFNγ when exposed to donor antigen indicating an attenuated response by the lymphocytes reminiscent of T cell responses seen in tolerant individuals. Flow cytometry of spleenocytes demonstrated a significant increase in the number of CD4+ Foxp3+ and CD25+ Foxp3+ lymphocytes indicating that the number of regulatory T cells was increased in the recipients which received costimulation blockade and MSCs. mRNA expression of IDO, TGFβ and Foxp3+ had a tendency towards increased expression in the livers of recipients treated with the combination of costimulation blockade and MSCs.

In order to study the effect of MSCs on DCs, the cells were co-cultured and the expression of co-stimulatory molecules and MHC class II was studied. Exposure to high numbers of MSCs reduced the expression of CD86 and increased the levels of CD80 indicating that the DC had a phenotype like immature DC. When MSCs were cultured with mature DC, T cell proliferation was almost completely abrogated. The addition of costimulation blockade reduced T cell proliferation when exposed to DC co-cultured with MSC indicating an additive effect of this combination. When studying the supernatants of these MLRs, an increased level of kyurenine was found implying substantial IDO activity and potential immune modulation by the MSCs and DCs.

MSCs may improve outcomes in syngeneic transplants by reducing inflammation and improving angiogenesis. These processes are most likely at work in the experiments demonstrated above because inflammation and immunity are not two separate phenomena but integrally linked. A reduction of inflammation may subsequently lead to a reduction in DC activation and immune activation. However, these studies suggest that MSCs are also effecting DC maturation directly.

Co-stimulation blockade, by limiting the availability of co-stimulatory molecules, leads the reactive T cell population to interpret interactions with DCs as if it was in cell-cell contact with a tolerogenic or immature DC. This interaction leads to an anergic response and the peripheral conversion of T cells to regulatory T cells. MSC have the ability to modulate DC differentiation into a tolerogenic or immature DC with the subsequent effect that the DC then induces regulatory T cells. In this manner both costimulation blockade and MSCs are converging on the maturation of DCs and how they are perceived by T cells. MSCs are also capable of directly inducing regulatory T cells by tryptophan degradation and the production of kynurenine metabolites. Tryptophan catabolism is an immune regulatory pathway which the co-stimulation blockade and MSCs also have in common. One of the major pathways in which CTLA4Ig induces the generation of regulatory T cells is through the production of IDO by DCs after binding to B7 on the DC surface. The synergy seen in this model between MSCs infusion and costimulatory blockade could be partially due to the increased IDO activity by the MSC and costimulation blockade manipulated DCs working in concert.

The present invention thus clearly demonstrates the broad utility of combining MSCs (preferably MSCs that have been validated for immuno-modulatory capacity) and at least one co-stimulation inhibitor (for instance CTLA4Ig, anti-LFA1, anti-CD40L, anti-CD40, etc.) in various transplantation settings, in autoimmunity, and in inflammation. The present inventors have above-described successfully applied this combinatorial modality also in cardiac transplantation, in the treatment of myocardial infarction, the treatment of IBS, in the treatment of rheumatoid arthritis, etc.

CTLA4Ig recently received FDA approval as maintenance therapy for renal transplantation. A combination of MSC administration and co-stimulation blockade (i.e. administration of at least one agent inhibiting at least one co-stimulatory signal) is shown in the present application to potentiate the immuno-modulatory effects of co-stimulation inhibition in a number of autoimmune diseases where co-stimulation therapies are already being studied individually. The combination of co-stimulation blockade (i.e. at least one agent inhibiting co-stimulatory signal(s)) with MSCs may thus be used to inhibit immune responses in various different settings, for inducing (FoxP3-positive) regulatory T cells (both in vitro and in vivo), and for treating numerous immune-mediated diseases, and consequently could have pivotal implications for the field of regenerative medicine.

The invention claimed is:

1. A method for therapeutic and/or prophylactic modulation and/or suppression of the immune system of a subject, the method comprising the steps of:
   (a) administering to the subject an MSC population; and,
   (b) administering to the subject an exogeneous co-stimulation inhibitor CTLA4Ig and at least one further exogenous co-stimulation inhibitor,
   wherein steps (a) and (b) may be carried out simultaneously or sequentially in any sequence or order.

2. The method of claim 1, wherein the therapeutic and/or prophylactic modulation is for the treatment and/or prophylaxis of diabetes type I, ulcerative colitis, Crohn's disease, multiple sclerosis, ALS, autoimmune hepatitis, acute respiratory distress syndrome (ARDS), graft-vs-host disease (GvHD), kidney failure, autoimmune kidney diseases, liver failure, autoimmune liver diseases, rheumatoid arthritis, Parkinson's disease, hematopoietic cell transplantation, SLE, Alzheimer's disease, arteriosclerosis, chronic or acute inflammatory diseases, arthritis, asthma, chronic obstructive pulmonary disease, post-cardiotomy cardiac failure, allergic diseases of the skin or airways, autoimmune vasculitis, islet cell transplant rejection, pancreas transplant rejection, kidney transplant rejection, kidney cell transplant rejection, liver transplant rejection, hepatocyte transplant rejection, heart transplant rejection, cardiac cell transplant rejection, skin transplant rejection, dermatocyte transplant rejection, or other similar or related diseases, disorders, and conditions.

3. The method according to claim 1, further comprising the step (c) of administering to the subject a therapeutic transplant in the form of a cell, tissue, and/or organ, wherein steps (a), (b), and (c) may be carried out simultaneously or sequentially in any sequence or order.

4. A method of therapeutic and/or prophylactic treatment of a subject, the method comprising the step of administering to the subject an MSC population and an exogenous co-stimulation inhibitor CTLA4Ig, wherein the subject was previously administered at least one further exogenous co-stimulation inhibitor.

5. A method of therapeutic and/or prophylactic treatment of a subject, the method comprising the step of administering to the subject an exogenous co-stimulation inhibitor CTLA4Ig and at least one further exogenous co-stimulation inhibitor, wherein the subject was previously administered an MSC population.

* * * * *

SEQUENCE LISTING

<160> NUMBER OF SEQ ID NOS: 49

<210> SEQ ID NO 1
<211> LENGTH: 466
<212> TYPE: PRT
<213> ORGANISM: Homo sapiens

<400> SEQUENCE: 1

-continued

```
Met Ser Thr Arg Ser Val Ser Ser Ser Tyr Arg Arg Met Phe Gly
1               5                   10                  15

Gly Pro Gly Thr Ala Ser Arg Pro Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
```

```
                    420                 425                 430
Leu Val Asp Thr His Ser Lys Arg Thr Leu Ile Lys Thr Val Glu
            435                 440                 445

Thr Arg Asp Gly Gln Val Ile Asn Glu Thr Ser Gln His His Asp Asp
        450                 455                 460

Leu Glu
465

<210> SEQ ID NO 2
<211> LENGTH: 793
<212> TYPE: PRT
<213> ORGANISM: Homo sapiens

<400> SEQUENCE: 2

Met Asp Asp Phe Glu Arg Arg Arg Glu Leu Arg Arg Gln Lys Arg Glu
1               5                   10                  15

Glu Met Arg Leu Glu Ala Glu Arg Ile Ala Tyr Gln Arg Asn Asp Asp
            20                  25                  30

Asp Glu Glu Glu Ala Ala Arg Glu Arg Arg Arg Ala Arg Gln Glu
        35                  40                  45

Arg Leu Arg Gln Lys Gln Glu Glu Ser Leu Gly Gln Val Thr Asp
    50                  55                  60

Gln Val Glu Val Asn Ala Gln Asn Ser Val Pro Asp Glu Glu Ala Lys
65                  70                  75                  80

Thr Thr Thr Thr Asn Thr Gln Val Glu Gly Asp Asp Glu Ala Ala Phe
                85                  90                  95

Leu Glu Arg Leu Ala Arg Arg Glu Glu Arg Arg Gln Lys Arg Leu Gln
            100                 105                 110

Glu Ala Leu Glu Arg Gln Lys Glu Phe Asp Pro Thr Ile Thr Asp Ala
        115                 120                 125

Ser Leu Ser Leu Pro Ser Arg Arg Met Gln Asn Asp Thr Ala Glu Asn
    130                 135                 140

Glu Thr Thr Glu Lys Glu Glu Lys Ser Glu Ser Arg Gln Glu Arg Tyr
145                 150                 155                 160

Glu Ile Glu Glu Thr Glu Thr Val Thr Lys Ser Tyr Gln Lys Asn Asp
                165                 170                 175

Trp Arg Asp Ala Glu Glu Asn Lys Lys Glu Asp Lys Glu Lys Glu Glu
            180                 185                 190

Glu Glu Glu Glu Lys Pro Lys Arg Gly Ser Ile Gly Glu Asn Gln Val
        195                 200                 205

Glu Val Met Val Glu Glu Lys Thr Thr Glu Ser Gln Glu Thr Val
    210                 215                 220

Val Met Ser Leu Lys Asn Gly Gln Ile Ser Ser Glu Pro Lys Gln
225                 230                 235                 240

Glu Glu Glu Arg Glu Gln Gly Ser Asp Glu Ile Ser His His Glu Lys
                245                 250                 255

Met Glu Glu Glu Asp Lys Glu Arg Ala Glu Ala Glu Arg Ala Arg Leu
            260                 265                 270

Glu Ala Glu Glu Arg Glu Arg Ile Lys Ala Glu Gln Asp Lys Lys Ile
        275                 280                 285

Ala Asp Glu Arg Ala Arg Ile Glu Ala Glu Lys Ala Ala Ala Gln
    290                 295                 300

Glu Arg Glu Arg Arg Glu Ala Glu Glu Arg Glu Arg Met Arg Glu Glu
305                 310                 315                 320
```

-continued

```
Glu Lys Arg Ala Ala Glu Glu Arg Gln Arg Ile Lys Glu Glu Lys
                325                 330                 335
Arg Ala Ala Glu Glu Arg Gln Arg Ile Lys Glu Glu Lys Arg Ala
            340                 345                 350
Ala Glu Glu Arg Gln Arg Ile Lys Glu Glu Lys Arg Ala Ala Glu
        355                 360                 365
Glu Arg Gln Arg Ala Arg Ala Glu Glu Glu Lys Ala Lys Val Glu
    370                 375                 380
Glu Gln Lys Arg Asn Lys Gln Leu Glu Glu Lys His Ala Met Gln
385                 390                 395                 400
Glu Thr Lys Ile Lys Gly Glu Lys Val Glu Gln Lys Ile Glu Gly Lys
                405                 410                 415
Trp Val Asn Glu Lys Lys Ala Gln Glu Asp Lys Leu Gln Thr Ala Val
                420                 425                 430
Leu Lys Lys Gln Gly Glu Glu Lys Gly Thr Lys Val Gln Ala Lys Arg
            435                 440                 445
Glu Lys Leu Gln Glu Asp Lys Pro Thr Phe Lys Lys Glu Glu Ile Lys
        450                 455                 460
Asp Glu Lys Ile Lys Lys Asp Lys Glu Pro Lys Glu Glu Val Lys Ser
465                 470                 475                 480
Phe Met Asp Arg Lys Lys Gly Phe Thr Glu Val Lys Ser Gln Asn Gly
                485                 490                 495
Glu Phe Met Thr His Lys Leu Lys His Thr Glu Asn Thr Phe Ser Arg
                500                 505                 510
Pro Gly Gly Arg Ala Ser Val Asp Thr Lys Glu Ala Glu Gly Ala Pro
            515                 520                 525
Gln Val Glu Ala Gly Lys Arg Leu Glu Glu Leu Arg Arg Arg Gly
        530                 535                 540
Glu Thr Glu Ser Glu Glu Phe Glu Lys Leu Lys Gln Lys Gln Gln Glu
545                 550                 555                 560
Ala Ala Leu Glu Leu Glu Glu Leu Lys Lys Lys Arg Glu Glu Arg Arg
                565                 570                 575
Lys Val Leu Glu Glu Glu Glu Gln Arg Arg Lys Gln Glu Glu Ala Asp
            580                 585                 590
Arg Lys Leu Arg Glu Glu Glu Glu Lys Arg Arg Leu Lys Glu Glu Ile
        595                 600                 605
Glu Arg Arg Arg Ala Glu Ala Ala Glu Lys Arg Gln Lys Met Pro Glu
    610                 615                 620
Asp Gly Leu Ser Asp Asp Lys Lys Pro Phe Lys Cys Phe Thr Pro Lys
625                 630                 635                 640
Gly Ser Ser Leu Lys Ile Glu Glu Arg Ala Glu Phe Leu Asn Lys Ser
                645                 650                 655
Val Gln Lys Ser Ser Gly Val Lys Ser Thr His Gln Ala Ala Ile Val
            660                 665                 670
Ser Lys Ile Asp Ser Arg Leu Glu Gln Tyr Thr Ser Ala Ile Glu Gly
        675                 680                 685
Thr Lys Ser Ala Lys Pro Thr Lys Pro Ala Ala Ser Asp Leu Pro Val
    690                 695                 700
Pro Ala Glu Gly Val Arg Asn Ile Lys Ser Met Trp Glu Lys Gly Asn
705                 710                 715                 720
Val Phe Ser Ser Pro Thr Ala Ala Gly Thr Pro Asn Lys Glu Thr Ala
                725                 730                 735
Gly Leu Lys Val Gly Val Ser Ser Arg Ile Asn Glu Trp Leu Thr Lys
```

```
                    740                 745                 750
Thr Pro Asp Gly Asn Lys Ser Pro Ala Pro Lys Pro Ser Asp Leu Arg
                755                 760                 765

Pro Gly Asp Val Ser Ser Lys Arg Asn Leu Trp Glu Lys Gln Ser Val
            770                 775                 780

Asp Lys Val Thr Ser Pro Thr Lys Val
785                 790
```

<210> SEQ ID NO 3
<211> LENGTH: 346
<212> TYPE: PRT
<213> ORGANISM: Homo sapiens

<400> SEQUENCE: 3

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
        50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320
```

Ile Ser Leu Cys Gln Ala Ile Leu Asp Glu Thr Lys Gly Asp Tyr Glu
            325                 330                 335

Lys Ile Leu Val Ala Leu Cys Gly Gly Asn
            340                 345

<210> SEQ ID NO 4
<211> LENGTH: 255
<212> TYPE: PRT
<213> ORGANISM: Homo sapiens

<400> SEQUENCE: 4

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
                20                  25                  30

Met Asp Val Glu Leu Thr Val Glu Glu Arg Asn Leu Leu Ser Val Ala
            35                  40                  45

Tyr Lys Asn Val Ile Gly Ala Arg Arg Ala Ser Trp Arg Ile Ile Ser
        50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 5
<211> LENGTH: 181
<212> TYPE: PRT
<213> ORGANISM: Homo sapiens

<400> SEQUENCE: 5

Met Gly Asn Ile Phe Ala Asn Leu Phe Lys Gly Leu Phe Gly Lys Lys
1               5                   10                  15

Glu Met Arg Ile Leu Met Val Gly Leu Asp Ala Ala Gly Lys Thr Thr
                20                  25                  30

Ile Leu Tyr Lys Leu Lys Leu Gly Glu Ile Val Thr Thr Ile Pro Thr
        35                  40                  45

```
Ile Gly Phe Asn Val Glu Thr Val Glu Tyr Lys Asn Ile Ser Phe Thr
        50                  55                  60

Val Trp Asp Val Gly Gly Gln Asp Lys Ile Arg Pro Leu Trp Arg His
65                  70                  75                  80

Tyr Phe Gln Asn Thr Gln Gly Leu Ile Phe Val Val Asp Ser Asn Asp
                    85                  90                  95

Arg Glu Arg Val Asn Glu Ala Arg Glu Glu Leu Met Arg Met Leu Ala
                100                 105                 110

Glu Asp Glu Leu Arg Asp Ala Val Leu Leu Val Phe Ala Asn Lys Gln
                115                 120                 125

Asp Leu Pro Asn Ala Met Asn Ala Ala Glu Ile Thr Asp Lys Leu Gly
            130                 135                 140

Leu His Ser Leu Arg His Arg Asn Trp Tyr Ile Gln Ala Thr Cys Ala
145                 150                 155                 160

Thr Ser Gly Asp Gly Leu Tyr Glu Gly Leu Asp Trp Leu Ser Asn Gln
                    165                 170                 175

Leu Arg Asn Gln Lys
                180

<210> SEQ ID NO 6
<211> LENGTH: 592
<212> TYPE: PRT
<213> ORGANISM: Homo sapiens

<400> SEQUENCE: 6

Met Glu Gly Lys Trp Leu Leu Cys Met Leu Leu Val Leu Gly Thr Ala
1               5                   10                  15

Ile Val Glu Ala His Asp Gly His Asp Asp Val Ile Asp Ile Glu
                20                  25                  30

Asp Asp Leu Asp Asp Val Ile Glu Val Glu Asp Ser Lys Pro Asp
            35                  40                  45

Thr Thr Ala Pro Pro Ser Ser Pro Lys Val Thr Tyr Lys Ala Pro Val
50                  55                  60

Pro Thr Gly Glu Val Tyr Phe Ala Asp Ser Phe Asp Arg Gly Thr Leu
65                  70                  75                  80

Ser Gly Trp Ile Leu Ser Lys Ala Lys Lys Asp Asp Thr Asp Asp Glu
                85                  90                  95

Ile Ala Lys Tyr Asp Gly Lys Trp Glu Val Glu Glu Met Lys Glu Ser
                100                 105                 110

Lys Leu Pro Gly Asp Lys Gly Leu Val Leu Met Ser Arg Ala Lys His
                115                 120                 125

His Ala Ile Ser Ala Lys Leu Asn Lys Pro Phe Leu Phe Asp Thr Lys
            130                 135                 140

Pro Leu Ile Val Gln Tyr Glu Val Asn Phe Gln Asn Gly Ile Glu Cys
145                 150                 155                 160

Gly Gly Ala Tyr Val Lys Leu Leu Ser Lys Thr Pro Glu Leu Asn Leu
                165                 170                 175

Asp Gln Phe His Asp Lys Thr Pro Tyr Thr Ile Met Phe Gly Pro Asp
                180                 185                 190

Lys Cys Gly Glu Asp Tyr Lys Leu His Phe Ile Phe Arg His Lys Asn
                195                 200                 205

Pro Lys Thr Gly Ile Tyr Glu Glu Lys His Ala Lys Arg Pro Asp Ala
            210                 215                 220

Asp Leu Lys Thr Tyr Phe Thr Asp Lys Lys Thr His Leu Tyr Thr Leu
225                 230                 235                 240
```

```
Ile Leu Asn Pro Asp Asn Ser Phe Glu Ile Leu Val Asp Gln Ser Val
                245                 250                 255

Val Asn Ser Gly Asn Leu Leu Asn Asp Met Thr Pro Pro Val Asn Pro
            260                 265                 270

Ser Arg Glu Ile Glu Asp Pro Glu Asp Arg Lys Pro Glu Asp Trp Asp
        275                 280                 285

Glu Arg Pro Lys Ile Pro Asp Pro Glu Ala Val Lys Pro Asp Asp Trp
    290                 295                 300

Asp Glu Asp Ala Pro Ala Lys Ile Pro Asp Glu Glu Ala Thr Lys Pro
305                 310                 315                 320

Glu Gly Trp Leu Asp Asp Glu Pro Glu Tyr Val Pro Asp Pro Asp Ala
                325                 330                 335

Glu Lys Pro Glu Asp Trp Asp Glu Asp Met Asp Gly Glu Trp Glu Ala
            340                 345                 350

Pro Gln Ile Ala Asn Pro Arg Cys Glu Ser Ala Pro Gly Cys Gly Val
        355                 360                 365

Trp Gln Arg Pro Val Ile Asp Asn Pro Asn Tyr Lys Gly Lys Trp Lys
    370                 375                 380

Pro Pro Met Ile Asp Asn Pro Ser Tyr Gln Gly Ile Trp Lys Pro Arg
385                 390                 395                 400

Lys Ile Pro Asn Pro Asp Phe Phe Glu Asp Leu Glu Pro Phe Arg Met
                405                 410                 415

Thr Pro Phe Ser Ala Ile Gly Leu Glu Leu Trp Ser Met Thr Ser Asp
            420                 425                 430

Ile Phe Phe Asp Asn Phe Ile Ile Cys Ala Asp Arg Arg Ile Val Asp
        435                 440                 445

Asp Trp Ala Asn Asp Gly Trp Gly Leu Lys Lys Ala Ala Asp Gly Ala
    450                 455                 460

Ala Glu Pro Gly Val Val Gly Gln Met Ile Glu Ala Ala Glu Glu Arg
465                 470                 475                 480

Pro Trp Leu Trp Val Val Tyr Ile Leu Thr Val Ala Leu Pro Val Phe
                485                 490                 495

Leu Val Ile Leu Phe Cys Cys Ser Gly Lys Lys Gln Thr Ser Gly Met
            500                 505                 510

Glu Tyr Lys Lys Thr Asp Ala Pro Gln Pro Asp Val Lys Glu Glu Glu
        515                 520                 525

Glu Glu Lys Glu Glu Glu Lys Asp Lys Gly Asp Glu Glu Glu Glu Gly
    530                 535                 540

Glu Glu Lys Leu Glu Glu Lys Gln Lys Ser Asp Ala Glu Glu Asp Gly
545                 550                 555                 560

Gly Thr Val Ser Gln Glu Glu Asp Arg Lys Pro Lys Ala Glu Glu
                565                 570                 575

Asp Glu Ile Leu Asn Arg Ser Pro Arg Asn Arg Lys Pro Arg Arg Glu
            580                 585                 590

<210> SEQ ID NO 7
<211> LENGTH: 180
<212> TYPE: PRT
<213> ORGANISM: Homo sapiens

<400> SEQUENCE: 7

Met Gly Leu Thr Val Ser Ala Leu Phe Ser Arg Ile Phe Gly Lys Lys
1               5                   10                  15

Gln Met Arg Ile Leu Met Val Gly Leu Asp Ala Ala Gly Lys Thr Thr
```

```
                   20                  25                  30
Ile Leu Tyr Lys Leu Lys Leu Gly Glu Ile Val Thr Thr Ile Pro Thr
                35                  40                  45
Ile Gly Phe Asn Val Glu Thr Val Glu Tyr Lys Asn Ile Cys Phe Thr
            50                  55                  60
Val Trp Asp Val Gly Gly Gln Asp Lys Ile Arg Pro Leu Trp Arg His
 65                  70                  75                  80
Tyr Phe Gln Asn Thr Gln Gly Leu Ile Phe Val Val Asp Ser Asn Asp
                85                  90                  95
Arg Glu Arg Val Gln Glu Ser Ala Asp Glu Leu Gln Lys Met Leu Gln
                100                 105                 110
Glu Asp Glu Leu Arg Asp Ala Val Leu Leu Val Phe Ala Asn Lys Gln
                115                 120                 125
Asp Met Pro Asn Ala Met Pro Val Ser Glu Leu Thr Asp Lys Leu Gly
                130                 135                 140
Leu Gln His Leu Arg Ser Arg Thr Trp Tyr Val Gln Ala Thr Cys Ala
145                 150                 155                 160
Thr Gln Gly Thr Gly Leu Tyr Asp Gly Leu Asp Trp Leu Ser His Glu
                165                 170                 175
Leu Ser Lys Arg
            180

<210> SEQ ID NO 8
<211> LENGTH: 193
<212> TYPE: PRT
<213> ORGANISM: Homo sapiens

<400> SEQUENCE: 8

Met Ala Ala Ile Arg Lys Lys Leu Val Ile Val Gly Asp Gly Ala Cys
 1               5                  10                  15
Gly Lys Thr Cys Leu Leu Ile Val Phe Ser Lys Asp Gln Phe Pro Glu
                20                  25                  30
Val Tyr Val Pro Thr Val Phe Glu Asn Tyr Val Ala Asp Ile Glu Val
                35                  40                  45
Asp Gly Lys Gln Val Glu Leu Ala Leu Trp Asp Thr Ala Gly Gln Glu
            50                  55                  60
Asp Tyr Asp Arg Leu Arg Pro Leu Ser Tyr Pro Asp Thr Asp Val Ile
 65                  70                  75                  80
Leu Met Cys Phe Ser Ile Asp Ser Pro Asp Ser Leu Glu Asn Ile Pro
                85                  90                  95
Glu Lys Trp Thr Pro Glu Val Lys His Phe Cys Pro Asn Val Pro Ile
                100                 105                 110
Ile Leu Val Gly Asn Lys Lys Asp Leu Arg Asn Asp Glu His Thr Arg
                115                 120                 125
Arg Glu Leu Ala Lys Met Lys Gln Glu Pro Val Lys Pro Glu Glu Gly
                130                 135                 140
Arg Asp Met Ala Asn Arg Ile Gly Ala Phe Gly Tyr Met Glu Cys Ser
145                 150                 155                 160
Ala Lys Thr Lys Asp Gly Val Arg Glu Val Phe Glu Met Ala Thr Arg
                165                 170                 175
Ala Ala Leu Gln Ala Arg Arg Gly Lys Lys Lys Ser Gly Cys Leu Val
                180                 185                 190
Leu
```

```
<210> SEQ ID NO 9
<211> LENGTH: 206
<212> TYPE: PRT
<213> ORGANISM: Homo sapiens

<400> SEQUENCE: 9

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Gly Ala Asn Thr Thr Ser Gly Pro Ile Arg Thr Pro Gln Ile Pro
            100                 105                 110

Glu Trp Leu Ile Ile Leu Ala Ser Leu Leu Ala Leu Ala Leu Ile Leu
        115                 120                 125

Ala Val Cys Ile Ala Val Asn Ser Arg Arg Arg Cys Gly Gln Lys Lys
    130                 135                 140

Lys Leu Val Ile Asn Ser Gly Asn Gly Ala Val Glu Asp Arg Lys Pro
145                 150                 155                 160

Ser Gly Leu Asn Gly Glu Ala Ser Lys Ser Gln Glu Met Val His Leu
                165                 170                 175

Val Asn Lys Glu Ser Ser Glu Thr Pro Asp Gln Phe Met Thr Ala Asp
            180                 185                 190

Glu Thr Arg Asn Leu Gln Asn Val Asp Met Lys Ile Gly Val
        195                 200                 205

<210> SEQ ID NO 10
<211> LENGTH: 142
<212> TYPE: PRT
<213> ORGANISM: Homo sapiens

<400> SEQUENCE: 10

Met Ala Thr Lys Ile Asp Lys Glu Ala Cys Arg Ala Ala Tyr Asn Leu
1               5                   10                  15

Val Arg Asp Asp Gly Ser Ala Val Ile Trp Val Thr Phe Lys Tyr Asp
            20                  25                  30

Gly Ser Thr Ile Val Pro Gly Glu Gln Gly Ala Glu Tyr Gln His Phe
        35                  40                  45

Ile Gln Gln Cys Thr Asp Asp Val Arg Leu Phe Ala Phe Val Arg Phe
    50                  55                  60

Thr Thr Gly Asp Ala Met Ser Lys Arg Ser Lys Phe Ala Leu Ile Thr
65                  70                  75                  80

Trp Ile Gly Glu Asn Val Ser Gly Leu Gln Arg Ala Lys Thr Gly Thr
                85                  90                  95

Asp Lys Thr Leu Val Lys Glu Val Val Gln Asn Phe Ala Lys Glu Phe
            100                 105                 110

Val Ile Ser Asp Arg Lys Glu Leu Glu Glu Asp Phe Ile Lys Ser Glu
        115                 120                 125

Leu Lys Lys Ala Gly Gly Ala Asn Tyr Asp Ala Gln Thr Glu
```

<210> SEQ ID NO 11
<211> LENGTH: 379
<212> TYPE: PRT
<213> ORGANISM: Homo sapiens

<400> SEQUENCE: 11

Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
                20                  25                  30

Gly Gln Pro Phe Asp Val Gly Pro Arg Tyr Thr Gln Leu Gln Tyr Ile
            35                  40                  45

Gly Glu Gly Ala Tyr Gly Met Val Ser Ser Ala Tyr Asp His Val Arg
        50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Pro Phe Thr Phe Ala Met Glu Leu
            340                 345                 350

Asp Asp Leu Pro Lys Glu Arg Leu Lys Glu Leu Ile Phe Gln Glu Thr
355                 360                 365

Ala Arg Phe Gln Pro Gly Val Leu Glu Ala Pro
    370                 375

<210> SEQ ID NO 12
<211> LENGTH: 282
<212> TYPE: PRT
<213> ORGANISM: Homo sapiens

<400> SEQUENCE: 12

Met Glu Arg Pro Ser Leu Arg Ala Leu Leu Leu Gly Ala Ala Gly Leu
1               5                   10                  15

Leu Leu Leu Leu Leu Pro Leu Ser Ser Ser Ser Ser Asp Thr Cys
            20                  25                  30

Gly Pro Cys Glu Pro Ala Ser Cys Pro Pro Leu Pro Pro Leu Gly Cys
        35                  40                  45

Leu Leu Gly Glu Thr Arg Asp Ala Cys Gly Cys Cys Pro Met Cys Ala
    50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
        115                 120                 125

Ser Gly Cys Gln Leu Arg Ala Ala Ser Gln Arg Ala Glu Ser Arg Gly
    130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
        275                 280

<210> SEQ ID NO 13
<211> LENGTH: 552
<212> TYPE: PRT
<213> ORGANISM: Homo sapiens

<400> SEQUENCE: 13

Met Arg Leu Leu Pro Leu Ala Pro Gly Arg Leu Arg Arg Gly Ser Pro
1               5                   10                  15

Arg His Leu Pro Ser Cys Ser Pro Ala Leu Leu Leu Val Leu Gly
            20                  25                  30

```
Gly Cys Leu Gly Val Phe Val Ala Ala Gly Thr Arg Arg Pro Asn
             35                  40                  45

Val Val Leu Leu Leu Thr Asp Asp Gln Asp Glu Val Leu Gly Gly Met
 50                      55                  60

Thr Pro Leu Lys Lys Thr Lys Ala Leu Ile Gly Glu Met Gly Met Thr
 65                  70                  75                  80

Phe Ser Ser Ala Tyr Val Pro Ser Ala Leu Cys Cys Pro Ser Arg Ala
                 85                  90                  95

Ser Ile Leu Thr Gly Lys Tyr Pro His Asn His Val Val Asn Asn
             100                 105                 110

Thr Leu Glu Gly Asn Cys Ser Ser Lys Ser Trp Gln Lys Ile Gln Glu
         115                 120                 125

Pro Asn Thr Phe Pro Ala Ile Leu Arg Ser Met Cys Gly Tyr Gln Thr
         130                 135                 140

Phe Phe Ala Gly Lys Tyr Leu Asn Glu Tyr Gly Ala Pro Asp Ala Gly
145                 150                 155                 160

Gly Leu Glu His Val Pro Leu Gly Trp Ser Tyr Trp Tyr Ala Leu Glu
                 165                 170                 175

Lys Asn Ser Lys Tyr Tyr Asn Tyr Thr Leu Ser Ile Asn Gly Lys Ala
             180                 185                 190

Arg Lys His Gly Glu Asn Tyr Ser Val Asp Tyr Leu Thr Asp Val Leu
         195                 200                 205

Ala Asn Val Ser Leu Asp Phe Leu Asp Tyr Lys Ser Asn Phe Glu Pro
         210                 215                 220

Phe Phe Met Met Ile Ala Thr Pro Ala Pro His Ser Pro Trp Thr Ala
225                 230                 235                 240

Ala Pro Gln Tyr Gln Lys Ala Phe Gln Asn Val Phe Ala Pro Arg Asn
                 245                 250                 255

Lys Asn Phe Asn Ile His Gly Thr Asn Lys His Trp Leu Ile Arg Gln
             260                 265                 270

Ala Lys Thr Pro Met Thr Asn Ser Ser Ile Gln Phe Leu Asp Asn Ala
         275                 280                 285

Phe Arg Lys Arg Trp Gln Thr Leu Leu Ser Val Asp Asp Leu Val Glu
290                 295                 300

Lys Leu Val Lys Arg Leu Glu Phe Thr Gly Glu Leu Asn Asn Thr Tyr
305                 310                 315                 320

Ile Phe Tyr Thr Ser Asp Asn Gly Tyr His Thr Gly Gln Phe Ser Leu
                 325                 330                 335

Pro Ile Asp Lys Arg Gln Leu Tyr Glu Phe Asp Ile Lys Val Pro Leu
             340                 345                 350

Leu Val Arg Gly Pro Gly Ile Lys Pro Asn Gln Thr Ser Lys Met Leu
         355                 360                 365

Val Ala Asn Ile Asp Leu Gly Pro Thr Ile Leu Asp Ile Ala Gly Tyr
         370                 375                 380

Asp Leu Asn Lys Thr Gln Met Asp Gly Met Ser Leu Leu Pro Ile Leu
385                 390                 395                 400

Arg Gly Ala Ser Asn Leu Thr Trp Arg Ser Asp Val Leu Val Glu Tyr
                 405                 410                 415

Gln Gly Glu Gly Arg Asn Val Thr Asp Pro Thr Cys Pro Ser Leu Ser
             420                 425                 430

Pro Gly Val Ser Gln Cys Phe Pro Asp Cys Val Cys Glu Asp Ala Tyr
         435                 440                 445

Asn Asn Thr Tyr Ala Cys Val Arg Thr Met Ser Ala Leu Trp Asn Leu
```

```
                   450               455              460
Gln Tyr Cys Glu Phe Asp Asp Gln Glu Val Phe Val Glu Val Tyr Asn
465                 470                 475                 480

Leu Thr Ala Asp Pro Asp Gln Ile Thr Asn Ile Ala Lys Thr Ile Asp
                485                 490                 495

Pro Glu Leu Leu Gly Lys Met Asn Tyr Arg Leu Met Met Leu Gln Ser
                500                 505                 510

Cys Ser Gly Pro Thr Cys Arg Thr Pro Gly Val Phe Asp Pro Gly Tyr
                515                 520                 525

Arg Phe Asp Pro Arg Leu Met Phe Ser Asn Arg Gly Ser Val Arg Thr
                530                 535                 540

Arg Arg Phe Ser Lys His Leu Leu
545                 550

<210> SEQ ID NO 14
<211> LENGTH: 138
<212> TYPE: PRT
<213> ORGANISM: Homo sapiens

<400> SEQUENCE: 14

Met Pro Asn Phe Ser Gly Asn Trp Lys Ile Ile Arg Ser Glu Asn Phe
1               5                   10                  15

Glu Glu Leu Leu Lys Val Leu Gly Val Asn Val Met Leu Arg Lys Ile
                20                  25                  30

Ala Val Ala Ala Ala Ser Lys Pro Ala Val Glu Ile Lys Gln Glu Gly
            35                  40                  45

Asp Thr Phe Tyr Ile Lys Thr Ser Thr Thr Val Arg Thr Thr Glu Ile
        50                  55                  60

Asn Phe Lys Val Gly Glu Glu Phe Glu Glu Gln Thr Val Asp Gly Arg
65                  70                  75                  80

Pro Cys Lys Ser Leu Val Lys Trp Glu Ser Glu Asn Lys Met Val Cys
                85                  90                  95

Glu Gln Lys Leu Leu Lys Gly Glu Gly Pro Lys Thr Ser Trp Thr Arg
                100                 105                 110

Glu Leu Thr Asn Asp Gly Glu Leu Ile Leu Thr Met Thr Ala Asp Asp
            115                 120                 125

Val Val Cys Thr Arg Val Tyr Val Arg Glu
        130                 135

<210> SEQ ID NO 15
<211> LENGTH: 89
<212> TYPE: PRT
<213> ORGANISM: Homo sapiens

<400> SEQUENCE: 15

Met Asp Gly Glu Glu Lys Thr Tyr Gly Gly Cys Glu Gly Pro Asp Ala
1               5                   10                  15

Met Tyr Val Lys Leu Ile Ser Ser Asp Gly His Glu Phe Ile Val Lys
                20                  25                  30

Arg Glu His Ala Leu Thr Ser Gly Thr Ile Lys Ala Met Leu Ser Gly
            35                  40                  45

Pro Gly Gln Phe Ala Glu Asn Glu Thr Asn Glu Val Asn Phe Arg Glu
        50                  55                  60

Ile Pro Ser His Val Leu Ser Lys Val Cys Met Tyr Phe Thr Tyr Lys
65                  70                  75                  80

Val Arg Tyr Thr Asn Ser Ser Thr Glu
```

-continued

```
                85

<210> SEQ ID NO 16
<211> LENGTH: 50
<212> TYPE: PRT
<213> ORGANISM: Homo sapiens

<400> SEQUENCE: 16

Met Leu Ile Lys Val Lys Thr Leu Thr Gly Lys Glu Ile Glu Ile Asp
1               5                   10                  15

Ile Glu Pro Thr Asp Lys Val Glu Arg Ile Lys Glu Arg Val Glu Glu
            20                  25                  30

Lys Glu Gly Ile Pro Pro Gln Gln Arg Leu Ile Tyr Ser Gly Lys
        35                  40                  45

Gln Met
    50

<210> SEQ ID NO 17
<211> LENGTH: 132
<212> TYPE: PRT
<213> ORGANISM: Homo sapiens

<400> SEQUENCE: 17

Met Val Asp Ala Phe Leu Gly Thr Trp Lys Leu Val Asp Ser Lys Asn
1               5                   10                  15

Phe Asp Asp Tyr Met Lys Ser Leu Gly Val Gly Phe Ala Thr Arg Gln
            20                  25                  30

Val Ala Ser Met Thr Lys Pro Thr Thr Ile Ile Glu Lys Asn Gly Asp
        35                  40                  45

Ile Leu Thr Leu Lys Thr His Ser Thr Phe Lys Asn Thr Glu Ile Ser
    50                  55                  60

Phe Lys Leu Gly Val Glu Phe Asp Glu Thr Thr Ala Asp Asp Arg Lys
65                  70                  75                  80

Val Lys Ser Ile Val Thr Leu Asp Gly Gly Lys Leu Val His Leu Gln
                85                  90                  95

Lys Trp Asp Gly Gln Glu Thr Thr Leu Val Arg Glu Leu Ile Asp Gly
            100                 105                 110

Lys Leu Ile Leu Thr Leu Thr His Gly Thr Ala Val Cys Thr Arg Thr
        115                 120                 125

Tyr Glu Lys Glu
    130

<210> SEQ ID NO 18
<211> LENGTH: 698
<212> TYPE: PRT
<213> ORGANISM: Homo sapiens

<400> SEQUENCE: 18

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80
```

```
Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
            115                 120                 125

Asn Gln Leu Arg Gly Lys Lys Ser Cys His Thr Gly Leu Gly Arg Ser
130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
            195                 200                 205

Gly Ala Phe Lys Cys Leu Lys Asp Gly Ala Gly Asp Val Ala Phe Val
            210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
            275                 280                 285

Ala Gln Glu His Phe Gly Lys Asp Lys Ser Lys Glu Phe Gln Leu Phe
            290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
            355                 360                 365

His Glu Arg Leu Lys Cys Asp Glu Trp Ser Val Asn Ser Val Gly Lys
        370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Ile
            435                 440                 445

Ala Val Val Lys Lys Ser Ala Ser Asp Leu Thr Trp Asp Asn Leu Lys
            450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495
```

-continued

```
Glu Phe Phe Ser Gly Cys Ala Pro Gly Ser Lys Lys Asp Ser Ser
                500                 505                 510
Leu Cys Lys Leu Cys Met Gly Ser Gly Leu Asn Leu Cys Glu Pro Asn
    515                 520                 525
Asn Lys Glu Gly Tyr Tyr Gly Tyr Thr Gly Ala Phe Arg Cys Leu Val
530                 535                 540
Glu Lys Gly Asp Val Ala Phe Val Lys His Gln Thr Val Pro Gln Asn
545                 550                 555                 560
Thr Gly Gly Lys Asn Pro Asp Pro Trp Ala Lys Asn Leu Asn Glu Lys
                565                 570                 575
Asp Tyr Glu Leu Leu Cys Leu Asp Gly Thr Arg Lys Pro Val Glu Glu
            580                 585                 590
Tyr Ala Asn Cys His Leu Ala Arg Ala Pro Asn His Ala Val Val Thr
        595                 600                 605
Arg Lys Asp Lys Glu Ala Cys Val His Lys Ile Leu Arg Gln Gln Gln
    610                 615                 620
His Leu Phe Gly Ser Asn Val Thr Asp Cys Ser Gly Asn Phe Cys Leu
625                 630                 635                 640
Phe Arg Ser Glu Thr Lys Asp Leu Leu Phe Arg Asp Asp Thr Val Cys
                645                 650                 655
Leu Ala Lys Leu His Asp Arg Asn Thr Tyr Glu Lys Tyr Leu Gly Glu
            660                 665                 670
Glu Tyr Val Lys Ala Val Gly Asn Leu Arg Lys Cys Ser Thr Ser Ser
        675                 680                 685
Leu Leu Glu Ala Cys Thr Phe Arg Arg Pro
    690                 695

<210> SEQ ID NO 19
<211> LENGTH: 3396
<212> TYPE: PRT
<213> ORGANISM: Homo sapiens

<400> SEQUENCE: 19

Met Phe Ile Asn Ile Lys Ser Ile Leu Trp Met Cys Ser Thr Leu Ile
1               5                   10                  15
Val Thr His Ala Leu His Lys Val Lys Val Gly Lys Ser Pro Pro Val
            20                  25                  30
Arg Gly Ser Leu Ser Gly Lys Val Ser Leu Pro Cys His Phe Ser Thr
        35                  40                  45
Met Pro Thr Leu Pro Pro Ser Tyr Asn Thr Ser Glu Phe Leu Arg Ile
    50                  55                  60
Lys Trp Ser Lys Ile Glu Val Asp Lys Asn Gly Lys Asp Leu Lys Glu
65                  70                  75                  80
Thr Thr Val Leu Val Ala Gln Asn Gly Asn Ile Lys Ile Gly Gln Asp
                85                  90                  95
Tyr Lys Gly Arg Val Ser Val Pro Thr His Pro Glu Ala Val Gly Asp
            100                 105                 110
Ala Ser Leu Thr Val Val Lys Leu Leu Ala Ser Asp Ala Gly Leu Tyr
        115                 120                 125
Arg Cys Asp Val Met Tyr Gly Ile Glu Asp Thr Gln Asp Thr Val Ser
    130                 135                 140
Leu Thr Val Asp Gly Val Val Phe His Tyr Arg Ala Ala Thr Ser Arg
145                 150                 155                 160
Tyr Thr Leu Asn Phe Glu Ala Ala Gln Lys Ala Cys Leu Asp Val Gly
                165                 170                 175
```

-continued

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

Pro Ile Arg Ala Pro Arg Val Gly Cys Tyr Gly Asp Lys Met Gly Lys
    210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Ala Lys Glu Cys Glu Asn
            260                 265                 270

Gln Asp Ala Arg Leu Ala Thr Val Gly Glu Leu Gln Ala Ala Trp Arg
        275                 280                 285

Asn Gly Phe Asp Gln Cys Asp Tyr Gly Trp Leu Ser Asp Ala Ser Val
    290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Pro Lys Glu Ala Thr
            340                 345                 350

Thr Ile Asp Leu Ser Ile Leu Ala Glu Thr Ala Ser Pro Ser Leu Ser
        355                 360                 365

Lys Glu Pro Gln Met Val Ser Asp Arg Thr Thr Pro Ile Ile Pro Leu
    370                 375                 380

Val Asp Glu Leu Pro Val Ile Pro Thr Glu Phe Pro Pro Val Gly Asn
385                 390                 395                 400

Ile Val Ser Phe Glu Gln Lys Ala Thr Val Gln Pro Gln Ala Ile Thr
                405                 410                 415

Asp Ser Leu Ala Thr Lys Leu Pro Thr Pro Thr Gly Ser Thr Lys Lys
            420                 425                 430

Pro Trp Asp Met Asp Asp Tyr Ser Pro Ser Ala Ser Gly Pro Leu Gly
        435                 440                 445

Lys Leu Asp Ile Ser Glu Ile Lys Glu Glu Val Leu Gln Ser Thr Thr
    450                 455                 460

Gly Val Ser His Tyr Ala Thr Asp Ser Trp Asp Gly Val Val Glu Asp
465                 470                 475                 480

Lys Gln Thr Gln Glu Ser Val Thr Gln Ile Glu Gln Ile Glu Val Gly
                485                 490                 495

Pro Leu Val Thr Ser Met Glu Ile Leu Lys His Ile Pro Ser Lys Glu
            500                 505                 510

Phe Pro Val Thr Glu Thr Pro Leu Val Thr Ala Arg Met Ile Leu Glu
        515                 520                 525

Ser Lys Thr Glu Lys Lys Met Val Ser Thr Val Ser Glu Leu Val Thr
    530                 535                 540

Thr Gly His Tyr Gly Phe Thr Leu Gly Glu Glu Asp Asp Glu Asp Arg
545                 550                 555                 560

Thr Leu Thr Val Gly Ser Asp Glu Ser Thr Leu Ile Phe Asp Gln Ile
                565                 570                 575

Pro Glu Val Ile Thr Val Ser Lys Thr Ser Glu Asp Thr Ile His Thr
            580                 585                 590

-continued

His Leu Glu Asp Leu Glu Ser Val Ser Ala Ser Thr Thr Val Ser Pro
595                     600                 605

Leu Ile Met Pro Asp Asn Asn Gly Ser Ser Met Asp Asp Trp Glu Glu
610                     615                 620

Arg Gln Thr Ser Gly Arg Ile Thr Glu Glu Phe Leu Gly Lys Tyr Leu
625                 630                     635                 640

Ser Thr Thr Pro Phe Pro Ser Gln His Arg Thr Glu Ile Glu Leu Phe
                645                 650                 655

Pro Tyr Ser Gly Asp Lys Ile Leu Val Glu Gly Ile Ser Thr Val Ile
                660                 665                 670

Tyr Pro Ser Leu Gln Thr Glu Met Thr His Arg Arg Glu Arg Thr Glu
675                     680                 685

Thr Leu Ile Pro Glu Met Arg Thr Asp Thr Tyr Thr Asp Glu Ile Gln
690                     695                 700

Glu Glu Ile Thr Lys Ser Pro Phe Met Gly Lys Thr Glu Glu Glu Val
705                 710                     715                 720

Phe Ser Gly Met Lys Leu Ser Thr Ser Leu Ser Glu Pro Ile His Val
                725                 730                 735

Thr Glu Ser Ser Val Glu Met Thr Lys Ser Phe Asp Phe Pro Thr Leu
                740                 745                 750

Ile Thr Lys Leu Ser Ala Glu Pro Thr Glu Val Arg Asp Met Glu Glu
                755                 760                 765

Asp Phe Thr Ala Thr Pro Gly Thr Thr Lys Tyr Asp Glu Asn Ile Thr
770                 775                     780

Thr Val Leu Leu Ala His Gly Thr Leu Ser Val Glu Ala Ala Thr Val
785                     790                 795                 800

Ser Lys Trp Ser Trp Asp Glu Asp Asn Thr Thr Ser Lys Pro Leu Glu
                805                 810                 815

Ser Thr Glu Pro Ser Ala Ser Ser Lys Leu Pro Pro Ala Leu Leu Thr
                820                 825                 830

Thr Val Gly Met Asn Gly Lys Asp Lys Asp Ile Pro Ser Phe Thr Glu
                835                 840                 845

Asp Gly Ala Asp Glu Phe Thr Leu Ile Pro Asp Ser Thr Gln Lys Gln
850                     855                 860

Leu Glu Glu Val Thr Asp Glu Asp Ile Ala Ala His Gly Lys Phe Thr
865                     870                 875                 880

Ile Arg Phe Gln Pro Thr Thr Ser Thr Gly Ile Ala Glu Lys Ser Thr
                885                 890                 895

Leu Arg Asp Ser Thr Thr Glu Glu Lys Val Pro Pro Ile Thr Ser Thr
                900                 905                 910

Glu Gly Gln Val Tyr Ala Thr Met Glu Gly Ser Ala Leu Gly Glu Val
                915                 920                 925

Glu Asp Val Asp Leu Ser Lys Pro Val Ser Thr Val Pro Gln Phe Ala
930                     935                 940

His Thr Ser Glu Val Glu Gly Leu Ala Phe Val Ser Tyr Ser Ser Thr
945                     950                 955                 960

Gln Glu Pro Thr Thr Tyr Val Asp Ser Ser His Thr Ile Pro Leu Ser
                965                 970                 975

Val Ile Pro Lys Thr Asp Trp Gly Val Leu Val Pro Ser Val Pro Ser
                980                 985                 990

Glu Asp Glu Val Leu Gly Glu Pro Ser Gln Asp Ile Leu Val Ile Asp
995                     1000                1005

Gln Thr Arg Leu Glu Ala Thr Ile Ser Pro Glu Thr Met Arg Thr

-continued

```
            1010                1015                1020
Thr Lys Ile Thr Glu Gly Thr Thr Gln Glu Glu Phe Pro Trp Lys
        1025                1030                1035
Glu Gln Thr Ala Glu Lys Pro Val Pro Ala Leu Ser Ser Thr Ala
        1040                1045                1050
Trp Thr Pro Lys Glu Ala Val Thr Pro Leu Asp Glu Gln Glu Gly
        1055                1060                1065
Asp Gly Ser Ala Tyr Thr Val Ser Glu Asp Glu Leu Leu Thr Gly
        1070                1075                1080
Ser Glu Arg Val Pro Val Leu Glu Thr Thr Pro Val Gly Lys Ile
        1085                1090                1095
Asp His Ser Val Ser Tyr Pro Pro Gly Ala Val Thr Glu His Lys
        1100                1105                1110
Val Lys Thr Asp Glu Val Val Thr Leu Thr Pro Arg Ile Gly Pro
        1115                1120                1125
Lys Val Ser Leu Ser Pro Gly Pro Glu Gln Lys Tyr Glu Thr Glu
        1130                1135                1140
Gly Ser Ser Thr Thr Gly Phe Thr Ser Ser Leu Ser Pro Phe Ser
        1145                1150                1155
Thr His Ile Thr Gln Leu Met Glu Glu Thr Thr Thr Glu Lys Thr
        1160                1165                1170
Ser Leu Glu Asp Ile Asp Leu Gly Ser Gly Leu Phe Glu Lys Pro
        1175                1180                1185
Lys Ala Thr Glu Leu Ile Glu Phe Ser Thr Ile Lys Val Thr Val
        1190                1195                1200
Pro Ser Asp Ile Thr Thr Ala Phe Ser Ser Val Asp Arg Leu His
        1205                1210                1215
Thr Thr Ser Ala Phe Lys Pro Ser Ser Ala Ile Thr Lys Lys Pro
        1220                1225                1230
Pro Leu Ile Asp Arg Glu Pro Gly Glu Glu Thr Thr Ser Asp Met
        1235                1240                1245
Val Ile Ile Gly Glu Ser Thr Ser His Val Pro Pro Thr Thr Leu
        1250                1255                1260
Glu Asp Ile Val Ala Lys Glu Thr Glu Thr Asp Ile Asp Arg Glu
        1265                1270                1275
Tyr Phe Thr Thr Ser Ser Pro Pro Ala Thr Gln Pro Thr Arg Pro
        1280                1285                1290
Pro Thr Val Glu Asp Lys Glu Ala Phe Gly Pro Gln Ala Leu Ser
        1295                1300                1305
Thr Pro Gln Pro Pro Ala Ser Thr Lys Phe His Pro Asp Ile Asn
        1310                1315                1320
Val Tyr Ile Ile Glu Val Arg Glu Asn Lys Thr Gly Arg Met Ser
        1325                1330                1335
Asp Leu Ser Val Ile Gly His Pro Ile Asp Ser Glu Ser Lys Glu
        1340                1345                1350
Asp Glu Pro Cys Ser Glu Glu Thr Asp Pro Val His Asp Leu Met
        1355                1360                1365
Ala Glu Ile Leu Pro Glu Phe Pro Asp Ile Ile Glu Ile Asp Leu
        1370                1375                1380
Tyr His Ser Glu Glu Asn Glu Glu Glu Glu Glu Cys Ala Asn
        1385                1390                1395
Ala Thr Asp Val Thr Thr Thr Pro Ser Val Gln Tyr Ile Asn Gly
        1400                1405                1410
```

```
Lys His Leu Val Thr Thr Val Pro Lys Asp Pro Glu Ala Ala Glu
1415                1420                1425

Ala Arg Arg Gly Gln Phe Glu Ser Val Ala Pro Ser Gln Asn Phe
1430                1435                1440

Ser Asp Ser Ser Glu Ser Asp Thr His Pro Phe Val Ile Ala Lys
1445                1450                1455

Thr Glu Leu Ser Thr Ala Val Gln Pro Asn Glu Ser Thr Glu Thr
1460                1465                1470

Thr Glu Ser Leu Glu Val Thr Trp Lys Pro Glu Thr Tyr Pro Glu
1475                1480                1485

Thr Ser Glu His Phe Ser Gly Gly Glu Pro Asp Val Phe Pro Thr
1490                1495                1500

Val Pro Phe His Glu Glu Phe Glu Ser Gly Thr Ala Lys Lys Gly
1505                1510                1515

Ala Glu Ser Val Thr Glu Arg Asp Thr Glu Val Gly His Gln Ala
1520                1525                1530

His Glu His Thr Glu Pro Val Ser Leu Phe Pro Glu Glu Ser Ser
1535                1540                1545

Gly Glu Ile Ala Ile Asp Gln Glu Ser Gln Lys Ile Ala Phe Ala
1550                1555                1560

Arg Ala Thr Glu Val Thr Phe Gly Glu Glu Val Glu Lys Ser Thr
1565                1570                1575

Ser Val Thr Tyr Thr Pro Thr Ile Val Pro Ser Ser Ala Ser Ala
1580                1585                1590

Tyr Val Ser Glu Glu Glu Ala Val Thr Leu Ile Gly Asn Pro Trp
1595                1600                1605

Pro Asp Asp Leu Leu Ser Thr Lys Glu Ser Trp Val Glu Ala Thr
1610                1615                1620

Pro Arg Gln Val Val Glu Leu Ser Gly Ser Ser Ser Ile Pro Ile
1625                1630                1635

Thr Glu Gly Ser Gly Glu Ala Glu Glu Asp Glu Asp Thr Met Phe
1640                1645                1650

Thr Met Val Thr Asp Leu Ser Gln Arg Asn Thr Thr Asp Thr Leu
1655                1660                1665

Ile Thr Leu Asp Thr Ser Arg Ile Ile Thr Glu Ser Phe Phe Glu
1670                1675                1680

Val Pro Ala Thr Thr Ile Tyr Pro Val Ser Glu Gln Pro Ser Ala
1685                1690                1695

Lys Val Val Pro Thr Lys Phe Val Ser Glu Thr Asp Thr Ser Glu
1700                1705                1710

Trp Ile Ser Ser Thr Thr Val Glu Glu Lys Lys Arg Lys Glu Glu
1715                1720                1725

Glu Gly Thr Thr Gly Thr Ala Ser Thr Phe Glu Val Tyr Ser Ser
1730                1735                1740

Thr Gln Arg Ser Asp Gln Leu Ile Leu Pro Phe Glu Leu Glu Ser
1745                1750                1755

Pro Asn Val Ala Thr Ser Ser Asp Ser Gly Thr Arg Lys Ser Phe
1760                1765                1770

Met Ser Leu Thr Thr Pro Thr Gln Ser Glu Arg Glu Met Thr Asp
1775                1780                1785

Ser Thr Pro Val Phe Thr Glu Thr Asn Thr Leu Glu Asn Leu Gly
1790                1795                1800
```

```
Ala Gln Thr Thr Glu His Ser Ser Ile His Gln Pro Gly Val Gln
1805                1810                1815
Glu Gly Leu Thr Thr Leu Pro Arg Ser Pro Ala Ser Val Phe Met
1820                1825                1830
Glu Gln Gly Ser Gly Glu Ala Ala Ala Asp Pro Glu Thr Thr Thr
1835                1840                1845
Val Ser Ser Phe Ser Leu Asn Val Glu Tyr Ala Ile Gln Ala Glu
1850                1855                1860
Lys Glu Val Ala Gly Thr Leu Ser Pro His Val Glu Thr Thr Phe
1865                1870                1875
Ser Thr Glu Pro Thr Gly Leu Val Leu Ser Thr Val Met Asp Arg
1880                1885                1890
Val Val Ala Glu Asn Ile Thr Gln Thr Ser Arg Glu Ile Val Ile
1895                1900                1905
Ser Glu Arg Leu Gly Glu Pro Asn Tyr Gly Ala Glu Ile Arg Gly
1910                1915                1920
Phe Ser Thr Gly Phe Pro Leu Glu Glu Asp Phe Ser Gly Asp Phe
1925                1930                1935
Arg Glu Tyr Ser Thr Val Ser His Pro Ile Ala Lys Glu Glu Thr
1940                1945                1950
Val Met Met Glu Gly Ser Gly Asp Ala Ala Phe Arg Asp Thr Gln
1955                1960                1965
Thr Ser Pro Ser Thr Val Pro Thr Ser Val His Ile Ser His Ile
1970                1975                1980
Ser Asp Ser Glu Gly Pro Ser Ser Thr Met Val Ser Thr Ser Ala
1985                1990                1995
Phe Pro Trp Glu Glu Phe Thr Ser Ser Ala Glu Gly Ser Gly Glu
2000                2005                2010
Gln Leu Val Thr Val Ser Ser Ser Val Val Pro Val Leu Pro Ser
2015                2020                2025
Ala Val Gln Lys Phe Ser Gly Thr Ala Ser Ser Ile Ile Asp Glu
2030                2035                2040
Gly Leu Gly Glu Val Gly Thr Val Asn Glu Ile Asp Arg Arg Ser
2045                2050                2055
Thr Ile Leu Pro Thr Ala Glu Val Glu Gly Thr Lys Ala Pro Val
2060                2065                2070
Glu Lys Glu Glu Val Lys Val Ser Gly Thr Val Ser Thr Asn Phe
2075                2080                2085
Pro Gln Thr Ile Glu Pro Ala Lys Leu Trp Ser Arg Gln Glu Val
2090                2095                2100
Asn Pro Val Arg Gln Glu Ile Glu Ser Glu Thr Thr Ser Glu Glu
2105                2110                2115
Gln Ile Gln Glu Glu Lys Ser Phe Glu Ser Pro Gln Asn Ser Pro
2120                2125                2130
Ala Thr Glu Gln Thr Ile Phe Asp Ser Gln Thr Phe Thr Glu Thr
2135                2140                2145
Glu Leu Lys Thr Thr Asp Tyr Ser Val Leu Thr Thr Lys Lys Thr
2150                2155                2160
Tyr Ser Asp Asp Lys Glu Met Lys Glu Glu Asp Thr Ser Leu Val
2165                2170                2175
Asn Met Ser Thr Pro Asp Pro Asp Ala Asn Gly Leu Glu Ser Tyr
2180                2185                2190
Thr Thr Leu Pro Glu Ala Thr Glu Lys Ser His Phe Phe Leu Ala
```

-continued

```
            2195                2200                 2205

Thr Ala Leu Val Thr Glu Ser Ile Pro Ala Glu His Val Val Thr
            2210                2215                2220

Asp Ser Pro Ile Lys Lys Glu Glu Ser Thr Lys His Phe Pro Lys
            2225                2230                2235

Gly Met Arg Pro Thr Ile Gln Glu Ser Asp Thr Glu Leu Leu Phe
            2240                2245                2250

Ser Gly Leu Gly Ser Gly Glu Glu Val Leu Pro Thr Leu Pro Thr
            2255                2260                2265

Glu Ser Val Asn Phe Thr Glu Val Glu Gln Ile Asn Asn Thr Leu
            2270                2275                2280

Tyr Pro His Thr Ser Gln Val Glu Ser Thr Ser Ser Asp Lys Ile
            2285                2290                2295

Glu Asp Phe Asn Arg Met Glu Asn Val Ala Lys Glu Val Gly Pro
            2300                2305                2310

Leu Val Ser Gln Thr Asp Ile Phe Glu Gly Ser Gly Ser Val Thr
            2315                2320                2325

Ser Thr Thr Leu Ile Glu Ile Leu Ser Asp Thr Gly Ala Glu Gly
            2330                2335                2340

Pro Thr Val Ala Pro Leu Pro Phe Ser Thr Asp Ile Gly His Pro
            2345                2350                2355

Gln Asn Gln Thr Val Arg Trp Ala Glu Glu Ile Gln Thr Ser Arg
            2360                2365                2370

Pro Gln Thr Ile Thr Glu Gln Asp Ser Asn Lys Asn Ser Ser Thr
            2375                2380                2385

Ala Glu Ile Asn Glu Thr Thr Thr Ser Ser Thr Asp Phe Leu Ala
            2390                2395                2400

Arg Ala Tyr Gly Phe Glu Met Ala Lys Glu Phe Val Thr Ser Ala
            2405                2410                2415

Pro Lys Pro Ser Asp Leu Tyr Tyr Glu Pro Ser Gly Glu Gly Ser
            2420                2425                2430

Gly Glu Val Asp Ile Val Asp Ser Phe His Thr Ser Ala Thr Thr
            2435                2440                2445

Gln Ala Thr Arg Gln Glu Ser Ser Thr Thr Phe Val Ser Asp Gly
            2450                2455                2460

Ser Leu Glu Lys His Pro Glu Val Pro Ser Ala Lys Ala Val Thr
            2465                2470                2475

Ala Asp Gly Phe Pro Thr Val Ser Val Met Leu Pro Leu His Ser
            2480                2485                2490

Glu Gln Asn Lys Ser Ser Pro Asp Pro Thr Ser Thr Leu Ser Asn
            2495                2500                2505

Thr Val Ser Tyr Glu Arg Ser Thr Asp Gly Ser Phe Gln Asp Arg
            2510                2515                2520

Phe Arg Glu Phe Glu Asp Ser Thr Leu Lys Pro Asn Arg Lys Lys
            2525                2530                2535

Pro Thr Glu Asn Ile Ile Ile Asp Leu Asp Lys Glu Asp Lys Asp
            2540                2545                2550

Leu Ile Leu Thr Ile Thr Glu Ser Thr Ile Leu Glu Ile Leu Pro
            2555                2560                2565

Glu Leu Thr Ser Asp Lys Asn Thr Ile Ile Asp Ile Asp His Thr
            2570                2575                2580

Lys Pro Val Tyr Glu Asp Ile Leu Gly Met Gln Thr Asp Ile Asp
            2585                2590                2595
```

```
Thr Glu Val Pro Ser Glu Pro His Asp Ser Asn Asp Glu Ser Asn
    2600            2605            2610

Asp Asp Ser Thr Gln Val Gln Glu Ile Tyr Glu Ala Ala Val Asn
    2615            2620            2625

Leu Ser Leu Thr Glu Glu Thr Phe Glu Gly Ser Ala Asp Val Leu
    2630            2635            2640

Ala Ser Tyr Thr Gln Ala Thr His Asp Glu Ser Met Thr Tyr Glu
    2645            2650            2655

Asp Arg Ser Gln Leu Asp His Met Gly Phe His Phe Thr Thr Gly
    2660            2665            2670

Ile Pro Ala Pro Ser Thr Glu Thr Glu Leu Asp Val Leu Leu Pro
    2675            2680            2685

Thr Ala Thr Ser Leu Pro Ile Pro Arg Lys Ser Ala Thr Val Ile
    2690            2695            2700

Pro Glu Ile Glu Gly Ile Lys Ala Glu Ala Lys Ala Leu Asp Asp
    2705            2710            2715

Met Phe Glu Ser Ser Thr Leu Ser Asp Gly Gln Ala Ile Ala Asp
    2720            2725            2730

Gln Ser Glu Ile Ile Pro Thr Leu Gly Gln Phe Glu Arg Thr Gln
    2735            2740            2745

Glu Glu Tyr Glu Asp Lys Lys His Ala Gly Pro Ser Phe Gln Pro
    2750            2755            2760

Glu Phe Ser Ser Gly Ala Glu Glu Ala Leu Val Asp His Thr Pro
    2765            2770            2775

Tyr Leu Ser Ile Ala Thr Thr His Leu Met Asp Gln Ser Val Thr
    2780            2785            2790

Glu Val Pro Asp Val Met Glu Gly Ser Asn Pro Tyr Tyr Thr
    2795            2800            2805

Asp Thr Thr Leu Ala Val Ser Thr Phe Ala Lys Leu Ser Ser Gln
    2810            2815            2820

Thr Pro Ser Ser Pro Leu Thr Ile Tyr Ser Gly Ser Glu Ala Ser
    2825            2830            2835

Gly His Thr Glu Ile Pro Gln Pro Ser Ala Leu Pro Gly Ile Asp
    2840            2845            2850

Val Gly Ser Ser Val Met Ser Pro Gln Asp Ser Phe Lys Glu Ile
    2855            2860            2865

His Val Asn Ile Glu Ala Thr Phe Lys Pro Ser Ser Glu Glu Tyr
    2870            2875            2880

Leu His Ile Thr Glu Pro Pro Ser Leu Ser Pro Asp Thr Lys Leu
    2885            2890            2895

Glu Pro Ser Glu Asp Asp Gly Lys Pro Glu Leu Leu Glu Glu Met
    2900            2905            2910

Glu Ala Ser Pro Thr Glu Leu Ile Ala Val Glu Gly Thr Glu Ile
    2915            2920            2925

Leu Gln Asp Phe Gln Asn Lys Thr Asp Gly Gln Val Ser Gly Glu
    2930            2935            2940

Ala Ile Lys Met Phe Pro Thr Ile Lys Thr Pro Glu Ala Gly Thr
    2945            2950            2955

Val Ile Thr Thr Ala Asp Glu Ile Glu Leu Glu Gly Ala Thr Gln
    2960            2965            2970

Trp Pro His Ser Thr Ser Ala Ser Ala Thr Tyr Gly Val Glu Ala
    2975            2980            2985
```

```
Gly Val Val Pro Trp Leu Ser Pro Gln Thr Ser Glu Arg Pro Thr
2990            2995                3000

Leu Ser Ser Ser Pro Glu Ile Asn Pro Glu Thr Gln Ala Ala Leu
3005            3010                3015

Ile Arg Gly Gln Asp Ser Thr Ile Ala Ala Ser Glu Gln Gln Val
3020            3025                3030

Ala Ala Arg Ile Leu Asp Ser Asn Asp Gln Ala Thr Val Asn Pro
3035            3040                3045

Val Glu Phe Asn Thr Glu Val Ala Thr Pro Pro Phe Ser Leu Leu
3050            3055                3060

Glu Thr Ser Asn Glu Thr Asp Phe Leu Ile Gly Ile Asn Glu Glu
3065            3070                3075

Ser Val Glu Gly Thr Ala Ile Tyr Leu Pro Gly Pro Asp Arg Cys
3080            3085                3090

Lys Met Asn Pro Cys Leu Asn Gly Gly Thr Cys Tyr Pro Thr Glu
3095            3100                3105

Thr Ser Tyr Val Cys Thr Cys Val Pro Gly Tyr Ser Gly Asp Gln
3110            3115                3120

Cys Glu Leu Asp Phe Asp Glu Cys His Ser Asn Pro Cys Arg Asn
3125            3130                3135

Gly Ala Thr Cys Val Asp Gly Phe Asn Thr Phe Arg Cys Leu Cys
3140            3145                3150

Leu Pro Ser Tyr Val Gly Ala Leu Cys Glu Gln Asp Thr Glu Thr
3155            3160                3165

Cys Asp Tyr Gly Trp His Lys Phe Gln Gly Gln Cys Tyr Lys Tyr
3170            3175                3180

Phe Ala His Arg Arg Thr Trp Asp Ala Ala Glu Arg Glu Cys Arg
3185            3190                3195

Leu Gln Gly Ala His Leu Thr Ser Ile Leu Ser His Glu Glu Gln
3200            3205                3210

Met Phe Val Asn Arg Val Gly His Asp Tyr Gln Trp Ile Gly Leu
3215            3220                3225

Asn Asp Lys Met Phe Glu His Asp Phe Arg Trp Thr Asp Gly Ser
3230            3235                3240

Thr Leu Gln Tyr Glu Asn Trp Arg Pro Asn Gln Pro Asp Ser Phe
3245            3250                3255

Phe Ser Ala Gly Glu Asp Cys Val Val Ile Ile Trp His Glu Asn
3260            3265                3270

Gly Gln Trp Asn Asp Val Pro Cys Asn Tyr His Leu Thr Tyr Thr
3275            3280                3285

Cys Lys Lys Gly Thr Val Ala Cys Gly Gln Pro Pro Val Val Glu
3290            3295                3300

Asn Ala Lys Thr Phe Gly Lys Met Lys Pro Arg Tyr Glu Ile Asn
3305            3310                3315

Ser Leu Ile Arg Tyr His Cys Lys Asp Gly Phe Ile Gln Arg His
3320            3325                3330

Leu Pro Thr Ile Arg Cys Leu Gly Asn Gly Arg Trp Ala Ile Pro
3335            3340                3345

Lys Ile Thr Cys Met Asn Pro Ser Ala Tyr Gln Arg Thr Tyr Ser
3350            3355                3360

Met Lys Tyr Phe Lys Asn Ser Ser Ser Ala Lys Asp Asn Ser Ile
3365            3370                3375

Asn Thr Ser Lys His Asp His Arg Trp Ser Arg Arg Trp Gln Glu
```

Ser Arg Arg
    3395

<210> SEQ ID NO 20
<211> LENGTH: 339
<212> TYPE: PRT
<213> ORGANISM: Homo sapiens

<400> SEQUENCE: 20

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
    210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
    290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp

<210> SEQ ID NO 21
<211> LENGTH: 480
<212> TYPE: PRT
<213> ORGANISM: Homo sapiens

<400> SEQUENCE: 21

Met Gln Ile Pro Arg Ala Ala Leu Leu Pro Leu Leu Leu Leu Leu Leu
1               5                   10                  15

Ala Ala Pro Ala Ser Ala Gln Leu Ser Arg Ala Gly Arg Ser Ala Pro
            20                  25                  30

Leu Ala Ala Gly Cys Pro Asp Arg Cys Glu Pro Ala Arg Cys Pro Pro
        35                  40                  45

Gln Pro Glu His Cys Glu Gly Gly Arg Ala Arg Asp Ala Cys Gly Cys
    50                  55                  60

Cys Glu Val Cys Gly Ala Pro Glu Gly Ala Ala Cys Gly Leu Gln Glu
65                  70                  75                  80

Gly Pro Cys Gly Glu Gly Leu Gln Cys Val Val Pro Phe Gly Val Pro
                85                  90                  95

Ala Ser Ala Thr Val Arg Arg Arg Ala Gln Ala Gly Leu Cys Val Cys
            100                 105                 110

Ala Ser Ser Glu Pro Val Cys Gly Ser Asp Ala Asn Thr Tyr Ala Asn
        115                 120                 125

Leu Cys Gln Leu Arg Ala Ala Ser Arg Arg Ser Glu Arg Leu His Arg
    130                 135                 140

Pro Pro Val Ile Val Leu Gln Arg Gly Ala Cys Gly Gln Gly Gln Glu
145                 150                 155                 160

Asp Pro Asn Ser Leu Arg His Lys Tyr Asn Phe Ile Ala Asp Val Val
                165                 170                 175

Glu Lys Ile Ala Pro Ala Val Val His Ile Glu Leu Phe Arg Lys Leu
            180                 185                 190

Pro Phe Ser Lys Arg Glu Val Pro Val Ala Ser Gly Ser Gly Phe Ile
        195                 200                 205

Val Ser Glu Asp Gly Leu Ile Val Thr Asn Ala His Val Val Thr Asn
    210                 215                 220

Lys His Arg Val Lys Val Glu Leu Lys Asn Gly Ala Thr Tyr Glu Ala
225                 230                 235                 240

Lys Ile Lys Asp Val Asp Glu Lys Ala Asp Ile Ala Leu Ile Lys Ile
                245                 250                 255

Asp His Gln Gly Lys Leu Pro Val Leu Leu Leu Gly Arg Ser Ser Glu
            260                 265                 270

Leu Arg Pro Gly Glu Phe Val Val Ala Ile Gly Ser Pro Phe Ser Leu
        275                 280                 285

Gln Asn Thr Val Thr Thr Gly Ile Val Ser Thr Thr Gln Arg Gly Gly
    290                 295                 300

Lys Glu Leu Gly Leu Arg Asn Ser Asp Met Asp Tyr Ile Gln Thr Asp
305                 310                 315                 320

Ala Ile Ile Asn Tyr Gly Asn Ser Gly Gly Pro Leu Val Asn Leu Asp
                325                 330                 335

Gly Glu Val Ile Gly Ile Asn Thr Leu Lys Val Thr Ala Gly Ile Ser
            340                 345                 350

Phe Ala Ile Pro Ser Asp Lys Ile Lys Lys Phe Leu Thr Glu Ser His
        355                 360                 365

Asp Arg Gln Ala Lys Gly Lys Ala Ile Thr Lys Lys Lys Tyr Ile Gly
    370                 375                 380

```
Ile Arg Met Met Ser Leu Thr Ser Ser Lys Ala Lys Glu Leu Lys Asp
385                 390                 395                 400

Arg His Arg Asp Phe Pro Asp Val Ile Ser Gly Ala Tyr Ile Ile Glu
            405                 410                 415

Val Ile Pro Asp Thr Pro Ala Glu Ala Gly Gly Leu Lys Glu Asn Asp
        420                 425                 430

Val Ile Ile Ser Ile Asn Gly Gln Ser Val Val Ser Ala Asn Asp Val
            435                 440                 445

Ser Asp Val Ile Lys Arg Glu Ser Thr Leu Asn Met Val Val Arg Arg
450                 455                 460

Gly Asn Glu Asp Ile Met Ile Thr Val Ile Pro Glu Glu Ile Asp Pro
465                 470                 475                 480
```

<210> SEQ ID NO 22
<211> LENGTH: 291
<212> TYPE: PRT
<213> ORGANISM: Homo sapiens

<400> SEQUENCE: 22

```
Met Gln Arg Ala Arg Pro Thr Leu Trp Ala Ala Ala Leu Thr Leu Leu
1               5                   10                  15

Val Leu Leu Arg Gly Pro Pro Val Ala Arg Ala Gly Ala Ser Ser Ala
            20                  25                  30

Gly Leu Gly Pro Val Val Arg Cys Glu Pro Cys Asp Ala Arg Ala Leu
        35                  40                  45

Ala Gln Cys Ala Pro Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
        115                 120                 125

Pro Ala Pro Pro Ala Pro Gly Asn Ala Ser Glu Ser Glu Glu Asp Arg
    130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Ile Lys
                165                 170                 175

Lys Gly His Ala Lys Asp Ser Gln Arg Tyr Lys Val Asp Tyr Glu Ser
            180                 185                 190

Gln Ser Thr Asp Thr Gln Asn Phe Ser Ser Glu Ser Lys Arg Glu Thr
        195                 200                 205

Glu Tyr Gly Pro Cys Arg Arg Glu Met Glu Asp Thr Leu Asn His Leu
    210                 215                 220

Lys Phe Leu Asn Val Leu Ser Pro Arg Gly Val His Ile Pro Asn Cys
225                 230                 235                 240

Asp Lys Lys Gly Phe Tyr Lys Lys Lys Gln Cys Arg Pro Ser Lys Gly
                245                 250                 255

Arg Lys Arg Gly Phe Cys Trp Cys Val Asp Lys Tyr Gly Gln Pro Leu
            260                 265                 270

Pro Gly Tyr Thr Thr Lys Gly Lys Glu Asp Val His Cys Tyr Ser Met
        275                 280                 285
```

Gln Ser Lys
    290

<210> SEQ ID NO 23
<211> LENGTH: 349
<212> TYPE: PRT
<213> ORGANISM: Homo sapiens

<400> SEQUENCE: 23

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys His Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345

-continued

```
<210> SEQ ID NO 24
<211> LENGTH: 1134
<212> TYPE: PRT
<213> ORGANISM: Homo sapiens

<400> SEQUENCE: 24
```

Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110

Arg Gly Ile Leu Ser Gly Thr Ser Asp Leu Leu Leu Thr Phe Asp Glu
        115                 120                 125

Ala Glu Val Arg Lys Ile Ile Arg Val Cys Lys Gly Ile Leu Glu Tyr
    130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
            180                 185                 190

Asn Ser Met Asn Thr Val Lys Glu Leu Leu Pro Val Leu Ile Ser Ala
        195                 200                 205

Met Lys Ile Phe Val Thr Thr Lys Asn Ser Lys Asn Gln Gly Ile Glu
    210                 215                 220

Glu Ala Leu Lys Asn Arg Asn Phe Thr Val Glu Lys Met Ser Ala Glu
225                 230                 235                 240

Ile Asn Glu Ile Ile Arg Val Leu Gln Leu Thr Ser Trp Asp Glu Asp
                245                 250                 255

Ala Trp Ala Ser Lys Asp Thr Glu Ala Met Lys Arg Ala Leu Ala Ser
            260                 265                 270

Ile Asp Ser Lys Leu Asn Gln Ala Lys Gly Trp Leu Arg Asp Pro Ser
        275                 280                 285

Ala Ser Pro Gly Asp Ala Gly Glu Gln Ala Ile Arg Gln Ile Leu Asp
    290                 295                 300

Glu Ala Gly Lys Val Gly Glu Leu Cys Ala Gly Lys Glu Arg Arg Glu
305                 310                 315                 320

Ile Leu Gly Thr Cys Lys Met Leu Gly Gln Met Thr Asp Gln Val Ala
                325                 330                 335

Asp Leu Arg Ala Arg Gly Gln Gly Ser Ser Pro Val Ala Met Gln Lys
            340                 345                 350

Ala Gln Gln Val Ser Gln Gly Leu Asp Val Leu Thr Ala Lys Val Glu
        355                 360                 365

Asn Ala Ala Arg Lys Leu Glu Ala Met Thr Asn Ser Lys Gln Ser Ile
    370                 375                 380

```
Ala Lys Lys Ile Asp Ala Gln Asn Trp Leu Ala Asp Pro Asn Gly
385                 390                 395                 400

Gly Pro Glu Gly Glu Glu Gln Ile Arg Gly Ala Leu Ala Glu Ala Arg
            405                 410                 415

Lys Ile Ala Glu Leu Cys Asp Asp Pro Lys Glu Arg Asp Asp Ile Leu
            420                 425                 430

Arg Ser Leu Gly Glu Ile Ser Ala Leu Thr Ser Lys Leu Ala Asp Leu
            435                 440                 445

Arg Arg Gln Gly Lys Gly Asp Ser Pro Glu Ala Arg Ala Leu Ala Lys
450                 455                 460

Gln Val Ala Thr Ala Leu Gln Asn Leu Gln Thr Lys Thr Asn Arg Ala
465                 470                 475                 480

Val Ala Asn Ser Arg Pro Ala Lys Ala Ala Val His Leu Glu Gly Lys
            485                 490                 495

Ile Glu Gln Ala Gln Arg Trp Ile Asp Asn Pro Thr Val Asp Asp Arg
            500                 505                 510

Gly Val Gly Gln Ala Ala Ile Arg Gly Leu Val Ala Glu Gly His Arg
            515                 520                 525

Leu Ala Asn Val Met Met Gly Pro Tyr Arg Gln Asp Leu Leu Ala Lys
530                 535                 540

Cys Asp Arg Val Asp Gln Leu Thr Ala Gln Leu Ala Asp Leu Ala Ala
545                 550                 555                 560

Arg Gly Glu Gly Glu Ser Pro Gln Ala Arg Ala Leu Ala Ser Gln Leu
            565                 570                 575

Gln Asp Ser Leu Lys Asp Leu Lys Ala Arg Met Gln Glu Ala Met Thr
            580                 585                 590

Gln Glu Val Ser Asp Val Phe Ser Asp Thr Thr Pro Ile Lys Leu
            595                 600                 605

Leu Ala Val Ala Ala Thr Ala Pro Pro Asp Ala Pro Asn Arg Glu Glu
610                 615                 620

Val Phe Asp Glu Arg Ala Ala Asn Phe Glu Asn His Ser Gly Lys Leu
625                 630                 635                 640

Gly Ala Thr Ala Glu Lys Ala Ala Ala Val Gly Thr Ala Asn Lys Ser
            645                 650                 655

Thr Val Glu Gly Ile Gln Ala Ser Val Lys Thr Ala Arg Glu Leu Thr
            660                 665                 670

Pro Gln Val Val Ser Ala Ala Arg Ile Leu Leu Arg Asn Pro Gly Asn
            675                 680                 685

Gln Ala Ala Tyr Glu His Phe Glu Thr Met Lys Asn Gln Trp Ile Asp
            690                 695                 700

Asn Val Glu Lys Met Thr Gly Leu Val Asp Glu Ala Ile Asp Thr Lys
705                 710                 715                 720

Ser Leu Leu Asp Ala Ser Glu Glu Ala Ile Lys Lys Asp Leu Asp Lys
            725                 730                 735

Cys Lys Val Ala Met Ala Asn Ile Gln Pro Gln Met Leu Val Ala Gly
            740                 745                 750

Ala Thr Ser Ile Ala Arg Arg Ala Asn Arg Ile Leu Leu Val Ala Lys
            755                 760                 765

Arg Glu Val Glu Asn Ser Glu Asp Pro Lys Phe Arg Glu Ala Val Lys
            770                 775                 780

Ala Ala Ser Asp Glu Leu Ser Lys Thr Ile Ser Pro Met Val Met Asp
785                 790                 795                 800

Ala Lys Ala Val Ala Gly Asn Ile Ser Asp Pro Gly Leu Gln Lys Ser
```

```
                    805                 810                 815
Phe Leu Asp Ser Gly Tyr Arg Ile Leu Gly Ala Val Ala Lys Val Arg
            820                 825                 830
Glu Ala Phe Gln Pro Gln Pro Asp Phe Pro Pro Pro Pro Asp
        835                 840                 845
Leu Glu Gln Leu Arg Leu Thr Asp Glu Leu Ala Pro Pro Lys Pro Pro
    850                 855                 860
Leu Pro Glu Gly Glu Val Pro Pro Arg Pro Pro Pro Glu Glu
865                 870                 875                 880
Lys Asp Glu Glu Phe Pro Glu Gln Lys Ala Gly Glu Val Ile Asn Gln
                885                 890                 895
Pro Met Met Met Ala Ala Arg Gln Leu His Asp Glu Ala Arg Lys Trp
            900                 905                 910
Ser Ser Lys Pro Gly Ile Pro Ala Ala Glu Val Gly Ile Gly Val Val
        915                 920                 925
Ala Glu Ala Asp Ala Ala Asp Ala Ala Gly Phe Pro Val Pro Pro Asp
    930                 935                 940
Met Glu Asp Asp Tyr Glu Pro Glu Leu Leu Leu Met Pro Ser Asn Gln
945                 950                 955                 960
Pro Val Asn Gln Pro Ile Leu Ala Ala Ala Gln Ser Leu His Arg Glu
                965                 970                 975
Ala Thr Lys Trp Ser Ser Lys Gly Asn Asp Ile Ile Ala Ala Ala Lys
            980                 985                 990
Arg Met Ala Leu Leu Met Ala Glu Met Ser Arg Leu Val Arg Gly Gly
        995                 1000                1005
Ser Gly Thr Lys Arg Ala Leu Ile Gln Cys Ala Lys Asp Ile Ala
    1010                1015                1020
Lys Ala Ser Asp Glu Val Thr Arg Leu Ala Lys Glu Val Ala Lys
    1025                1030                1035
Gln Cys Thr Asp Lys Arg Ile Arg Thr Asn Leu Leu Gln Val Cys
    1040                1045                1050
Glu Arg Ile Pro Thr Ile Ser Thr Gln Leu Lys Ile Leu Ser Thr
    1055                1060                1065
Val Lys Ala Thr Met Leu Gly Arg Thr Asn Ile Ser Asp Glu Glu
    1070                1075                1080
Ser Glu Gln Ala Thr Glu Met Leu Val His Asn Ala Gln Asn Leu
    1085                1090                1095
Met Gln Ser Val Lys Glu Thr Val Arg Glu Ala Glu Ala Ala Ser
    1100                1105                1110
Ile Lys Ile Arg Thr Asp Ala Gly Phe Thr Leu Arg Trp Val Arg
    1115                1120                1125
Lys Thr Pro Trp Tyr Gln
    1130

<210> SEQ ID NO 25
<211> LENGTH: 5890
<212> TYPE: PRT
<213> ORGANISM: Homo sapiens

<400> SEQUENCE: 25

Met Glu Lys Glu Glu Thr Thr Arg Glu Leu Leu Leu Pro Asn Trp Gln
1               5                   10                  15
Gly Ser Gly Ser His Gly Leu Thr Ile Ala Gln Arg Asp Asp Gly Val
            20                  25                  30
```

-continued

```
Phe Val Gln Glu Val Thr Gln Asn Ser Pro Ala Ala Arg Thr Gly Val
             35                  40                  45

Val Lys Glu Gly Asp Gln Ile Val Gly Ala Thr Ile Tyr Phe Asp Asn
 50                  55                  60

Leu Gln Ser Gly Glu Val Thr Gln Leu Leu Asn Thr Met Gly His His
 65                  70                  75                  80

Thr Val Gly Leu Lys Leu His Arg Lys Gly Asp Arg Ser Pro Glu Pro
                 85                  90                  95

Gly Gln Thr Trp Thr Arg Glu Val Phe Ser Ser Cys Ser Ser Glu Val
                100                 105                 110

Val Leu Ser Gly Asp Asp Glu Glu Tyr Gln Arg Ile Tyr Thr Thr Lys
                115                 120                 125

Ile Lys Pro Arg Leu Lys Ser Glu Asp Gly Val Glu Gly Asp Leu Gly
130                 135                 140

Glu Thr Gln Ser Arg Thr Ile Thr Val Thr Arg Arg Val Thr Ala Tyr
145                 150                 155                 160

Thr Val Asp Val Thr Gly Arg Glu Gly Ala Lys Asp Ile Asp Ile Ser
                165                 170                 175

Ser Pro Glu Phe Lys Ile Lys Ile Pro Arg His Glu Leu Thr Glu Ile
                180                 185                 190

Ser Asn Val Asp Val Glu Thr Gln Ser Gly Lys Thr Val Ile Arg Leu
                195                 200                 205

Pro Ser Gly Ser Gly Ala Ala Ser Pro Thr Gly Ser Ala Val Asp Ile
                210                 215                 220

Arg Ala Gly Ala Ile Ser Ala Ser Gly Pro Glu Leu Gln Gly Ala Gly
225                 230                 235                 240

His Ser Lys Leu Gln Val Thr Met Pro Gly Ile Lys Val Gly Gly Ser
                245                 250                 255

Gly Val Asn Val Asn Ala Lys Gly Leu Asp Leu Gly Gly Arg Gly Gly
                260                 265                 270

Val Gln Val Pro Ala Val Asp Ile Ser Ser Ser Leu Gly Gly Arg Ala
                275                 280                 285

Val Glu Val Gln Gly Pro Ser Leu Glu Ser Gly Asp His Gly Lys Ile
                290                 295                 300

Lys Phe Pro Thr Met Lys Val Pro Lys Phe Gly Val Ser Thr Gly Arg
305                 310                 315                 320

Glu Gly Gln Thr Pro Lys Ala Gly Leu Arg Val Ser Ala Pro Glu Val
                325                 330                 335

Ser Val Gly His Lys Gly Gly Lys Pro Gly Leu Thr Ile Gln Ala Pro
                340                 345                 350

Gln Leu Glu Val Ser Val Pro Ser Ala Asn Ile Glu Gly Leu Glu Gly
                355                 360                 365

Lys Leu Lys Gly Pro Gln Ile Thr Gly Pro Ser Leu Glu Gly Asp Leu
370                 375                 380

Gly Leu Lys Gly Ala Lys Pro Gln Gly His Ile Gly Val Asp Ala Ser
385                 390                 395                 400

Ala Pro Gln Ile Gly Gly Ser Ile Thr Gly Pro Ser Val Glu Val Gln
                405                 410                 415

Ala Pro Asp Ile Asp Val Gln Gly Gly Ser Lys Leu Asn Val Pro
                420                 425                 430

Lys Met Lys Val Pro Lys Phe Ser Val Ser Gly Ala Lys Gly Glu Glu
                435                 440                 445

Thr Gly Ile Asp Val Thr Leu Pro Thr Gly Glu Val Thr Val Pro Gly
```

```
            450                 455                 460
Val Ser Gly Asp Val Ser Leu Pro Glu Ile Ala Thr Gly Gly Leu Glu
465                 470                 475                 480

Gly Lys Met Lys Gly Thr Lys Val Lys Thr Pro Glu Met Ile Ile Gln
                485                 490                 495

Lys Pro Lys Ile Ser Met Gln Asp Val Asp Leu Ser Leu Gly Ser Pro
                500                 505                 510

Lys Leu Lys Gly Asp Ile Lys Val Ser Ala Pro Gly Val Gln Gly Asp
                515                 520                 525

Val Lys Gly Pro Gln Val Ala Leu Lys Gly Ser Arg Val Asp Ile Glu
            530                 535                 540

Thr Pro Asn Leu Glu Gly Thr Leu Thr Gly Pro Arg Leu Gly Ser Pro
545                 550                 555                 560

Ser Gly Lys Thr Gly Thr Cys Arg Ile Ser Met Ser Glu Val Asp Leu
                565                 570                 575

Asn Val Ala Ala Pro Lys Val Lys Gly Gly Val Asp Val Thr Leu Pro
                580                 585                 590

Arg Val Glu Gly Lys Val Lys Val Pro Glu Val Asp Val Arg Gly Pro
                595                 600                 605

Lys Val Asp Val Ser Ala Pro Asp Val Glu Ala His Gly Pro Glu Trp
            610                 615                 620

Asn Leu Lys Met Pro Lys Met Lys Met Pro Thr Phe Ser Thr Pro Gly
625                 630                 635                 640

Ala Lys Gly Glu Gly Pro Asp Val His Met Thr Leu Pro Lys Gly Asp
                645                 650                 655

Ile Ser Ile Ser Gly Pro Lys Val Asn Val Glu Ala Pro Asp Val Asn
                660                 665                 670

Leu Glu Gly Leu Gly Gly Lys Leu Lys Gly Pro Asp Val Lys Leu Pro
                675                 680                 685

Asp Met Ser Val Lys Thr Pro Lys Ile Ser Met Pro Asp Val Asp Leu
            690                 695                 700

His Val Lys Gly Thr Lys Val Lys Gly Glu Tyr Asp Val Thr Val Pro
705                 710                 715                 720

Lys Leu Glu Gly Glu Leu Lys Gly Pro Lys Val Asp Ile Asp Ala Pro
                725                 730                 735

Asp Val Asp Val His Gly Pro Asp Trp His Leu Lys Met Pro Lys Met
                740                 745                 750

Lys Met Pro Lys Phe Ser Val Pro Gly Phe Lys Ala Glu Gly Pro Glu
                755                 760                 765

Val Asp Val Asn Leu Pro Lys Ala Asp Val Asp Ile Ser Gly Pro Lys
            770                 775                 780

Ile Asp Val Thr Ala Pro Asp Val Ser Ile Glu Pro Glu Gly Lys
785                 790                 795                 800

Leu Lys Gly Pro Lys Phe Lys Met Pro Glu Met Asn Ile Lys Val Pro
                805                 810                 815

Lys Ile Ser Met Pro Asp Val Asp Leu His Leu Lys Gly Pro Asn Val
                820                 825                 830

Lys Gly Glu Tyr Asp Val Thr Met Pro Lys Val Glu Ser Glu Ile Lys
                835                 840                 845

Val Pro Asp Val Glu Leu Lys Ser Ala Lys Met Asp Ile Asp Val Pro
            850                 855                 860

Asp Val Glu Val Gln Gly Pro Asp Trp His Leu Lys Met Pro Lys Met
865                 870                 875                 880
```

```
Lys Met Pro Lys Phe Ser Met Pro Gly Phe Lys Ala Glu Gly Pro Glu
            885                 890                 895

Val Asp Val Asn Leu Pro Lys Ala Asp Val Asp Ile Ser Gly Pro Lys
            900                 905                 910

Val Gly Val Glu Val Pro Asp Val Asn Ile Glu Gly Pro Gly Lys
            915                 920                 925

Leu Lys Gly Pro Lys Phe Lys Met Pro Glu Met Asn Ile Lys Ala Pro
    930                 935                 940

Lys Ile Ser Met Pro Asp Val Asp Leu His Met Lys Gly Pro Lys Val
945                 950                 955                 960

Lys Gly Glu Tyr Asp Met Thr Val Pro Lys Leu Glu Gly Asp Leu Lys
            965                 970                 975

Gly Pro Lys Val Asp Val Ser Ala Pro Asp Val Glu Met Gln Gly Pro
            980                 985                 990

Asp Trp Asn Leu Lys Met Pro Lys Ile Lys Met Pro Lys Phe Ser Met
            995                 1000                1005

Pro Ser Leu Lys Gly Glu Gly Pro Glu Phe Asp Val Asn Leu Ser
    1010                1015                1020

Lys Ala Asn Val Asp Ile Ser Ala Pro Lys Val Asp Thr Asn Ala
    1025                1030                1035

Pro Asp Leu Ser Leu Glu Gly Pro Glu Gly Lys Leu Lys Gly Pro
    1040                1045                1050

Lys Phe Lys Met Pro Glu Met His Phe Arg Ala Pro Lys Met Ser
    1055                1060                1065

Leu Pro Asp Val Asp Leu Asp Leu Lys Gly Pro Lys Met Lys Gly
    1070                1075                1080

Asn Val Asp Ile Ser Ala Pro Lys Ile Glu Gly Glu Met Gln Val
    1085                1090                1095

Pro Asp Val Asp Ile Arg Gly Pro Lys Val Asp Ile Lys Ala Pro
    1100                1105                1110

Asp Val Glu Gly Gln Gly Leu Asp Trp Ser Leu Lys Ile Pro Lys
    1115                1120                1125

Met Lys Met Pro Lys Phe Ser Met Pro Ser Leu Lys Gly Glu Gly
    1130                1135                1140

Pro Glu Val Asp Val Asn Leu Pro Lys Ala Asp Val Val Val Ser
    1145                1150                1155

Gly Pro Lys Val Asp Ile Glu Ala Pro Asp Val Ser Leu Glu Gly
    1160                1165                1170

Pro Glu Gly Lys Leu Lys Gly Pro Lys Phe Lys Met Pro Glu Met
    1175                1180                1185

His Phe Lys Thr Pro Lys Ile Ser Met Pro Asp Val Asp Leu His
    1190                1195                1200

Leu Lys Gly Pro Lys Val Lys Gly Asp Val Asp Val Ser Val Pro
    1205                1210                1215

Lys Val Glu Gly Glu Met Lys Val Pro Asp Val Glu Ile Lys Gly
    1220                1225                1230

Pro Lys Met Asp Ile Asp Ala Pro Asp Val Glu Val Gln Gly Pro
    1235                1240                1245

Asp Trp His Leu Lys Met Pro Lys Met Lys Met Pro Lys Phe Ser
    1250                1255                1260

Met Pro Gly Phe Lys Gly Glu Gly Arg Val Asp Val Asn Leu
    1265                1270                1275
```

```
Pro Lys Ala Asp Ile Asp Val Ser Gly Pro Lys Val  Asp Val Glu
    1280                1285                1290

Val Pro Asp Val Ser Leu Glu Gly Pro Glu Gly Lys  Leu Lys Gly
    1295                1300                1305

Pro Lys Phe Lys Met Pro Glu Met His Phe Lys Ala  Pro Lys Ile
    1310                1315                1320

Ser Met Pro Asp Val Asp Leu Asn Leu Lys Gly Pro  Lys Leu Lys
    1325                1330                1335

Gly Asp Val Asp Val Ser Leu Pro Glu Val Glu Gly  Glu Met Lys
    1340                1345                1350

Val Pro Asp Val Asp Ile Lys Gly Pro Lys Val Asp  Ile Ser Ala
    1355                1360                1365

Pro Asp Val Asp Val His Gly Pro Asp Trp His Leu  Lys Met Pro
    1370                1375                1380

Lys Val Lys Met Pro Lys Phe Ser Met Pro Gly Phe  Lys Gly Glu
    1385                1390                1395

Gly Pro Glu Val Asp Val Lys Leu Pro Lys Ala Asp  Val Asp Val
    1400                1405                1410

Ser Gly Pro Lys Met Asp Ala Glu Val Pro Asp Val  Asn Ile Glu
    1415                1420                1425

Gly Pro Asp Ala Lys Leu Lys Gly Pro Lys Phe Lys  Met Pro Glu
    1430                1435                1440

Met Ser Ile Lys Pro Gln Lys Ile Ser Ile Pro Asp  Val Gly Leu
    1445                1450                1455

His Leu Lys Gly Pro Lys Met Lys Gly Asp Tyr Asp  Val Thr Val
    1460                1465                1470

Pro Lys Val Glu Gly Glu Ile Lys Ala Pro Asp Val  Asp Ile Lys
    1475                1480                1485

Gly Pro Lys Val Asp Ile Asn Ala Pro Asp Val Glu  Val His Gly
    1490                1495                1500

Pro Asp Trp His Leu Lys Met Pro Lys Val Lys Met  Pro Lys Phe
    1505                1510                1515

Ser Met Pro Gly Phe Lys Gly Glu Gly Pro Glu Val  Asp Met Asn
    1520                1525                1530

Leu Pro Lys Ala Asp Leu Gly Val Ser Gly Pro Lys  Val Asp Ile
    1535                1540                1545

Asp Val Pro Asp Val Asn Leu Glu Ala Pro Glu Gly  Lys Leu Lys
    1550                1555                1560

Gly Pro Lys Phe Lys Met Pro Ser Met Asn Ile Gln  Thr His Lys
    1565                1570                1575

Ile Ser Met Pro Asp Val Gly Leu Asn Leu Lys Ala  Pro Lys Leu
    1580                1585                1590

Lys Thr Asp Val Asp Val Ser Leu Pro Lys Val Glu  Gly Asp Leu
    1595                1600                1605

Lys Gly Pro Glu Ile Asp Val Lys Ala Pro Lys Met  Asp Val Asn
    1610                1615                1620

Val Gly Asp Ile Asp Ile Glu Gly Pro Glu Gly Lys  Leu Lys Gly
    1625                1630                1635

Pro Lys Phe Lys Met Pro Glu Met His Phe Lys Ala  Pro Lys Ile
    1640                1645                1650

Ser Met Pro Asp Val Asp Leu His Leu Lys Gly Pro  Lys Val Lys
    1655                1660                1665

Gly Asp Met Asp Val Ser Val Pro Lys Val Glu Gly  Glu Met Lys
```

-continued

```
              1670                1675                1680
Val Pro Asp Val Asp Ile Lys Gly Pro Lys Val Asp Ile Asp Ala
    1685                1690                1695

Pro Asp Val Glu Val His Asp Pro Asp Trp His Leu Lys Met Pro
    1700                1705                1710

Lys Met Lys Met Pro Lys Phe Ser Met Pro Gly Phe Lys Ala Glu
    1715                1720                1725

Gly Pro Glu Val Asp Val Asn Leu Pro Lys Ala Asp Ile Asp Val
    1730                1735                1740

Ser Gly Pro Ser Val Asp Thr Asp Ala Pro Asp Leu Asp Ile Glu
    1745                1750                1755

Gly Pro Glu Gly Lys Leu Lys Gly Ser Lys Phe Lys Met Pro Lys
    1760                1765                1770

Leu Asn Ile Lys Ala Pro Lys Val Ser Met Pro Asp Val Asp Leu
    1775                1780                1785

Asn Leu Lys Gly Pro Lys Leu Lys Gly Glu Ile Asp Ala Ser Val
    1790                1795                1800

Pro Glu Leu Glu Gly Asp Leu Arg Gly Pro Gln Val Asp Val Lys
    1805                1810                1815

Gly Pro Phe Val Glu Ala Glu Val Pro Asp Val Asp Leu Glu Cys
    1820                1825                1830

Pro Asp Ala Lys Leu Lys Gly Pro Lys Phe Lys Met Pro Glu Met
    1835                1840                1845

His Phe Lys Ala Pro Lys Ile Ser Met Pro Asp Val Asp Leu His
    1850                1855                1860

Leu Lys Gly Pro Lys Val Lys Gly Asp Ala Asp Val Ser Val Pro
    1865                1870                1875

Lys Leu Glu Gly Asp Leu Thr Gly Pro Ser Val Gly Val Glu Val
    1880                1885                1890

Pro Asp Val Glu Leu Glu Cys Pro Asp Ala Lys Leu Lys Gly Pro
    1895                1900                1905

Lys Phe Lys Met Pro Asp Met His Phe Lys Ala Pro Lys Ile Ser
    1910                1915                1920

Met Pro Asp Val Asp Leu His Leu Lys Gly Pro Lys Val Lys Gly
    1925                1930                1935

Asp Val Asp Val Ser Val Pro Lys Leu Glu Gly Asp Leu Thr Gly
    1940                1945                1950

Pro Ser Val Gly Val Glu Val Pro Asp Val Glu Leu Glu Cys Pro
    1955                1960                1965

Asp Ala Lys Leu Lys Gly Pro Lys Phe Lys Met Pro Glu Met His
    1970                1975                1980

Phe Lys Thr Pro Lys Ile Ser Met Pro Asp Val Asp Leu His Leu
    1985                1990                1995

Lys Gly Pro Lys Val Lys Gly Asp Met Asp Val Ser Val Pro Lys
    2000                2005                2010

Val Glu Gly Glu Met Lys Val Pro Asp Val Asp Ile Lys Gly Pro
    2015                2020                2025

Lys Met Asp Ile Asp Ala Pro Asp Val Asp Val His Gly Pro Asp
    2030                2035                2040

Trp His Leu Lys Met Pro Met Lys Met Pro Lys Phe Ser Met
    2045                2050                2055

Pro Gly Phe Lys Ala Glu Gly Pro Glu Val Asp Val Asn Leu Pro
    2060                2065                2070
```

```
Lys Ala Asp Val Val Ser Gly Pro Lys Val Asp Val Glu Val
2075             2080                 2085

Pro Asp Val Ser Leu Glu Gly Pro Glu Gly Lys Leu Lys Gly Pro
2090                 2095                 2100

Lys Leu Lys Met Pro Glu Met His Phe Lys Ala Pro Lys Ile Ser
2105                 2110                 2115

Met Pro Asp Val Asp Leu His Leu Lys Gly Pro Lys Val Lys Gly
2120                 2125                 2130

Asp Val Asp Val Ser Leu Pro Lys Leu Glu Gly Asp Leu Thr Gly
2135                 2140                 2145

Pro Ser Val Asp Val Glu Val Pro Asp Val Glu Leu Glu Cys Pro
2150                 2155                 2160

Asp Ala Lys Leu Lys Gly Pro Lys Phe Lys Met Pro Glu Met His
2165                 2170                 2175

Phe Lys Thr Pro Lys Ile Ser Met Pro Asp Val Asn Leu Asn Leu
2180                 2185                 2190

Lys Gly Pro Lys Val Lys Gly Asp Met Asp Val Ser Val Pro Lys
2195                 2200                 2205

Val Glu Gly Glu Met Lys Val Pro Asp Val Asp Ile Arg Gly Pro
2210                 2215                 2220

Lys Val Asp Ile Asp Ala Pro Asp Val Asp Val His Gly Pro Asp
2225                 2230                 2235

Trp His Leu Lys Met Pro Lys Met Lys Met Pro Lys Phe Ser Met
2240                 2245                 2250

Pro Gly Phe Lys Gly Glu Gly Pro Glu Val Asp Val Asn Leu Pro
2255                 2260                 2265

Lys Ala Asp Val Asp Val Ser Gly Pro Lys Val Asp Val Glu Val
2270                 2275                 2280

Pro Asp Val Ser Leu Glu Gly Pro Glu Gly Lys Leu Lys Gly Pro
2285                 2290                 2295

Lys Phe Lys Met Pro Glu Met His Phe Lys Thr Pro Lys Ile Ser
2300                 2305                 2310

Met Pro Asp Val Asp Phe Asn Leu Lys Gly Pro Lys Ile Lys Gly
2315                 2320                 2325

Asp Val Asp Val Ser Ala Pro Lys Leu Glu Gly Glu Leu Lys Gly
2330                 2335                 2340

Pro Glu Leu Asp Val Lys Gly Pro Lys Leu Asp Ala Asp Met Pro
2345                 2350                 2355

Glu Val Ala Val Glu Gly Pro Asn Gly Lys Trp Lys Thr Pro Lys
2360                 2365                 2370

Phe Lys Met Pro Asp Met His Phe Lys Ala Pro Lys Ile Ser Met
2375                 2380                 2385

Pro Asp Leu Asp Leu His Leu Lys Ser Pro Lys Ala Lys Gly Glu
2390                 2395                 2400

Val Asp Val Asp Val Pro Lys Leu Glu Gly Asp Leu Lys Gly Pro
2405                 2410                 2415

His Val Asp Val Ser Gly Pro Asp Ile Asp Ile Glu Gly Pro Glu
2420                 2425                 2430

Gly Lys Leu Lys Gly Pro Lys Phe Lys Met Pro Asp Met His Phe
2435                 2440                 2445

Lys Ala Pro Asn Ile Ser Met Pro Asp Val Asp Leu Asn Leu Lys
2450                 2455                 2460
```

-continued

```
Gly Pro Lys Ile Lys Gly Asp Val Asp Val Ser Val Pro Glu Val
    2465            2470                2475
Glu Gly Lys Leu Glu Val Pro Asp Met Asn Ile Arg Gly Pro Lys
    2480            2485                2490
Val Asp Val Asn Ala Pro Val Gln Ala Pro Trp His Leu
    2495            2500                2505
Lys Met Pro Lys Met Lys Met Pro Lys Phe Ser Met Pro Gly Phe
    2510            2515                2520
Lys Ala Glu Gly Pro Glu Val Asp Val Asn Leu Pro Lys Ala Asp
    2525            2530                2535
Val Asp Ile Ser Gly Pro Lys Val Asp Ile Glu Gly Pro Asp Val
    2540            2545                2550
Asn Ile Glu Gly Pro Glu Gly Lys Leu Lys Gly Pro Lys Leu Lys
    2555            2560                2565
Met Pro Glu Met Asn Ile Lys Ala Pro Lys Ile Ser Met Pro Asp
    2570            2575                2580
Phe Asp Leu His Leu Lys Gly Pro Lys Val Lys Gly Asp Val Asp
    2585            2590                2595
Val Ser Leu Pro Lys Val Glu Gly Asp Leu Lys Gly Pro Glu Val
    2600            2605                2610
Asp Ile Lys Gly Pro Lys Val Asp Ile Asn Ala Pro Asp Val Gly
    2615            2620                2625
Val Gln Gly Pro Asp Trp His Leu Lys Met Pro Lys Val Lys Met
    2630            2635                2640
Pro Lys Phe Ser Met Pro Gly Phe Lys Gly Glu Gly Pro Asp Gly
    2645            2650                2655
Asp Val Lys Leu Pro Lys Ala Asp Ile Asp Val Ser Gly Pro Lys
    2660            2665                2670
Val Asp Ile Glu Gly Pro Asp Val Asn Ile Glu Gly Pro Glu Gly
    2675            2680                2685
Lys Leu Lys Gly Pro Lys Phe Lys Met Pro Glu Met Asn Ile Lys
    2690            2695                2700
Ala Pro Lys Ile Ser Met Pro Asp Ile Asp Leu Asn Leu Lys Gly
    2705            2710                2715
Pro Lys Val Lys Gly Asp Val Asp Val Ser Leu Pro Lys Val Glu
    2720            2725                2730
Gly Asp Leu Lys Gly Pro Glu Val Asp Ile Lys Gly Pro Lys Val
    2735            2740                2745
Asp Ile Asp Ala Pro Asp Val Asp Val His Gly Pro Asp Trp His
    2750            2755                2760
Leu Lys Met Pro Lys Ile Lys Met Pro Lys Ile Ser Met Pro Gly
    2765            2770                2775
Phe Lys Gly Glu Gly Pro Asp Val Asp Val Asn Leu Pro Lys Ala
    2780            2785                2790
Asp Ile Asp Val Ser Gly Pro Lys Val Asp Val Glu Cys Pro Asp
    2795            2800                2805
Val Asn Ile Glu Gly Pro Glu Gly Lys Trp Lys Ser Pro Lys Phe
    2810            2815                2820
Lys Met Pro Glu Met His Phe Lys Thr Pro Lys Ile Ser Met Pro
    2825            2830                2835
Asp Ile Asp Leu Asn Leu Thr Gly Pro Lys Ile Lys Gly Asp Val
    2840            2845                2850
Asp Val Thr Gly Pro Lys Val Glu Gly Asp Leu Lys Gly Pro Glu
```

-continued

```
                2855                2860                2865

Val Asp Leu Lys Gly Pro Lys Val Asp Ile Asp Val Pro Asp Val
    2870                2875                2880

Asn Val Gln Gly Pro Asp Trp His Leu Lys Met Pro Lys Met Lys
    2885                2890                2895

Met Pro Lys Phe Ser Met Pro Gly Phe Lys Ala Glu Gly Pro Glu
    2900                2905                2910

Val Asp Val Asn Leu Pro Lys Ala Asp Val Asp Val Ser Gly Pro
    2915                2920                2925

Lys Val Asp Val Glu Gly Pro Asp Val Asn Ile Glu Gly Pro Glu
    2930                2935                2940

Gly Lys Leu Lys Gly Pro Lys Phe Lys Met Pro Glu Met Asn Ile
    2945                2950                2955

Lys Ala Pro Lys Ile Pro Met Pro Asp Phe Asp Leu His Leu Lys
    2960                2965                2970

Gly Pro Lys Val Lys Gly Asp Val Asp Ile Ser Leu Pro Lys Val
    2975                2980                2985

Glu Gly Asp Leu Lys Gly Pro Glu Val Asp Ile Arg Gly Pro Gln
    2990                2995                3000

Val Asp Ile Asp Val Pro Asp Val Gly Val Gln Gly Pro Asp Trp
    3005                3010                3015

His Leu Lys Met Pro Lys Val Lys Met Pro Lys Phe Ser Met Pro
    3020                3025                3030

Gly Phe Lys Gly Glu Gly Pro Asp Val Asp Val Asn Leu Pro Lys
    3035                3040                3045

Ala Asp Leu Asp Val Ser Gly Pro Lys Val Asp Ile Asp Val Pro
    3050                3055                3060

Asp Val Asn Ile Glu Gly Pro Glu Gly Lys Leu Lys Gly Pro Lys
    3065                3070                3075

Phe Lys Met Pro Glu Met Asn Ile Lys Ala Pro Lys Ile Ser Met
    3080                3085                3090

Pro Asp Ile Asp Leu Asn Leu Lys Gly Pro Lys Val Lys Gly Asp
    3095                3100                3105

Met Asp Val Ser Leu Pro Lys Val Glu Gly Asp Met Lys Val Pro
    3110                3115                3120

Asp Val Asp Ile Lys Gly Pro Lys Val Asp Ile Asn Ala Pro Asp
    3125                3130                3135

Val Asp Val Gln Gly Pro Asp Trp His Leu Lys Met Pro Lys Ile
    3140                3145                3150

Lys Met Pro Lys Ile Ser Met Pro Gly Phe Lys Gly Glu Gly Pro
    3155                3160                3165

Glu Val Asp Val Asn Leu Pro Lys Ala Asp Leu Asp Val Ser Gly
    3170                3175                3180

Pro Lys Val Asp Val Asp Val Pro Asp Val Asn Ile Glu Gly Pro
    3185                3190                3195

Asp Ala Lys Leu Lys Gly Pro Lys Phe Lys Met Pro Glu Met Asn
    3200                3205                3210

Ile Lys Ala Pro Lys Ile Ser Met Pro Asp Leu Asp Leu Asn Leu
    3215                3220                3225

Lys Gly Pro Lys Met Lys Gly Glu Val Asp Val Ser Leu Ala Asn
    3230                3235                3240

Val Glu Gly Asp Leu Lys Gly Pro Ala Leu Asp Ile Lys Gly Pro
    3245                3250                3255
```

-continued

```
Lys Ile Asp Val Asp Ala Pro Asp Ile Asp Ile His Gly Pro Asp
3260                3265                3270

Ala Lys Leu Lys Gly Pro Lys Leu Lys Met Pro Asp Met His Val
3275                3280                3285

Asn Met Pro Lys Ile Ser Met Pro Glu Ile Asp Leu Asn Leu Lys
3290                3295                3300

Gly Ser Lys Leu Lys Gly Asp Val Asp Val Ser Gly Pro Lys Leu
3305                3310                3315

Glu Gly Asp Ile Lys Ala Pro Ser Leu Asp Ile Lys Gly Pro Glu
3320                3325                3330

Val Asp Val Ser Gly Pro Lys Leu Asn Ile Glu Gly Lys Ser Lys
3335                3340                3345

Lys Ser Arg Phe Lys Leu Pro Lys Phe Asn Phe Ser Gly Ser Lys
3350                3355                3360

Val Gln Thr Pro Glu Val Asp Val Lys Gly Lys Lys Pro Asp Ile
3365                3370                3375

Asp Ile Thr Gly Pro Lys Val Asp Ile Asn Ala Pro Asp Val Glu
3380                3385                3390

Val Gln Gly Lys Val Lys Gly Ser Lys Phe Lys Met Pro Phe Leu
3395                3400                3405

Ser Ile Ser Ser Pro Lys Val Ser Met Pro Asp Val Glu Leu Asn
3410                3415                3420

Leu Lys Ser Pro Lys Val Lys Gly Asp Leu Asp Ile Ala Gly Pro
3425                3430                3435

Asn Leu Glu Gly Asp Phe Lys Gly Pro Lys Val Asp Ile Lys Ala
3440                3445                3450

Pro Glu Val Asn Leu Asn Ala Pro Asp Val Asp Val His Gly Pro
3455                3460                3465

Asp Trp Asn Leu Lys Met Pro Lys Met Lys Met Pro Lys Phe Ser
3470                3475                3480

Val Ser Gly Leu Lys Ala Glu Gly Pro Asp Val Ala Val Asp Leu
3485                3490                3495

Pro Lys Gly Asp Ile Asn Ile Glu Gly Pro Ser Met Asn Ile Glu
3500                3505                3510

Gly Pro Asp Leu Asn Val Glu Gly Pro Glu Gly Gly Leu Lys Gly
3515                3520                3525

Pro Lys Phe Lys Met Pro Asp Met Asn Ile Lys Ala Pro Lys Ile
3530                3535                3540

Ser Met Pro Asp Ile Asp Leu Asn Leu Lys Gly Pro Lys Val Lys
3545                3550                3555

Gly Asp Val Asp Ile Ser Leu Pro Lys Leu Glu Gly Asp Leu Lys
3560                3565                3570

Gly Pro Glu Val Asp Ile Lys Gly Pro Lys Val Asp Ile Asn Ala
3575                3580                3585

Pro Asp Val Asp Val His Gly Pro Asp Trp His Leu Lys Met Pro
3590                3595                3600

Lys Val Lys Met Pro Lys Phe Ser Met Pro Gly Phe Lys Gly Glu
3605                3610                3615

Gly Pro Glu Val Asp Val Thr Leu Pro Lys Ala Asp Ile Asp Ile
3620                3625                3630

Ser Gly Pro Asn Val Asp Val Asp Val Pro Asp Val Asn Ile Glu
3635                3640                3645
```

-continued

```
Gly Pro Asp Ala Lys Leu Lys Gly Pro Lys Phe Lys Met Pro Glu
    3650                3655                3660
Met Asn Ile Lys Ala Pro Lys Ile Ser Met Pro Asp Phe Asp Leu
    3665                3670                3675
Asn Leu Lys Gly Pro Lys Met Lys Gly Asp Val Val Val Ser Leu
    3680                3685                3690
Pro Lys Val Glu Gly Asp Leu Lys Gly Pro Glu Val Asp Ile Lys
    3695                3700                3705
Gly Pro Lys Val Asp Ile Asp Thr Pro Asp Ile Asn Ile Glu Gly
    3710                3715                3720
Ser Glu Gly Lys Phe Lys Gly Pro Lys Phe Lys Ile Pro Glu Met
    3725                3730                3735
His Leu Lys Ala Pro Lys Ile Ser Met Pro Asp Ile Asp Leu Asn
    3740                3745                3750
Leu Lys Gly Pro Lys Val Lys Gly Asp Val Asp Val Ser Leu Pro
    3755                3760                3765
Lys Met Glu Gly Asp Leu Lys Gly Pro Glu Val Asp Ile Lys Gly
    3770                3775                3780
Pro Lys Val Asp Ile Asn Ala Pro Asp Val Asp Val Gln Gly Pro
    3785                3790                3795
Asp Trp His Leu Lys Met Pro Lys Val Lys Met Pro Lys Phe Ser
    3800                3805                3810
Met Pro Gly Phe Lys Gly Glu Gly Pro Asp Val Asp Val Asn Leu
    3815                3820                3825
Pro Lys Ala Asp Leu Asp Val Ser Gly Pro Lys Val Asp Ile Asp
    3830                3835                3840
Val Pro Asp Val Asn Ile Glu Gly Pro Glu Gly Lys Leu Lys Gly
    3845                3850                3855
Pro Lys Phe Lys Met Pro Glu Met Asn Ile Lys Ala Pro Lys Ile
    3860                3865                3870
Ser Met Pro Asp Ile Asp Leu Asn Leu Lys Gly Pro Lys Val Lys
    3875                3880                3885
Gly Asp Met Asp Val Ser Leu Pro Lys Val Glu Gly Asp Met Gln
    3890                3895                3900
Val Pro Asp Leu Asp Ile Lys Gly Pro Lys Val Asp Ile Asn Ala
    3905                3910                3915
Pro Asp Val Asp Val Arg Gly Pro Asp Trp His Leu Lys Met Pro
    3920                3925                3930
Lys Ile Lys Met Pro Lys Ile Ser Met Pro Gly Phe Lys Gly Glu
    3935                3940                3945
Gly Pro Glu Val Asp Val Asn Leu Pro Lys Ala Asp Leu Asp Val
    3950                3955                3960
Ser Gly Pro Lys Val Asp Val Asp Val Pro Asp Val Asn Ile Glu
    3965                3970                3975
Gly Pro Asp Ala Lys Leu Lys Gly Pro Lys Phe Lys Met Pro Glu
    3980                3985                3990
Met Asn Ile Lys Ala Pro Lys Ile Ser Met Pro Asp Phe Asp Leu
    3995                4000                4005
His Leu Lys Gly Pro Lys Val Lys Gly Asp Val Asp Val Ser Leu
    4010                4015                4020
Pro Lys Met Glu Gly Asp Leu Lys Ala Pro Glu Val Asp Ile Lys
    4025                4030                4035
Gly Pro Lys Val Asp Ile Asp Ala Pro Asp Val Asp Val His Gly
```

-continued

```
            4040                4045                4050
Pro Asp Trp His Leu Lys Met Pro Lys Val Lys Met Pro Lys Phe
    4055                4060                4065
Ser Met Pro Gly Phe Lys Gly Glu Gly Pro Glu Val Asp Val Asn
    4070                4075                4080
Leu Pro Lys Ala Asp Ile Asp Val Ser Gly Pro Lys Val Asp Ile
    4085                4090                4095
Asp Thr Pro Asp Ile Asp Ile His Gly Pro Glu Gly Lys Leu Lys
    4100                4105                4110
Gly Pro Lys Phe Lys Met Pro Asp Leu His Leu Lys Ala Pro Lys
    4115                4120                4125
Ile Ser Met Pro Glu Val Asp Leu Asn Leu Lys Gly Pro Lys Met
    4130                4135                4140
Lys Gly Asp Val Asp Val Ser Leu Pro Lys Val Glu Gly Asp Leu
    4145                4150                4155
Lys Gly Pro Glu Val Asp Ile Lys Gly Pro Lys Val Asp Ile Asp
    4160                4165                4170
Val Pro Asp Val Asp Val Gln Gly Pro Asp Trp His Leu Lys Met
    4175                4180                4185
Pro Lys Val Lys Met Pro Lys Phe Ser Met Pro Gly Phe Lys Gly
    4190                4195                4200
Glu Gly Pro Asp Val Asp Val Asn Leu Pro Lys Ala Asp Leu Asp
    4205                4210                4215
Val Ser Gly Pro Lys Val Asp Ile Asp Val Pro Asp Val Asn Ile
    4220                4225                4230
Glu Gly Pro Asp Ala Lys Leu Lys Gly Pro Lys Phe Lys Met Pro
    4235                4240                4245
Glu Met Asn Ile Lys Ala Pro Lys Ile Ser Met Pro Asp Phe Asp
    4250                4255                4260
Leu His Leu Lys Gly Pro Lys Val Lys Gly Asp Val Asp Val Ser
    4265                4270                4275
Leu Pro Lys Val Glu Gly Asp Leu Lys Gly Pro Glu Val Asp Ile
    4280                4285                4290
Lys Gly Pro Lys Val Asp Ile Asp Ala Pro Asp Val Asp Val His
    4295                4300                4305
Gly Pro Asp Trp His Leu Lys Met Pro Lys Val Lys Met Pro Lys
    4310                4315                4320
Phe Ser Met Pro Gly Phe Lys Gly Glu Gly Pro Asp Val Asp Val
    4325                4330                4335
Thr Leu Pro Lys Ala Asp Ile Glu Ile Ser Gly Pro Lys Val Asp
    4340                4345                4350
Ile Asp Ala Pro Asp Val Ser Ile Glu Gly Pro Asp Ala Lys Leu
    4355                4360                4365
Lys Gly Pro Lys Phe Lys Met Pro Glu Met Asn Ile Lys Ala Pro
    4370                4375                4380
Lys Ile Ser Met Pro Asp Ile Asp Phe Asn Leu Lys Gly Pro Lys
    4385                4390                4395
Val Lys Gly Asp Val Asp Val Ser Leu Pro Lys Val Glu Gly Asp
    4400                4405                4410
Leu Lys Gly Pro Glu Ile Asp Ile Lys Gly Pro Ser Leu Asp Ile
    4415                4420                4425
Asp Thr Pro Asp Val Asn Ile Glu Gly Pro Glu Gly Lys Leu Lys
    4430                4435                4440
```

Gly Pro Lys Phe Lys Met Pro Glu Met Asn Ile Lys Ala Pro Lys
    4445              4450              4455

Ile Ser Met Pro Asp Phe Asp Leu His Leu Lys Gly Pro Lys Val
    4460              4465              4470

Lys Gly Asp Val Asp Val Ser Leu Pro Lys Val Glu Ser Asp Leu
    4475              4480              4485

Lys Gly Pro Glu Val Asp Ile Glu Gly Pro Gly Lys Leu Lys
    4490              4495              4500

Gly Pro Lys Phe Lys Met Pro Asp Val His Phe Lys Ser Pro Gln
    4505              4510              4515

Ile Ser Met Ser Asp Ile Asp Leu Asn Leu Lys Gly Pro Lys Ile
    4520              4525              4530

Lys Gly Asp Met Asp Ile Ser Val Pro Lys Leu Glu Gly Asp Leu
    4535              4540              4545

Lys Gly Pro Lys Val Asp Val Lys Gly Pro Lys Val Gly Ile Asp
    4550              4555              4560

Thr Pro Asp Ile Asp Ile His Gly Pro Glu Gly Lys Leu Lys Gly
    4565              4570              4575

Pro Lys Phe Lys Met Pro Asp Leu His Leu Lys Ala Pro Lys Ile
    4580              4585              4590

Ser Met Pro Glu Val Asp Leu Asn Leu Lys Gly Pro Lys Val Lys
    4595              4600              4605

Gly Asp Met Asp Ile Ser Leu Pro Lys Val Glu Gly Asp Leu Lys
    4610              4615              4620

Gly Pro Glu Val Asp Ile Arg Asp Pro Lys Val Asp Ile Asp Val
    4625              4630              4635

Pro Asp Val Asp Val Gln Gly Pro Asp Trp His Leu Lys Met Pro
    4640              4645              4650

Lys Val Lys Met Pro Lys Phe Ser Met Pro Gly Phe Lys Gly Glu
    4655              4660              4665

Gly Pro Asp Val Asp Val Asn Leu Pro Lys Ala Asp Ile Asp Val
    4670              4675              4680

Ser Gly Pro Lys Val Asp Val Asp Val Pro Asp Val Asn Ile Glu
    4685              4690              4695

Gly Pro Asp Ala Lys Leu Lys Gly Pro Lys Phe Lys Met Pro Glu
    4700              4705              4710

Met Ser Ile Lys Ala Pro Lys Ile Ser Met Pro Asp Ile Asp Leu
    4715              4720              4725

Asn Leu Lys Gly Pro Lys Val Lys Gly Asp Val Asp Val Thr Leu
    4730              4735              4740

Pro Lys Val Glu Gly Asp Leu Lys Gly Pro Glu Ala Asp Ile Lys
    4745              4750              4755

Gly Pro Lys Val Asp Ile Asn Thr Pro Asp Val Asp Val His Gly
    4760              4765              4770

Pro Asp Trp His Leu Lys Met Pro Lys Val Lys Met Pro Lys Phe
    4775              4780              4785

Ser Met Pro Gly Phe Lys Gly Glu Gly Pro Asp Val Asp Val Ser
    4790              4795              4800

Leu Pro Lys Ala Asp Ile Asp Val Ser Gly Pro Lys Val Asp Val
    4805              4810              4815

Asp Ile Pro Asp Val Asn Ile Glu Gly Pro Asp Ala Lys Leu Lys
    4820              4825              4830

```
Gly Pro Lys Phe Lys Met Pro Glu Ile Asn Ile Lys Ala Pro Lys
4835                4840                4845

Ile Ser Ile Pro Asp Val Asp Leu Asp Leu Lys Gly Pro Lys Val
4850                4855                4860

Lys Gly Asp Phe Asp Val Ser Val Pro Lys Val Glu Gly Thr Leu
4865                4870                4875

Lys Gly Pro Glu Val Asp Leu Lys Gly Pro Arg Leu Asp Phe Glu
4880                4885                4890

Gly Pro Asp Ala Lys Leu Ser Gly Pro Ser Leu Lys Met Pro Ser
4895                4900                4905

Leu Glu Ile Ser Ala Pro Lys Val Thr Ala Pro Asp Val Asp Leu
4910                4915                4920

His Leu Lys Ala Pro Lys Ile Gly Phe Ser Gly Pro Lys Leu Glu
4925                4930                4935

Gly Gly Glu Val Asp Leu Lys Gly Pro Lys Val Glu Ala Pro Ser
4940                4945                4950

Leu Asp Val His Met Asp Ser Pro Asp Ile Asn Ile Glu Gly Pro
4955                4960                4965

Asp Val Lys Ile Pro Lys Phe Lys Lys Pro Lys Phe Gly Phe Gly
4970                4975                4980

Ala Lys Ser Pro Lys Ala Asp Ile Lys Ser Pro Ser Leu Asp Val
4985                4990                4995

Thr Val Pro Glu Ala Glu Leu Asn Leu Glu Thr Pro Glu Ile Ser
5000                5005                5010

Val Gly Gly Lys Gly Lys Lys Ser Lys Phe Lys Met Pro Lys Ile
5015                5020                5025

His Met Ser Gly Pro Lys Ile Lys Ala Lys Lys Gln Gly Phe Asp
5030                5035                5040

Leu Asn Val Pro Gly Gly Glu Ile Asp Ala Ser Leu Lys Ala Pro
5045                5050                5055

Asp Val Asp Val Asn Ile Ala Gly Pro Asp Ala Ala Leu Lys Val
5060                5065                5070

Asp Val Lys Ser Pro Lys Thr Lys Lys Thr Met Phe Gly Lys Met
5075                5080                5085

Tyr Phe Pro Asp Val Glu Phe Asp Ile Lys Ser Pro Lys Phe Lys
5090                5095                5100

Ala Glu Ala Pro Leu Pro Ser Pro Lys Leu Glu Gly Glu Leu Gln
5105                5110                5115

Ala Pro Asp Leu Glu Leu Ser Leu Pro Ala Ile His Val Glu Gly
5120                5125                5130

Leu Asp Ile Lys Ala Lys Ala Pro Lys Val Lys Met Pro Asp Val
5135                5140                5145

Asp Ile Ser Val Pro Lys Ile Glu Gly Asp Leu Lys Gly Pro Lys
5150                5155                5160

Val Gln Ala Asn Leu Gly Ala Pro Asp Ile Asn Ile Glu Gly Leu
5165                5170                5175

Asp Ala Lys Val Lys Thr Pro Ser Phe Gly Ile Ser Ala Pro Gln
5180                5185                5190

Val Ser Ile Pro Asp Val Asn Val Asn Leu Lys Gly Pro Lys Ile
5195                5200                5205

Lys Gly Asp Val Pro Ser Val Gly Leu Glu Gly Pro Asp Val Asp
5210                5215                5220

Leu Gln Gly Pro Glu Ala Lys Ile Lys Phe Pro Lys Phe Ser Met
```

-continued

```
            5225                5230                5235
Pro Lys Ile Gly Ile Pro Gly Val Lys Met Glu Gly Gly Gly Ala
            5240                5245                5250
Glu Val His Ala Gln Leu Pro Ser Leu Glu Gly Asp Leu Arg Gly
            5255                5260                5265
Pro Asp Val Lys Leu Glu Gly Pro Asp Val Ser Leu Lys Gly Pro
            5270                5275                5280
Gly Val Asp Leu Pro Ser Val Asn Leu Ser Met Pro Lys Val Ser
            5285                5290                5295
Gly Pro Asp Leu Asp Leu Asn Leu Lys Gly Pro Ser Leu Lys Gly
            5300                5305                5310
Asp Leu Asp Ala Ser Val Pro Ser Met Lys Val His Ala Pro Gly
            5315                5320                5325
Leu Asn Leu Ser Gly Val Gly Gly Lys Met Gln Val Gly Gly Asp
            5330                5335                5340
Gly Val Lys Val Pro Gly Ile Asp Ala Thr Thr Lys Leu Asn Val
            5345                5350                5355
Gly Ala Pro Asp Val Thr Leu Arg Gly Pro Ser Leu Gln Gly Asp
            5360                5365                5370
Leu Ala Val Ser Gly Asp Ile Lys Cys Pro Lys Val Ser Val Gly
            5375                5380                5385
Ala Pro Asp Leu Ser Leu Glu Ala Ser Glu Gly Ser Ile Lys Leu
            5390                5395                5400
Pro Lys Met Lys Leu Pro Gln Phe Gly Ile Ser Thr Pro Gly Ser
            5405                5410                5415
Asp Leu His Val Asn Ala Lys Gly Pro Gln Val Ser Gly Glu Leu
            5420                5425                5430
Lys Gly Pro Gly Val Asp Val Asn Leu Lys Gly Pro Arg Ile Ser
            5435                5440                5445
Ala Pro Asn Val Asp Phe Asn Leu Glu Gly Pro Lys Val Lys Gly
            5450                5455                5460
Ser Leu Gly Ala Thr Gly Glu Ile Lys Gly Pro Thr Val Gly Gly
            5465                5470                5475
Gly Leu Pro Gly Ile Gly Val Gln Gly Leu Glu Gly Asn Leu Gln
            5480                5485                5490
Met Pro Gly Ile Lys Ser Ser Gly Cys Asp Val Asn Leu Pro Gly
            5495                5500                5505
Val Asn Val Lys Leu Pro Thr Gly Gln Ile Ser Gly Pro Glu Ile
            5510                5515                5520
Lys Gly Gly Leu Lys Gly Ser Glu Val Gly Phe His Gly Ala Ala
            5525                5530                5535
Pro Asp Ile Ser Val Lys Gly Pro Ala Phe Asn Met Ala Ser Pro
            5540                5545                5550
Glu Ser Asp Phe Gly Ile Asn Leu Lys Gly Pro Lys Ile Lys Gly
            5555                5560                5565
Gly Ala Asp Val Ser Gly Gly Val Ser Ala Pro Asp Ile Ser Leu
            5570                5575                5580
Gly Glu Gly His Leu Ser Val Lys Gly Ser Gly Gly Glu Trp Lys
            5585                5590                5595
Gly Pro Gln Val Ser Ser Ala Leu Asn Leu Asp Thr Ser Lys Phe
            5600                5605                5610
Ala Gly Gly Leu His Phe Ser Gly Pro Lys Val Glu Gly Gly Val
            5615                5620                5625
```

-continued

```
Lys Gly Gly Gln Ile Gly Leu Gln Ala Pro Gly Leu Ser Val Ser
    5630                5635                5640

Gly Pro Gln Gly His Leu Glu Ser Gly Ser Gly Lys Val Thr Phe
    5645                5650                5655

Pro Lys Met Lys Ile Pro Lys Phe Thr Phe Ser Gly Arg Glu Leu
    5660                5665                5670

Val Gly Arg Glu Met Gly Val Asp Val His Phe Pro Lys Ala Glu
    5675                5680                5685

Ala Ser Ile Gln Ala Gly Ala Gly Asp Gly Glu Trp Glu Glu Ser
    5690                5695                5700

Glu Val Lys Leu Lys Lys Ser Lys Ile Lys Met Pro Lys Phe Asn
    5705                5710                5715

Phe Ser Lys Pro Lys Gly Lys Gly Gly Val Thr Gly Ser Pro Glu
    5720                5725                5730

Ala Ser Ile Ser Gly Ser Lys Gly Asp Leu Lys Ser Ser Lys Ala
    5735                5740                5745

Ser Leu Gly Ser Leu Glu Gly Glu Ala Glu Ala Glu Ala Ser Ser
    5750                5755                5760

Pro Lys Gly Lys Phe Ser Leu Phe Lys Ser Lys Lys Pro Arg His
    5765                5770                5775

Arg Ser Asn Ser Phe Ser Asp Glu Arg Glu Phe Ser Gly Pro Ser
    5780                5785                5790

Thr Pro Thr Gly Thr Leu Glu Phe Glu Gly Gly Glu Val Ser Leu
    5795                5800                5805

Glu Gly Gly Lys Val Lys Gly Lys His Gly Lys Leu Lys Phe Gly
    5810                5815                5820

Thr Phe Gly Gly Leu Gly Ser Lys Ser Lys Gly His Tyr Glu Val
    5825                5830                5835

Thr Gly Ser Asp Asp Glu Thr Gly Lys Leu Gln Gly Ser Gly Val
    5840                5845                5850

Ser Leu Ala Ser Lys Lys Ser Arg Leu Ser Ser Ser Ser Ser Asn
    5855                5860                5865

Asp Ser Gly Asn Lys Val Gly Ile Gln Leu Pro Glu Val Glu Leu
    5870                5875                5880

Ser Val Ser Thr Lys Lys Glu
    5885                5890

<210> SEQ ID NO 26
<211> LENGTH: 2468
<212> TYPE: PRT
<213> ORGANISM: Homo sapiens

<400> SEQUENCE: 26

Met Ala Thr Val Val Glu Ala Thr Glu Pro Glu Pro Ser Gly Ser
1               5                   10                  15

Ile Ala Asn Pro Ala Ala Ser Thr Ser Pro Ser Leu Ser His Arg Phe
                20                  25                  30

Leu Asp Ser Lys Phe Tyr Leu Leu Val Val Val Gly Glu Ile Val Thr
            35                  40                  45

Glu Glu His Leu Arg Arg Ala Ile Gly Asn Ile Glu Leu Gly Ile Arg
        50                  55                  60

Ser Trp Asp Thr Asn Leu Ile Glu Cys Asn Leu Asp Gln Glu Leu Lys
65                  70                  75                  80

Leu Phe Val Ser Arg His Ser Ala Arg Phe Ser Pro Glu Val Pro Gly
```

```
                    85                  90                  95
Gln Lys Ile Leu His His Arg Ser Asp Val Leu Glu Thr Val Val Leu
            100                 105                 110

Ile Asn Pro Ser Asp Glu Ala Val Ser Thr Glu Val Arg Leu Met Ile
            115                 120                 125

Thr Asp Ala Ala Arg His Lys Leu Leu Val Leu Thr Gly Gln Cys Phe
            130                 135                 140

Glu Asn Thr Gly Glu Leu Ile Leu Gln Ser Gly Ser Phe Ser Phe Gln
145                 150                 155                 160

Asn Phe Ile Glu Ile Phe Thr Asp Gln Glu Ile Gly Glu Leu Leu Ser
                165                 170                 175

Thr Thr His Pro Ala Asn Lys Ala Ser Leu Thr Leu Phe Cys Pro Glu
                180                 185                 190

Glu Gly Asp Trp Lys Asn Ser Asn Leu Asp Arg His Asn Leu Gln Asp
                195                 200                 205

Phe Ile Asn Ile Lys Leu Asn Ser Ala Ser Ile Leu Pro Glu Met Glu
210                 215                 220

Gly Leu Ser Glu Phe Thr Glu Tyr Leu Ser Glu Ser Val Glu Val Pro
225                 230                 235                 240

Ser Pro Phe Asp Ile Leu Glu Pro Pro Thr Ser Gly Gly Phe Leu Lys
                245                 250                 255

Leu Ser Lys Pro Cys Cys Tyr Ile Phe Pro Gly Gly Arg Gly Asp Ser
                260                 265                 270

Ala Leu Phe Ala Val Asn Gly Phe Asn Met Leu Ile Asn Gly Gly Ser
                275                 280                 285

Glu Arg Lys Ser Cys Phe Trp Lys Leu Ile Arg His Leu Asp Arg Val
                290                 295                 300

Asp Ser Ile Leu Leu Thr His Ile Gly Asp Asp Asn Leu Pro Gly Ile
305                 310                 315                 320

Asn Ser Met Leu Gln Arg Lys Ile Ala Glu Leu Glu Glu Glu Gln Ser
                325                 330                 335

Gln Gly Ser Thr Thr Asn Ser Asp Trp Met Lys Asn Leu Ile Ser Pro
                340                 345                 350

Asp Leu Gly Val Val Phe Leu Asn Val Pro Glu Asn Leu Lys Asn Pro
                355                 360                 365

Glu Pro Asn Ile Lys Met Lys Arg Ser Ile Glu Glu Ala Cys Phe Thr
                370                 375                 380

Leu Gln Tyr Leu Asn Lys Leu Ser Met Lys Pro Glu Pro Leu Phe Arg
385                 390                 395                 400

Ser Val Gly Asn Thr Ile Asp Pro Val Ile Leu Phe Gln Lys Met Gly
                405                 410                 415

Val Gly Lys Leu Glu Met Tyr Val Leu Asn Pro Val Lys Ser Ser Lys
                420                 425                 430

Glu Met Gln Tyr Phe Met Gln Gln Trp Thr Gly Thr Asn Lys Asp Lys
                435                 440                 445

Ala Glu Phe Ile Leu Pro Asn Gly Gln Glu Val Asp Leu Pro Ile Ser
                450                 455                 460

Tyr Leu Thr Ser Val Ser Ser Leu Ile Val Trp His Pro Ala Asn Pro
465                 470                 475                 480

Ala Glu Lys Ile Ile Arg Val Leu Phe Pro Gly Asn Ser Thr Gln Tyr
                485                 490                 495

Asn Ile Leu Glu Gly Leu Glu Lys Leu Lys His Leu Asp Phe Leu Lys
                500                 505                 510
```

```
Gln Pro Leu Ala Thr Gln Lys Asp Leu Thr Gly Gln Val Pro Thr Pro
            515                 520                 525
Val Val Lys Gln Thr Lys Leu Lys Gln Arg Ala Asp Ser Arg Glu Ser
530                 535                 540
Leu Lys Pro Ala Ala Lys Pro Leu Pro Ser Lys Ser Val Arg Lys Glu
545                 550                 555                 560
Ser Lys Glu Glu Thr Pro Glu Val Thr Lys Val Asn His Val Glu Lys
                565                 570                 575
Pro Pro Lys Val Glu Ser Lys Glu Lys Val Met Val Lys Lys Asp Lys
                580                 585                 590
Pro Ile Lys Thr Glu Thr Lys Pro Ser Val Thr Glu Lys Glu Val Pro
            595                 600                 605
Ser Lys Glu Glu Pro Ser Pro Val Lys Ala Glu Val Ala Glu Lys Gln
            610                 615                 620
Ala Thr Asp Val Lys Pro Lys Ala Ala Lys Glu Lys Thr Val Lys Lys
625                 630                 635                 640
Glu Thr Lys Val Lys Pro Glu Asp Lys Lys Glu Lys Glu Lys Lys Pro
                645                 650                 655
Lys Lys Glu Val Ala Lys Lys Glu Asp Lys Thr Pro Ile Lys Lys Glu
                660                 665                 670
Glu Lys Pro Lys Lys Glu Val Lys Glu Val Lys Lys Glu Ile
                675                 680                 685
Lys Lys Glu Glu Lys Lys Glu Pro Lys Lys Val Lys Lys Glu Thr
            690                 695                 700
Pro Pro Lys Glu Val Lys Lys Glu Val Lys Glu Glu Lys Lys Glu
705                 710                 715                 720
Val Lys Lys Glu Glu Lys Glu Pro Lys Lys Glu Ile Lys Lys Leu Pro
                725                 730                 735
Lys Asp Ala Lys Lys Ser Ser Thr Pro Leu Ser Glu Ala Lys Lys Pro
                740                 745                 750
Ala Ala Leu Lys Pro Lys Val Pro Lys Lys Glu Glu Ser Val Lys Lys
            755                 760                 765
Asp Ser Val Ala Ala Gly Lys Pro Lys Glu Lys Gly Lys Ile Lys Val
            770                 775                 780
Ile Lys Lys Glu Gly Lys Ala Ala Glu Ala Val Ala Ala Ala Val Gly
785                 790                 795                 800
Thr Gly Ala Thr Thr Ala Ala Val Met Ala Ala Gly Ile Ala Ala
                805                 810                 815
Ile Gly Pro Ala Lys Glu Leu Glu Ala Glu Arg Ser Leu Met Ser Ser
            820                 825                 830
Pro Glu Asp Leu Thr Lys Asp Phe Glu Glu Leu Lys Ala Glu Glu Val
            835                 840                 845
Asp Val Thr Lys Asp Ile Lys Pro Gln Leu Glu Leu Ile Glu Asp Glu
850                 855                 860
Glu Lys Leu Lys Glu Thr Glu Pro Val Glu Ala Tyr Val Ile Gln Lys
865                 870                 875                 880
Glu Arg Glu Val Thr Lys Gly Pro Ala Glu Ser Pro Asp Glu Gly Ile
                885                 890                 895
Thr Thr Thr Glu Gly Glu Gly Glu Cys Glu Gln Thr Pro Glu Glu Leu
                900                 905                 910
Glu Pro Val Glu Lys Gln Gly Val Asp Asp Ile Glu Lys Phe Glu Asp
                915                 920                 925
```

```
Glu Gly Ala Gly Phe Glu Glu Ser Ser Glu Thr Gly Asp Tyr Glu Glu
    930                 935                 940

Lys Ala Glu Thr Glu Glu Ala Glu Glu Pro Glu Glu Asp Gly Glu Glu
945                 950                 955                 960

His Val Cys Val Ser Ala Ser Lys His Ser Pro Thr Glu Asp Glu Glu
                965                 970                 975

Ser Ala Lys Ala Glu Ala Asp Ala Tyr Ile Arg Glu Lys Arg Glu Ser
            980                 985                 990

Val Ala Ser Gly Asp Asp Arg Ala Glu Glu Asp Met Asp Glu Ala Ile
        995                 1000                1005

Glu Lys Gly Glu Ala Glu Gln Ser Glu Glu Ala Asp Glu Glu
    1010                1015                1020

Asp Lys Ala Glu Asp Ala Arg Glu Glu Glu Tyr Glu Pro Glu Lys
    1025                1030                1035

Met Glu Ala Glu Asp Tyr Val Met Ala Val Val Asp Lys Ala Ala
    1040                1045                1050

Glu Ala Gly Gly Ala Glu Glu Gln Tyr Gly Phe Leu Thr Thr Pro
    1055                1060                1065

Thr Lys Gln Leu Gly Ala Gln Ser Pro Gly Arg Glu Pro Ala Ser
    1070                1075                1080

Ser Ile His Asp Glu Thr Leu Pro Gly Gly Ser Glu Ser Glu Ala
    1085                1090                1095

Thr Ala Ser Asp Glu Glu Asn Arg Glu Asp Gln Pro Glu Glu Phe
    1100                1105                1110

Thr Ala Thr Ser Gly Tyr Thr Gln Ser Thr Ile Glu Ile Ser Ser
    1115                1120                1125

Glu Pro Thr Pro Met Asp Glu Met Ser Thr Pro Arg Asp Val Met
    1130                1135                1140

Ser Asp Glu Thr Asn Asn Glu Glu Thr Glu Ser Pro Ser Gln Glu
    1145                1150                1155

Phe Val Asn Ile Thr Lys Tyr Glu Ser Ser Leu Tyr Ser Gln Glu
    1160                1165                1170

Tyr Ser Lys Pro Ala Asp Val Thr Pro Leu Asn Gly Phe Ser Glu
    1175                1180                1185

Gly Ser Lys Thr Asp Ala Thr Asp Gly Lys Asp Tyr Asn Ala Ser
    1190                1195                1200

Ala Ser Thr Ile Ser Pro Pro Ser Ser Met Glu Glu Asp Lys Phe
    1205                1210                1215

Ser Arg Ser Ala Leu Arg Asp Ala Tyr Cys Ser Glu Val Lys Ala
    1220                1225                1230

Ser Thr Thr Leu Asp Ile Lys Asp Ser Ile Ser Ala Val Ser Ser
    1235                1240                1245

Glu Lys Val Ser Pro Ser Lys Ser Pro Ser Leu Ser Pro Ser Pro
    1250                1255                1260

Pro Ser Pro Leu Glu Lys Thr Pro Leu Gly Glu Arg Ser Val Asn
    1265                1270                1275

Phe Ser Leu Thr Pro Asn Glu Ile Lys Val Ser Ala Glu Ala Glu
    1280                1285                1290

Val Ala Pro Val Ser Pro Glu Val Thr Gln Glu Val Val Glu Glu
    1295                1300                1305

His Cys Ala Ser Pro Glu Asp Lys Thr Leu Glu Val Val Ser Pro
    1310                1315                1320

Ser Gln Ser Val Thr Gly Ser Ala Gly His Thr Pro Tyr Tyr Gln
```

-continued

```
                1325                1330                1335

Ser Pro Thr Asp Glu Lys Ser His Leu Pro Thr Glu Val Ile
    1340                1345                1350

Glu Lys Pro Pro Ala Val Pro Val Ser Phe Glu Phe Ser Asp Ala
    1355                1360                1365

Lys Asp Glu Asn Glu Arg Ala Ser Val Ser Pro Met Asp Glu Pro
    1370                1375                1380

Val Pro Asp Ser Glu Ser Pro Ile Glu Lys Val Leu Ser Pro Leu
    1385                1390                1395

Arg Ser Pro Pro Leu Ile Gly Ser Glu Ser Ala Tyr Glu Ser Phe
    1400                1405                1410

Leu Ser Ala Asp Asp Lys Ala Ser Gly Arg Gly Ala Glu Ser Pro
    1415                1420                1425

Phe Glu Glu Lys Ser Gly Lys Gln Gly Ser Pro Asp Gln Val Ser
    1430                1435                1440

Pro Val Ser Glu Met Thr Ser Thr Ser Leu Tyr Gln Asp Lys Gln
    1445                1450                1455

Glu Gly Lys Ser Thr Asp Phe Ala Pro Ile Lys Glu Asp Phe Gly
    1460                1465                1470

Gln Glu Lys Lys Thr Asp Asp Val Glu Ala Met Ser Ser Gln Pro
    1475                1480                1485

Ala Leu Ala Leu Asp Glu Arg Lys Leu Gly Asp Val Ser Pro Thr
    1490                1495                1500

Gln Ile Asp Val Ser Gln Phe Gly Ser Phe Lys Glu Asp Thr Lys
    1505                1510                1515

Met Ser Ile Ser Glu Gly Thr Val Ser Asp Lys Ser Ala Thr Pro
    1520                1525                1530

Val Asp Glu Gly Val Ala Glu Asp Thr Tyr Ser His Met Glu Gly
    1535                1540                1545

Val Ala Ser Val Ser Thr Ala Ser Val Ala Thr Ser Ser Phe Pro
    1550                1555                1560

Glu Pro Thr Thr Asp Asp Val Ser Pro Ser Leu His Ala Glu Val
    1565                1570                1575

Gly Ser Pro His Ser Thr Glu Val Asp Asp Ser Leu Ser Val Ser
    1580                1585                1590

Val Val Gln Thr Pro Thr Thr Phe Gln Glu Thr Glu Met Ser Pro
    1595                1600                1605

Ser Lys Glu Glu Cys Pro Arg Pro Met Ser Ile Ser Pro Pro Asp
    1610                1615                1620

Phe Ser Pro Lys Thr Ala Lys Ser Arg Thr Pro Val Gln Asp His
    1625                1630                1635

Arg Ser Glu Gln Ser Ser Met Ser Ile Glu Phe Gly Gln Glu Ser
    1640                1645                1650

Pro Glu Gln Ser Leu Ala Met Asp Phe Ser Arg Gln Ser Pro Asp
    1655                1660                1665

His Pro Thr Val Gly Ala Gly Val Leu His Ile Thr Glu Asn Gly
    1670                1675                1680

Pro Thr Glu Val Asp Tyr Ser Pro Ser Asp Met Gln Asp Ser Ser
    1685                1690                1695

Leu Ser His Lys Ile Pro Pro Met Glu Glu Pro Ser Tyr Thr Gln
    1700                1705                1710

Asp Asn Asp Leu Ser Glu Leu Ile Ser Val Ser Gln Val Glu Ala
    1715                1720                1725
```

Ser Pro Ser Thr Ser Ser Ala His Thr Pro Ser Gln Ile Ala Ser
1730                    1735                    1740

Pro Leu Gln Glu Asp Thr Leu Ser Asp Val Ala Pro Pro Arg Asp
1745                    1750                    1755

Met Ser Leu Tyr Ala Ser Leu Thr Ser Glu Lys Val Gln Ser Leu
1760                    1765                    1770

Glu Gly Glu Lys Leu Ser Pro Lys Ser Asp Ile Ser Pro Leu Thr
1775                    1780                    1785

Pro Arg Glu Ser Ser Pro Leu Tyr Ser Pro Thr Phe Ser Asp Ser
1790                    1795                    1800

Thr Ser Ala Val Lys Glu Lys Thr Ala Thr Cys His Ser Ser Ser
1805                    1810                    1815

Ser Pro Pro Ile Asp Ala Ala Ser Ala Glu Pro Tyr Gly Phe Arg
1820                    1825                    1830

Ala Ser Val Leu Phe Asp Thr Met Gln His His Leu Ala Leu Asn
1835                    1840                    1845

Arg Asp Leu Ser Thr Pro Gly Leu Glu Lys Asp Ser Gly Gly Lys
1850                    1855                    1860

Thr Pro Gly Asp Phe Ser Tyr Ala Tyr Gln Lys Pro Glu Glu Thr
1865                    1870                    1875

Thr Arg Ser Pro Asp Glu Glu Asp Tyr Asp Tyr Glu Ser Tyr Glu
1880                    1885                    1890

Lys Thr Thr Arg Thr Ser Asp Val Gly Gly Tyr Tyr Tyr Glu Lys
1895                    1900                    1905

Ile Glu Arg Thr Thr Lys Ser Pro Ser Asp Ser Gly Tyr Ser Tyr
1910                    1915                    1920

Glu Thr Ile Gly Lys Thr Thr Lys Thr Pro Glu Asp Gly Asp Tyr
1925                    1930                    1935

Ser Tyr Glu Ile Ile Glu Lys Thr Thr Arg Thr Pro Glu Glu Gly
1940                    1945                    1950

Gly Tyr Ser Tyr Asp Ile Ser Glu Lys Thr Thr Ser Pro Pro Glu
1955                    1960                    1965

Val Ser Gly Tyr Ser Tyr Glu Lys Thr Glu Arg Ser Arg Arg Leu
1970                    1975                    1980

Leu Asp Asp Ile Ser Asn Gly Tyr Asp Asp Ser Glu Asp Gly Gly
1985                    1990                    1995

His Thr Leu Gly Asp Pro Ser Tyr Ser Tyr Glu Thr Thr Glu Lys
2000                    2005                    2010

Ile Thr Ser Phe Pro Glu Ser Glu Gly Tyr Ser Tyr Glu Thr Ser
2015                    2020                    2025

Thr Lys Thr Thr Arg Thr Pro Asp Thr Ser Thr Tyr Cys Tyr Glu
2030                    2035                    2040

Thr Ala Glu Lys Ile Thr Arg Thr Pro Gln Ala Ser Thr Tyr Ser
2045                    2050                    2055

Tyr Glu Thr Ser Asp Leu Cys Tyr Thr Ala Glu Lys Lys Ser Pro
2060                    2065                    2070

Ser Glu Ala Arg Gln Asp Val Asp Leu Cys Leu Val Ser Ser Cys
2075                    2080                    2085

Glu Tyr Lys His Pro Lys Thr Glu Leu Ser Pro Ser Phe Ile Asn
2090                    2095                    2100

Pro Asn Pro Leu Glu Trp Phe Ala Ser Glu Glu Pro Thr Glu Glu
2105                    2110                    2115

Ser Glu Lys Pro Leu Thr Gln Ser Gly Gly Ala Pro Pro Pro Pro
    2120                2125                2130

Gly Gly Lys Gln Gln Gly Arg Gln Cys Asp Glu Thr Pro Pro Thr
    2135                2140                2145

Ser Val Ser Glu Ser Ala Pro Ser Gln Thr Asp Ser Asp Val Pro
    2150                2155                2160

Pro Glu Thr Glu Glu Cys Pro Ser Ile Thr Ala Asp Ala Asn Ile
    2165                2170                2175

Asp Ser Glu Asp Glu Ser Glu Thr Ile Pro Thr Asp Lys Thr Val
    2180                2185                2190

Thr Tyr Lys His Met Asp Pro Pro Ala Pro Val Gln Asp Arg
    2195                2200                2205

Ser Pro Ser Pro Arg His Pro Asp Val Ser Met Val Asp Pro Glu
    2210                2215                2220

Ala Leu Ala Ile Glu Gln Asn Leu Gly Lys Ala Leu Lys Lys Asp
    2225                2230                2235

Leu Lys Glu Lys Thr Lys Thr Lys Lys Pro Gly Thr Lys Thr Lys
    2240                2245                2250

Ser Ser Ser Pro Val Lys Lys Ser Asp Gly Lys Ser Lys Pro Leu
    2255                2260                2265

Ala Ala Ser Pro Lys Pro Ala Gly Leu Lys Glu Ser Ser Asp Lys
    2270                2275                2280

Val Ser Arg Val Ala Ser Pro Lys Lys Lys Glu Ser Val Glu Lys
    2285                2290                2295

Ala Ala Lys Pro Thr Thr Thr Pro Glu Val Lys Ala Ala Arg Gly
    2300                2305                2310

Glu Glu Lys Asp Lys Glu Thr Lys Asn Ala Ala Asn Ala Ser Ala
    2315                2320                2325

Ser Lys Ser Ala Lys Thr Ala Thr Ala Gly Pro Gly Thr Thr Lys
    2330                2335                2340

Thr Thr Lys Ser Ser Ala Val Pro Pro Gly Leu Pro Val Tyr Leu
    2345                2350                2355

Asp Leu Cys Tyr Ile Pro Asn His Ser Asn Ser Lys Asn Val Asp
    2360                2365                2370

Val Glu Phe Phe Lys Arg Val Arg Ser Ser Tyr Tyr Val Val Ser
    2375                2380                2385

Gly Asn Asp Pro Ala Ala Glu Glu Pro Ser Arg Ala Val Leu Asp
    2390                2395                2400

Ala Leu Leu Glu Gly Lys Ala Gln Trp Gly Ser Asn Met Gln Val
    2405                2410                2415

Thr Leu Ile Pro Thr His Asp Ser Glu Val Met Arg Glu Trp Tyr
    2420                2425                2430

Gln Glu Thr His Glu Lys Gln Gln Asp Leu Asn Ile Met Val Leu
    2435                2440                2445

Ala Ser Ser Ser Thr Val Val Met Gln Asp Glu Ser Phe Pro Ala
    2450                2455                2460

Cys Lys Ile Glu Leu
    2465

<210> SEQ ID NO 27
<211> LENGTH: 2511
<212> TYPE: PRT
<213> ORGANISM: Homo sapiens

<400> SEQUENCE: 27

```
Met Glu Glu Val Val Ile Ala Gly Met Ser Gly Lys Leu Pro Glu Ser
1               5                   10                  15

Glu Asn Leu Gln Glu Phe Trp Asp Asn Leu Ile Gly Gly Val Asp Met
            20                  25                  30

Val Thr Asp Asp Arg Arg Trp Lys Ala Gly Leu Tyr Gly Leu Pro
        35                  40                  45

Arg Arg Ser Gly Lys Leu Lys Asp Leu Ser Arg Phe Asp Ala Ser Phe
    50                  55                  60

Phe Gly Val His Pro Lys Gln Ala His Thr Met Asp Pro Gln Leu Arg
65              70                  75                  80

Leu Leu Leu Glu Val Thr Tyr Glu Ala Ile Val Asp Gly Gly Ile Asn
            85                  90                  95

Pro Asp Ser Leu Arg Gly Thr His Thr Gly Val Trp Val Gly Val Ser
            100                 105                 110

Gly Ser Glu Thr Ser Glu Ala Leu Ser Arg Asp Pro Glu Thr Leu Val
        115                 120                 125

Gly Tyr Ser Met Val Gly Cys Gln Arg Ala Met Met Ala Asn Arg Leu
        130                 135                 140

Ser Phe Phe Phe Asp Phe Arg Gly Pro Ser Ile Ala Leu Asp Thr Ala
145                 150                 155                 160

Cys Ser Ser Ser Leu Met Ala Leu Gln Asn Ala Tyr Gln Ala Ile His
                165                 170                 175

Ser Gly Gln Cys Pro Ala Ala Ile Val Gly Gly Ile Asn Val Leu Leu
            180                 185                 190

Lys Pro Asn Thr Ser Val Gln Phe Leu Arg Leu Gly Met Leu Ser Pro
            195                 200                 205

Glu Gly Thr Cys Lys Ala Phe Asp Thr Ala Gly Asn Gly Tyr Cys Arg
            210                 215                 220

Ser Glu Gly Val Val Ala Val Leu Leu Thr Lys Lys Ser Leu Ala Arg
225                 230                 235                 240

Arg Val Tyr Ala Thr Ile Leu Asn Ala Gly Thr Asn Thr Asp Gly Phe
                245                 250                 255

Lys Glu Gln Gly Val Thr Phe Pro Ser Gly Asp Ile Gln Glu Gln Leu
            260                 265                 270

Ile Arg Ser Leu Tyr Gln Ser Ala Gly Val Ala Pro Glu Ser Phe Glu
        275                 280                 285

Tyr Ile Glu Ala His Gly Thr Gly Thr Lys Val Gly Asp Pro Gln Glu
        290                 295                 300

Leu Asn Gly Ile Thr Arg Ala Leu Cys Ala Thr Arg Gln Glu Pro Leu
305                 310                 315                 320

Leu Ile Gly Ser Thr Lys Ser Asn Met Gly His Pro Glu Pro Ala Ser
            325                 330                 335

Gly Leu Ala Ala Leu Ala Lys Val Leu Leu Ser Leu Glu His Gly Leu
            340                 345                 350

Trp Ala Pro Asn Leu His Phe His Ser Pro Asn Pro Glu Ile Pro Ala
            355                 360                 365

Leu Leu Asp Gly Arg Leu Gln Val Val Asp Gln Pro Leu Pro Val Arg
    370                 375                 380

Gly Gly Asn Val Gly Ile Asn Ser Phe Gly Phe Gly Gly Ser Asn Val
385                 390                 395                 400

His Ile Ile Leu Arg Pro Asn Thr Gln Pro Pro Ala Pro Ala Pro
                405                 410                 415
```

```
His Ala Thr Leu Pro Arg Leu Leu Arg Ala Ser Gly Arg Thr Pro Glu
            420                 425                 430

Ala Val Gln Lys Leu Leu Glu Gln Gly Leu Arg His Ser Gln Asp Leu
            435                 440                 445

Ala Phe Leu Ser Met Leu Asn Asp Ile Ala Ala Val Pro Ala Thr Ala
            450                 455                 460

Met Pro Phe Arg Gly Tyr Ala Val Leu Gly Gly Glu Arg Gly Gly Pro
465                 470                 475                 480

Glu Val Gln Gln Val Pro Ala Gly Glu Arg Pro Leu Trp Phe Ile Cys
            485                 490                 495

Ser Gly Met Gly Thr Gln Trp Arg Gly Met Gly Leu Ser Leu Met Arg
            500                 505                 510

Leu Asp Arg Phe Arg Asp Ser Ile Leu Arg Ser Asp Glu Ala Val Lys
            515                 520                 525

Pro Phe Gly Leu Lys Val Ser Gln Leu Leu Leu Ser Thr Asp Glu Ser
            530                 535                 540

Thr Phe Asp Asp Ile Val His Ser Phe Val Ser Leu Thr Ala Ile Gln
545                 550                 555                 560

Ile Gly Leu Ile Asp Leu Leu Ser Cys Met Gly Leu Arg Pro Asp Gly
            565                 570                 575

Ile Val Gly His Ser Leu Gly Glu Val Ala Cys Gly Tyr Ala Asp Gly
            580                 585                 590

Cys Leu Ser Gln Glu Glu Ala Val Leu Ala Ala Tyr Trp Arg Gly Gln
            595                 600                 605

Cys Ile Lys Glu Ala His Leu Pro Pro Gly Ala Met Ala Ala Val Gly
            610                 615                 620

Leu Ser Trp Glu Glu Cys Lys Gln Arg Cys Pro Pro Gly Val Val Pro
625                 630                 635                 640

Ala Cys His Asn Ser Lys Asp Thr Val Thr Ile Ser Gly Pro Gln Ala
            645                 650                 655

Pro Val Phe Glu Phe Val Glu Gln Leu Arg Lys Glu Gly Val Phe Ala
            660                 665                 670

Lys Glu Val Arg Thr Gly Gly Met Ala Phe His Ser Tyr Phe Met Glu
            675                 680                 685

Ala Ile Ala Pro Pro Leu Leu Gln Glu Leu Lys Lys Val Ile Arg Glu
            690                 695                 700

Pro Lys Pro Arg Ser Ala Arg Trp Leu Ser Thr Ser Ile Pro Glu Ala
705                 710                 715                 720

Gln Trp His Ser Ser Leu Ala Arg Thr Ser Ser Ala Glu Tyr Asn Val
            725                 730                 735

Asn Asn Leu Val Ser Pro Val Leu Phe Gln Glu Ala Leu Trp His Val
            740                 745                 750

Pro Glu His Ala Val Val Leu Glu Ile Ala Pro His Ala Leu Leu Gln
            755                 760                 765

Ala Val Leu Lys Arg Gly Leu Lys Pro Ser Cys Thr Ile Ile Pro Leu
            770                 775                 780

Met Lys Lys Asp His Arg Asp Asn Leu Glu Phe Phe Leu Ala Gly Ile
785                 790                 795                 800

Gly Arg Leu His Leu Ser Gly Ile Asp Ala Asn Pro Asn Ala Leu Phe
            805                 810                 815

Pro Pro Val Glu Phe Pro Ala Pro Arg Gly Thr Pro Leu Ile Ser Pro
            820                 825                 830

Leu Ile Lys Trp Asp His Ser Leu Ala Trp Asp Val Pro Ala Ala Glu
```

-continued

```
                835                 840                 845
Asp Phe Pro Asn Gly Ser Gly Ser Pro Ser Ala Ala Ile Tyr Asn Ile
    850                 855                 860
Asp Thr Ser Ser Glu Ser Pro Asp His Tyr Leu Val Asp His Thr Leu
865                 870                 875                 880
Asp Gly Arg Val Leu Phe Pro Ala Thr Gly Tyr Leu Ser Ile Val Trp
                885                 890                 895
Lys Thr Leu Ala Arg Ala Leu Gly Leu Gly Val Glu Gln Leu Pro Val
            900                 905                 910
Val Phe Glu Asp Val Val Leu His Gln Ala Thr Ile Leu Pro Lys Thr
        915                 920                 925
Gly Thr Val Ser Leu Glu Val Arg Leu Leu Glu Ala Ser Arg Ala Phe
930                 935                 940
Glu Val Ser Glu Asn Gly Asn Leu Val Val Ser Gly Lys Val Tyr Gln
945                 950                 955                 960
Trp Asp Asp Pro Asp Pro Arg Leu Phe Asp His Pro Glu Ser Pro Thr
                965                 970                 975
Pro Asn Pro Thr Glu Pro Leu Phe Leu Ala Gln Ala Glu Val Tyr Lys
            980                 985                 990
Glu Leu Arg Leu Arg Gly Tyr Asp Tyr Gly Pro His Phe Gln Gly Ile
                995                1000                1005
Leu Glu Ala Ser Leu Glu Gly Asp Ser Gly Arg Leu Leu Trp Lys
           1010                1015                1020
Asp Asn Trp Val Ser Phe Met Asp Thr Met Leu Gln Met Ser Ile
           1025                1030                1035
Leu Gly Ser Ala Lys His Gly Leu Tyr Leu Pro Thr Arg Val Thr
           1040                1045                1050
Ala Ile His Ile Asp Pro Ala Thr His Arg Gln Lys Leu Tyr Thr
           1055                1060                1065
Leu Gln Asp Lys Ala Gln Val Ala Asp Val Val Ser Arg Trp
           1070                1075                1080
Leu Arg Val Thr Val Ala Gly Gly Val His Ile Ser Gly Leu His
           1085                1090                1095
Thr Glu Ser Ala Pro Arg Arg Gln Gln Glu Gln Gln Val Pro Ile
           1100                1105                1110
Leu Glu Lys Phe Cys Phe Thr Pro His Thr Glu Glu Gly Cys Leu
           1115                1120                1125
Ser Glu Arg Ala Ala Leu Gln Glu Glu Leu Gln Leu Cys Lys Gly
           1130                1135                1140
Leu Val Gln Ala Leu Gln Thr Lys Val Thr Gln Gln Gly Leu Lys
           1145                1150                1155
Met Val Val Pro Gly Leu Asp Gly Ala Gln Ile Pro Arg Asp Pro
           1160                1165                1170
Ser Gln Gln Glu Leu Pro Arg Leu Leu Ser Ala Ala Cys Arg Leu
           1175                1180                1185
Gln Leu Asn Gly Asn Leu Gln Leu Glu Leu Ala Gln Val Leu Ala
           1190                1195                1200
Gln Glu Arg Pro Lys Leu Pro Glu Asp Pro Leu Leu Ser Gly Leu
           1205                1210                1215
Leu Asp Ser Pro Ala Leu Lys Ala Cys Leu Asp Thr Ala Val Glu
           1220                1225                1230
Asn Met Pro Ser Leu Lys Met Lys Val Val Glu Val Leu Ala Gly
           1235                1240                1245
```

His Gly His Leu Tyr Ser Arg Ile Pro Gly Leu Leu Ser Pro His
1250                1255                1260

Pro Leu Leu Gln Leu Ser Tyr Thr Ala Thr Asp Arg His Pro Gln
1265                1270                1275

Ala Leu Glu Ala Ala Gln Ala Glu Leu Gln Gln His Asp Val Ala
1280                1285                1290

Gln Gly Gln Trp Asp Pro Ala Asp Pro Ala Pro Ser Ala Leu Gly
1295                1300                1305

Ser Ala Asp Leu Leu Val Cys Asn Cys Ala Val Ala Ala Leu Gly
1310                1315                1320

Asp Pro Ala Ser Ala Leu Ser Asn Met Val Ala Ala Leu Arg Glu
1325                1330                1335

Gly Gly Phe Leu Leu Leu His Thr Leu Leu Arg Gly His Pro Leu
1340                1345                1350

Gly Asp Ile Val Ala Phe Leu Thr Ser Thr Glu Pro Gln Tyr Gly
1355                1360                1365

Gln Gly Ile Leu Ser Gln Asp Ala Trp Glu Ser Leu Phe Ser Arg
1370                1375                1380

Val Ser Leu Arg Leu Val Gly Leu Lys Lys Ser Phe Tyr Gly Ser
1385                1390                1395

Thr Leu Phe Leu Cys Arg Arg Pro Thr Pro Gln Asp Ser Pro Ile
1400                1405                1410

Phe Leu Pro Val Asp Asp Thr Ser Phe Arg Trp Val Glu Ser Leu
1415                1420                1425

Lys Gly Ile Leu Ala Asp Glu Asp Ser Ser Arg Pro Val Trp Leu
1430                1435                1440

Lys Ala Ile Asn Cys Ala Thr Ser Gly Val Val Gly Leu Val Asn
1445                1450                1455

Cys Leu Arg Arg Glu Pro Gly Gly Asn Arg Leu Arg Cys Val Leu
1460                1465                1470

Leu Ser Asn Leu Ser Ser Thr Ser His Val Pro Glu Val Asp Pro
1475                1480                1485

Gly Ser Ala Glu Leu Gln Lys Val Leu Gln Gly Asp Leu Val Met
1490                1495                1500

Asn Val Tyr Arg Asp Gly Ala Trp Gly Ala Phe Arg His Phe Leu
1505                1510                1515

Leu Glu Glu Asp Lys Pro Glu Glu Pro Thr Ala His Ala Phe Val
1520                1525                1530

Ser Thr Leu Thr Arg Gly Asp Leu Ser Ser Ile Arg Trp Val Cys
1535                1540                1545

Ser Ser Leu Arg His Ala Gln Pro Thr Cys Pro Gly Ala Gln Leu
1550                1555                1560

Cys Thr Val Tyr Tyr Ala Ser Leu Asn Phe Arg Asp Ile Met Leu
1565                1570                1575

Ala Thr Gly Lys Leu Ser Pro Asp Ala Ile Pro Gly Lys Trp Thr
1580                1585                1590

Ser Gln Asp Ser Leu Leu Gly Met Glu Phe Ser Gly Arg Asp Ala
1595                1600                1605

Ser Gly Lys Arg Val Met Gly Leu Val Pro Ala Lys Gly Leu Ala
1610                1615                1620

Thr Ser Val Leu Leu Ser Pro Asp Phe Leu Trp Asp Val Pro Ser
1625                1630                1635

```
Asn Trp Thr Leu Glu Glu Ala Ala Ser Val Pro Val Val Tyr Ser
1640                1645                1650

Thr Ala Tyr Tyr Ala Leu Val Val Arg Gly Arg Val Arg Pro Gly
1655                1660                1665

Glu Thr Leu Leu Ile His Ser Gly Ser Gly Gly Val Gly Gln Ala
1670                1675                1680

Ala Ile Ala Ile Ala Leu Ser Leu Gly Cys Arg Val Phe Thr Thr
1685                1690                1695

Val Gly Ser Ala Glu Lys Arg Ala Tyr Leu Gln Ala Arg Phe Pro
1700                1705                1710

Gln Leu Asp Ser Thr Ser Phe Ala Asn Ser Arg Asp Thr Ser Phe
1715                1720                1725

Glu Gln His Val Leu Trp His Thr Gly Gly Lys Gly Val Asp Leu
1730                1735                1740

Val Leu Asn Ser Leu Ala Glu Glu Lys Leu Gln Ala Ser Val Arg
1745                1750                1755

Cys Leu Ala Thr His Gly Arg Phe Leu Glu Ile Gly Lys Phe Asp
1760                1765                1770

Leu Ser Gln Asn His Pro Leu Gly Met Ala Ile Phe Leu Lys Asn
1775                1780                1785

Val Thr Phe His Gly Val Leu Leu Asp Ala Phe Phe Asn Glu Ser
1790                1795                1800

Ser Ala Asp Trp Arg Glu Val Trp Ala Leu Val Gln Ala Gly Ile
1805                1810                1815

Arg Asp Gly Val Val Arg Pro Leu Lys Cys Thr Val Phe His Gly
1820                1825                1830

Ala Gln Val Glu Asp Ala Phe Arg Tyr Met Ala Gln Gly Lys His
1835                1840                1845

Ile Gly Lys Val Val Val Gln Val Leu Ala Glu Glu Pro Glu Ala
1850                1855                1860

Val Leu Lys Gly Ala Lys Pro Lys Leu Met Ser Ala Ile Ser Lys
1865                1870                1875

Thr Phe Cys Pro Ala His Lys Ser Tyr Ile Ile Ala Gly Gly Leu
1880                1885                1890

Gly Gly Phe Gly Leu Glu Leu Ala Gln Trp Leu Ile Gln Arg Gly
1895                1900                1905

Val Gln Lys Leu Val Leu Thr Ser Arg Ser Gly Ile Arg Thr Gly
1910                1915                1920

Tyr Gln Ala Lys Gln Val Arg Arg Trp Arg Arg Gln Gly Val Gln
1925                1930                1935

Val Gln Val Ser Thr Ser Asn Ile Ser Ser Leu Glu Gly Ala Arg
1940                1945                1950

Gly Leu Ile Ala Glu Ala Ala Gln Leu Gly Pro Val Gly Gly Val
1955                1960                1965

Phe Asn Leu Ala Val Val Leu Arg Asp Gly Leu Leu Glu Asn Gln
1970                1975                1980

Thr Pro Glu Phe Phe Gln Asp Val Cys Lys Pro Lys Tyr Ser Gly
1985                1990                1995

Thr Leu Asn Leu Asp Arg Val Thr Arg Glu Ala Cys Pro Glu Leu
2000                2005                2010

Asp Tyr Phe Val Val Phe Ser Ser Val Ser Cys Gly Arg Gly Asn
2015                2020                2025

Ala Gly Gln Ser Asn Tyr Gly Phe Ala Asn Ser Ala Met Glu Arg
```

```
            2030                2035                2040
Ile Cys Glu Lys Arg Arg His Glu Gly Leu Pro Gly Leu Ala Val
    2045                2050                2055

Gln Trp Gly Ala Ile Gly Asp Val Gly Ile Leu Val Glu Thr Met
    2060                2065                2070

Ser Thr Asn Asp Thr Ile Val Ser Gly Thr Leu Pro Gln Arg Met
    2075                2080                2085

Ala Ser Cys Leu Glu Val Leu Asp Leu Phe Leu Asn Gln Pro His
    2090                2095                2100

Met Val Leu Ser Ser Phe Val Leu Ala Glu Lys Ala Ala Ala Tyr
    2105                2110                2115

Arg Asp Arg Asp Ser Gln Arg Asp Leu Val Glu Ala Val Ala His
    2120                2125                2130

Ile Leu Gly Ile Arg Asp Leu Ala Ala Val Asn Leu Asp Ser Ser
    2135                2140                2145

Leu Ala Asp Leu Gly Leu Asp Ser Leu Met Ser Val Glu Val Arg
    2150                2155                2160

Gln Thr Leu Glu Arg Glu Leu Asn Leu Val Leu Ser Val Arg Glu
    2165                2170                2175

Val Arg Gln Leu Thr Leu Arg Lys Leu Gln Glu Leu Ser Ser Lys
    2180                2185                2190

Ala Asp Glu Ala Ser Glu Leu Ala Cys Pro Thr Pro Lys Glu Asp
    2195                2200                2205

Gly Leu Ala Gln Gln Gln Thr Gln Leu Asn Leu Arg Ser Leu Leu
    2210                2215                2220

Val Asn Pro Glu Gly Pro Thr Leu Met Arg Leu Asn Ser Val Gln
    2225                2230                2235

Ser Ser Glu Arg Pro Leu Phe Leu Val His Pro Ile Glu Gly Ser
    2240                2245                2250

Thr Thr Val Phe His Ser Leu Ala Ser Arg Leu Ser Ile Pro Thr
    2255                2260                2265

Tyr Gly Leu Gln Cys Thr Arg Ala Ala Pro Leu Asp Ser Ile His
    2270                2275                2280

Ser Leu Ala Ala Tyr Tyr Ile Asp Cys Ile Arg Gln Val Gln Pro
    2285                2290                2295

Glu Gly Pro Tyr Arg Val Ala Gly Tyr Ser Tyr Gly Ala Cys Val
    2300                2305                2310

Ala Phe Glu Met Cys Ser Gln Leu Gln Ala Gln Ser Pro Ala
    2315                2320                2325

Pro Thr His Asn Ser Leu Phe Leu Phe Asp Gly Ser Pro Thr Tyr
    2330                2335                2340

Val Leu Ala Tyr Thr Gln Ser Tyr Arg Ala Lys Leu Thr Pro Gly
    2345                2350                2355

Cys Glu Ala Glu Ala Glu Thr Glu Ala Ile Cys Phe Phe Val Gln
    2360                2365                2370

Gln Phe Thr Asp Met Glu His Asn Arg Val Leu Glu Ala Leu Leu
    2375                2380                2385

Pro Leu Lys Gly Leu Glu Glu Arg Val Ala Ala Ala Val Asp Leu
    2390                2395                2400

Ile Ile Lys Ser His Gln Gly Leu Asp Arg Gln Glu Leu Ser Phe
    2405                2410                2415

Ala Ala Arg Ser Phe Tyr Tyr Lys Leu Arg Ala Ala Glu Gln Tyr
    2420                2425                2430
```

```
Thr Pro Lys Ala Lys Tyr His Gly Asn Val Met Leu Leu Arg Ala
    2435            2440                2445

Lys Thr Gly Gly Ala Tyr Gly Glu Asp Leu Gly Ala Asp Tyr Asn
    2450            2455                2460

Leu Ser Gln Val Cys Asp Gly Lys Val Ser Val His Val Ile Glu
    2465            2470                2475

Gly Asp His Arg Thr Leu Leu Glu Gly Ser Gly Leu Glu Ser Ile
    2480            2485                2490

Ile Ser Ile Ile His Ser Ser Leu Ala Glu Pro Arg Val Ser Val
    2495            2500                2505

Arg Glu Gly
    2510

<210> SEQ ID NO 28
<211> LENGTH: 286
<212> TYPE: PRT
<213> ORGANISM: Homo sapiens

<400> SEQUENCE: 28

Met Ala Glu Asp Gly Glu Ala Glu Phe His Phe Ala Ala Leu Tyr
1               5                   10                  15

Ile Ser Gly Gln Trp Pro Arg Leu Arg Ala Asp Thr Asp Leu Gln Arg
                20                  25                  30

Leu Gly Ser Ser Ala Met Ala Pro Ser Arg Lys Phe Val Gly Gly
            35                  40                  45

Asn Trp Lys Met Asn Gly Arg Lys Gln Ser Leu Gly Glu Leu Ile Gly
    50                  55                  60

Thr Leu Asn Ala Ala Lys Val Pro Ala Asp Thr Glu Val Val Cys Ala
65                  70                  75                  80

Pro Pro Thr Ala Tyr Ile Asp Phe Ala Arg Gln Lys Leu Asp Pro Lys
                85                  90                  95

Ile Ala Val Ala Ala Gln Asn Cys Tyr Lys Val Thr Asn Gly Ala Phe
            100                 105                 110

Thr Gly Glu Ile Ser Pro Gly Met Ile Lys Asp Cys Gly Ala Thr Trp
        115                 120                 125

Val Val Leu Gly His Ser Glu Arg Arg His Val Phe Gly Glu Ser Asp
    130                 135                 140

Glu Leu Ile Gly Gln Lys Val Ala His Ala Leu Ala Glu Gly Leu Gly
145                 150                 155                 160

Val Ile Ala Cys Ile Gly Glu Lys Leu Asp Glu Arg Glu Ala Gly Ile
                165                 170                 175

Thr Glu Lys Val Val Phe Glu Gln Thr Lys Val Ile Ala Asp Asn Val
            180                 185                 190

Lys Asp Trp Ser Lys Val Val Leu Ala Tyr Glu Pro Val Trp Ala Ile
        195                 200                 205

Gly Thr Gly Lys Thr Ala Thr Pro Gln Gln Ala Gln Glu Val His Glu
    210                 215                 220

Lys Leu Arg Gly Trp Leu Lys Ser Asn Val Ser Asp Ala Val Ala Gln
225                 230                 235                 240

Ser Thr Arg Ile Ile Tyr Gly Gly Ser Val Thr Gly Ala Thr Cys Lys
                245                 250                 255

Glu Leu Ala Ser Gln Pro Asp Val Asp Gly Phe Leu Val Gly Gly Ala
            260                 265                 270

Ser Leu Lys Pro Glu Phe Val Asp Ile Ile Asn Ala Lys Gln
```

275              280              285

<210> SEQ ID NO 29
<211> LENGTH: 1101
<212> TYPE: PRT
<213> ORGANISM: Homo sapiens

<400> SEQUENCE: 29

Met Ser Ala Lys Ala Ile Ser Glu Gln Thr Gly Lys Glu Leu Leu Tyr
1               5                   10                  15

Lys Phe Ile Cys Thr Thr Ser Ala Ile Gln Asn Arg Phe Lys Tyr Ala
            20                  25                  30

Arg Val Thr Pro Asp Thr Asp Trp Ala Arg Leu Leu Gln Asp His Pro
        35                  40                  45

Trp Leu Leu Ser Gln Asn Leu Val Val Lys Pro Asp Gln Leu Ile Lys
    50                  55                  60

Arg Arg Gly Lys Leu Gly Leu Val Gly Val Asn Leu Thr Leu Asp Gly
65                  70                  75                  80

Val Lys Ser Trp Leu Lys Pro Arg Leu Gly Gln Glu Ala Thr Val Gly
                85                  90                  95

Lys Ala Thr Gly Phe Leu Lys Asn Phe Leu Ile Glu Pro Phe Val Pro
            100                 105                 110

His Ser Gln Ala Glu Glu Phe Tyr Val Cys Ile Tyr Ala Thr Arg Glu
        115                 120                 125

Gly Asp Tyr Val Leu Phe His His Glu Gly Gly Val Asp Val Gly Asp
130                 135                 140

Val Asp Ala Lys Ala Gln Lys Leu Leu Val Gly Val Asp Glu Lys Leu
145                 150                 155                 160

Asn Pro Glu Asp Ile Lys Lys His Leu Leu Val His Ala Pro Glu Asp
                165                 170                 175

Lys Lys Glu Ile Leu Ala Ser Phe Ile Ser Gly Leu Phe Asn Phe Tyr
            180                 185                 190

Glu Asp Leu Tyr Phe Thr Tyr Leu Glu Ile Asn Pro Leu Val Val Thr
        195                 200                 205

Lys Asp Gly Val Tyr Val Leu Asp Leu Ala Ala Lys Val Asp Ala Thr
    210                 215                 220

Ala Asp Tyr Ile Cys Lys Val Lys Trp Gly Asp Ile Glu Phe Pro Pro
225                 230                 235                 240

Pro Phe Gly Arg Glu Ala Tyr Pro Glu Glu Ala Tyr Ile Ala Asp Leu
                245                 250                 255

Asp Ala Lys Ser Gly Ala Ser Leu Lys Leu Thr Leu Leu Asn Pro Lys
            260                 265                 270

Gly Arg Ile Trp Thr Met Val Ala Gly Gly Ala Ser Val Val Tyr
        275                 280                 285

Ser Asp Thr Ile Cys Asp Leu Gly Gly Val Asn Glu Leu Ala Asn Tyr
    290                 295                 300

Gly Glu Tyr Ser Gly Ala Pro Ser Glu Gln Gln Thr Tyr Asp Tyr Ala
305                 310                 315                 320

Lys Thr Ile Leu Ser Leu Met Thr Arg Glu Lys His Pro Asp Gly Lys
                325                 330                 335

Ile Leu Ile Ile Gly Gly Ser Ile Ala Asn Phe Thr Asn Val Ala Ala
            340                 345                 350

Thr Phe Lys Gly Ile Val Arg Ala Ile Arg Asp Tyr Gln Gly Pro Leu
        355                 360                 365

```
Lys Glu His Glu Val Thr Ile Phe Val Arg Arg Gly Pro Asn Tyr
370                 375                 380

Gln Glu Gly Leu Arg Val Met Gly Glu Val Gly Lys Thr Thr Gly Ile
385                 390                 395                 400

Pro Ile His Val Phe Gly Thr Glu Thr His Met Thr Ala Ile Val Gly
                405                 410                 415

Met Ala Leu Gly His Arg Pro Ile Pro Asn Gln Pro Pro Thr Ala Ala
                420                 425                 430

His Thr Ala Asn Phe Leu Leu Asn Ala Ser Gly Ser Thr Ser Thr Pro
                435                 440                 445

Ala Pro Ser Arg Thr Ala Ser Phe Ser Glu Ser Arg Ala Asp Glu Val
450                 455                 460

Ala Pro Ala Lys Lys Ala Lys Pro Ala Met Pro Gln Asp Ser Val Pro
465                 470                 475                 480

Ser Pro Arg Ser Leu Gln Gly Lys Ser Thr Thr Leu Phe Ser Arg His
                485                 490                 495

Thr Lys Ala Ile Val Trp Gly Met Gln Thr Arg Ala Val Gln Gly Met
                500                 505                 510

Leu Asp Phe Asp Tyr Val Cys Ser Arg Asp Glu Pro Ser Val Ala Ala
                515                 520                 525

Met Val Tyr Pro Phe Thr Gly Asp His Lys Gln Lys Phe Tyr Trp Gly
                530                 535                 540

His Lys Glu Ile Leu Ile Pro Val Phe Lys Asn Met Ala Asp Ala Met
545                 550                 555                 560

Arg Lys His Pro Glu Val Asp Val Leu Ile Asn Phe Ala Ser Leu Arg
                565                 570                 575

Ser Ala Tyr Asp Ser Thr Met Glu Thr Met Asn Tyr Ala Gln Ile Arg
                580                 585                 590

Thr Ile Ala Ile Ile Ala Glu Gly Ile Pro Glu Ala Leu Thr Arg Lys
                595                 600                 605

Leu Ile Lys Lys Ala Asp Gln Lys Gly Val Thr Ile Ile Gly Pro Ala
610                 615                 620

Thr Val Gly Gly Ile Lys Pro Gly Cys Phe Lys Ile Gly Asn Thr Gly
625                 630                 635                 640

Gly Met Leu Asp Asn Ile Leu Ala Ser Lys Leu Tyr Arg Pro Gly Ser
                645                 650                 655

Val Ala Tyr Val Ser Arg Ser Gly Gly Met Ser Asn Glu Leu Asn Asn
                660                 665                 670

Ile Ile Ser Arg Thr Thr Asp Gly Val Tyr Glu Gly Val Ala Ile Gly
                675                 680                 685

Gly Asp Arg Tyr Pro Gly Ser Thr Phe Met Asp His Val Leu Arg Tyr
690                 695                 700

Gln Asp Thr Pro Gly Val Lys Met Ile Val Val Leu Gly Glu Ile Gly
705                 710                 715                 720

Gly Thr Glu Glu Tyr Lys Ile Cys Arg Gly Ile Lys Glu Gly Arg Leu
                725                 730                 735

Thr Lys Pro Ile Val Cys Trp Cys Ile Gly Thr Cys Ala Thr Met Phe
                740                 745                 750

Ser Ser Glu Val Gln Phe Gly His Ala Gly Ala Cys Ala Asn Gln Ala
                755                 760                 765

Ser Glu Thr Ala Val Ala Lys Asn Gln Ala Leu Lys Glu Ala Gly Val
770                 775                 780

Phe Val Pro Arg Ser Phe Asp Glu Leu Gly Glu Ile Ile Gln Ser Val
```

```
                785                 790                 795                 800
Tyr Glu Asp Leu Val Ala Asn Gly Val Ile Val Pro Ala Gln Glu Val
                    805                 810                 815

Pro Pro Pro Thr Val Pro Met Asp Tyr Ser Trp Ala Arg Glu Leu Gly
                820                 825                 830

Leu Ile Arg Lys Pro Ala Ser Phe Met Thr Ser Ile Cys Asp Glu Arg
                835                 840                 845

Gly Gln Glu Leu Ile Tyr Ala Gly Met Pro Ile Thr Glu Val Phe Lys
                850                 855                 860

Glu Glu Met Gly Ile Gly Gly Val Leu Gly Leu Leu Trp Phe Gln Lys
865                 870                 875                 880

Arg Leu Pro Lys Tyr Ser Cys Gln Phe Ile Glu Met Cys Leu Met Val
                885                 890                 895

Thr Ala Asp His Gly Pro Ala Val Ser Gly Ala His Asn Thr Ile Ile
                900                 905                 910

Cys Ala Arg Ala Gly Lys Asp Leu Val Ser Ser Leu Thr Ser Gly Leu
                915                 920                 925

Leu Thr Ile Gly Asp Arg Phe Gly Gly Ala Leu Asp Ala Ala Ala Lys
                930                 935                 940

Met Phe Ser Lys Ala Phe Asp Ser Gly Ile Ile Pro Met Glu Phe Val
945                 950                 955                 960

Asn Lys Met Lys Lys Glu Gly Lys Leu Ile Met Gly Ile Gly His Arg
                965                 970                 975

Val Lys Ser Ile Asn Asn Pro Asp Met Arg Val Gln Ile Leu Lys Asp
                980                 985                 990

Tyr Val Arg Gln His Phe Pro Ala Thr Pro Leu Leu Asp Tyr Ala Leu
                995                 1000                1005

Glu Val Glu Lys Ile Thr Thr Ser Lys Lys Pro Asn Leu Ile Leu
        1010                1015                1020

Asn Val Asp Gly Leu Ile Gly Val Ala Phe Val Asp Met Leu Arg
        1025                1030                1035

Asn Cys Gly Ser Phe Thr Arg Glu Glu Ala Asp Glu Tyr Ile Asp
        1040                1045                1050

Ile Gly Ala Leu Asn Gly Ile Phe Val Leu Gly Arg Ser Met Gly
        1055                1060                1065

Phe Ile Gly His Tyr Leu Asp Gln Lys Arg Leu Lys Gln Gly Leu
        1070                1075                1080

Tyr Arg His Pro Trp Asp Asp Ile Ser Tyr Val Leu Pro Glu His
        1085                1090                1095

Met Ser Met
        1100

<210> SEQ ID NO 30
<211> LENGTH: 417
<212> TYPE: PRT
<213> ORGANISM: Homo sapiens

<400> SEQUENCE: 30

Met Leu Leu Ser Val Pro Leu Leu Leu Gly Leu Leu Gly Leu Ala Val
1               5                   10                  15

Ala Glu Pro Ala Val Tyr Phe Lys Glu Gln Phe Leu Asp Gly Asp Gly
                20                  25                  30

Trp Thr Ser Arg Trp Ile Glu Ser Lys His Lys Ser Asp Phe Gly Lys
            35                  40                  45
```

```
Phe Val Leu Ser Ser Gly Lys Phe Tyr Gly Asp Glu Lys Asp Lys
     50                  55                  60

Gly Leu Gln Thr Ser Gln Asp Ala Arg Phe Tyr Ala Leu Ser Ala Ser
 65                  70                  75                  80

Phe Glu Pro Phe Ser Asn Lys Gly Gln Thr Leu Val Val Gln Phe Thr
                 85                  90                  95

Val Lys His Glu Gln Asn Ile Asp Cys Gly Gly Tyr Val Lys Leu
            100                 105                 110

Phe Pro Asn Ser Leu Asp Gln Thr Asp Met His Gly Asp Ser Glu Tyr
            115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Ala Glu Asp
370                 375                 380

Lys Glu Asp Asp Glu Asp Lys Asp Glu Asp Glu Glu Asp Glu Glu Asp
385                 390                 395                 400

Lys Glu Glu Asp Glu Glu Glu Asp Val Pro Gly Gln Ala Lys Asp Glu
                405                 410                 415

Leu
```

<210> SEQ ID NO 31
<211> LENGTH: 1268
<212> TYPE: PRT
<213> ORGANISM: Homo sapiens

<400> SEQUENCE: 31

-continued

```
Met Ser Ser Val Ala Val Leu Thr Gln Glu Ser Phe Ala Glu His Arg
1               5                   10                  15

Ser Gly Leu Val Pro Gln Gln Ile Lys Val Ala Thr Leu Asn Ser Glu
            20                  25                  30

Glu Glu Ser Asp Pro Pro Thr Tyr Lys Asp Ala Phe Pro Pro Leu Pro
        35                  40                  45

Glu Lys Ala Ala Cys Leu Glu Ser Ala Gln Glu Pro Ser Gly Ala Trp
50                  55                  60

Gly Asn Lys Ile Arg Pro Ile Lys Ala Ser Val Ile Thr Gln Val Phe
65                  70                  75                  80

His Val Pro Leu Glu Glu Arg Lys Tyr Lys Asp Met Asn Gln Phe Gly
                85                  90                  95

Glu Gly Glu Gln Ala Lys Ile Cys Leu Glu Ile Met Gln Arg Thr Gly
            100                 105                 110

Ala His Leu Glu Leu Ser Leu Ala Lys Asp Gln Gly Leu Ser Ile Met
        115                 120                 125

Val Ser Gly Lys Leu Asp Ala Val Met Lys Ala Arg Lys Asp Ile Val
    130                 135                 140

Ala Arg Leu Gln Thr Gln Ala Ser Ala Thr Val Ala Ile Pro Lys Glu
145                 150                 155                 160

His His Arg Phe Val Ile Gly Lys Asn Gly Glu Lys Leu Gln Asp Leu
                165                 170                 175

Glu Leu Lys Thr Ala Thr Lys Ile Gln Ile Pro Arg Pro Asp Asp Pro
            180                 185                 190

Ser Asn Gln Ile Lys Ile Thr Gly Thr Lys Glu Gly Ile Glu Lys Ala
        195                 200                 205

Arg His Glu Val Leu Leu Ile Ser Ala Glu Gln Asp Lys Arg Ala Val
    210                 215                 220

Glu Arg Leu Glu Val Glu Lys Ala Phe His Pro Phe Ile Ala Gly Pro
225                 230                 235                 240

Tyr Asn Arg Leu Val Gly Glu Ile Met Gln Glu Thr Gly Thr Arg Ile
                245                 250                 255

Asn Ile Pro Pro Pro Ser Val Asn Arg Thr Glu Ile Val Phe Thr Gly
            260                 265                 270

Glu Lys Glu Gln Leu Ala Gln Ala Val Ala Arg Ile Lys Lys Ile Tyr
        275                 280                 285

Glu Glu Lys Lys Lys Lys Thr Thr Ile Ala Val Glu Val Lys Lys
    290                 295                 300

Ser Gln His Lys Tyr Val Ile Gly Pro Lys Gly Asn Ser Leu Gln Glu
305                 310                 315                 320

Ile Leu Glu Arg Thr Gly Val Ser Val Glu Ile Pro Pro Ser Asp Ser
                325                 330                 335

Ile Ser Glu Thr Val Ile Leu Arg Gly Glu Pro Glu Lys Leu Gly Gln
            340                 345                 350

Ala Leu Thr Glu Val Tyr Ala Lys Ala Asn Ser Phe Thr Val Ser Ser
        355                 360                 365

Val Ala Ala Pro Ser Trp Leu His Arg Phe Ile Ile Gly Lys Lys Gly
    370                 375                 380

Gln Asn Leu Ala Lys Ile Thr Gln Gln Met Pro Lys Val His Ile Glu
385                 390                 395                 400

Phe Thr Glu Gly Glu Asp Lys Ile Thr Leu Glu Gly Pro Thr Glu Asp
                405                 410                 415

Val Asn Val Ala Gln Glu Gln Ile Glu Gly Met Val Lys Asp Leu Ile
```

-continued

```
               420             425             430
Asn Arg Met Asp Tyr Val Glu Ile Asn Ile Asp His Lys Phe His Arg
            435             440             445

His Leu Ile Gly Lys Ser Gly Ala Asn Ile Asn Arg Ile Lys Asp Gln
450             455             460

Tyr Lys Val Ser Val Arg Ile Pro Pro Asp Ser Glu Lys Ser Asn Leu
465             470             475             480

Ile Arg Ile Glu Gly Asp Pro Gln Gly Val Gln Gln Ala Lys Arg Glu
            485             490             495

Leu Leu Glu Leu Ala Ser Arg Met Glu Asn Glu Arg Thr Lys Asp Leu
            500             505             510

Ile Ile Glu Gln Arg Phe His Arg Thr Ile Gly Gln Lys Gly Glu
            515             520             525

Arg Ile Arg Glu Ile Arg Asp Lys Phe Pro Val Ile Ile Asn Phe
            530             535             540

Pro Asp Pro Ala Gln Lys Ser Asp Ile Val Gln Leu Arg Gly Pro Lys
545             550             555             560

Asn Glu Val Glu Lys Cys Thr Lys Tyr Met Gln Lys Met Val Ala Asp
            565             570             575

Leu Val Glu Asn Ser Tyr Ser Ile Ser Val Pro Ile Phe Lys Gln Phe
            580             585             590

His Lys Asn Ile Ile Gly Lys Gly Gly Ala Asn Ile Lys Lys Ile Arg
            595             600             605

Glu Glu Ser Asn Thr Lys Ile Asp Leu Pro Ala Glu Asn Ser Asn Ser
            610             615             620

Glu Thr Ile Ile Ile Thr Gly Lys Arg Ala Asn Cys Glu Ala Ala Arg
625             630             635             640

Ser Arg Ile Leu Ser Ile Gln Lys Asp Leu Ala Asn Ile Ala Glu Val
            645             650             655

Glu Val Ser Ile Pro Ala Lys Leu His Asn Ser Leu Ile Gly Thr Lys
            660             665             670

Gly Arg Leu Ile Arg Ser Ile Met Glu Glu Cys Gly Gly Val His Ile
            675             680             685

His Phe Pro Val Glu Gly Ser Gly Ser Asp Thr Val Val Ile Arg Gly
            690             695             700

Pro Ser Ser Asp Val Glu Lys Ala Lys Lys Gln Leu Leu His Leu Ala
705             710             715             720

Glu Glu Lys Gln Thr Lys Ser Phe Thr Val Asp Ile Arg Ala Lys Pro
            725             730             735

Glu Tyr His Lys Phe Leu Ile Gly Lys Gly Gly Lys Ile Arg Lys
            740             745             750

Val Arg Asp Ser Thr Gly Ala Arg Val Ile Phe Pro Ala Ala Glu Asp
            755             760             765

Lys Asp Gln Asp Leu Ile Thr Ile Ile Gly Lys Glu Asp Ala Val Arg
            770             775             780

Glu Ala Gln Lys Glu Leu Glu Ala Leu Ile Gln Asn Leu Asp Asn Val
785             790             795             800

Val Glu Asp Ser Met Leu Val Asp Pro Lys His His Arg His Phe Val
            805             810             815

Ile Arg Arg Gly Gln Val Leu Arg Glu Ile Ala Glu Glu Tyr Gly Gly
            820             825             830

Val Met Val Ser Phe Pro Arg Ser Gly Thr Gln Ser Asp Lys Val Thr
            835             840             845
```

```
Leu Lys Gly Ala Lys Asp Cys Val Glu Ala Lys Lys Arg Ile Gln
    850                 855                 860
Glu Ile Ile Glu Asp Leu Glu Ala Gln Val Thr Leu Glu Cys Ala Ile
865                 870                 875                 880
Pro Gln Lys Phe His Arg Ser Val Met Gly Pro Lys Gly Ser Arg Ile
                885                 890                 895
Gln Gln Ile Thr Arg Asp Phe Ser Val Gln Ile Lys Phe Pro Asp Arg
            900                 905                 910
Glu Glu Asn Ala Val His Ser Thr Glu Pro Val Val Gln Glu Asn Gly
        915                 920                 925
Asp Glu Ala Gly Glu Gly Arg Glu Ala Lys Asp Cys Asp Pro Gly Ser
    930                 935                 940
Pro Arg Arg Cys Asp Ile Ile Ile Ser Gly Arg Lys Glu Lys Cys
945                 950                 955                 960
Glu Ala Ala Lys Glu Ala Leu Glu Ala Leu Val Pro Val Thr Ile Glu
                965                 970                 975
Val Glu Val Pro Phe Asp Leu His Arg Tyr Val Ile Gly Gln Lys Gly
            980                 985                 990
Ser Gly Ile Arg Lys Met Met Asp Glu Phe Glu Val Asn Ile His Val
        995                 1000                1005
Pro Ala Pro Glu Leu Gln Ser Asp Ile Ile Ala Ile Thr Gly Leu
    1010                1015                1020
Ala Ala Asn Leu Asp Arg Ala Lys Ala Gly Leu Leu Glu Arg Val
    1025                1030                1035
Lys Glu Leu Gln Ala Glu Gln Glu Asp Arg Ala Leu Arg Ser Phe
    1040                1045                1050
Lys Leu Ser Val Thr Val Asp Pro Lys Tyr His Pro Lys Ile Ile
    1055                1060                1065
Gly Arg Lys Gly Ala Val Ile Thr Gln Ile Arg Leu Glu His Asp
    1070                1075                1080
Val Asn Ile Gln Phe Pro Asp Lys Asp Asp Gly Asn Gln Pro Gln
    1085                1090                1095
Asp Gln Ile Thr Ile Thr Gly Tyr Glu Lys Asn Thr Glu Ala Ala
    1100                1105                1110
Arg Asp Ala Ile Leu Arg Ile Val Gly Glu Leu Glu Gln Met Val
    1115                1120                1125
Ser Glu Asp Val Pro Leu Asp His Arg Val His Ala Arg Ile Ile
    1130                1135                1140
Gly Ala Arg Gly Lys Ala Ile Arg Lys Ile Met Asp Glu Phe Lys
    1145                1150                1155
Val Asp Ile Arg Phe Pro Gln Ser Gly Ala Pro Asp Pro Asn Cys
    1160                1165                1170
Val Thr Val Thr Gly Leu Pro Glu Asn Val Glu Glu Ala Ile Asp
    1175                1180                1185
His Ile Leu Asn Leu Glu Glu Glu Tyr Leu Ala Asp Val Val Asp
    1190                1195                1200
Ser Glu Ala Leu Gln Val Tyr Met Lys Pro Pro Ala His Glu Glu
    1205                1210                1215
Ala Lys Ala Pro Ser Arg Gly Phe Val Val Arg Asp Ala Pro Trp
    1220                1225                1230
Thr Ala Ser Ser Ser Glu Lys Ala Pro Asp Met Ser Ser Ser Glu
    1235                1240                1245
```

Glu Phe Pro Ser Phe Gly Ala Gln Val Ala Pro Lys Thr Leu Pro
1250                1255                1260

Trp Gly Pro Lys Arg
    1265

<210> SEQ ID NO 32
<211> LENGTH: 4128
<212> TYPE: PRT
<213> ORGANISM: Homo sapiens

<400> SEQUENCE: 32

Met Ala Gly Ser Gly Ala Gly Val Arg Cys Ser Leu Leu Arg Leu Gln
1               5                   10                  15

Glu Thr Leu Ser Ala Ala Asp Arg Cys Gly Ala Ala Leu Ala Gly His
                20                  25                  30

Gln Leu Ile Arg Gly Leu Gly Gln Glu Cys Val Leu Ser Ser Ser Pro
            35                  40                  45

Ala Val Leu Ala Leu Gln Thr Ser Leu Val Phe Ser Arg Asp Phe Gly
        50                  55                  60

Leu Leu Val Phe Val Arg Lys Ser Leu Asn Ser Ile Glu Phe Arg Glu
65                  70                  75                  80

Cys Arg Glu Glu Ile Leu Lys Phe Leu Cys Ile Phe Leu Glu Lys Met
                85                  90                  95

Gly Gln Lys Ile Ala Pro Tyr Ser Val Glu Ile Lys Asn Thr Cys Thr
            100                 105                 110

Ser Val Tyr Thr Lys Asp Arg Ala Ala Lys Cys Lys Ile Pro Ala Leu
        115                 120                 125

Asp Leu Leu Ile Lys Leu Leu Gln Thr Phe Arg Ser Ser Arg Leu Met
    130                 135                 140

Asp Glu Phe Lys Ile Gly Glu Leu Phe Ser Lys Phe Tyr Gly Glu Leu
145                 150                 155                 160

Ala Leu Lys Lys Lys Ile Pro Asp Thr Val Leu Glu Lys Val Tyr Glu
                165                 170                 175

Leu Leu Gly Leu Leu Gly Glu Val His Pro Ser Glu Met Ile Asn Asn
            180                 185                 190

Ala Glu Asn Leu Phe Arg Ala Phe Leu Gly Glu Leu Lys Thr Gln Met
        195                 200                 205

Thr Ser Ala Val Arg Glu Pro Lys Leu Pro Val Leu Ala Gly Cys Leu
    210                 215                 220

Lys Gly Leu Ser Ser Leu Leu Cys Asn Phe Thr Lys Ser Met Glu Glu
225                 230                 235                 240

Asp Pro Gln Thr Ser Arg Glu Ile Phe Asn Phe Val Leu Lys Ala Ile
                245                 250                 255

Arg Pro Gln Ile Asp Leu Lys Arg Tyr Ala Val Pro Ser Ala Gly Leu
            260                 265                 270

Arg Leu Phe Ala Leu His Ala Ser Gln Phe Ser Thr Cys Leu Leu Asp
        275                 280                 285

Asn Tyr Val Ser Leu Phe Glu Val Leu Leu Lys Trp Cys Ala His Thr
    290                 295                 300

Asn Val Glu Leu Lys Lys Ala Ala Leu Ser Ala Leu Glu Ser Phe Leu
305                 310                 315                 320

Lys Gln Val Ser Asn Met Val Ala Lys Asn Ala Glu Met His Lys Asn
                325                 330                 335

Lys Leu Gln Tyr Phe Met Glu Gln Phe Tyr Gly Ile Ile Arg Asn Val
            340                 345                 350

```
Asp Ser Asn Asn Lys Glu Leu Ser Ile Ala Ile Arg Gly Tyr Gly Leu
            355                 360                 365

Phe Ala Gly Pro Cys Lys Val Ile Asn Ala Lys Asp Val Asp Phe Met
    370                 375                 380

Tyr Val Glu Leu Ile Gln Arg Cys Lys Gln Met Phe Leu Thr Gln Thr
385                 390                 395                 400

Asp Thr Gly Asp Asp Arg Val Tyr Gln Met Pro Ser Phe Leu Gln Ser
                405                 410                 415

Val Ala Ser Val Leu Leu Tyr Leu Asp Thr Val Pro Glu Val Tyr Thr
            420                 425                 430

Pro Val Leu Glu His Leu Val Val Met Gln Ile Asp Ser Phe Pro Gln
        435                 440                 445

Tyr Ser Pro Lys Met Gln Leu Val Cys Cys Arg Ala Ile Val Lys Val
        450                 455                 460

Phe Leu Ala Leu Ala Ala Lys Gly Pro Val Leu Arg Asn Cys Ile Ser
465                 470                 475                 480

Thr Val His Gln Gly Leu Ile Arg Ile Cys Ser Lys Pro Val Val
                485                 490                 495

Leu Pro Lys Gly Pro Glu Ser Glu Ser Glu Asp His Arg Ala Ser Gly
            500                 505                 510

Glu Val Arg Thr Gly Lys Trp Lys Val Pro Thr Tyr Lys Asp Tyr Val
        515                 520                 525

Asp Leu Phe Arg His Leu Leu Ser Ser Asp Gln Met Met Asp Ser Ile
    530                 535                 540

Leu Ala Asp Glu Ala Phe Phe Ser Val Asn Ser Ser Glu Ser Leu
545                 550                 555                 560

Asn His Leu Leu Tyr Asp Glu Phe Val Lys Ser Val Leu Lys Ile Val
                565                 570                 575

Glu Lys Leu Asp Leu Thr Leu Glu Ile Gln Thr Val Gly Glu Gln Glu
            580                 585                 590

Asn Gly Asp Glu Ala Pro Gly Val Trp Met Ile Pro Thr Ser Asp Pro
        595                 600                 605

Ala Ala Asn Leu His Pro Ala Lys Pro Lys Asp Phe Ser Ala Phe Ile
    610                 615                 620

Asn Leu Val Glu Phe Cys Arg Glu Ile Leu Pro Glu Lys Gln Ala Glu
625                 630                 635                 640

Phe Phe Glu Pro Trp Val Tyr Ser Phe Ser Tyr Glu Leu Ile Leu Gln
                645                 650                 655

Ser Thr Arg Leu Pro Leu Ile Ser Gly Phe Tyr Lys Leu Leu Ser Ile
            660                 665                 670

Thr Val Arg Asn Ala Lys Lys Ile Lys Tyr Phe Glu Gly Val Ser Pro
        675                 680                 685

Lys Ser Leu Lys His Ser Pro Glu Asp Pro Glu Lys Tyr Ser Cys Phe
    690                 695                 700

Ala Leu Phe Val Lys Phe Gly Lys Glu Val Ala Val Lys Met Lys Gln
705                 710                 715                 720

Tyr Lys Asp Glu Leu Leu Ala Ser Cys Leu Thr Phe Leu Leu Ser Leu
                725                 730                 735

Pro His Asn Ile Ile Glu Leu Asp Val Arg Ala Tyr Val Pro Ala Leu
            740                 745                 750

Gln Met Ala Phe Lys Leu Gly Leu Ser Tyr Thr Pro Leu Ala Glu Val
        755                 760                 765
```

```
Gly Leu Asn Ala Leu Glu Glu Trp Ser Ile Tyr Ile Asp Arg His Val
770                 775                 780
Met Gln Pro Tyr Tyr Lys Asp Ile Leu Pro Cys Leu Asp Gly Tyr Leu
785                 790                 795                 800
Lys Thr Ser Ala Leu Ser Asp Glu Thr Lys Asn Asn Trp Glu Val Ser
                805                 810                 815
Ala Leu Ser Arg Ala Ala Gln Lys Gly Phe Asn Lys Val Val Leu Lys
                820                 825                 830
His Leu Lys Lys Thr Lys Asn Leu Ser Ser Asn Glu Ala Ile Ser Leu
                835                 840                 845
Glu Glu Ile Arg Ile Arg Val Val Gln Met Leu Gly Ser Leu Gly Gly
850                 855                 860
Gln Ile Asn Lys Asn Leu Leu Thr Val Thr Ser Ser Asp Glu Met Met
865                 870                 875                 880
Lys Ser Tyr Val Ala Trp Asp Arg Glu Lys Arg Leu Ser Phe Ala Val
                885                 890                 895
Pro Phe Arg Glu Met Lys Pro Val Ile Phe Leu Asp Val Phe Leu Pro
            900                 905                 910
Arg Val Thr Glu Leu Ala Leu Thr Ala Ser Asp Arg Gln Thr Lys Val
            915                 920                 925
Ala Ala Cys Glu Leu Leu His Ser Met Val Met Phe Met Leu Gly Lys
930                 935                 940
Ala Thr Gln Met Pro Glu Gly Gly Gln Gly Ala Pro Pro Met Tyr Gln
945                 950                 955                 960
Leu Tyr Lys Arg Thr Phe Pro Val Leu Leu Arg Leu Ala Cys Asp Val
                965                 970                 975
Asp Gln Val Thr Arg Gln Leu Tyr Glu Pro Leu Val Met Gln Leu Ile
                980                 985                 990
His Trp Phe Thr Asn Asn Lys Lys Phe Glu Ser Gln Asp Thr Val Ala
            995                 1000                1005
Leu Leu Glu Ala Ile Leu Asp Gly Ile Val Asp Pro Val Asp Ser
    1010                1015                1020
Thr Leu Arg Asp Phe Cys Gly Arg Cys Ile Arg Glu Phe Leu Lys
    1025                1030                1035
Trp Ser Ile Lys Gln Ile Thr Pro Gln Gln Glu Lys Ser Pro
    1040                1045                1050
Val Asn Thr Lys Ser Leu Phe Lys Arg Leu Tyr Ser Leu Ala Leu
    1055                1060                1065
His Pro Asn Ala Phe Lys Arg Leu Gly Ala Ser Leu Ala Phe Asn
    1070                1075                1080
Asn Ile Tyr Arg Glu Phe Arg Glu Glu Glu Ser Leu Val Glu Gln
    1085                1090                1095
Phe Val Phe Glu Ala Leu Val Ile Tyr Met Glu Ser Leu Ala Leu
    1100                1105                1110
Ala His Ala Asp Glu Lys Ser Leu Gly Thr Ile Gln Gln Cys Cys
    1115                1120                1125
Asp Ala Ile Asp His Leu Cys Arg Ile Ile Glu Lys Lys His Val
    1130                1135                1140
Ser Leu Asn Lys Ala Lys Lys Arg Arg Leu Pro Arg Gly Phe Pro
    1145                1150                1155
Pro Ser Ala Ser Leu Cys Leu Leu Asp Leu Val Lys Trp Leu Leu
    1160                1165                1170
Ala His Cys Gly Arg Pro Gln Thr Glu Cys Arg His Lys Ser Ile
```

```
                1175                1180                1185
Glu Leu Phe Tyr Lys Phe Val Pro Leu Leu Pro Gly Asn Arg Ser
    1190                1195                1200
Pro Asn Leu Trp Leu Lys Asp Val Leu Lys Glu Glu Gly Val Ser
    1205                1210                1215
Phe Leu Ile Asn Thr Phe Glu Gly Gly Gly Cys Gly Gln Pro Ser
    1220                1225                1230
Gly Ile Leu Ala Gln Pro Thr Leu Leu Tyr Leu Arg Gly Pro Phe
    1235                1240                1245
Ser Leu Gln Ala Thr Leu Cys Trp Leu Asp Leu Leu Ala Ala
    1250                1255                1260
Leu Glu Cys Tyr Asn Thr Phe Ile Gly Glu Arg Thr Val Gly Ala
    1265                1270                1275
Leu Gln Val Leu Gly Thr Glu Ala Gln Ser Ser Leu Leu Lys Ala
    1280                1285                1290
Val Ala Phe Phe Leu Glu Ser Ile Ala Met His Asp Ile Ile Ala
    1295                1300                1305
Ala Glu Lys Cys Phe Gly Thr Gly Ala Ala Gly Asn Arg Thr Ser
    1310                1315                1320
Pro Gln Glu Gly Glu Arg Tyr Asn Tyr Ser Lys Cys Thr Val Val
    1325                1330                1335
Val Arg Ile Met Glu Phe Thr Thr Thr Leu Leu Asn Thr Ser Pro
    1340                1345                1350
Glu Gly Trp Lys Leu Leu Lys Lys Asp Leu Cys Asn Thr His Leu
    1355                1360                1365
Met Arg Val Leu Val Gln Thr Leu Cys Glu Pro Ala Ser Ile Gly
    1370                1375                1380
Phe Asn Ile Gly Asp Val Gln Val Met Ala His Leu Pro Asp Val
    1385                1390                1395
Cys Val Asn Leu Met Lys Ala Leu Lys Met Ser Pro Tyr Lys Asp
    1400                1405                1410
Ile Leu Glu Thr His Leu Arg Glu Lys Ile Thr Ala Gln Ser Ile
    1415                1420                1425
Glu Glu Leu Cys Ala Val Asn Leu Tyr Gly Pro Asp Ala Gln Val
    1430                1435                1440
Asp Arg Ser Arg Leu Ala Ala Val Val Ser Ala Cys Lys Gln Leu
    1445                1450                1455
His Arg Ala Gly Leu Leu His Asn Ile Leu Pro Ser Gln Ser Thr
    1460                1465                1470
Asp Leu His His Ser Val Gly Thr Glu Leu Leu Ser Leu Val Tyr
    1475                1480                1485
Lys Gly Ile Ala Pro Gly Asp Glu Arg Gln Cys Leu Pro Ser Leu
    1490                1495                1500
Asp Leu Ser Cys Lys Gln Leu Ala Ser Gly Leu Leu Glu Leu Ala
    1505                1510                1515
Phe Ala Phe Gly Gly Leu Cys Glu Arg Leu Val Ser Leu Leu Leu
    1520                1525                1530
Asn Pro Ala Val Leu Ser Thr Ala Ser Leu Gly Ser Ser Gln Gly
    1535                1540                1545
Ser Val Ile His Phe Ser His Gly Glu Tyr Phe Tyr Ser Leu Phe
    1550                1555                1560
Ser Glu Thr Ile Asn Thr Glu Leu Leu Lys Asn Leu Asp Leu Ala
    1565                1570                1575
```

```
Val Leu Glu Leu Met Gln Ser Ser Val Asp Asn Thr Lys Met Val
    1580            1585                1590

Ser Ala Val Leu Asn Gly Met Leu Asp Gln Ser Phe Arg Glu Arg
    1595            1600                1605

Ala Asn Gln Lys His Gln Gly Leu Lys Leu Ala Thr Thr Ile Leu
    1610            1615                1620

Gln His Trp Lys Lys Cys Asp Ser Trp Trp Ala Lys Asp Ser Pro
    1625            1630                1635

Leu Glu Thr Lys Met Ala Val Leu Ala Leu Leu Ala Lys Ile Leu
    1640            1645                1650

Gln Ile Asp Ser Ser Val Ser Phe Asn Thr Ser His Gly Ser Phe
    1655            1660                1665

Pro Glu Val Phe Thr Thr Tyr Ile Ser Leu Leu Ala Asp Thr Lys
    1670            1675                1680

Leu Asp Leu His Leu Lys Gly Gln Ala Val Thr Leu Leu Pro Phe
    1685            1690                1695

Phe Thr Ser Leu Thr Gly Gly Ser Leu Glu Glu Leu Arg Arg Val
    1700            1705                1710

Leu Glu Gln Leu Ile Val Ala His Phe Pro Met Gln Ser Arg Glu
    1715            1720                1725

Phe Pro Pro Gly Thr Pro Arg Phe Asn Asn Tyr Val Asp Cys Met
    1730            1735                1740

Lys Lys Phe Leu Asp Ala Leu Glu Leu Ser Gln Ser Pro Met Leu
    1745            1750                1755

Leu Glu Leu Met Thr Glu Val Leu Cys Arg Glu Gln Gln His Val
    1760            1765                1770

Met Glu Glu Leu Phe Gln Ser Ser Phe Arg Arg Ile Ala Arg Arg
    1775            1780                1785

Gly Ser Cys Val Thr Gln Val Gly Leu Leu Glu Ser Val Tyr Glu
    1790            1795                1800

Met Phe Arg Lys Asp Asp Pro Arg Leu Ser Phe Thr Arg Gln Ser
    1805            1810                1815

Phe Val Asp Arg Ser Leu Leu Thr Leu Leu Trp His Cys Ser Leu
    1820            1825                1830

Asp Ala Leu Arg Glu Phe Phe Ser Thr Ile Val Val Asp Ala Ile
    1835            1840                1845

Asp Val Leu Lys Ser Arg Phe Thr Lys Leu Asn Glu Ser Thr Phe
    1850            1855                1860

Asp Thr Gln Ile Thr Lys Lys Met Gly Tyr Tyr Lys Ile Leu Asp
    1865            1870                1875

Val Met Tyr Ser Arg Leu Pro Lys Asp Asp Val His Ala Lys Glu
    1880            1885                1890

Ser Lys Ile Asn Gln Val Phe His Gly Ser Cys Ile Thr Glu Gly
    1895            1900                1905

Asn Glu Leu Thr Lys Thr Leu Ile Lys Leu Cys Tyr Asp Ala Phe
    1910            1915                1920

Thr Glu Asn Met Ala Gly Glu Asn Gln Leu Leu Glu Arg Arg Arg
    1925            1930                1935

Leu Tyr His Cys Ala Ala Tyr Asn Cys Ala Ile Ser Val Ile Cys
    1940            1945                1950

Cys Val Phe Asn Glu Leu Lys Phe Tyr Gln Gly Phe Leu Phe Ser
    1955            1960                1965
```

```
Glu Lys Pro Glu Lys Asn Leu Leu Ile Phe Glu Asn Leu Ile Asp
1970                1975                1980

Leu Lys Arg Arg Tyr Asn Phe Pro Val Glu Val Glu Val Pro Met
1985                1990                1995

Glu Arg Lys Lys Lys Tyr Ile Glu Ile Arg Lys Glu Ala Arg Glu
2000                2005                2010

Ala Ala Asn Gly Asp Ser Asp Gly Pro Ser Tyr Met Ser Ser Leu
2015                2020                2025

Ser Tyr Leu Ala Asp Ser Thr Leu Ser Glu Glu Met Ser Gln Phe
2030                2035                2040

Asp Phe Ser Thr Gly Val Gln Ser Tyr Ser Tyr Ser Ser Gln Asp
2045                2050                2055

Pro Arg Pro Ala Thr Gly Arg Phe Arg Arg Glu Gln Arg Asp
2060                2065                2070

Pro Thr Val His Asp Asp Val Leu Glu Leu Glu Met Asp Glu Leu
2075                2080                2085

Asn Arg His Glu Cys Met Ala Pro Leu Thr Ala Leu Val Lys His
2090                2095                2100

Met His Arg Ser Leu Gly Pro Pro Gln Gly Glu Asp Ser Val
2105                2110                2115

Pro Arg Asp Leu Pro Ser Trp Met Lys Phe Leu His Gly Lys Leu
2120                2125                2130

Gly Asn Pro Ile Val Pro Leu Asn Ile Arg Leu Phe Leu Ala Lys
2135                2140                2145

Leu Val Ile Asn Thr Glu Glu Val Phe Arg Pro Tyr Ala Lys His
2150                2155                2160

Trp Leu Ser Pro Leu Leu Gln Leu Ala Ala Ser Glu Asn Asn Gly
2165                2170                2175

Gly Glu Gly Ile His Tyr Met Val Val Glu Ile Val Ala Thr Ile
2180                2185                2190

Leu Ser Trp Thr Gly Leu Ala Thr Pro Thr Gly Val Pro Lys Asp
2195                2200                2205

Glu Val Leu Ala Asn Arg Leu Leu Asn Phe Leu Met Lys His Val
2210                2215                2220

Phe His Pro Lys Arg Ala Val Phe Arg His Asn Leu Glu Ile Ile
2225                2230                2235

Lys Thr Leu Val Glu Cys Trp Lys Asp Cys Leu Ser Ile Pro Tyr
2240                2245                2250

Arg Leu Ile Phe Glu Lys Phe Ser Gly Lys Asp Pro Asn Ser Lys
2255                2260                2265

Asp Asn Ser Val Gly Ile Gln Leu Leu Gly Ile Val Met Ala Asn
2270                2275                2280

Asp Leu Pro Pro Tyr Asp Pro Gln Cys Gly Ile Gln Ser Ser Glu
2285                2290                2295

Tyr Phe Gln Ala Leu Val Asn Asn Met Ser Phe Val Arg Tyr Lys
2300                2305                2310

Glu Val Tyr Ala Ala Ala Glu Val Leu Gly Leu Ile Leu Arg
2315                2320                2325

Tyr Val Met Glu Arg Lys Asn Ile Leu Glu Glu Ser Leu Cys Glu
2330                2335                2340

Leu Val Ala Lys Gln Leu Lys Gln His Gln Asn Thr Met Glu Asp
2345                2350                2355

Lys Phe Ile Val Cys Leu Asn Lys Val Thr Lys Ser Phe Pro Pro
```

```
                2360                2365                2370
Leu Ala Asp Arg Phe Met Asn Ala Val Phe Leu Leu Pro Lys
        2375                2380                2385
Phe His Gly Val Leu Lys Thr Leu Cys Leu Glu Val Val Leu Cys
        2390                2395                2400
Arg Val Glu Gly Met Thr Glu Leu Tyr Phe Gln Leu Lys Ser Lys
        2405                2410                2415
Asp Phe Val Gln Val Met Arg His Arg Asp Glu Arg Gln Lys
        2420                2425                2430
Val Cys Leu Asp Ile Ile Tyr Lys Met Met Pro Lys Leu Lys Pro
        2435                2440                2445
Val Glu Leu Arg Glu Leu Leu Asn Pro Val Val Glu Phe Val Ser
        2450                2455                2460
His Pro Ser Thr Thr Cys Arg Glu Gln Met Tyr Asn Ile Leu Met
        2465                2470                2475
Trp Ile His Asp Asn Tyr Arg Asp Pro Glu Ser Glu Thr Asp Asn
        2480                2485                2490
Asp Ser Gln Glu Ile Phe Lys Leu Ala Lys Asp Val Leu Ile Gln
        2495                2500                2505
Gly Leu Ile Asp Glu Asn Pro Gly Leu Gln Leu Ile Ile Arg Asn
        2510                2515                2520
Phe Trp Ser His Glu Thr Arg Leu Pro Ser Asn Thr Leu Asp Arg
        2525                2530                2535
Leu Leu Ala Leu Asn Ser Leu Tyr Ser Pro Lys Ile Glu Val His
        2540                2545                2550
Phe Leu Ser Leu Ala Thr Asn Phe Leu Leu Glu Met Thr Ser Met
        2555                2560                2565
Ser Pro Asp Tyr Pro Asn Pro Met Phe Glu His Pro Leu Ser Glu
        2570                2575                2580
Cys Glu Phe Gln Glu Tyr Thr Ile Asp Ser Asp Trp Arg Phe Arg
        2585                2590                2595
Ser Thr Val Leu Thr Pro Met Phe Val Glu Thr Gln Ala Ser Gln
        2600                2605                2610
Gly Thr Leu Gln Thr Arg Thr Gln Glu Gly Ser Leu Ser Ala Arg
        2615                2620                2625
Trp Pro Val Ala Gly Gln Ile Arg Ala Thr Gln Gln His Asp
        2630                2635                2640
Phe Thr Leu Thr Gln Thr Ala Asp Gly Arg Ser Ser Phe Asp Trp
        2645                2650                2655
Leu Thr Gly Ser Ser Thr Asp Pro Leu Val Asp His Thr Ser Pro
        2660                2665                2670
Ser Ser Asp Ser Leu Leu Phe Ala His Lys Arg Ser Glu Arg Leu
        2675                2680                2685
Gln Arg Ala Pro Leu Lys Ser Val Gly Pro Asp Phe Gly Lys Lys
        2690                2695                2700
Arg Leu Gly Leu Pro Gly Asp Glu Val Asp Asn Lys Val Lys Gly
        2705                2710                2715
Ala Ala Gly Arg Thr Asp Leu Leu Arg Leu Arg Arg Phe Met
        2720                2725                2730
Arg Asp Gln Glu Lys Leu Ser Leu Met Tyr Ala Arg Lys Gly Val
        2735                2740                2745
Ala Glu Gln Lys Arg Glu Lys Glu Ile Lys Ser Glu Leu Lys Met
        2750                2755                2760
```

-continued

```
Lys Gln Asp Ala Gln Val Val Leu Tyr Arg Ser Tyr Arg His Gly
2765                2770                2775

Asp Leu Pro Asp Ile Gln Ile Lys His Ser Ser Leu Ile Thr Pro
        2780                2785                2790

Leu Gln Ala Val Ala Gln Arg Asp Pro Ile Ile Ala Lys Gln Leu
    2795                2800                2805

Phe Ser Ser Leu Phe Ser Gly Ile Leu Lys Glu Met Asp Lys Phe
    2810                2815                2820

Lys Thr Leu Ser Glu Lys Asn Asn Ile Thr Gln Lys Leu Leu Gln
2825                2830                2835

Asp Phe Asn Arg Phe Leu Asn Thr Thr Phe Ser Phe Phe Pro Pro
        2840                2845                2850

Phe Val Ser Cys Ile Gln Asp Ile Ser Cys Gln His Ala Ala Leu
    2855                2860                2865

Leu Ser Leu Asp Pro Ala Ala Val Ser Ala Gly Cys Leu Ala Ser
    2870                2875                2880

Leu Gln Gln Pro Val Gly Ile Arg Leu Leu Glu Glu Ala Leu Leu
    2885                2890                2895

Arg Leu Leu Pro Ala Glu Leu Pro Ala Lys Arg Val Arg Gly Lys
2900                2905                2910

Ala Arg Leu Pro Pro Asp Val Leu Arg Trp Val Glu Leu Ala Lys
        2915                2920                2925

Leu Tyr Arg Ser Ile Gly Glu Tyr Asp Val Leu Arg Gly Ile Phe
    2930                2935                2940

Thr Ser Glu Ile Gly Thr Lys Gln Ile Thr Gln Ser Ala Leu Leu
    2945                2950                2955

Ala Glu Ala Arg Ser Asp Tyr Ser Glu Ala Ala Lys Gln Tyr Asp
2960                2965                2970

Glu Ala Leu Asn Lys Gln Asp Trp Val Asp Gly Glu Pro Thr Glu
        2975                2980                2985

Ala Glu Lys Asp Phe Trp Glu Leu Ala Ser Leu Asp Cys Tyr Asn
    2990                2995                3000

His Leu Ala Glu Trp Lys Ser Leu Glu Tyr Cys Ser Thr Ala Ser
    3005                3010                3015

Ile Asp Ser Glu Asn Pro Pro Asp Leu Asn Lys Ile Trp Ser Glu
3020                3025                3030

Pro Phe Tyr Gln Glu Thr Tyr Leu Pro Tyr Met Ile Arg Ser Lys
        3035                3040                3045

Leu Lys Leu Leu Leu Gln Gly Glu Ala Asp Gln Ser Leu Leu Thr
    3050                3055                3060

Phe Ile Asp Lys Ala Met His Gly Glu Leu Gln Lys Ala Ile Leu
    3065                3070                3075

Glu Leu His Tyr Ser Gln Glu Leu Ser Leu Leu Tyr Leu Leu Gln
3080                3085                3090

Asp Asp Val Asp Arg Ala Lys Tyr Tyr Ile Gln Asn Gly Ile Gln
        3095                3100                3105

Ser Phe Met Gln Asn Tyr Ser Ser Ile Asp Val Leu Leu His Gln
    3110                3115                3120

Ser Arg Leu Thr Lys Leu Gln Ser Val Gln Ala Leu Thr Glu Ile
    3125                3130                3135

Gln Glu Phe Ile Ser Phe Ile Ser Lys Gln Gly Asn Leu Ser Ser
3140                3145                3150
```

-continued

```
Gln Val Pro Leu Lys Arg Leu Leu Asn Thr Trp Thr Asn Arg Tyr
    3155                3160                3165

Pro Asp Ala Lys Met Asp Pro Met Asn Ile Trp Asp Asp Ile Ile
    3170                3175                3180

Thr Asn Arg Cys Phe Phe Leu Ser Lys Ile Glu Glu Lys Leu Thr
    3185                3190                3195

Pro Leu Pro Glu Asp Asn Ser Met Asn Val Asp Gln Asp Gly Asp
    3200                3205                3210

Pro Ser Asp Arg Met Glu Val Gln Glu Gln Glu Asp Ile Ser
    3215                3220                3225

Ser Leu Ile Arg Ser Cys Lys Phe Ser Met Lys Met Lys Met Ile
    3230                3235                3240

Asp Ser Ala Arg Lys Gln Asn Asn Phe Ser Leu Ala Met Lys Leu
    3245                3250                3255

Leu Lys Glu Leu His Lys Glu Ser Lys Thr Arg Asp Asp Trp Leu
    3260                3265                3270

Val Ser Trp Val Gln Ser Tyr Cys Arg Leu Ser His Cys Arg Ser
    3275                3280                3285

Arg Ser Gln Gly Cys Ser Glu Gln Val Leu Thr Val Leu Lys Thr
    3290                3295                3300

Val Ser Leu Leu Asp Glu Asn Asn Val Ser Ser Tyr Leu Ser Lys
    3305                3310                3315

Asn Ile Leu Ala Phe Arg Asp Gln Asn Ile Leu Leu Gly Thr Thr
    3320                3325                3330

Tyr Arg Ile Ile Ala Asn Ala Leu Ser Ser Glu Pro Ala Cys Leu
    3335                3340                3345

Ala Glu Ile Glu Glu Asp Lys Ala Arg Arg Ile Leu Glu Leu Ser
    3350                3355                3360

Gly Ser Ser Ser Glu Asp Ser Glu Lys Val Ile Ala Gly Leu Tyr
    3365                3370                3375

Gln Arg Ala Phe Gln His Leu Ser Glu Ala Val Gln Ala Ala Glu
    3380                3385                3390

Glu Glu Ala Gln Pro Pro Ser Trp Ser Cys Gly Pro Ala Ala Gly
    3395                3400                3405

Val Ile Asp Ala Tyr Met Thr Leu Ala Asp Phe Cys Asp Gln Gln
    3410                3415                3420

Leu Arg Lys Glu Glu Glu Asn Ala Ser Val Ile Asp Ser Ala Glu
    3425                3430                3435

Leu Gln Ala Tyr Pro Ala Leu Val Val Glu Lys Met Leu Lys Ala
    3440                3445                3450

Leu Lys Leu Asn Ser Asn Glu Ala Arg Leu Lys Phe Pro Arg Leu
    3455                3460                3465

Leu Gln Ile Ile Glu Arg Tyr Pro Glu Glu Thr Leu Ser Leu Met
    3470                3475                3480

Thr Lys Glu Ile Ser Ser Val Pro Cys Trp Gln Phe Ile Ser Trp
    3485                3490                3495

Ile Ser His Met Val Ala Leu Leu Asp Lys Asp Gln Ala Val Ala
    3500                3505                3510

Val Gln His Ser Val Glu Glu Ile Thr Asp Asn Tyr Pro Gln Ala
    3515                3520                3525

Ile Val Tyr Pro Phe Ile Ile Ser Ser Glu Ser Tyr Ser Phe Lys
    3530                3535                3540

Asp Thr Ser Thr Gly His Lys Asn Lys Glu Phe Val Ala Arg Ile
```

-continued

|  | 3545 |  |  | 3550 |  |  | 3555 |  |  |
| --- | --- | --- | --- | --- | --- | --- | --- | --- | --- |

Lys Ser Lys Leu Asp Gln Gly Gly Val Ile Gln Asp Phe Ile Asn
3560                3565                3570

Ala Leu Asp Gln Leu Ser Asn Pro Glu Leu Leu Phe Lys Asp Trp
3575                3580                3585

Ser Asn Asp Val Arg Ala Glu Leu Ala Lys Thr Pro Val Asn Lys
3590                3595                3600

Lys Asn Ile Glu Lys Met Tyr Glu Arg Met Tyr Ala Ala Leu Gly
3605                3610                3615

Asp Pro Lys Ala Pro Gly Leu Gly Ala Phe Arg Arg Lys Phe Ile
3620                3625                3630

Gln Thr Phe Gly Lys Glu Phe Asp Lys His Phe Gly Lys Gly Gly
3635                3640                3645

Ser Lys Leu Leu Arg Met Lys Leu Ser Asp Phe Asn Asp Ile Thr
3650                3655                3660

Asn Met Leu Leu Leu Lys Met Asn Lys Asp Ser Lys Pro Pro Gly
3665                3670                3675

Asn Leu Lys Glu Cys Ser Pro Trp Met Ser Asp Phe Lys Val Glu
3680                3685                3690

Phe Leu Arg Asn Glu Leu Glu Ile Pro Gly Gln Tyr Asp Gly Arg
3695                3700                3705

Gly Lys Pro Leu Pro Glu Tyr His Val Arg Ile Ala Gly Phe Asp
3710                3715                3720

Glu Arg Val Thr Val Met Ala Ser Leu Arg Arg Pro Lys Arg Ile
3725                3730                3735

Ile Ile Arg Gly His Asp Glu Arg Glu His Pro Phe Leu Val Lys
3740                3745                3750

Gly Gly Glu Asp Leu Arg Gln Asp Gln Arg Val Glu Gln Leu Phe
3755                3760                3765

Gln Val Met Asn Gly Ile Leu Ala Gln Asp Ser Ala Cys Ser Gln
3770                3775                3780

Arg Ala Leu Gln Leu Arg Thr Tyr Ser Val Val Pro Met Thr Ser
3785                3790                3795

Arg Leu Gly Leu Ile Glu Trp Leu Glu Asn Thr Val Thr Leu Lys
3800                3805                3810

Asp Leu Leu Leu Asn Thr Met Ser Gln Glu Glu Lys Ala Ala Tyr
3815                3820                3825

Leu Ser Asp Pro Arg Ala Pro Pro Cys Glu Tyr Lys Asp Trp Leu
3830                3835                3840

Thr Lys Met Ser Gly Lys His Asp Val Gly Ala Tyr Met Leu Met
3845                3850                3855

Tyr Lys Gly Ala Asn Arg Thr Glu Thr Val Thr Ser Phe Arg Lys
3860                3865                3870

Arg Glu Ser Lys Val Pro Ala Asp Leu Leu Lys Arg Ala Phe Val
3875                3880                3885

Arg Met Ser Thr Ser Pro Glu Ala Phe Leu Ala Leu Arg Ser His
3890                3895                3900

Phe Ala Ser Ser His Ala Leu Ile Cys Ile Ser His Trp Ile Leu
3905                3910                3915

Gly Ile Gly Asp Arg His Leu Asn Asn Phe Met Val Ala Met Glu
3920                3925                3930

Thr Gly Gly Val Ile Gly Ile Asp Phe Gly His Ala Phe Gly Ser
3935                3940                3945

-continued

```
Ala Thr Gln Phe Leu Pro Val Pro Glu Leu Met Pro Phe Arg Leu
3950                3955                3960

Thr Arg Gln Phe Ile Asn Leu Met Leu Pro Met Lys Glu Thr Gly
    3965                3970                3975

Leu Met Tyr Ser Ile Met Val His Ala Leu Arg Ala Phe Arg Ser
3980                3985                3990

Asp Pro Gly Leu Leu Thr Asn Thr Met Asp Val Phe Val Lys Glu
    3995                4000                4005

Pro Ser Phe Asp Trp Lys Asn Phe Glu Gln Lys Met Leu Lys Lys
4010                4015                4020

Gly Gly Ser Trp Ile Gln Glu Ile Asn Val Ala Glu Lys Asn Trp
4025                4030                4035

Tyr Pro Arg Gln Lys Ile Cys Tyr Ala Lys Arg Lys Leu Ala Gly
    4040                4045                4050

Ala Asn Pro Ala Val Ile Thr Cys Asp Glu Leu Leu Leu Gly His
4055                4060                4065

Glu Lys Ala Pro Ala Phe Arg Asp Tyr Val Ala Val Ala Arg Gly
    4070                4075                4080

Ser Lys Asp His Asn Ile Arg Ala Gln Glu Pro Glu Ser Gly Leu
4085                4090                4095

Ser Glu Glu Thr Gln Val Lys Cys Leu Met Asp Gln Ala Thr Asp
4100                4105                4110

Pro Asn Ile Leu Gly Arg Thr Trp Glu Gly Trp Glu Pro Trp Met
4115                4120                4125

<210> SEQ ID NO 33
<211> LENGTH: 445
<212> TYPE: PRT
<213> ORGANISM: Homo sapiens

<400> SEQUENCE: 33

Met Asn Glu Glu Tyr Asp Val Ile Val Leu Gly Thr Gly Leu Thr Glu
1               5                   10                  15

Cys Ile Leu Ser Gly Ile Met Ser Val Asn Gly Lys Lys Val Leu His
                20                  25                  30

Met Asp Arg Asn Pro Tyr Tyr Gly Gly Glu Ser Ala Ser Ile Thr Pro
            35                  40                  45

Leu Glu Asp Leu Tyr Lys Arg Phe Lys Ile Pro Gly Ser Pro Pro Glu
    50                  55                  60

Ser Met Gly Arg Gly Arg Asp Trp Asn Val Asp Leu Ile Pro Lys Phe
65                  70                  75                  80

Leu Met Ala Asn Gly Gln Leu Val Lys Met Leu Leu Tyr Thr Glu Val
                85                  90                  95

Thr Arg Tyr Leu Asp Phe Lys Val Thr Glu Gly Ser Phe Val Tyr Lys
            100                 105                 110

Gly Gly Lys Ile Tyr Lys Val Pro Ser Thr Glu Ala Glu Ala Leu Ala
        115                 120                 125

Ser Ser Leu Met Gly Leu Phe Glu Lys Arg Arg Phe Arg Lys Phe Leu
    130                 135                 140

Val Tyr Val Ala Asn Phe Asp Glu Lys Asp Pro Arg Thr Phe Glu Gly
145                 150                 155                 160

Ile Asp Pro Lys Lys Thr Thr Met Arg Asp Val Tyr Lys Lys Phe Asp
                165                 170                 175

Leu Gly Gln Asp Val Ile Asp Phe Thr Gly His Ala Leu Ala Leu Tyr
```

```
                180                 185                 190
Arg Thr Asp Asp Tyr Leu Asp Gln Pro Cys Tyr Glu Thr Ile Asn Arg
            195                 200                 205

Ile Lys Leu Tyr Ser Glu Ser Leu Ala Arg Tyr Gly Lys Ser Pro Tyr
        210                 215                 220

Leu Tyr Pro Leu Tyr Gly Leu Gly Glu Leu Pro Gln Gly Phe Ala Arg
225                 230                 235                 240

Leu Ser Ala Ile Tyr Gly Gly Thr Tyr Met Leu Asn Lys Pro Ile Glu
                245                 250                 255

Glu Ile Ile Val Gln Asn Gly Lys Val Ile Gly Val Lys Ser Glu Gly
            260                 265                 270

Glu Ile Ala Arg Cys Lys Gln Leu Ile Cys Asp Pro Ser Tyr Val Lys
        275                 280                 285

Asp Arg Val Glu Lys Val Gly Gln Val Ile Arg Val Ile Cys Ile Leu
290                 295                 300

Ser His Pro Ile Lys Asn Thr Asn Asp Ala Asn Ser Cys Gln Ile Ile
305                 310                 315                 320

Ile Pro Gln Asn Gln Val Asn Arg Lys Ser Asp Ile Tyr Val Cys Met
                325                 330                 335

Ile Ser Phe Ala His Asn Val Ala Ala Gln Gly Lys Tyr Ile Ala Ile
            340                 345                 350

Val Ser Thr Thr Val Glu Thr Lys Glu Pro Glu Lys Glu Ile Arg Pro
        355                 360                 365

Ala Leu Glu Leu Leu Glu Pro Ile Glu Gln Lys Phe Val Ser Ile Ser
370                 375                 380

Asp Leu Leu Val Pro Lys Asp Leu Gly Thr Glu Ser Gln Ile Phe Ile
385                 390                 395                 400

Ser Arg Thr Tyr Asp Ala Thr Thr His Phe Glu Thr Thr Cys Asp Asp
                405                 410                 415

Ile Lys Asn Ile Tyr Lys Arg Met Thr Gly Ser Glu Phe Asp Phe Glu
            420                 425                 430

Glu Met Lys Arg Lys Lys Asn Asp Ile Tyr Gly Glu Asp
        435                 440                 445

<210> SEQ ID NO 34
<211> LENGTH: 529
<212> TYPE: PRT
<213> ORGANISM: Homo sapiens

<400> SEQUENCE: 34

Met Leu Gly Phe Val Gly Arg Val Ala Ala Pro Ala Ser Gly Ala
1               5                   10                  15

Leu Arg Arg Leu Thr Pro Ser Ala Ser Leu Pro Pro Ala Gln Leu Leu
            20                  25                  30

Leu Arg Ala Ala Pro Thr Ala Val His Pro Val Arg Asp Tyr Ala Ala
        35                  40                  45

Gln Thr Ser Pro Ser Pro Lys Ala Gly Ala Ala Thr Gly Arg Ile Val
    50                  55                  60

Ala Val Ile Gly Ala Val Val Asp Val Gln Phe Asp Glu Gly Leu Pro
65                  70                  75                  80

Pro Ile Leu Asn Ala Leu Glu Val Gln Gly Arg Glu Thr Arg Leu Val
                85                  90                  95

Leu Glu Val Ala Gln His Leu Gly Glu Ser Thr Val Arg Thr Ile Ala
            100                 105                 110
```

-continued

Met Asp Gly Thr Glu Gly Leu Val Arg Gly Gln Lys Val Leu Asp Ser
            115                 120                 125

Gly Ala Pro Ile Lys Ile Pro Val Gly Pro Glu Thr Leu Gly Arg Ile
130                 135                 140

Met Asn Val Ile Gly Glu Pro Ile Asp Glu Arg Gly Pro Ile Lys Thr
145                 150                 155                 160

Lys Gln Phe Ala Pro Ile His Ala Glu Ala Pro Glu Phe Met Glu Met
                165                 170                 175

Ser Val Glu Gln Glu Ile Leu Val Thr Gly Ile Lys Val Val Asp Leu
            180                 185                 190

Leu Ala Pro Tyr Ala Lys Gly Gly Lys Ile Gly Leu Phe Gly Gly Ala
            195                 200                 205

Gly Val Gly Lys Thr Val Leu Ile Met Glu Leu Ile Asn Asn Val Ala
210                 215                 220

Lys Ala His Gly Gly Tyr Ser Val Phe Ala Gly Val Gly Glu Arg Thr
225                 230                 235                 240

Arg Glu Gly Asn Asp Leu Tyr His Glu Met Ile Glu Ser Gly Val Ile
                245                 250                 255

Asn Leu Lys Asp Ala Thr Ser Lys Val Ala Leu Val Tyr Gly Gln Met
            260                 265                 270

Asn Glu Pro Pro Gly Ala Arg Ala Arg Val Ala Leu Thr Gly Leu Thr
            275                 280                 285

Val Ala Glu Tyr Phe Arg Asp Gln Glu Gly Gln Asp Val Leu Leu Phe
        290                 295                 300

Ile Asp Asn Ile Phe Arg Phe Thr Gln Ala Gly Ser Glu Val Ser Ala
305                 310                 315                 320

Leu Leu Gly Arg Ile Pro Ser Ala Val Gly Tyr Gln Pro Thr Leu Ala
                325                 330                 335

Thr Asp Met Gly Thr Met Gln Glu Arg Ile Thr Thr Lys Lys Gly
            340                 345                 350

Ser Ile Thr Ser Val Gln Ala Ile Tyr Val Pro Ala Asp Asp Leu Thr
            355                 360                 365

Asp Pro Ala Pro Ala Thr Thr Phe Ala His Leu Asp Ala Thr Thr Val
370                 375                 380

Leu Ser Arg Ala Ile Ala Glu Leu Gly Ile Tyr Pro Ala Val Asp Pro
385                 390                 395                 400

Leu Asp Ser Thr Ser Arg Ile Met Asp Pro Asn Ile Val Gly Ser Glu
                405                 410                 415

His Tyr Asp Val Ala Arg Gly Val Gln Lys Ile Leu Gln Asp Tyr Lys
            420                 425                 430

Ser Leu Gln Asp Ile Ile Ala Ile Leu Gly Met Asp Glu Leu Ser Glu
            435                 440                 445

Glu Asp Lys Leu Thr Val Ser Arg Ala Arg Lys Ile Gln Arg Phe Leu
        450                 455                 460

Ser Gln Pro Phe Gln Val Ala Glu Val Phe Thr Gly His Met Gly Lys
465                 470                 475                 480

Leu Val Pro Leu Lys Glu Thr Ile Lys Gly Phe Gln Gln Ile Leu Ala
                485                 490                 495

Gly Glu Tyr Asp His Leu Pro Glu Gln Ala Phe Tyr Met Val Gly Pro
            500                 505                 510

Ile Glu Glu Ala Val Ala Lys Ala Asp Lys Leu Ala Glu Glu His Ser
            515                 520                 525

Ser

<210> SEQ ID NO 35
<211> LENGTH: 1045
<212> TYPE: PRT
<213> ORGANISM: Homo sapiens

<400> SEQUENCE: 35

```
Met Glu Gly Leu Glu Glu Ala Glu Ala Asn Cys Ser Val Ala Phe Ala
1               5                   10                  15

Glu Ala Gln Arg Trp Val Glu Ala Val Thr Glu Lys Asn Phe Glu Thr
            20                  25                  30

Lys Asp Phe Arg Ala Ser Leu Glu Asn Gly Val Leu Leu Cys Asp Leu
        35                  40                  45

Ile Asn Lys Leu Lys Pro Gly Val Ile Lys Lys Ile Asn Arg Leu Ser
    50                  55                  60

Thr Pro Ile Ala Gly Leu Asp Asn Ile Asn Val Phe Leu Lys Ala Cys
65                  70                  75                  80

Glu Gln Ile Gly Leu Lys Glu Ala Gln Leu Phe His Pro Gly Asp Leu
                85                  90                  95

Gln Asp Leu Ser Asn Arg Val Thr Val Lys Gln Glu Glu Thr Asp Arg
            100                 105                 110

Arg Val Lys Asn Val Leu Ile Thr Leu Tyr Trp Leu Gly Arg Lys Ala
        115                 120                 125

Gln Ser Asn Pro Tyr Tyr Asn Gly Pro His Leu Asn Leu Lys Ala Phe
    130                 135                 140

Glu Asn Leu Leu Gly Gln Ala Leu Thr Lys Ala Leu Glu Asp Ser Ser
145                 150                 155                 160

Phe Leu Lys Arg Ser Gly Arg Asp Ser Gly Tyr Gly Asp Ile Trp Cys
                165                 170                 175

Pro Glu Arg Gly Glu Phe Leu Ala Pro Pro Arg His His Lys Arg Glu
            180                 185                 190

Asp Ser Phe Glu Ser Leu Asp Ser Leu Gly Ser Arg Ser Leu Thr Ser
        195                 200                 205

Cys Ser Ser Asp Ile Thr Leu Arg Gly Gly Arg Glu Gly Phe Glu Ser
    210                 215                 220

Asp Thr Asp Ser Glu Phe Thr Phe Lys Met Gln Asp Tyr Asn Lys Asp
225                 230                 235                 240

Asp Met Ser Tyr Arg Arg Ile Ser Ala Val Glu Pro Lys Thr Ala Leu
                245                 250                 255

Pro Phe Asn Arg Phe Leu Pro Asn Lys Ser Arg Gln Pro Ser Tyr Val
            260                 265                 270

Pro Ala Pro Leu Arg Lys Lys Lys Pro Asp Lys His Glu Asp Asn Arg
        275                 280                 285

Arg Ser Trp Ala Ser Pro Val Tyr Thr Glu Ala Asp Gly Thr Phe Ser
    290                 295                 300

Arg Leu Phe Gln Lys Ile Tyr Gly Glu Asn Gly Ser Lys Ser Met Ser
305                 310                 315                 320

Asp Val Ser Ala Glu Asp Val Gln Asn Leu Arg Gln Leu Arg Tyr Glu
                325                 330                 335

Glu Met Gln Lys Ile Lys Ser Gln Leu Lys Glu Gln Asp Gln Lys Trp
            340                 345                 350

Gln Asp Asp Leu Ala Lys Trp Lys Asp Arg Arg Lys Ser Tyr Thr Ser
        355                 360                 365

Asp Leu Gln Lys Lys Lys Glu Glu Arg Glu Glu Ile Glu Lys Gln Ala
```

```
              370                 375                 380
Leu Glu Lys Ser Lys Arg Ser Ser Lys Thr Phe Lys Glu Met Leu Gln
385                 390                 395                 400

Asp Arg Glu Ser Gln Asn Gln Lys Ser Thr Val Pro Ser Arg Arg Arg
                405                 410                 415

Met Tyr Ser Phe Asp Asp Val Leu Glu Gly Lys Arg Pro Pro Thr
                420                 425                 430

Met Thr Val Ser Glu Ala Ser Tyr Gln Ser Glu Arg Val Glu Glu Lys
                435                 440                 445

Gly Ala Thr Tyr Pro Ser Glu Ile Pro Lys Glu Asp Ser Thr Thr Phe
                450                 455                 460

Ala Lys Arg Glu Asp Arg Val Thr Thr Glu Ile Gln Leu Pro Ser Gln
465                 470                 475                 480

Ser Pro Val Glu Glu Gln Ser Pro Ala Ser Leu Ser Ser Leu Arg Ser
                485                 490                 495

Arg Ser Thr Gln Met Glu Ser Thr Arg Val Ser Ala Ser Leu Pro Arg
                500                 505                 510

Ser Tyr Arg Lys Thr Asp Thr Val Arg Leu Thr Ser Val Val Thr Pro
                515                 520                 525

Arg Pro Phe Gly Ser Gln Thr Arg Gly Ile Ser Ser Leu Pro Arg Ser
                530                 535                 540

Tyr Thr Met Asp Asp Ala Trp Lys Tyr Asn Gly Asp Val Glu Asp Ile
545                 550                 555                 560

Lys Arg Thr Pro Asn Asn Val Val Ser Thr Pro Ala Pro Ser Pro Asp
                565                 570                 575

Ala Ser Gln Leu Ala Ser Ser Leu Ser Ser Gln Lys Glu Val Ala Ala
                580                 585                 590

Thr Glu Glu Asp Val Thr Arg Leu Pro Ser Pro Thr Ser Pro Phe Ser
                595                 600                 605

Ser Leu Ser Gln Asp Gln Ala Ala Thr Ser Lys Ala Thr Leu Ser Ser
                610                 615                 620

Thr Ser Gly Leu Asp Leu Met Ser Glu Ser Gly Glu Gly Glu Ile Ser
625                 630                 635                 640

Pro Gln Arg Glu Val Ser Arg Ser Gln Gln Phe Ser Asp Met Arg
                645                 650                 655

Ile Ser Ile Asn Gln Thr Pro Gly Lys Ser Leu Asp Phe Gly Phe Thr
                660                 665                 670

Ile Lys Trp Asp Ile Pro Gly Ile Phe Val Ala Ser Val Glu Ala Gly
                675                 680                 685

Ser Pro Ala Glu Phe Ser Gln Leu Gln Val Asp Asp Glu Ile Ile Ala
                690                 695                 700

Ile Asn Asn Thr Lys Phe Ser Tyr Asn Asp Ser Lys Glu Trp Glu Glu
705                 710                 715                 720

Ala Met Ala Lys Ala Gln Glu Thr Gly His Leu Val Met Asp Val Arg
                725                 730                 735

Arg Tyr Gly Lys Ala Gly Ser Pro Glu Thr Lys Trp Ile Asp Ala Thr
                740                 745                 750

Ser Gly Ile Tyr Asn Ser Glu Lys Ser Ser Asn Leu Ser Val Thr Thr
                755                 760                 765

Asp Phe Ser Glu Ser Leu Gln Ser Ser Asn Ile Glu Ser Lys Glu Ile
                770                 775                 780

Asn Gly Ile His Asp Glu Ser Asn Ala Phe Glu Ser Lys Ala Ser Glu
785                 790                 795                 800
```

-continued

```
Ser Ile Ser Leu Lys Asn Leu Lys Arg Arg Ser Gln Phe Phe Glu Gln
                805                 810                 815
Gly Ser Ser Asp Ser Val Val Pro Asp Leu Pro Val Pro Thr Ile Ser
            820                 825                 830
Ala Pro Ser Arg Trp Val Trp Asp Gln Glu Glu Glu Arg Lys Arg Gln
        835                 840                 845
Glu Arg Trp Gln Lys Glu Gln Asp Arg Leu Leu Gln Glu Lys Tyr Gln
    850                 855                 860
Arg Glu Gln Glu Lys Leu Arg Glu Glu Trp Gln Arg Ala Lys Gln Glu
865                 870                 875                 880
Ala Glu Arg Glu Asn Ser Lys Tyr Leu Asp Glu Leu Met Val Leu
                885                 890                 895
Ser Ser Asn Ser Met Ser Leu Thr Thr Arg Glu Pro Ser Leu Ala Thr
                900                 905                 910
Trp Glu Ala Thr Trp Ser Glu Gly Ser Lys Ser Ser Asp Arg Glu Gly
        915                 920                 925
Thr Arg Ala Gly Glu Glu Arg Arg Gln Pro Gln Glu Glu Val Val
    930                 935                 940
His Glu Asp Gln Gly Lys Lys Pro Gln Asp Gln Leu Val Ile Glu Arg
945                 950                 955                 960
Glu Arg Lys Trp Glu Gln Gln Leu Gln Glu Gln Glu Gln Lys Arg
                965                 970                 975
Leu Gln Ala Glu Ala Glu Gln Lys Arg Pro Ala Glu Glu Gln Lys
                980                 985                 990
Arg Gln Ala Glu Ile Glu Arg Glu Thr Ser Val Arg Ile Tyr Gln Tyr
            995                 1000                1005
Arg Arg Pro Val Asp Ser Tyr Asp Ile Pro Lys Thr Glu Glu Ala
        1010                1015                1020
Ser Ser Gly Phe Leu Pro Gly Asp Arg Asn Lys Ser Arg Ser Thr
        1025                1030                1035
Thr Glu Leu Asp Asp Tyr Ser
        1040                1045

<210> SEQ ID NO 36
<211> LENGTH: 759
<212> TYPE: PRT
<213> ORGANISM: Homo sapiens

<400> SEQUENCE: 36

Met Glu Ser Ser Pro Phe Asn Arg Arg Gln Trp Thr Ser Leu Ser Leu
1               5                   10                  15
Arg Val Thr Ala Lys Glu Leu Ser Leu Val Asn Lys Asn Lys Ser Ser
                20                  25                  30
Ala Ile Val Glu Ile Phe Ser Lys Tyr Gln Lys Ala Ala Glu Glu Thr
            35                  40                  45
Asn Met Glu Lys Lys Arg Ser Asn Thr Glu Asn Leu Ser Gln His Phe
        50                  55                  60
Arg Lys Gly Thr Leu Thr Val Leu Lys Lys Trp Glu Asn Pro Gly
65                  70                  75                  80
Leu Gly Ala Glu Ser His Thr Asp Ser Leu Arg Asn Ser Ser Thr Glu
                85                  90                  95
Ile Arg His Arg Ala Asp His Pro Pro Ala Glu Val Thr Ser His Ala
            100                 105                 110
Ala Ser Gly Ala Lys Ala Asp Gln Glu Glu Gln Ile His Pro Arg Ser
```

```
            115                 120                 125
Arg Leu Arg Ser Pro Glu Ala Leu Val Gln Gly Arg Tyr Pro His
    130                 135                 140
Ile Lys Asp Gly Glu Asp Leu Lys Asp His Ser Thr Glu Ser Lys Lys
145                 150                 155                 160
Met Glu Asn Cys Leu Gly Glu Ser Arg His Glu Val Glu Lys Ser Glu
                165                 170                 175
Ile Ser Glu Asn Thr Asp Ala Ser Gly Lys Ile Glu Lys Tyr Asn Val
            180                 185                 190
Pro Leu Asn Arg Leu Lys Met Met Phe Glu Lys Gly Glu Pro Thr Gln
            195                 200                 205
Thr Lys Ile Leu Arg Ala Gln Ser Arg Ser Ala Ser Gly Arg Lys Ile
    210                 215                 220
Ser Glu Asn Ser Tyr Ser Leu Asp Asp Leu Glu Ile Gly Pro Gly Gln
225                 230                 235                 240
Leu Ser Ser Ser Thr Phe Asp Ser Glu Lys Asn Glu Ser Arg Arg Asn
                245                 250                 255
Leu Glu Leu Pro Arg Leu Ser Glu Thr Ser Ile Lys Asp Arg Met Ala
            260                 265                 270
Lys Tyr Gln Ala Ala Val Ser Lys Gln Ser Ser Ser Thr Asn Tyr Thr
    275                 280                 285
Asn Glu Leu Lys Ala Ser Gly Gly Glu Ile Lys Ile His Lys Met Glu
290                 295                 300
Gln Lys Glu Asn Val Pro Pro Gly Pro Glu Val Cys Ile Thr His Gln
305                 310                 315                 320
Glu Gly Glu Lys Ile Ser Ala Asn Glu Asn Ser Leu Ala Val Arg Ser
                325                 330                 335
Thr Pro Ala Glu Asp Asp Ser Arg Asp Ser Gln Val Lys Ser Glu Val
            340                 345                 350
Gln Gln Pro Val His Pro Lys Pro Leu Ser Pro Asp Ser Arg Ala Ser
    355                 360                 365
Ser Leu Ser Glu Ser Ser Pro Pro Lys Ala Met Lys Lys Phe Gln Ala
370                 375                 380
Pro Ala Arg Glu Thr Cys Val Glu Cys Gln Lys Thr Val Tyr Pro Met
385                 390                 395                 400
Glu Arg Leu Leu Ala Asn Gln Gln Val Phe His Ile Ser Cys Phe Arg
                405                 410                 415
Cys Ser Tyr Cys Asn Asn Lys Leu Ser Leu Gly Thr Tyr Ala Ser Leu
            420                 425                 430
His Gly Arg Ile Tyr Cys Lys Pro His Phe Asn Gln Leu Phe Lys Ser
    435                 440                 445
Lys Gly Asn Tyr Asp Glu Gly Phe Gly His Arg Pro His Lys Asp Leu
450                 455                 460
Trp Ala Ser Lys Asn Glu Asn Glu Glu Ile Leu Glu Arg Pro Ala Gln
465                 470                 475                 480
Leu Ala Asn Ala Arg Glu Thr Pro His Ser Pro Gly Val Glu Asp Ala
                485                 490                 495
Pro Ile Ala Lys Val Gly Val Leu Ala Ala Ser Met Glu Ala Lys Ala
            500                 505                 510
Ser Ser Gln Gln Glu Lys Glu Asp Lys Pro Ala Glu Thr Lys Lys Leu
    515                 520                 525
Arg Ile Ala Trp Pro Pro Pro Thr Glu Leu Gly Ser Ser Gly Ser Ala
530                 535                 540
```

```
Leu Glu Glu Gly Ile Lys Met Ser Lys Pro Lys Trp Pro Glu Asp
545                 550                 555                 560

Glu Ile Ser Lys Pro Glu Val Pro Glu Asp Val Asp Leu Asp Leu Lys
            565                 570                 575

Lys Leu Arg Arg Ser Ser Ser Leu Lys Glu Arg Ser Arg Pro Phe Thr
            580                 585                 590

Val Ala Ala Ser Phe Gln Ser Thr Ser Val Lys Ser Pro Lys Thr Val
            595                 600                 605

Ser Pro Pro Ile Arg Lys Gly Trp Ser Met Ser Glu Gln Ser Glu Glu
            610                 615                 620

Ser Val Gly Gly Arg Val Ala Glu Arg Lys Gln Val Glu Asn Ala Lys
625                 630                 635                 640

Ala Ser Lys Lys Asn Gly Asn Val Gly Lys Thr Thr Trp Gln Asn Lys
                645                 650                 655

Glu Ser Lys Gly Glu Thr Gly Lys Arg Ser Lys Glu Gly His Ser Leu
            660                 665                 670

Glu Met Glu Asn Glu Asn Leu Val Glu Asn Gly Ala Asp Ser Asp Glu
            675                 680                 685

Asp Asp Asn Ser Phe Leu Lys Gln Gln Ser Pro Gln Glu Pro Lys Ser
690                 695                 700

Leu Asn Trp Ser Ser Phe Val Asp Asn Thr Phe Ala Glu Glu Phe Thr
705                 710                 715                 720

Thr Gln Asn Gln Lys Ser Gln Asp Val Glu Leu Trp Glu Gly Glu Val
                725                 730                 735

Val Lys Glu Leu Ser Val Glu Glu Gln Ile Lys Arg Asn Arg Tyr Tyr
            740                 745                 750

Asp Glu Asp Glu Asp Glu Glu
            755

<210> SEQ ID NO 37
<211> LENGTH: 877
<212> TYPE: PRT
<213> ORGANISM: Homo sapiens

<400> SEQUENCE: 37

Met Leu Ala Ser Leu Tyr Asn Gly Ser Val Cys Val Trp Asn His Glu
1               5                   10                  15

Thr Gln Thr Leu Val Lys Thr Phe Glu Val Cys Asp Leu Pro Val Arg
            20                  25                  30

Ala Ala Lys Phe Val Ala Arg Lys Asn Trp Val Val Thr Gly Ala Asp
            35                  40                  45

Asp Met Gln Ile Arg Val Phe Asn Tyr Asn Thr Leu Glu Arg Val His
            50                  55                  60

Met Phe Glu Ala His Ser Asp Tyr Ile Arg Cys Ile Ala Val His Pro
65              70                  75                  80

Thr Gln Pro Phe Ile Leu Thr Ser Ser Asp Asp Met Leu Ile Lys Leu
            85                  90                  95

Trp Asp Trp Asp Lys Lys Trp Ser Cys Ser Gln Val Phe Glu Gly His
            100                 105                 110

Thr His Tyr Val Met Gln Ile Val Ile Asn Pro Lys Asp Asn Asn Gln
            115                 120                 125

Phe Ala Ser Ala Ser Leu Asp Arg Thr Ile Lys Val Trp Gln Leu Gly
            130                 135                 140

Ser Ser Ser Pro Asn Phe Thr Leu Glu Gly His Glu Lys Gly Val Asn
```

-continued

```
            145                 150                 155                 160
Cys Ile Asp Tyr Tyr Ser Gly Gly Asp Lys Pro Tyr Leu Ile Ser Gly
                165                 170                 175
Ala Asp Asp Arg Leu Val Lys Ile Trp Asp Tyr Gln Asn Lys Thr Cys
                180                 185                 190
Val Gln Thr Leu Glu Gly His Ala Gln Asn Val Ser Cys Ala Ser Phe
                195                 200                 205
His Pro Glu Leu Pro Ile Ile Ile Thr Gly Ser Glu Asp Gly Thr Val
            210                 215                 220
Arg Ile Trp His Ser Ser Thr Tyr Arg Leu Glu Ser Thr Leu Asn Tyr
225                 230                 235                 240
Gly Met Glu Arg Val Trp Cys Val Ala Ser Leu Arg Gly Ser Asn Asn
                245                 250                 255
Val Ala Leu Gly Tyr Asp Glu Gly Ser Ile Ile Val Lys Leu Gly Arg
                260                 265                 270
Glu Glu Pro Ala Met Ser Met Asp Ala Asn Gly Lys Ile Ile Trp Ala
                275                 280                 285
Lys His Ser Glu Val Gln Gln Ala Asn Leu Lys Ala Met Gly Asp Ala
            290                 295                 300
Glu Ile Lys Asp Gly Glu Arg Leu Pro Leu Ala Val Lys Asp Met Gly
305                 310                 315                 320
Ser Cys Glu Ile Tyr Pro Gln Thr Ile Gln His Asn Pro Asn Gly Arg
                325                 330                 335
Phe Val Val Val Cys Gly Asp Gly Glu Tyr Ile Ile Tyr Thr Ala Met
                340                 345                 350
Ala Leu Arg Asn Lys Ser Phe Gly Ser Ala Gln Glu Phe Ala Trp Ala
                355                 360                 365
His Asp Ser Ser Glu Tyr Ala Ile Arg Glu Ser Asn Ser Ile Val Lys
            370                 375                 380
Ile Phe Lys Asn Phe Lys Glu Lys Lys Ser Phe Lys Pro Asp Phe Gly
385                 390                 395                 400
Ala Glu Ser Ile Tyr Gly Gly Phe Leu Leu Gly Val Arg Ser Val Asn
                405                 410                 415
Gly Leu Ala Phe Tyr Asp Trp Asp Asn Thr Glu Leu Ile Arg Arg Ile
                420                 425                 430
Glu Ile Gln Pro Lys His Ile Phe Trp Ser Asp Ser Gly Glu Leu Val
                435                 440                 445
Cys Ile Ala Thr Glu Glu Ser Phe Phe Ile Leu Lys Tyr Leu Ser Glu
            450                 455                 460
Lys Val Leu Ala Ala Gln Glu Thr His Glu Gly Val Thr Glu Asp Gly
465                 470                 475                 480
Ile Glu Asp Ala Phe Glu Val Leu Gly Glu Ile Gln Glu Ile Val Lys
                485                 490                 495
Thr Gly Leu Trp Val Gly Asp Cys Phe Ile Tyr Thr Ser Ser Val Asn
                500                 505                 510
Arg Leu Asn Tyr Tyr Val Gly Gly Glu Ile Val Thr Ile Ala His Leu
            515                 520                 525
Asp Arg Thr Met Tyr Leu Leu Gly Tyr Ile Pro Lys Asp Asn Arg Leu
            530                 535                 540
Tyr Leu Gly Asp Lys Glu Leu Asn Ile Ile Ser Tyr Ser Leu Leu Val
545                 550                 555                 560
Ser Val Leu Glu Tyr Gln Thr Ala Val Met Arg Arg Asp Phe Ser Met
                565                 570                 575
```

```
Ala Asp Lys Val Leu Pro Thr Ile Pro Lys Glu Gln Arg Thr Arg Val
            580                 585                 590

Ala His Phe Leu Glu Lys Gln Gly Phe Lys Gln Gln Ala Leu Thr Val
            595                 600                 605

Ser Thr Asp Pro Glu His Arg Phe Glu Leu Ala Leu Gln Leu Gly Glu
            610                 615                 620

Leu Lys Ile Ala Tyr Gln Leu Ala Val Glu Ala Glu Ser Glu Gln Lys
625                 630                 635                 640

Trp Lys Gln Leu Ala Glu Leu Ala Ile Ser Lys Cys Gln Phe Gly Leu
                645                 650                 655

Ala Gln Glu Cys Leu His His Ala Gln Asp Tyr Gly Gly Leu Leu Leu
            660                 665                 670

Leu Ala Thr Ala Ser Gly Asn Ala Asn Met Val Asn Lys Leu Ala Glu
            675                 680                 685

Gly Ala Glu Arg Asp Gly Lys Asn Asn Val Ala Phe Met Ser Tyr Phe
690                 695                 700

Leu Gln Gly Lys Val Asp Ala Cys Leu Glu Leu Ile Arg Thr Gly
705                 710                 715                 720

Arg Leu Pro Glu Ala Ala Phe Leu Ala Arg Thr Tyr Leu Pro Ser Gln
            725                 730                 735

Val Ser Arg Val Val Lys Leu Trp Arg Glu Asn Leu Ser Lys Val Asn
            740                 745                 750

Gln Lys Ala Ala Glu Ser Leu Ala Asp Pro Thr Glu Tyr Glu Asn Leu
            755                 760                 765

Phe Pro Gly Leu Lys Glu Ala Phe Val Val Glu Trp Val Lys Glu
            770                 775                 780

Thr His Ala Asp Leu Trp Pro Ala Lys Gln Tyr Pro Leu Val Thr Pro
785                 790                 795                 800

Asn Glu Glu Arg Asn Val Met Glu Glu Gly Lys Asp Phe Gln Pro Ser
                805                 810                 815

Arg Ser Thr Ala Gln Gln Glu Leu Asp Gly Lys Pro Ala Ser Pro Thr
            820                 825                 830

Pro Val Ile Val Ala Ser His Thr Ala Asn Lys Glu Glu Lys Ser Leu
            835                 840                 845

Leu Glu Leu Glu Val Asp Leu Asp Asn Leu Gly Leu Glu Asp Ile Asp
850                 855                 860

Thr Thr Asp Ile Asn Leu Asp Glu Asp Ile Leu Asp
865                 870                 875

<210> SEQ ID NO 38
<211> LENGTH: 461
<212> TYPE: PRT
<213> ORGANISM: Homo sapiens

<400> SEQUENCE: 38

Met Ser Leu Asp Ile Gln Ser Leu Asp Ile Gln Cys Glu Glu Leu Ser
1               5                   10                  15

Asp Ala Arg Trp Ala Glu Leu Leu Pro Leu Leu Gln Gln Cys Gln Val
            20                  25                  30

Val Arg Leu Asp Asp Cys Gly Leu Thr Glu Ala Arg Cys Lys Asp Ile
            35                  40                  45

Ser Ser Ala Leu Arg Val Asn Pro Ala Leu Ala Glu Leu Asn Leu Arg
        50                  55                  60

Ser Asn Glu Leu Gly Asp Val Gly Val His Cys Val Leu Gln Gly Leu
```

```
            65                  70                  75                  80
        Gln Thr Pro Ser Cys Lys Ile Gln Lys Leu Ser Leu Gln Asn Cys Cys
                        85                  90                  95

Leu Thr Gly Ala Gly Cys Gly Val Leu Ser Ser Thr Leu Arg Thr Leu
                    100                 105                 110

Pro Thr Leu Gln Glu Leu His Leu Ser Asp Asn Leu Leu Gly Asp Ala
                    115                 120                 125

Gly Leu Gln Leu Leu Cys Glu Gly Leu Leu Asp Pro Gln Cys Arg Leu
                130                 135                 140

Glu Lys Leu Gln Leu Glu Tyr Cys Ser Leu Ser Ala Ala Ser Cys Glu
        145                 150                 155                 160

Pro Leu Ala Ser Val Leu Arg Ala Lys Pro Asp Phe Lys Glu Leu Thr
                        165                 170                 175

Val Ser Asn Asn Asp Ile Asn Glu Ala Gly Val Arg Val Leu Cys Gln
                    180                 185                 190

Gly Leu Lys Asp Ser Pro Cys Gln Leu Glu Ala Leu Lys Leu Glu Ser
                    195                 200                 205

Cys Gly Val Thr Ser Asp Asn Cys Arg Asp Leu Cys Gly Ile Val Ala
                    210                 215                 220

Ser Lys Ala Ser Leu Arg Glu Leu Ala Leu Gly Ser Asn Lys Leu Gly
        225                 230                 235                 240

Asp Val Gly Met Ala Glu Leu Cys Pro Gly Leu Leu His Pro Ser Ser
                        245                 250                 255

Arg Leu Arg Thr Leu Trp Ile Trp Glu Cys Gly Ile Thr Ala Lys Gly
                    260                 265                 270

Cys Gly Asp Leu Cys Arg Val Leu Arg Ala Lys Glu Ser Leu Lys Glu
                    275                 280                 285

Leu Ser Leu Ala Gly Asn Glu Leu Gly Asp Glu Gly Ala Arg Leu Leu
                    290                 295                 300

Cys Glu Thr Leu Leu Glu Pro Gly Cys Gln Leu Glu Ser Leu Trp Val
        305                 310                 315                 320

Lys Ser Cys Ser Phe Thr Ala Ala Cys Cys Ser His Phe Ser Ser Val
                        325                 330                 335

Leu Ala Gln Asn Arg Phe Leu Leu Glu Leu Gln Ile Ser Asn Asn Arg
                    340                 345                 350

Leu Glu Asp Ala Gly Val Arg Glu Leu Cys Gln Gly Leu Gly Gln Pro
                    355                 360                 365

Gly Ser Val Leu Arg Val Leu Trp Leu Ala Asp Cys Asp Val Ser Asp
                    370                 375                 380

Ser Ser Cys Ser Ser Leu Ala Ala Thr Leu Leu Ala Asn His Ser Leu
        385                 390                 395                 400

Arg Glu Leu Asp Leu Ser Asn Asn Cys Leu Gly Asp Ala Gly Ile Leu
                        405                 410                 415

Gln Leu Val Glu Ser Val Arg Gln Pro Gly Cys Leu Leu Glu Gln Leu
                    420                 425                 430

Val Leu Tyr Asp Ile Tyr Trp Ser Glu Glu Met Glu Asp Arg Leu Gln
                    435                 440                 445

Ala Leu Glu Lys Asp Lys Pro Ser Leu Arg Val Ile Ser
                450                 455                 460

<210> SEQ ID NO 39
<211> LENGTH: 596
<212> TYPE: PRT
<213> ORGANISM: Homo sapiens
```

<400> SEQUENCE: 39

Met Ser Asn Tyr Ser Val Ser Leu Val Gly Pro Ala Pro Trp Gly Phe
1               5                   10                  15

Arg Leu Gln Gly Gly Lys Asp Phe Asn Met Pro Leu Thr Ile Ser Ser
                20                  25                  30

Leu Lys Asp Gly Gly Lys Ala Ala Gln Ala Asn Val Arg Ile Gly Asp
            35                  40                  45

Val Val Leu Ser Ile Asp Gly Ile Asn Ala Gln Gly Met Thr His Leu
50                  55                  60

Glu Ala Gln Asn Lys Ile Lys Gly Cys Thr Gly Ser Leu Asn Met Thr
65                  70                  75                  80

Leu Gln Arg Ala Ser Ala Ala Pro Lys Pro Glu Pro Val Pro Val Gln
                85                  90                  95

Lys Gly Glu Pro Lys Glu Val Val Lys Pro Val Pro Ile Thr Ser Pro
                100                 105                 110

Ala Val Ser Lys Val Thr Ser Thr Asn Asn Met Ala Tyr Asn Lys Ala
            115                 120                 125

Pro Arg Pro Phe Gly Ser Val Ser Ser Pro Lys Val Thr Ser Ile Pro
130                 135                 140

Ser Pro Ser Ser Ala Phe Thr Pro Ala His Ala Thr Thr Ser Ser His
145                 150                 155                 160

Ala Ser Pro Ser Pro Val Ala Ala Val Thr Pro Pro Leu Phe Ala Ala
                165                 170                 175

Ser Gly Leu His Ala Asn Ala Asn Leu Ser Ala Asp Gln Ser Pro Ser
                180                 185                 190

Ala Leu Ser Ala Gly Lys Thr Ala Val Asn Val Pro Arg Gln Pro Thr
            195                 200                 205

Val Thr Ser Val Cys Ser Glu Thr Ser Gln Glu Leu Ala Glu Gly Gln
210                 215                 220

Arg Arg Gly Ser Gln Gly Asp Ser Lys Gln Gln Asn Gly Pro Pro Arg
225                 230                 235                 240

Lys His Ile Val Glu Arg Tyr Thr Glu Phe Tyr His Val Pro Thr His
                245                 250                 255

Ser Asp Ala Ser Lys Lys Arg Leu Ile Glu Asp Thr Glu Asp Trp Arg
                260                 265                 270

Pro Arg Thr Gly Thr Thr Gln Ser Arg Ser Phe Arg Ile Leu Ala Gln
            275                 280                 285

Ile Thr Gly Thr Glu His Leu Lys Glu Ser Glu Ala Asp Asn Thr Lys
290                 295                 300

Lys Ala Asn Asn Ser Gln Glu Pro Ser Pro Gln Leu Ala Ser Ser Val
305                 310                 315                 320

Ala Ser Thr Arg Ser Met Pro Glu Ser Leu Asp Ser Pro Thr Ser Gly
                325                 330                 335

Arg Pro Gly Val Thr Ser Leu Thr Ala Ala Ala Phe Lys Pro Val
                340                 345                 350

Gly Ser Thr Gly Val Ile Lys Ser Pro Ser Trp Gln Arg Pro Asn Gln
            355                 360                 365

Gly Val Pro Ser Thr Gly Arg Ile Ser Asn Ser Ala Thr Tyr Ser Gly
370                 375                 380

Ser Val Ala Pro Ala Asn Ser Ala Leu Gly Gln Thr Gln Pro Ser Asp
385                 390                 395                 400

Gln Asp Thr Leu Val Gln Arg Ala Glu His Ile Pro Ala Gly Lys Arg

```
                    405                 410                 415
Thr Pro Met Cys Ala His Cys Asn Gln Val Ile Arg Gly Pro Phe Leu
        420                 425                 430

Val Ala Leu Gly Lys Ser Trp His Pro Glu Glu Phe Asn Cys Ala His
        435                 440                 445

Cys Lys Asn Thr Met Ala Tyr Ile Gly Phe Val Glu Lys Gly Ala
        450                 455                 460

Leu Tyr Cys Glu Leu Cys Tyr Glu Lys Phe Phe Ala Pro Glu Cys Gly
465                 470                 475                 480

Arg Cys Gln Arg Lys Ile Leu Gly Glu Val Ile Ser Ala Leu Lys Gln
                485                 490                 495

Thr Trp His Val Ser Cys Phe Val Cys Val Ala Cys Gly Lys Pro Ile
            500                 505                 510

Arg Asn Asn Val Phe His Leu Glu Asp Gly Pro Tyr Cys Glu Thr
            515                 520                 525

Asp Tyr Tyr Ala Leu Phe Gly Thr Ile Cys His Gly Cys Glu Phe Pro
        530                 535                 540

Ile Glu Ala Gly Asp Met Phe Leu Glu Ala Leu Gly Tyr Thr Trp His
545                 550                 555                 560

Asp Thr Cys Phe Val Cys Ser Val Cys Cys Glu Ser Leu Glu Gly Gln
                565                 570                 575

Thr Phe Phe Ser Lys Lys Asp Lys Pro Leu Cys Lys Lys His Ala His
                580                 585                 590

Ser Val Asn Phe
        595

<210> SEQ ID NO 40
<211> LENGTH: 331
<212> TYPE: PRT
<213> ORGANISM: Homo sapiens

<400> SEQUENCE: 40

Met Ala Arg Gly Gly Arg Gly Arg Arg Leu Gly Leu Ala Leu Gly Leu
1               5                   10                  15

Leu Leu Ala Leu Val Leu Ala Pro Arg Val Leu Arg Ala Lys Pro Thr
                20                  25                  30

Val Arg Lys Glu Arg Val Val Arg Pro Asp Ser Glu Leu Gly Glu Arg
            35                  40                  45

Pro Pro Glu Asp Asn Gln Ser Phe Gln Tyr Asp His Glu Ala Phe Leu
        50                  55                  60

Gly Lys Glu Asp Ser Lys Thr Phe Asp Gln Leu Thr Pro Asp Glu Ser
65                  70                  75                  80

Lys Glu Arg Leu Gly Lys Ile Val Asp Arg Ile Asp Asn Asp Gly Asp
                85                  90                  95

Gly Phe Val Thr Thr Glu Glu Leu Lys Thr Trp Ile Lys Arg Val Gln
            100                 105                 110

Lys Arg Tyr Ile Phe Asp Asn Val Ala Lys Val Trp Lys Asp Tyr Asp
        115                 120                 125

Arg Asp Lys Asp Asp Lys Ile Ser Trp Glu Glu Tyr Lys Gln Ala Thr
    130                 135                 140

Tyr Gly Tyr Tyr Leu Gly Asn Pro Ala Glu Phe His Asp Ser Ser Asp
145                 150                 155                 160

His His Thr Phe Lys Lys Met Leu Pro Arg Asp Glu Arg Arg Phe Lys
                165                 170                 175
```

```
Ala Ala Asp Leu Asn Gly Asp Leu Thr Ala Thr Arg Glu Glu Phe Thr
            180                 185                 190

Ala Phe Leu His Pro Glu Glu Phe Glu His Met Lys Glu Ile Val Val
        195                 200                 205

Leu Glu Thr Leu Glu Asp Ile Asp Lys Asn Gly Asp Gly Phe Val Asp
    210                 215                 220

Gln Asp Glu Tyr Ile Ala Asp Met Phe Ser His Glu Glu Asn Gly Pro
225                 230                 235                 240

Glu Pro Asp Trp Val Leu Ser Glu Arg Glu Gln Phe Asn Glu Phe Arg
                245                 250                 255

Asp Leu Asn Lys Asp Gly Lys Leu Asp Lys Asp Glu Ile Arg His Trp
            260                 265                 270

Ile Leu Pro Gln Asp Tyr Asp His Ala Gln Ala Glu Ala Arg His Leu
        275                 280                 285

Val Tyr Glu Ser Asp Lys Asn Lys Asp Glu Lys Leu Thr Lys Glu Glu
    290                 295                 300

Ile Leu Glu Asn Trp Asn Met Phe Val Gly Ser Gln Ala Thr Asn Tyr
305                 310                 315                 320

Gly Glu Asp Leu Thr Lys Asn His Asp Glu Leu
                325                 330

<210> SEQ ID NO 41
<211> LENGTH: 1411
<212> TYPE: PRT
<213> ORGANISM: Homo sapiens

<400> SEQUENCE: 41

Met Leu Arg Arg Ile Leu Gln Arg Thr Pro Gly Arg Val Gly Ser Gln
1               5                   10                  15

Gly Ser Asp Leu Asp Ser Ser Ala Thr Pro Ile Asn Thr Val Asp Val
            20                  25                  30

Asn Asn Glu Ser Ser Ser Glu Gly Phe Ile Cys Pro Gln Cys Met Lys
        35                  40                  45

Ser Leu Gly Ser Ala Asp Glu Leu Phe Lys His Tyr Glu Ala Val His
    50                  55                  60

Asp Ala Gly Asn Asp Ser Gly His Gly Gly Glu Ser Asn Leu Ala Leu
65                  70                  75                  80

Lys Arg Asp Asp Val Thr Leu Leu Arg Gln Glu Val Gln Asp Leu Gln
                85                  90                  95

Ala Ser Leu Lys Glu Glu Lys Trp Tyr Ser Glu Glu Leu Lys Lys Glu
            100                 105                 110

Leu Glu Lys Tyr Gln Gly Leu Gln Gln Gln Glu Ala Lys Pro Asp Gly
        115                 120                 125

Leu Val Thr Asp Ser Ser Ala Glu Leu Gln Ser Leu Glu Gln Gln Leu
    130                 135                 140

Glu Glu Ala Gln Thr Glu Asn Phe Asn Ile Lys Gln Met Lys Asp Leu
145                 150                 155                 160

Phe Glu Gln Lys Ala Ala Gln Leu Ala Thr Glu Ile Ala Asp Ile Lys
                165                 170                 175

Ser Lys Tyr Asp Glu Glu Arg Ser Leu Arg Glu Ala Ala Glu Gln Lys
            180                 185                 190

Val Thr Arg Leu Thr Glu Glu Leu Asn Lys Glu Ala Thr Val Ile Gln
        195                 200                 205

Asp Leu Lys Thr Glu Leu Leu Gln Arg Pro Gly Ile Glu Asp Val Ala
    210                 215                 220
```

```
Val Leu Lys Lys Glu Leu Val Gln Val Gln Thr Leu Met Asp Asn Met
225                 230                 235                 240

Thr Leu Glu Arg Glu Arg Glu Ser Glu Lys Leu Lys Asp Glu Cys Lys
            245                 250                 255

Lys Leu Gln Ser Gln Tyr Ala Ser Ser Glu Ala Thr Ile Ser Gln Leu
        260                 265                 270

Arg Ser Glu Leu Ala Lys Gly Pro Gln Glu Val Ala Val Tyr Val Gln
    275                 280                 285

Glu Leu Gln Lys Leu Lys Ser Ser Val Asn Glu Leu Thr Gln Lys Asn
290                 295                 300

Gln Thr Leu Thr Glu Asn Leu Lys Lys Glu Gln Asp Tyr Thr Lys
305                 310                 315                 320

Leu Glu Glu Lys His Asn Glu Ser Val Ser Lys Lys Asn Ile Gln
                325                 330                 335

Ala Thr Leu His Gln Lys Asp Leu Asp Cys Gln Gln Leu Gln Ser Arg
            340                 345                 350

Leu Ser Ala Ser Glu Thr Ser Leu His Arg Ile His Val Glu Leu Ser
    355                 360                 365

Glu Lys Gly Glu Ala Thr Gln Lys Leu Lys Glu Glu Leu Ser Glu Val
370                 375                 380

Glu Thr Lys Tyr Gln His Leu Lys Ala Glu Phe Lys Gln Leu Gln Gln
385                 390                 395                 400

Gln Arg Glu Glu Lys Glu Gln His Gly Leu Gln Leu Gln Ser Glu Ile
                405                 410                 415

Asn Gln Leu His Ser Lys Leu Leu Glu Thr Glu Arg Gln Leu Gly Glu
            420                 425                 430

Ala His Gly Arg Leu Lys Glu Gln Arg Gln Leu Ser Ser Glu Lys Leu
    435                 440                 445

Met Asp Lys Glu Gln Gln Val Ala Asp Leu Gln Leu Lys Leu Ser Arg
450                 455                 460

Leu Glu Glu Gln Leu Lys Glu Lys Val Thr Asn Ser Thr Glu Leu Gln
465                 470                 475                 480

His Gln Leu Asp Lys Thr Lys Gln Gln His Gln Glu Gln Gln Ala Leu
                485                 490                 495

Gln Gln Ser Thr Thr Ala Lys Leu Arg Glu Ala Gln Asn Asp Leu Glu
            500                 505                 510

Gln Val Leu Arg Gln Ile Gly Asp Lys Asp Gln Lys Ile Gln Asn Leu
    515                 520                 525

Glu Ala Leu Leu Gln Lys Ser Lys Glu Asn Ile Ser Leu Leu Glu Lys
530                 535                 540

Glu Arg Glu Asp Leu Tyr Ala Lys Ile Gln Ala Gly Glu Gly Glu Thr
545                 550                 555                 560

Ala Val Leu Asn Gln Leu Gln Glu Lys Asn His Thr Leu Gln Glu Gln
                565                 570                 575

Val Thr Gln Leu Thr Glu Lys Leu Lys Asn Gln Ser Glu Ser His Lys
            580                 585                 590

Gln Ala Gln Glu Asn Leu His Asp Gln Val Gln Glu Gln Lys Ala His
    595                 600                 605

Leu Arg Ala Ala Gln Asp Arg Val Leu Ser Leu Glu Thr Ser Val Asn
610                 615                 620

Glu Leu Asn Ser Gln Leu Asn Glu Ser Lys Glu Lys Val Ser Gln Leu
625                 630                 635                 640
```

-continued

```
Asp Ile Gln Ile Lys Ala Lys Thr Glu Leu Leu Ser Ala Glu Ala
                645                 650                 655

Ala Lys Thr Ala Gln Arg Ala Asp Leu Gln Asn His Leu Asp Thr Ala
        660                 665                 670

Gln Asn Ala Leu Gln Asp Lys Gln Glu Leu Asn Lys Ile Thr Thr
    675                 680                 685

Gln Leu Asp Gln Val Thr Ala Lys Leu Gln Asp Lys Gln Glu His Cys
    690                 695                 700

Ser Gln Leu Glu Ser His Leu Lys Glu Tyr Lys Glu Lys Tyr Leu Ser
705                 710                 715                 720

Leu Glu Gln Lys Thr Glu Glu Leu Glu Gly Gln Ile Lys Lys Leu Glu
                725                 730                 735

Ala Asp Ser Leu Glu Val Lys Ala Ser Lys Glu Gln Ala Leu Gln Asp
            740                 745                 750

Leu Gln Gln Gln Arg Gln Leu Asn Thr Asp Leu Glu Leu Arg Ala Thr
        755                 760                 765

Glu Leu Ser Lys Gln Leu Glu Met Glu Lys Glu Ile Val Ser Ser Thr
    770                 775                 780

Arg Leu Asp Leu Gln Lys Lys Ser Glu Ala Leu Glu Ser Ile Lys Gln
785                 790                 795                 800

Lys Leu Thr Lys Gln Glu Glu Lys Lys Ile Leu Lys Gln Asp Phe
                805                 810                 815

Glu Thr Leu Ser Gln Glu Thr Lys Ile Gln His Glu Leu Asn Asn
            820                 825                 830

Arg Ile Gln Thr Thr Val Thr Glu Leu Gln Lys Val Lys Met Glu Lys
        835                 840                 845

Glu Ala Leu Met Thr Glu Leu Ser Thr Val Lys Asp Lys Leu Ser Lys
    850                 855                 860

Val Ser Asp Ser Leu Lys Asn Ser Lys Ser Glu Phe Glu Lys Glu Asn
865                 870                 875                 880

Gln Lys Gly Lys Ala Ala Ile Leu Asp Leu Glu Lys Thr Cys Lys Glu
                885                 890                 895

Leu Lys His Gln Leu Gln Val Gln Met Glu Asn Thr Leu Lys Glu Gln
            900                 905                 910

Lys Glu Leu Lys Lys Ser Leu Glu Lys Glu Lys Glu Ala Ser His Gln
        915                 920                 925

Leu Lys Leu Glu Leu Asn Ser Met Gln Glu Gln Leu Ile Gln Ala Gln
    930                 935                 940

Asn Thr Leu Lys Gln Asn Glu Lys Glu Gln Gln Leu Gln Gly Asn
945                 950                 955                 960

Ile Asn Glu Leu Lys Gln Ser Ser Glu Gln Lys Lys Gln Ile Glu
                965                 970                 975

Ala Leu Gln Gly Glu Leu Lys Ile Ala Val Leu Gln Lys Thr Glu Leu
            980                 985                 990

Glu Asn Lys Leu Gln Gln Gln Leu  Thr Gln Ala Ala Gln  Glu Leu Ala
        995                 1000                1005

Ala Glu  Lys Glu Lys Ile Ser  Val Leu Gln Asn Asn  Tyr Glu Lys
        1010                1015                1020

Ser Gln  Glu Thr Phe Lys Gln  Leu Gln Ser Asp Phe  Tyr Gly Arg
        1025                1030                1035

Glu Ser  Glu Leu Leu Ala Thr  Arg Gln Asp Leu Lys  Ser Val Glu
        1040                1045                1050

Glu Lys  Leu Ser Leu Ala Gln  Glu Asp Leu Ile Ser  Asn Arg Asn
```

```
                1055                1060                1065
Gln Ile Gly Asn Gln Asn Lys Leu Ile Gln Glu Leu Lys Thr Ala
            1070                1075                1080
Lys Ala Thr Leu Glu Gln Asp Ser Ala Lys Lys Glu Gln Gln Leu
            1085                1090                1095
Gln Glu Arg Cys Lys Ala Leu Gln Asp Ile Gln Lys Glu Lys Ser
            1100                1105                1110
Leu Lys Glu Lys Glu Leu Val Asn Glu Lys Ser Lys Leu Ala Glu
            1115                1120                1125
Ile Glu Glu Ile Lys Cys Arg Gln Glu Lys Glu Ile Thr Lys Leu
            1130                1135                1140
Asn Glu Glu Leu Lys Ser His Lys Leu Glu Ser Ile Lys Glu Ile
            1145                1150                1155
Thr Asn Leu Lys Asp Ala Lys Gln Leu Leu Ile Gln Gln Lys Leu
            1160                1165                1170
Glu Leu Gln Gly Lys Ala Asp Ser Leu Lys Ala Ala Val Glu Gln
            1175                1180                1185
Glu Lys Arg Asn Gln Gln Ile Leu Lys Asp Gln Val Lys Lys Glu
            1190                1195                1200
Glu Glu Glu Leu Lys Lys Glu Phe Ile Glu Lys Glu Ala Lys Leu
            1205                1210                1215
His Ser Glu Ile Lys Glu Lys Glu Val Gly Met Lys Lys His Glu
            1220                1225                1230
Glu Asn Glu Ala Lys Leu Thr Met Gln Ile Thr Ala Leu Asn Glu
            1235                1240                1245
Asn Leu Gly Thr Val Lys Lys Glu Trp Gln Ser Ser Gln Arg Arg
            1250                1255                1260
Val Ser Glu Leu Glu Lys Gln Thr Asp Asp Leu Arg Gly Glu Ile
            1265                1270                1275
Ala Val Leu Glu Ala Thr Val Gln Asn Asn Gln Asp Glu Arg Arg
            1280                1285                1290
Ala Leu Leu Glu Arg Cys Leu Lys Gly Glu Gly Glu Ile Glu Lys
            1295                1300                1305
Leu Gln Thr Lys Val Leu Glu Leu Gln Arg Lys Leu Asp Asn Thr
            1310                1315                1320
Thr Ala Ala Val Gln Glu Leu Gly Arg Glu Asn Gln Ser Leu Gln
            1325                1330                1335
Ile Lys His Thr Gln Ala Leu Asn Arg Lys Trp Ala Glu Asp Asn
            1340                1345                1350
Glu Val Gln Asn Cys Met Ala Cys Gly Lys Gly Phe Ser Val Thr
            1355                1360                1365
Val Arg Arg His His Cys Arg Gln Cys Gly Asn Ile Phe Cys Ala
            1370                1375                1380
Glu Cys Ser Ala Lys Asn Ala Leu Thr Pro Ser Ser Lys Lys Pro
            1385                1390                1395
Val Arg Val Cys Asp Ala Cys Phe Asn Asp Leu Gln Gly
            1400                1405                1410

<210> SEQ ID NO 42
<211> LENGTH: 360
<212> TYPE: PRT
<213> ORGANISM: Homo sapiens

<400> SEQUENCE: 42
```

Met Ser Lys Gln Gln Pro Thr Gln Phe Ile Asn Pro Glu Thr Pro Gly
1               5                   10                  15

Tyr Val Gly Phe Ala Asn Leu Pro Asn Gln Val His Arg Lys Ser Val
            20                  25                  30

Lys Lys Gly Phe Glu Phe Thr Leu Met Val Val Gly Glu Ser Gly Leu
            35                  40                  45

Gly Lys Ser Thr Leu Ile Asn Ser Leu Phe Leu Thr Asp Leu Tyr Pro
        50                  55                  60

Glu Arg Val Ile Pro Gly Ala Ala Glu Lys Ile Glu Arg Thr Val Gln
65                  70                  75                  80

Ile Glu Ala Ser Thr Val Glu Ile Glu Arg Gly Val Lys Leu Arg
                85                  90                  95

Leu Thr Val Val Asp Thr Pro Gly Tyr Gly Asp Ala Ile Asn Cys Arg
                100                 105                 110

Asp Cys Phe Lys Thr Ile Ile Ser Tyr Ile Asp Glu Gln Phe Glu Arg
            115                 120                 125

Tyr Leu His Asp Glu Ser Gly Leu Asn Arg Arg His Ile Ile Asp Asn
        130                 135                 140

Arg Val His Cys Cys Phe Tyr Phe Ile Ser Pro Phe Gly His Gly Leu
145                 150                 155                 160

Lys Pro Leu Asp Val Ala Phe Met Lys Ala Ile His Asn Lys Val Asn
                165                 170                 175

Ile Val Pro Val Ile Ala Lys Ala Asp Thr Leu Thr Leu Lys Glu Arg
                180                 185                 190

Glu Arg Leu Lys Lys Arg Ile Leu Asp Glu Ile Glu Glu His Asn Ile
            195                 200                 205

Lys Ile Tyr His Leu Pro Asp Ala Glu Ser Asp Glu Asp Glu Asp Phe
        210                 215                 220

Lys Glu Gln Thr Arg Leu Leu Lys Ala Ser Ile Pro Phe Ser Val Val
225                 230                 235                 240

Gly Ser Asn Gln Leu Ile Glu Ala Lys Gly Lys Lys Val Arg Gly Arg
                245                 250                 255

Leu Tyr Pro Trp Gly Val Val Glu Val Glu Asn Pro Glu His Asn Asp
            260                 265                 270

Phe Leu Lys Leu Arg Thr Met Leu Ile Thr His Met Gln Asp Leu Gln
        275                 280                 285

Glu Val Thr Gln Asp Leu His Tyr Glu Asn Phe Arg Ser Glu Arg Leu
        290                 295                 300

Lys Arg Gly Gly Arg Lys Val Glu Asn Glu Asp Met Asn Lys Asp Gln
305                 310                 315                 320

Ile Leu Leu Glu Lys Glu Ala Glu Leu Arg Arg Met Gln Glu Met Ile
                325                 330                 335

Ala Arg Met Gln Ala Gln Met Gln Met Gln Met Gln Gly Gly Asp Gly
            340                 345                 350

Asp Gly Gly Ala Leu Gly His His
        355                 360

<210> SEQ ID NO 43
<211> LENGTH: 300
<212> TYPE: PRT
<213> ORGANISM: Homo sapiens

<400> SEQUENCE: 43

Met Ile Leu Leu Glu Val Asn Asn Arg Ile Ile Glu Glu Thr Leu Ala
1               5                   10                  15

```
Leu Lys Phe Glu Asn Ala Ala Gly Asn Lys Pro Glu Ala Val Glu
            20                  25                  30

Val Thr Phe Ala Asp Phe Asp Gly Val Leu Tyr His Ile Ser Asn Pro
        35                  40                  45

Asn Gly Asp Lys Thr Lys Val Met Val Ser Ile Ser Leu Lys Phe Tyr
    50                  55                  60

Lys Glu Leu Gln Ala His Gly Ala Asp Glu Leu Leu Lys Arg Val Tyr
65                  70                  75                  80

Gly Ser Phe Leu Val Asn Pro Glu Ser Gly Tyr Asn Val Ser Leu Leu
                85                  90                  95

Tyr Asp Leu Glu Asn Leu Pro Ala Ser Lys Asp Ser Ile Val His Gln
            100                 105                 110

Ala Gly Met Leu Lys Arg Asn Cys Phe Ala Ser Val Phe Glu Lys Tyr
        115                 120                 125

Phe Gln Phe Gln Glu Glu Gly Lys Glu Gly Glu Asn Arg Ala Val Ile
130                 135                 140

His Tyr Arg Asp Asp Glu Thr Met Tyr Val Glu Ser Lys Lys Asp Arg
145                 150                 155                 160

Val Thr Val Val Phe Ser Thr Val Phe Lys Asp Asp Asp Val Val
                165                 170                 175

Ile Gly Lys Val Phe Met Gln Glu Phe Lys Glu Gly Arg Arg Ala Ser
            180                 185                 190

His Thr Ala Pro Gln Val Leu Phe Ser His Arg Glu Pro Pro Leu Glu
        195                 200                 205

Leu Lys Asp Thr Asp Ala Ala Val Gly Asp Asn Ile Gly Tyr Ile Thr
    210                 215                 220

Phe Val Leu Phe Pro Arg His Thr Asn Ala Ser Ala Arg Asp Asn Thr
225                 230                 235                 240

Ile Asn Leu Ile His Thr Phe Arg Asp Tyr Leu His Tyr His Ile Lys
                245                 250                 255

Cys Ser Lys Ala Tyr Ile His Thr Arg Met Arg Ala Lys Thr Ser Asp
            260                 265                 270

Phe Leu Lys Val Leu Asn Arg Ala Arg Pro Asp Ala Glu Lys Lys Glu
        275                 280                 285

Met Lys Thr Ile Thr Gly Lys Thr Phe Ser Ser Arg
    290                 295                 300

<210> SEQ ID NO 44
<211> LENGTH: 425
<212> TYPE: PRT
<213> ORGANISM: Homo sapiens

<400> SEQUENCE: 44

Met Ala Val Ala Val Gly Arg Pro Ser Asn Glu Glu Leu Arg Asn Leu
1               5                   10                  15

Ser Leu Ser Gly His Val Gly Phe Asp Ser Leu Pro Asp Gln Leu Val
            20                  25                  30

Asn Lys Ser Thr Ser Gln Gly Phe Cys Phe Asn Ile Leu Cys Val Gly
        35                  40                  45

Glu Thr Gly Ile Gly Lys Ser Thr Leu Met Asp Thr Leu Phe Asn Thr
    50                  55                  60

Lys Phe Glu Ser Asp Pro Ala Thr His Asn Glu Pro Gly Val Arg Leu
65                  70                  75                  80

Lys Ala Arg Ser Tyr Glu Leu Gln Glu Ser Asn Val Arg Leu Lys Leu
```

```
                    85                  90                  95
Thr Ile Val Asp Thr Val Gly Phe Gly Asp Gln Ile Asn Lys Asp Asp
                100                 105                 110

Ser Tyr Lys Pro Ile Val Glu Tyr Ile Asp Ala Gln Phe Glu Ala Tyr
                115                 120                 125

Leu Gln Glu Glu Leu Lys Ile Lys Arg Ser Leu Phe Asn Tyr His Asp
                130                 135                 140

Thr Arg Ile His Ala Cys Leu Tyr Phe Ile Ala Pro Thr Gly His Ser
145                 150                 155                 160

Leu Lys Ser Leu Asp Leu Val Thr Met Lys Lys Leu Asp Ser Lys Val
                165                 170                 175

Asn Ile Ile Pro Ile Ile Ala Lys Ala Asp Thr Ile Ala Lys Asn Glu
                180                 185                 190

Leu His Lys Phe Lys Ser Lys Ile Met Ser Glu Leu Val Ser Asn Gly
                195                 200                 205

Val Gln Ile Tyr Gln Phe Pro Thr Asp Glu Glu Thr Val Ala Glu Ile
                210                 215                 220

Asn Ala Thr Met Ser Val His Leu Pro Phe Ala Val Val Gly Ser Thr
225                 230                 235                 240

Glu Glu Val Lys Ile Gly Asn Lys Met Ala Lys Ala Arg Gln Tyr Pro
                245                 250                 255

Trp Gly Val Val Gln Val Glu Asn Glu Asn His Cys Asp Phe Val Lys
                260                 265                 270

Leu Arg Glu Met Leu Ile Arg Val Asn Met Glu Asp Leu Arg Glu Gln
                275                 280                 285

Thr His Thr Arg His Tyr Glu Leu Tyr Arg Arg Cys Lys Leu Glu Glu
                290                 295                 300

Met Gly Phe Lys Asp Thr Asp Pro Asp Ser Lys Pro Phe Ser Leu Gln
305                 310                 315                 320

Glu Thr Tyr Glu Ala Lys Arg Asn Glu Phe Leu Gly Glu Leu Gln Lys
                325                 330                 335

Lys Glu Glu Glu Met Arg Gln Met Phe Val Met Arg Val Lys Glu Lys
                340                 345                 350

Glu Ala Glu Leu Lys Glu Ala Glu Lys Glu Leu His Glu Lys Phe Asp
                355                 360                 365

Leu Leu Lys Arg Thr His Gln Glu Glu Lys Lys Val Glu Asp Lys
                370                 375                 380

Lys Lys Glu Leu Glu Glu Val Asn Asn Phe Gln Lys Lys Lys Ala
385                 390                 395                 400

Ala Ala Gln Leu Leu Gln Ser Gln Ala Gln Gln Ser Gly Ala Gln Gln
                405                 410                 415

Thr Lys Lys Asp Lys Asp Lys Lys
                420                 425

<210> SEQ ID NO 45
<211> LENGTH: 325
<212> TYPE: PRT
<213> ORGANISM: Homo sapiens

<400> SEQUENCE: 45

Met Leu Pro Arg Val Gly Cys Pro Ala Leu Pro Leu Pro Pro Pro Pro
1               5                   10                  15

Leu Leu Pro Leu Leu Leu Leu Leu Gly Ala Ser Gly Gly Gly Gly Gly
                20                  25                  30
```

Gly Ala Arg Ala Glu Val Leu Phe Arg Cys Pro Cys Thr Pro Glu
            35                  40                  45

Arg Leu Ala Ala Cys Gly Pro Pro Val Ala Pro Ala Ala Val
 50                  55                  60

Ala Ala Val Ala Gly Gly Ala Arg Met Pro Cys Ala Glu Leu Val Arg
 65                  70                  75                  80

Glu Pro Gly Cys Gly Cys Ser Val Cys Ala Arg Leu Glu Gly Glu
                85                  90                  95

Ala Cys Gly Val Tyr Thr Pro Arg Cys Gly Gln Gly Leu Arg Cys Tyr
            100                 105                 110

Pro His Pro Gly Ser Glu Leu Pro Leu Gln Ala Leu Val Met Gly Glu
            115                 120                 125

Gly Thr Cys Glu Lys Arg Arg Asp Ala Glu Tyr Gly Ala Ser Pro Glu
130                 135                 140

Gln Val Ala Asp Asn Gly Asp Asp His Ser Glu Gly Leu Val Glu
145                 150                 155                 160

Asn His Val Asp Ser Thr Met Asn Met Leu Gly Gly Gly Ser Ala
                165                 170                 175

Gly Arg Lys Pro Leu Lys Ser Gly Met Lys Glu Leu Ala Val Phe Arg
            180                 185                 190

Glu Lys Val Thr Glu Gln His Arg Gln Met Gly Lys Gly Lys His
            195                 200                 205

His Leu Gly Leu Glu Glu Pro Lys Lys Leu Arg Pro Pro Ala Arg
210                 215                 220

Thr Pro Cys Gln Gln Glu Leu Asp Gln Val Leu Glu Arg Ile Ser Thr
225                 230                 235                 240

Met Arg Leu Pro Asp Glu Arg Gly Pro Leu Glu His Leu Tyr Ser Leu
                245                 250                 255

His Ile Pro Asn Cys Asp Lys His Gly Leu Tyr Asn Leu Lys Gln Cys
            260                 265                 270

Lys Met Ser Leu Asn Gly Gln Arg Gly Glu Cys Trp Cys Val Asn Pro
            275                 280                 285

Asn Thr Gly Lys Leu Ile Gln Gly Ala Pro Thr Ile Arg Gly Asp Pro
290                 295                 300

Glu Cys His Leu Phe Tyr Asn Glu Gln Glu Ala Arg Gly Val His
305                 310                 315                 320

Thr Gln Arg Met Gln
            325

<210> SEQ ID NO 46
<211> LENGTH: 357
<212> TYPE: PRT
<213> ORGANISM: Homo sapiens

<400> SEQUENCE: 46

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Glu Gly Ile Gly Asn Gly Thr Gln Ile
            100                 105                 110

Tyr Val Ile Asp Pro Glu Pro Cys Pro Asp Ser Asp Gln Glu Pro Lys
            115                 120                 125

Ser Ser Asp Lys Thr His Thr Ser Pro Pro Ser Pro Ala Pro Glu Leu
        130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 47
<211> LENGTH: 357
<212> TYPE: PRT
<213> ORGANISM: Homo sapiens

<400> SEQUENCE: 47

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu

```
                    85                  90                  95
Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Gln Glu Pro Lys
            115                 120                 125

Ser Ser Asp Lys Thr His Thr Ser Pro Pro Ser Pro Ala Pro Glu Leu
        130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Asp Val
                165                 170                 175

Ser His Glu Asp Pro Glu Val Lys Phe Asn Trp Tyr Val Asp Gly Val
                180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
        210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
        290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 48
<211> LENGTH: 125
<212> TYPE: PRT
<213> ORGANISM: Homo sapiens

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly His
            20                  25                  30

Trp Met Asn Trp Val Arg Gln Ala Pro Gly Lys Gly Leu Glu Trp Val
        35                  40                  45

Gly Ile Met Ile His Pro Ser Asp Ser Glu Thr Arg Tyr Asn Gln Lys
    50                  55                  60

Phe Lys Asp Ile Arg Phe Thr Ile Ser Val Asp Lys Ser Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Ala Arg Ile Gly Ile Tyr Phe Tyr Gly Thr Thr Tyr Phe Asp
            100                 105                 110

Tyr Ile Trp Gly Gln Gly Thr Leu Val Thr Val Ser Ser
        115                 120             125

<210> SEQ ID NO 49
<211> LENGTH: 108
<212> TYPE: PRT
<213> ORGANISM: Homo sapiens
<220> FEATURE:
<221> NAME/KEY: misc_feature
<222> LOCATION: (36)..(36)
<223> OTHER INFORMATION: Xaa can be any naturally occurring amino acid

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Thr Ile Ser Lys Tyr
            20                  25                  30

Leu Ala Trp Xaa Gln Gln Lys Pro Gly Lys Ala Pro Lys Leu Leu Ile
            35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Leu
                85                  90                  95

Thr Phe Gly Gln Gly Thr Lys Val Glu Ile Lys Arg
            100                 105
```